United States Patent
McCafferty et al.

(10) Patent No.: US 11,286,477 B2
(45) Date of Patent: *Mar. 29, 2022

(54) PREPARATION OF LIBRARIES OF PROTEIN VARIANTS EXPRESSED IN EUKARYOTIC CELLS AND USE FOR SELECTING BINDING MOLECULES

(71) Applicant: IONTAS LIMITED, Sawston (GB)

(72) Inventors: John McCafferty, Babraham (GB); Michael Dyson, Cambridge (GB); Kothai Parthiban, Cambridge (GB)

(73) Assignee: Iontas Limited, Sawston (GB)

(*) Notice: Subject to any disclaimer, the term of this patent is extended or adjusted under 35 U.S.C. 154(b) by 54 days.

This patent is subject to a terminal disclaimer.

(21) Appl. No.: 15/308,570

(22) PCT Filed: May 1, 2015

(86) PCT No.: PCT/GB2015/051287
§ 371 (c)(1),
(2) Date: Nov. 2, 2016

(87) PCT Pub. No.: WO2015/166272
PCT Pub. Date: Nov. 5, 2015

(65) Prior Publication Data
US 2017/0073664 A1  Mar. 16, 2017

(30) Foreign Application Priority Data
May 2, 2014 (GB) ..................................... 1407852

(51) Int. Cl.
| | |
|---|---|
| *C12Q 1/68* | (2018.01) |
| *G01N 33/567* | (2006.01) |
| *C12N 15/63* | (2006.01) |
| *C12N 15/87* | (2006.01) |
| *C12N 15/10* | (2006.01) |
| *C12N 15/90* | (2006.01) |
| *C07K 16/00* | (2006.01) |
| *A61K 48/00* | (2006.01) |

(52) U.S. Cl.
CPC .......... *C12N 15/102* (2013.01); *C07K 16/005* (2013.01); *C12N 15/1037* (2013.01); *C12N 15/907* (2013.01); *C07K 2317/24* (2013.01); *C07K 2317/622* (2013.01); *C07K 2317/64* (2013.01); *C07K 2319/03* (2013.01); *C07K 2319/035* (2013.01); *C07K 2319/036* (2013.01); *C12N 2310/20* (2017.05); *C12N 2800/30* (2013.01); *C12N 2800/80* (2013.01)

(58) Field of Classification Search
CPC .............. C12N 15/102; C12N 15/907; C12N 2800/30; C12N 2310/20; C07K 16/005; C07K 2319/036; C07K 2319/035; C07K 2317/24; C07K 2317/622; C07K 2317/64; C07K 2319/03
See application file for complete search history.

(56) References Cited

U.S. PATENT DOCUMENTS

| | | | |
|---|---|---|---|
| 6,528,313 B1 | 3/2003 | Le et al. | |
| 6,528,314 B1 | 3/2003 | Le et al. | |
| 6,638,768 B1 | 10/2003 | Le et al. | |
| 7,732,195 B2 | 6/2010 | Akamatsu et al. | |
| 7,884,054 B2 | 2/2011 | Chen et al. | |
| 8,163,546 B2 | 4/2012 | Akamatsu et al. | |
| 8,685,737 B2* | 4/2014 | Serber et al. | |
| 8,697,359 B1* | 4/2014 | Zhang et al. | |
| 8,771,960 B2 | 7/2014 | Breitling et al. | |
| 9,701,971 B2* | 7/2017 | Serber et al. | |
| 2003/0096401 A1 | 5/2003 | Huse | |
| 2009/0163379 A1 | 6/2009 | Wang et al. | |
| 2009/0263900 A1 | 10/2009 | Dekelver et al. | |
| 2010/0212035 A1 | 8/2010 | Buelow | |
| 2012/0277120 A1 | 11/2012 | Serber et al. | |
| 2014/0113375 A1 | 4/2014 | Liu | |

FOREIGN PATENT DOCUMENTS

| | | |
|---|---|---|
| EP | 2454376 B1 | 12/2015 |
| WO | 2002034929 A2 | 5/2002 |
| WO | 2002044361 A2 | 6/2002 |
| WO | 2002102855 A2 | 12/2002 |
| WO | 2003104415 A2 | 12/2003 |
| WO | 2005063817 A2 | 7/2005 |

(Continued)

OTHER PUBLICATIONS

Xu et al. The genomic sequence of the Chinese hamster ovary (CHO)-K1 cell line. Nature Biotechnology, vol. 29:735-741, (Year: 2011).*
Zhou et al. Four-way ligation for construction of a mammalian cell-based full-length antibody display library. Acta Biochim. Biophys. Sin. 43:232-238, (Year: 2011).*
Marks et al. By-passing immunization. Human antibodies from V-gene libraries displayed on phage. J. Mol. Biol. 222:581-597, (Year: 1991).*
Moehle et al. Targeted gene addition into a specified location in the human genome using designed zinc finger nucleases. PNAS 104:3055-3060, (Year: 2007).*
Hockemeyer et al. Genetic engineering of human pluripotent cells using TALE nucleases. Nature Biotechnology 29:731-734, (Year: 2011).*

(Continued)

*Primary Examiner* — Quang Nguyen
(74) *Attorney, Agent, or Firm* — Clark & Elbing LLP

(57) ABSTRACT

The invention relates to methods of producing eukaryotic cell libraries encoding a repertoire of binding molecules ("binders"), wherein the methods use a site-specific nuclease for targeted cleavage of cellular DNA to enhance site-specific integration of binder genes through endogenous cellular repair mechanisms. Populations of eukaryotic cells are produced in which a repertoire of genes encoding binders are integrated into a desired locus in cellular DNA (e.g., a genomic locus) allowing expression of the encoded binding molecule, thereby creating a population of cells expressing different binders.

15 Claims, 56 Drawing Sheets
Specification includes a Sequence Listing.

(56) References Cited

FOREIGN PATENT DOCUMENTS

| WO | 2007047578 A2 | 4/2007 |
|---|---|---|
| WO | 2007047859 A2 | 4/2007 |
| WO | 2008070367 A2 | 6/2008 |
| WO | 2008133938 A2 | 11/2008 |
| WO | 2009129247 A2 | 10/2009 |
| WO | 2010054007 A1 | 5/2010 |
| WO | 2010059981 A2 | 5/2010 |
| WO | 2011009080 A2 | 1/2011 |
| WO | 2011100058 A1 | 8/2011 |
| WO | 2011104382 A1 | 9/2011 |
| WO | 2012149470 A1 | 11/2012 |
| WO | 2012158739 A1 | 11/2012 |
| WO | 2012167192 A2 | 12/2012 |
| WO | 2013092720 A1 | 6/2013 |
| WO | 2013134880 A1 | 9/2013 |
| WO | 2013134881 A1 | 9/2013 |
| WO | 2013169802 A1 | 11/2013 |
| WO | 2013190032 A1 | 12/2013 |
| WO | 2014013026 A1 | 1/2014 |
| WO | 2014033644 A2 | 3/2014 |
| WO | 2014039872 A1 | 3/2014 |
| WO | 2014059173 A2 | 4/2014 |
| WO | 2015127439 A1 | 8/2015 |
| WO | 2015160683 A1 | 10/2015 |

OTHER PUBLICATIONS

Mali et al. RNA-guided human genome engineering via Cas9. Science 339:823-826, (Year: 2013).*
Le Cong et al. Multiplex genome engineering using CRISPR/Cas systems. Science 339:819-822, (Year: 2013).*
Gupta et al. Expanding the genetic editing tool kit: ZFNs, TALENs, and CRISPR-Cas9. J. Clin. Invest. 124:4154-4161, (Year: 2014).*
Akamatsu, et al., "Whole IgG surface display on mammalian cells: Application to isolation of neutralizing chicken monoclonal anti-IL-12 antibodies", Journal of Immunological Methods 327(1-2), 40-52 (2007).
Allen, et al., "Interactive competition between homologous recombination and non-homologous end joining", Molecular Cancer Research 1(12), 913-920 (2003).
Beerli, et al., "Isolation of human monoclonal antibodies by mammalian cell display", Proc Natl Acad Sci 105(38), 14336-14341 (2008).
Boublik, et al., "Eukaryotic Virus Display: Engineering the Major Surface Glycoprotein of the Autographa californica Nuclear Polyhedrosis Virus (AcNPV) for the Presentation of Foreign Proteins on the Virus Surface", Nature Biotechnology 13(10), 1079-1084 (1995).
Breous-Nystrom, et al., "Retrocyte Display® technology: generation and screening of a high diversity cellular antibody library", Methods 65(1), 57-67 (2014).
Buchholz, et al., "Different thermostabilities of FLP and Cre recombinases: implications for applied site-specific recombination", Nucleic Acids Res 24(21), 4256-4262 (1996).
Chao, et al., "Isolating and engineering human antibodies using yeast surface display", Nat Protoc 1(2), 755-768 (2006).
Cristea, et al., "In vivo cleavage of transgene donors promotes nuclease-mediated targeted integration", Biotechnology and Bioengineering 110(3), 871-880 (2013).
Cui, et al., "Targeted integration in rat and mouse embryos with zinc-finger nucleases", Nature Biotechnology 29(1), 64-67 (2011).
Edwards, et al., "The remarkable flexibility of the human antibody repertoire; isolation of over one thousand different antibodies to a single protein, BLyS", Journal of Molecular Biology 334(1), 103-118 (2003).
Grindley, et al., "Mechanisms of site-specific recombination", Annu Rev Biochem 75, 567-605 (2006).
Higuchi, et al., "Cell display library for gene cloning of variable regions of human antibodies to hepatitis B surface antigen", J Immunol Methods 202(2), 193-204 (1997).

Ho, et al., "Display and selection of scFv antibodies on HEK-293T cells", Methods Mol Biol 562, 99-113 (2009).
Ho, et al., "Isolation of anti-CD22 Fv with high affinity by Fv display on human cells", Proc Natl Acad Sci 103(25), 9637-9642 (2006).
Lee, et al., "Construction and characterization of a pseudo-immune human antibody library using yeast surface display". Biochemical and Biophysical Research Communications 346(3), 896-903 (2006).
Li, et al., "Identification of HBsAg-specific antibodies from a mammalian cell displayed full-length human antibody ibrary of healthy immunized donor", Cellular and Molecular Immunology 9(2), 184-190 (2012).
Maresca, et al., "Obligate ligation-gated recombination (ObLiGaRe): custom-designed nuclease-mediated targeted integration through nonhomologous end joining", Genome Research 23(3), 539-546 (2012).
Meyer, et al., "Gene targeting by homologous recombination in mouse zygotes mediated by zinc-finger nucleases", Proc Natl Acad of Sci 107(34), 15022-15026 (2010).
Moehle, et al., "Targeted gene addition into a specified location in the human genome using designed zinc finger nucleases", Proc Natl Acad Sci 104(9), 3055-3060 (2007).
Mottershead, et al., "Baculoviral Display of Functional scFv and Synthetic IgG-Binding Domains", Biochemical and Biophysical Research Communications 275(1), 84-90 (2000).
Okker-Blom, et al., "Baculovirus display strategies: Emerging tools for eukaryotic libraries and gene delivery", Briefings in Functional Genomics and Proteomics 2(3), 244-253 (2003).
Orlando, et al., "Zinc-finger nuclease-driven targeted integration into mammalian genomes using donors with limited chromosomal homology", Nucleic Acids Research 38(15), e152 (2010).
Pershad, et al., "Generating a panel of highly specific antibodies to 20 human SH2 domains by phage display", Protein Engineering, Design and Selection 23(4), 279-288 (2010).
Russell, et al., "Retroviral vectors displaying functional antibody fragments", Nucleic Acids Res 21(5), 1081-1085 (1993).
Salema, et al., "Selection of single domain antibodies from immune libraries displayed on the surface of E. coli cells with two β-domains of opposite topologies", PLoS One 8(9), e75126 (2013).
Schafi, et al., "Efficient FLP recombination in mouse ES cells and oocytes", Genesis 31(1), 6-10 (2001).
Schofield, et al., "Application of phage display to high throughput antibody generation and characterization", Genome Biol 8(11), R254 (2007).
Taube, et al., "Lentivirus display: stable expression of human antibodies on the surface of human cells and virus particles", PLOS Once 3(9), e3181 (2008).
Zhou, et al., "Development of a novel mammalian cell surface antibody display platform", MAbs 2(5), 508-518 (2010).
Duportet, X, et al., "A platform for rapid prototyping of synthetic gene networks in mammalian cells", Nucleic Acids Research 42(21), 13440-13451 (2014).
Fu, Y, et al., "High-frequency off-target mutagenesis induced by CRISPR-Cas nucleases in human cells", Nature Biotechnology 31(9), 822-827 (2013).
Gaj, T, et al., "ZFN, TALEN, and CRISPR/Cas-based methods for genome engineering", Trends in Biotechnology 31(7), 397-405 (2013).
Goffeau, A, et al., "Life with 6000 Genes", Science, 274 (5287), Genome Issue, 546+563-567 (1996).
Guilinger, J, et al., "Broad specificity profiling of TALENs results in engineered nucleases with improved DNA-cleavage specificity", Nature Methods 11(4), 429-437 (2014).
Higuchi, K, et al., "Cell display library for gene cloning of variable regions of human antibodies to hepatitis B surface antigen", Journal of Immunological Methods 202, 193-204, (1997).
Ho, M, et al., "Mammalian Cell Display for Antibody Engineering", Methods Mol. Biol. 525(337), 1-15 (2009).
Hsu, P, et al., "DNA targeting specificity of RNA-guided Cas9 nucleases", Nature Biotechnology 31(9), 827-834 (2013).
Ishibashi, K, et al., "Nonhomologous chromosomal integration of foreign DNA is completely dependent on MUS-53 (human Lig4 homolog) in Neurospora", PNAS 103(40), 14871-14876 (2006).

(56) References Cited

OTHER PUBLICATIONS

Jasin, M, et al., "Genetic manipulation of genomes with rare-cutting endonucleases", TIG 12(6) 224-228 (1996).

Kosicki, M, et al., "Repair of double-strand breaks induced by CRISPR-Cas9 leads to large deletions and complex rearrangements", Nature Biotechnology 36(8), 765-772 (2018).

Matreyek, K, et al., "A platform for functional assessment of large variant libraries in mammalian cells", Nucleic Acids Research 45(11), e102, 20 pages (2017).

Mehta, A, et al., "Sources of DNA Double-Strand Breaks and Models of Recombinational DNA Repair", Cold Spring Harb Perspect Biol 6:a016428, 1-17 (2014).

Parthiban, K, et al., "A comprehensive search of functional sequence space using large mammalian display libraries created by gene editing", MABS 11(5), 884-898 (2019).

Perelson, A, et al., "Theoretical Studies of Clonal Selection: Minimal Antibody Repertoire Size and Reliability of Self-Non-self Discrimination", J. Theor. Biol. 81, 645-670 (1979).

Tycko, J, et al., "Methods for Optimizing CRISPR-Cas9 Genome Editing Specificity", Molecular Cell 63, 355-370 (2016).

Bradbury, A, et al., "Beyond natural antibodies: the power of in vitro display technologies", Nat Biotechnol 29(3), 245-254(2011).

Choulika, A, et al., "Induction of Homologous Recombination in Mammalian Chromosomes by Using the I-ScеI System of *Saccharomyces cerevisiae*", Molecular and Cellular Biology 15(4), 1968-1973 (1995).

Horlick, R, et al., "Simultaneous Surface Display and Secretion of Proteins from Mammalian Cells Facilitate Efficient in Vitro Selection and Maturation of Antibodies", Journal of Biological Chemistry 288(27), 19861-19869 (2013).

Lin, A, et al., Affinity Maturation by CDR Targeted Protein Engineering, Abstract, 1 page (2013).

Luo, Y, et al., "Stable Enhanced Green Fluorescent Protein Expression After Differentiation and Transplantation of Reporter Human Induced Pluripotent Stem Cells Generated by AAVS1 Transcription Activator-Like Effector Nucleases", Stem Cells Translational Medicine 3, 821-835 (2014).

Mccafferty, J, et al., "Identification of optimal protein binders through the use of large genetically encoded display libraries", Current Opinion in Chemical Biology 2, 16-24 (2015).

McVey, M, et al., "MMEJ repair of double-strand breaks (director's cut): deleted sequences and alternative endings", Trends Genet 24(11), 529-538 (2008).

Melidoni, A, et al., "Selecting antagonistic antibodies that control differentiation through inducible expression in embryonic stem cells", PNAS 110(44), 17802-17807 (2013).

Pepper, L, et al., "A decade of yeast surface display technology: Where are we now?", Comb Chem High Throughput Screen 11(2), 127-134 (2008).

Porteus, M, et al., "Chimeric Nucleases Stimulate Gene Targeting in Human Cells", Science 300, 763 (2003).

Rouet, P, et al., "Introduction of Double-Strand Breaks into the Genome of Mouse Cells by Expression of a Rare-Cutting Endonuclease", Molecular and Cellular Biology 14(12), 8096-8106 (1994).

Sakuma, T, et al., "Homologous Recombination-Independent Large Gene Cassette Knock-in in CHO Cells Using TALEN and MMEJ-Directed Donor Plasmids", Int J Mol Sci 16, 23849-23866 (2015).

Sampson, T, et al., "Exploiting CRISPR/Cas systems for biotechnology", Bioessays 36(1), 34-38 (2014).

Shalem, O, et al., "Genome-Scale CRISPR-Cas9 Knockout Screening in Human Cells", Science 343(6166), 84-87 (2014).

Smith, E, et al., "Antibody Library Display on a Mammalian Virus Vector: Combining the Advantages of Both Phage and Yeast Display into One Technology", Current Drug Discovery Technology 11, 48-55 (2014).

Vilenchik, M, et al., "Endogenous DNA double-strand breaks: Production, fidelity of repair, and induction of cancer", PNAS 100(22), 12871-12876 (2003).

Wang, T, et al., "Genetic screens in human cells using the CRISPR/Cas9 system", Science 343(6166), 80-84 (2014).

Zhang, H, et al., "Selection of antibodies that regulate phenotype from intracellular combinatorial antibody libraries", PNAS 109(39), 1572-15733(2012).

Hockemeyer, D., et al., "Highly efficient gene targeting of expressed and silent genes in human ESCs and iPSCs using zinc finger nucleases", Nature Biotech 27, 851-857 (2009).

Zou, J, et al., "Gene targeting of a disease-related gene in human induced pluripotent stem and embryonic stem cells". Cell Stem Cell 5, 97-110 (2009).

\* cited by examiner

```
                          >"pEF promoter
"Acc65I"   >"EcoR1"      |
   |       |  10    |    20        30        40        50        60
   GGT ACC GAA TTC CGT GAG GCT CCG GTG CCC GTC AGT GGG CAG AGC GCA CAT CGC CCA CAG
   TCC CCG AGA AGT TGG GGG GAG GGG TCG GCA ATT GAA CCG GTG CCT AGA GAA GGT GGC GCG
   GGG TAA ACT GGG AAA GTG ATG TCG TGT ACT GGC TCC GCC TTT TTC CCG AGG GTG GGG GAG
   AAC CGT ATA TAA GTG CAG TAG TCG CCG TGA ACG TTC TTT TTC GCA ACG GGT TTG CCG CCA
   GAA CAC AGG TAA GTG CCG TGT GTG GTT CCC GCG GGC CTG GCC TCT TTA CGG GTT ATG GCC
   CTT GCG TGC CTT GAA TTA CTT CCA CCT GGC TCC AGT ACG TGA TTC TTG ATC CCG AGC TGG
   AGC CAG GGG CGG GCC TTG CGC TTT AGG AGC CCC TTC GCC TCG TGC TTG AGT TGA GGC CTG
   GCC TGG GCG CTG GGG CCG CCG CGT GCG AAT CTG GTG GCA CCT TCG CGC CTG TCT CGC TGC
   TTT CGA TAA GTC TCT AGC CAT TTA AAA TTT TTG ATG ACC TGC TGC GAC GCT TTT TTT CTG
   GCA AGA TAG TCT TGT AAA TGC GGG CCA GGA TCT GCA CAC TGG TAT TTC GGT TTT TGG GCC
   CGC GGC CGG CGA CGG GGC CGT GCG TCC ACG CAC ATG TTC GGC GAG GCG GGG CCT GCG
   AGC GCG GCC ACC GAG AAT CGG ACG GGG GTA GTC TCA AGC TGG CGC CGC TGC TCT GGT GCC
   TGG CCT CGC GCC GCC GTG TAT CGC CCC GCC CTG GGC GGC AAG GCT GGC CCG GTC GGC ACC
   AGT TGC GTG AGC GGA AAG ATG GCC GCT TCC CGG CCC TGC TCC AGG GGG CTC AAA ATG GAG
   GAC GCG GCG CTC GGG AGA GCG GGC GGG TGA GTC ACC CAC ACA AAG GAA AAG GGC CTT TCC
   GTC CTC AGC CGT CGC TTC ATG TGA CTC CAC GGA GTA CCG GGC GCC GTC CAG GCA CCT CGA
   TTA GTT CTG GAG CTT TTG GAG TAC GTC GTC TTT AGG TTG GGG GGA GGG GTT TTA TGC GAT
   GGA GTT TCC CCA CAC TGA GTG GGT GGA GAC TGA AGT TAG GCC AGC TTG GCA CTT GAT GTA
   ATT CTC GTT GGA ATT TGC CCT TTT TGA GTT TGG ATC TTG GTT CAT TCT CAA GCC TCA GAC
   AGT GGT TCA AAG TTT TTT TCT TCC ATT TCA GGT GTC GTG AGA CGT GGCACC ATG AGG GCC
                                                                     M   R   A>
                                                                     _a__a__>
                                                   >"NheI"           |
         1210      1220      1230      1240     |  1250      1260
   TGG ATC TTC TTT CTC CTT TGC CTG GCC GGG AGG GCT CTG GCA GCT AGC GAC ATC CAG ATG
    W   I   F   F   L   L   C   L   A   G   R   A   L   A   A   S>  D   I   Q   M>
   __a__a__a__a__a___"BM40 LEADER"__a__a__a__a__a__a__><__"D1.3 VL___>
         1270      1280      1290      1300      1310      1320
   ACC CAG AGC CCA AGC AGC CTG AGC GCC AGC GTG GGT GAC AGA GTG ACC ATC ACC TGT AGA
    T   Q   S   P   S   S   L   S   A   S   V   G   D   R   V   T   I   T   C   R>
   __b__b__b__b__b__b__b__b__"D1.3 VL"__b__b__b__b__b__b__b__b__>
         1330      1340      1350      1360      1370      1380
   GCC AGC GGT AAC ATC CAC AAC TAC CTG GCT TGG TAC CAG CAG AAG CCA GGT AAG GCT CCA
    A   S   G   N   I   H   N   Y   L   A   W   Y   Q   Q   K   P   G   K   A   P>
   __b__b__b__b__b__b__b__b__"D1.3 VL"__b__b__b__b__b__b__b__b__>
         1390      1400      1410      1420      1430      1440
   AAG CTG CTG ATC TAC TAC ACC ACC ACC CTG GCT GAC GGT GTG CCA AGC AGA TTC AGC GGT
    K   L   L   I   Y   Y   T   T   T   L   A   D   G   V   P   S   R   F   S   G>
   __b__b__b__b__b__b__b__b__"D1.3 VL"__b__b__b__b__b__b__b__b__>
         1450      1460      1470      1480      1490      1500
   AGC GGT AGC GGT ACC GAC TAC ACC TTC ACC ATC AGC AGC CTC CAG CCA GAG GAC ATC GCC
    S   G   S   G   T   D   Y   T   F   T   I   S   S   L   Q   P   E   D   I   A>
   __b__b__b__b__b__b__b__b__"D1.3 VL"__b__b__b__b__b__b__b__b__>
         1510      1520      1530      1540      1550      1560
   ACC TAC TAC TGC CAG CAC TTC TGG AGC ACC CCA AGG ACG TTC GGC CAA GGG ACC AAG GTG
    T   Y   Y   C   Q   H   F   W   S   T   P   R   T   F   G   Q   G   T   K   V>
   __b__b__b__b__b__b__b__b__"D1.3 VL"__b__b__b__b__b__b__b__b__>
```

Fig. 2

```
                                >"Not1"
        1570        | 1580       1590        1600        1610       1620
GAA ATC AAA CGT ACC GCG  GCC GCC CCT TCC GTG TTC ATC TTC CCT CCC TCC GAC GAG CAG
 E   I   K   R   T> A    A   A   P   S   V   F   I   F   P   P   S   D   E   Q>
___b__"D1.3 VL"b__>c___c___"CODON OPTIMISED HUMAN_C_KAPPA"_c___c___c___c___c
        1630        1640        1650        1660        1670       1680
CTG AAG TCC GGC ACC GCC TCT GTG GTG TGC CTG CTG AAC AAC TTC TAC CCT CGG GAG GCC
 L   K   S   G   T   A   S   V   V   C   L   L   N   N   F   Y   P   R   E   A>
___c___c___c___c___c___"CODON OPTIMISED HUMAN_C_KAPPA"_c___c___c___c___c___c___>
        1690        1700        1710        1720        1730       1740
AAG GTG CAG TGG AAG GTG GAC AAC GCC CTG CAG TCC GGC AAC TCC CAG GAA TCC GTC ACC
 K   V   Q   W   K   V   D   N   A   L   Q   S   G   N   S   Q   E   S   V   T>
___c___c___c___c___c___"CODON OPTIMISED HUMAN_C_KAPPA"_c___c___c___c___c___c___>
        1750        1760        1770        1780        1790       1800
GAG CAG GAC TCC AAG GAC TCT ACC TAC TCC CTG TCC TCC ACC CTG ACC CTG TCC AAG GCC
 E   Q   D   S   K   D   S   T   Y   S   L   S   S   T   L   T   L   S   K   A>
___c___c___c___c___c___"CODON OPTIMISED HUMAN_C_KAPPA"_c___c___c___c___c___c___>
        1810        1820        1830        1840        1850       1860
GAC TAC GAG AAG CAC AAG CTG TAC GCC TGC GAA GTG ACC CAC CAG GGC CTG TCC TCT CCC
 D   Y   E   K   H   K   L   Y   A   C   E   V   T   H   Q   G   L   S   S   P>
___c___c___c___c___c___"CODON OPTIMISED HUMAN_C_KAPPA"_c___c___c___c___c___c___>
                                              >"HindIII"    >"Bcl1"   >"BGH_pA→
        1870        1880        1890        1900        1910     | 1920
GTG ACC AAG TCC TTC AAC CGG GGC GAG TGC TA ATA AAA GCT TAC GAC GTG ATC AGC CTC
 V   T   K   S   F   N   R   G   E   C>
___"CODON OPTIMISED HUMAN_C_KAPPA"_c___>
        1930        1940        1950        1960        1970       1980
GAC TGT GCC TTC TAG TTG CCA GCC ATC TGT TGT TTG CCC CTC CCC CGT GCC TTC CTT GAC
        1990        2000        2010        2020        2030       2040
CCT GGA AGG TGC CAC TCC CAC TGT CCT TTC CTA ATA AAA TGA GGA AAT TGC ATC GCA TTG
        2050        2060        2070        2080        2090       2100
TCT GAG TAG GTG TCA TTC TAT TCT GGG GGG TGG GGT GGG GCA GGA CAG CAA GGG GGA GGA
                                                    >"Spe1 CMV_promoter"→
        2110        2120        2130        2140     |  | 2150       2160
TTG GGA AGA CAA TAG CAG GCA TGC TGG GGA ACA TTG ATT ATT GAC TAG TTA TTA ATA GTA
ATC AAT TAC GGG GTC ATT AGT TCA TAG CCC ATA TAT GGA GTT CCG CGT TAC ATA ACT TAC
GGT AAA TGG CCC GCC TGG CTG ACC GCC CAA CGA CCC CCG CCC ATT GAC GTC AAT AAT GAC
GTA TGT TCC ATA GTA ACG CCA ATA GGG ACT TTC CAT TGA CGT CAA TGG GTG GAG TAT TTA
CGG TAA ACT GCC CAC TTG GCA GTA CAT CAA GTG TAT CAT ATG CCA AGT CCG CCC CCT ATT
GAC GTC AAT GAC GGT AAA TGG CCC GCC TGG CAT TAT GCC CAG TAC ATG ACC TTA TGG GAC
                                             >"ex-Nco_site"
        2470        2480        2490        2500     |  2510       2520
TTT CCT ACT TGG CAG TAC ATC TAC GTA TTA GTC ATC GCT ATT ACC ATG GTG ATG CGG TTT
TTG GCA GTA CAC CAA TGG GCG TGG ATA GCG GTT TGA CTC ACG GGG ATT TCC AAG TCT CCA
CCC CAT TGA CGT CAA TGG GAG TTT GTT TTG GCA CCA AAA TCA ACG GGA CTT TCC AAA ATG
TCG TAA TAA CCC CGC CCC GTT GAC GCA AAT GGG CGG TAG GCG TGT ACG GTG GGA GGT CTA
                           ← end CMV promoter-II-Tri-partite leader→
        2650        2660        2670        2680        2690       2700
TAT AAG CAG AGC TCG TTT AGT GAA CCG TCA GATC CT CAC TCT CTT CCG CAT CGC TGT CTG
CGA GGG CCA GCT GTT GGG CTC GCG GTT GAG GAC AAA CTC TTC GCG GTC TTT CCA GTA CTC
TTG GAT CGG AAA CCC GTC GGC CTC CGA ACG TAC TCC GCC ACG AGG GAC CGA GCA AGT
                >"ex-Xho1_site"
        2890        2900     | 2910        2920        2930       2940
CCG CAT CGA CCG GAT CGG AAA ACC TCT CGT GAA AGG CGT CTA ACC AGT CAC AGT CGC AAG
GTA GGC TGA GCA CCG TGG CGG GCG GCA GCG GGT GGC GGT CGG GGT TGT TTC TGG CGG AGG
TGC TGC TGA TGA TGT AAT TAA AGT AGG CGG TCT TGA GAC GGC GGA TGG TCG AGG TGA GGT
GTG GCA GGC TTG AGA TCC AGC TGT TGG GGT GAG TAC TCC CTC TCA AAA GCG GGC ATT ACT
TCT GCG CTA AGA TTG TCA GTT TCC AAA AAC GAG GAG GAT TTG ATA TTC ACC TGG CCC GAT
CTG GCC ATA CAC TTG AGT GAC AAT GAC ATC CAC TTT GCC TTT CTC TCC ACA GGT GTC CAC
```

Fig. 2 (continued)

```
                >"Pme1_Pml1_junction"
        3250    |    3260         3270         3280         3290         3300
    TCC CAG GTC CAA GTT TGT GGA AAT TAA TAC GAC GTG GCC ACC ATG AGT TGG AGC TGT ATC
                                                         M   S   W   S   C   I>
                                                     __e__"LEADER1"____e___>

>"intron"
                         |
        3310         3320         3330         3340         3350         3360
    ATC CTC TTC TTG GTA GCA ACA GCT ACA GGT AAG GGG TTA ACA GTA GCA GGC TTG AGG TCT
     I   L   F   L   V   A   T   A   T>
    __e__e____"LEADER1"__e___e___e___> end intron  > Nco1
        3370         3380         3390         3400         3410    |
    GGA CAT ATA TAT GGG TGA CAA TGA CAT CCA CTT TGC CTT TCT CTC CAC A GGC GCC ATG
                                                                      G   A   M
                                                                          LEADER2
    3420         3430         3440         3450         3460         3470
    GCC CAG GTC CAA CTG CAG GAG AGC GGT CCA GGT CTT GTG AGA CCT AGC CAG ACC CTG AGC
     A  <Q   V   Q   L   Q   E   S   G   P   G   L   V   R   P   S   Q   T   L   S>
        __g___g___g___g___g___g___g___"D1.3 VH"__g___g___g___g___g___g___g___g__>
    3480         3490         3500         3510         3520         3530
    CTG ACC TGC ACC GTG TCT GGC AGC ACC TTC AGC GGC TAT GGT GTA AAC TGG GTG AGA CAG
     L   T   C   T   V   S   G   S   T   F   S   G   Y   G   V   N   W   V   R   Q>
    __g___g___g___g___g___g___g___g___"D1.3 VH"__g___g___g___g___g___g___g___g__>
    3540         3550         3560         3570         3580         3590
    CCA CCT GGA CGA GGT CTT GAG TGG ATT GGA ATG ATT TGG GGT GAT GGA AAC ACA GAC TAT
     P   P   G   R   G   L   E   W   I   G   M   I   W   G   D   G   N   T   D   Y>
    __g___g___g___g___g___g___g___g___"D1.3 VH"__g___g___g___g___g___g___g___g__>
    3600         3610         3620         3630         3640         3650
    AAT TCA GCT CTC AAA TCC AGA GTG ACA ATG CTG GTA GAC ACC AGC AAG AAC CAG TTC AGC
     N   S   A   L   K   S   R   V   T   M   L   V   D   T   S   K   N   Q   F   S>
    __g___g___g___g___g___g___g___g___"D1.3 VH"__g___g___g___g___g___g___g___g__>
    3660         3670         3680         3690         3700         3710
    CTG AGA CTC AGC AGC GTG ACA GCC GCC GAC ACC GCG GTC TAT TAT TGT GCA AGA GAG AGA
     L   R   L   S   S   V   T   A   A   D   T   A   V   Y   Y   C   A   R   E   R>
    __g___g___g___g___g___g___g___g___"D1.3 VH"__g___g___g___g___g___g___g___g__>
                                                                    Xho1
                                                                      |
    3720         3730         3740         3750         3760    |    3770
    GAT TAT AGG CTT GAC TAC TGG GGT CAA GGC AGC CTC GTC ACA GTC TCG AGT GCC AGC ACC
     D   Y   R   L   D   Y   W   G   Q   G   S   L   V   T   V   S   S>  A   S   T>

__g___g___g___g___g___g___"D1.3 VH"__g___g___g___g___g___g___g__>
    3780         3790         3800         3810         3820         3830
    AAG GGC CCC AGC GTG TTC CCT CTG GCC CCC TGT AGC AGA AGC ACC AGC GAG AGC ACA GCC
     K   G   P   S   V   F   P   L   A   P   C   S   R   S   T   S   E   S   T   A>
    __h___h___h___h___h___h___h___h___"CH1"__h___h___h___h___h___h___h___h___h__>
```

Fig. 2 (continued)

```
3840        3850        3860        3870        3880        3890
GCC CTG GGC TGC CTG GTC AAG GAC TAC TTC CCC GAG CCC GTG ACC GTG TCC TGG AAC TCT
 A   L   G   C   L   V   K   D   Y   F   P   E   P   V   T   V   S   W   N   S>
__h___h___h___h___h___h___h___h___h____"CH1"__h___h___h___h___h___h___h___h___h____>
3900        3910        3920        3930        3940        3950
GGC GCT CTG ACC AGC GGC GTG CAC ACC TTT CCA GCC GTG CTG CAG AGC AGC GGC CTG TAC
 G   A   L   T   S   G   V   H   T   F   P   A   V   L   Q   S   S   G   L   Y>
__h___h___h___h___h___h___h___h___h____"CH1"__h___h___h___h___h___h___h___h___h____>
3960        3970        3980        3990        4000        4010
AGC CTG AGC AGC GTG GTC ACC GTG CCC AGC AGC AAC TTC GGC ACC CAG ACC TAC ACC TGT
 S   L   S   S   V   V   T   V   P   S   S   N   F   G   T   Q   T   Y   T   C>
__h___h___h___h___h___h___h___h___h____"CH1"__h___h___h___h___h___h___h___h___h____>
4020        4030        4040        4050        4060        4070
AAC GTG GAC CAC AAG CCC AGC AAC ACC AAG GTG GAC AAG ACC GTG GAA CGG AAG TGC TGC
 N   V   D   H   K   P   S   N   T   K   V   D   K   T   V>  E   R   K   C   C>
__h___h___h___h___h___h___h___h__"CH1"___h___h___h___h___h___>     HINGE
4080        4090        4100        4110        4120        4130
GTG GAA TGC CCC CCC TGT CCC GCT CCT CCA GTG GCT GGA CCT TCC GTG TTC CTG TTC CCC
 V   E   C   P   P   C   P>  A   P   P   V   A   G   P   S   V   F   L   F   P>
__i___i_"HINGE"___i___i__><__j___j___j___j___j___j__"CH2"__j___j___j___j___j___j____>
4140        4150        4160        4170        4180        4190
CCA AAG CCC AAG GAC ACC CTG ATG ATC AGC CGG ACC CCC GAA GTG ACC TGC GTG GTG GTG
 P   K   P   K   D   T   L   M   I   S   R   T   P   E   V   T   C   V   V   V>
4200        4210        4220        4230        4240        4250
GAC GTG TCC CAC GAG GAC CCC GAG GTG CAG TTC AAT TGG TAC GTG GAC GGC GTG GAA GTG
 D   V   S   H   E   D   P   E   V   Q   F   N   W   Y   V   D   G   V   E   V>
__j___j___j___j___j___j___j___j___j____"CH2"__j___j___j___j___j___j___j___j___j____>
4260        4270        4280        4290        4300        4310
CAC AAC GCC AAG ACC AAG CCC AGA GAG GAA CAG TTC AAC AGC ACC TTC CGG GTG GTG TCC
 H   N   A   K   T   K   P   R   E   E   Q   F   N   S   T   F   R   V   V   S>
__j___j___j___j___j___j___j___j___j____"CH2"__j___j___j___j___j___j___j___j___j____>
4320        4330        4340        4350        4360        4370
GTG CTG ACC GTG GTG CAC CAG GAC TGG CTG AAC GGC AAA GAG TAC AAG TGC GCC GTC TCC
 V   L   T   V   V   H   Q   D   W   L   N   G   K   E   Y   K   C   A   V   S>
__j___j___j___j___j___j___j___j___j____"CH2"__j___j___j___j___j___j___j___j___j____>
4380        4390        4400        4410        4420        4430
AAC AAG GGC CTG CCT GCC CCC ATC GAG AAA ACC ATC AGC AAG ACC AAG GGC CAG CCT CGC
 N   K   G   L   P   A   P   I   E   K   T   I   S   K   T   K>  G   Q   P   R>
__j___j___j___j___j___j__"CH2"__j___j___j___j___j___j___j____>    CH3
```

Fig. 2 (continued)

```
       4440  Bsu36I            4460       4470       4480       4490
       GAG CCT CAG GTG TAC ACA CTG CCC CCC AGC CGG GAA GAG ATG ACC AAG AAC CAG GTG TCC
        E   P   Q   V   Y   T   L   P   P   S   R   E   E   M   T   K   N   Q   V   S>
       __k___k___k___k___k___k___k___k___"CH3"_k___k___k___k___k___k___k___k___k__>
       4500       4510       4520       4530       4540       4550
       CTG ACC TGC CTC GTG AAG GGC TTC TAC CCC AGC GAT ATC GCC GTG GAA TGG GAG AGC AAC
        L   T   C   L   V   K   G   F   Y   P   S   D   I   A   V   E   W   E   S   N>
       __k___k___k___k___k___k___k___k___"CH3"_k___k___k___k___k___k___k___k___k__>
       4560       4570       4580       4590       4600       4610
       GGC CAG CCC GAG AAC AAC TAC AAG ACC ACC CCC CCC ATG CTG GAC AGC GAC GGC TCA TTC
        G   Q   P   E   N   N   Y   K   T   T   P   P   M   L   D   S   D   G   S   F>
       __k___k___k___k___k___k___k___k___"CH3"_k___k___k___k___k___k___k___k___k__>
       4620       4630       4640       4650       4660       4670
       TTC CTG TAC AGC AAG CTG ACA GTG GAC AAG AGC CGG TGG CAG CAG GGC AAC GTG TTC AGC
        F   L   Y   S   K   L   T   V   D   K   S   R   W   Q   Q   G   N   V   F   S>
       __k___k___k___k___k___k___k___k___"CH3"_k___k___k___k___k___k___k___k___k__>
       4680       4690       4700       4710       4720       4730
       TGC AGC GTG ATG CAC GAG GCC CTG CAC AAC CAC TAC ACC CAG AAG TCC CTG AGC CTG AGC
        C   S   V   M   H   E   A   L   H   N   H   Y   T   Q   K   S   L   S   L   S>
       __k___k___k___k___k___k___k___k___"CH3"_k___k___k___k___k___k___k___k___k__>
                >"5'_Splice_site"   Pme1
       4740       4750    |  4760       4770       4780       ROX site
       CCC GGC AAG GGA TCC AAG GT AAG TTT AAA CAT ATA TA TAACTTTAAATAATTGGCATTATTTAAAGTTA
        P   G   K   G   S   K
                              __l___l___l___"ARTIFICIAL INTRON (PIC26)"___l___l___l___>
                                                                >"3'_Splice_site"
       4800       |4810|     4820       4830       4840       4850
                 CT ACT AAC TAA CCC TGA TTA TTT AAA TTT TCA G GAA CAA AAA CTC ATC TCA
       __l___l___l_"ARTIFICIAL INTRON (PIC26)"_l___l___l___l___>  E   Q   K   L   I   S>
                                                                   "MYC EPITOPE"__m__>
       4860       4870       4880       4890       4900       4910
       GAA GAG GAT CTG AAT GCT GTG GGC CAG GAC ACG CAG GAG GTC ATC GTG GTG CCA CAC TCC
        E   E   D   L>  N   A   V   G   Q   D   T   Q   E   V   I   V   V   P   H   S>
       _"MYC EPI___>  __n___n___n___n___n___n_"PDGFR spacer__n___n___n___n___n__>
       4920       4930       4940       4950       4960       4970
       TTG CCC TTT AAG GTG GTG GTG ATC TCA GCC ATC CTG GCC GTG GTG CTC ACC ATC ATC
        L   P   F   K   V   V   V   I   S   A   I   L   A   L   V   V   L   T   I   I>
       _PDGFR spacer_ _n___n___n___n___n__"PDGFR TM"__n___n___n___n___n___n___n__>
                                                            >"5'_Splice_site"
       4980       4990       5000       5010       5020       |5030
       TCC CTT ATC ATC CTC ATC ATG CTT TGG CAG AAG AAG CCA CGT TAG TAA CA GGT AAG AGTG
        S   L   I   I   L   I   M   L   W   Q   K   K   P   R   *   *>
       __n___n___n___n___n___n_"PDGFR TM"___n___n___n___n___n___n__>
       5040          ROX site
       TAACTTTAAATAATGCCAATTATTTA AAG TTA CTG ACT CTC TCT GCT TAC GAC GCT TCT
                   >"end_secreted_antibody"|
                   >"3'_Splice_site"        >"BGH_pA-→
       5100       5110   |  |5120       5130
       TCT TTT TTT TTT CCT GCA G GGG TAG TAA TCA GC CTC GAC TGT GCC TTC TAG TTG CCA GCC ATC
                           5170       5180       5190       5200       5210       5220
                   TGT TGT TTG CCC CTC CCC CGT GCC TTC CTT GAC CCT GGA AGG TGC CAC TCC CAC TGT CCT
                           5230       5240       5250       5260       |5270       5280
                   TTC CTA ATA AAA TGA GGA AAT TGC ATC GCA TTG TCT GAG TAG GTG TCA TTC TAT TCT GGG
                           5290       5300       5310       5320       5330       5340
                   GGG TGG GGT GGG GCA GGA CAG CAA GGG GGA GGA TTG GGA AGA CAA TAG CAG GCATGCTGGGGA
               End PolyA              loxP site                 BstZ171
       TGGCCCGGGCATG ATAACTTCGTATAATGTATGCTATACGAAGTTAT GTATAC
```

>"Acc65I"  >"EcoR1"   >"AAVS1_left_homology_arm"

```
            |       |          |
            |       | 10       | 20            30            40            50            60
            GGT ACC GAA TTC GCC CTT TGC TTT CTC TGA CCT GCA TTC TCT CCC CTG GGC CTG TGC CGC
            TTT CTG TCT GCA GCT TGT GGC CTG GGT CAC CTC TAC GGC TGG CCC AGA TCC TTC CCT GCC
            GCC TCC TTC AGG TTC CGT CTT CCT CCA CTC CCT CTT CCC CTT GCT CTC TGC TGT GTT GCT
            GCC CAA GGA TGC TCT TTC CGG AGC ACT TCC TTC TCG GCG CTG CAC CAC GTG ATG TCC TCT
            GAG CGG ATC CTC CCC GTG TCT GGG TCC TCT CCG GGC ATC TCT CCT CCC TCA CCC AAC CCC
            ATG CCG TCT TCA CTC GCT GGG TTC CCT TTT CCT TCT CCT TCT GGG GCC TGT GCC ATC TCT
            CGT TTC TTA GGA TGG CCT TCT CCG ACG GAT GTC TCC CTT GCG TCC CGC CTC CCC TTC TTG
            TAG GCC TGC ATC ATC ACC GTT TTT CTG GAC AAC CCC AAA GTA CCC CGT CTC CCT GGC TTT
            AGC CAC CTC TCC ATC CTC TTG CTT TCT TTG CCT GGA CAC CCC GTT CTC CTG TGG ATT CGG
            GTC ACC TCT CAC TCC TTT CAT TTG GGC AGC TCC CCT ACC CCC CTT ACC TCT CTA GTC TGT
            GCA AGC TCT TCC AGC CCC TCA TGG CAT CTT CCA GGG CTC CGA GAG CTC AGC TAG TCT
            TCT TCC TCC AAC CCG GGC CCC TAT GTC CAC TTC AGG ACA GCA TGT TTG CTG CCT CCA GGG
            ATC CTG TGT CCC CGA GCT GGG ACC ACC TTA TAT CCA GGC CGG TTA ATG TGG CTC TGG
```

>"NsiI"
```
                                                                              |
            790            800            810            820         | 830         | 840
            TTC TGG GTA CTT TTA TCT GTC CCC TCC ACC CCA CAG TGG GGC AAG ATG CAT CTT CTG ACC
```

>"Splice_acceptor"
```
            850      | 860            870            880            890            900
            TCT TCT CTT CCT CCC ACA GGG C ATG GCA AAA CCT CTG AGC CAG GAA GAA AGC ACA CTG ATT
                                         M   A   K   P   L   S   Q   E   E   S   T   L   I>
                                         _a__a__a__a____"BLASTICIDIN"____a__a__a__a__>
            910            920            930            940            950            960
            GAA AGA GCA ACC GCT ACT ATC AAC AGC ATC CCC ATC TCC GAA GAC TAT TCT GTG GCT AGT
             E   R   A   T   A   T   I   N   S   I   P   I   S   E   D   Y   S   V   A   S>
             _a__a__a__a__a__a__a____"BLASTICIDIN"_a__a__a__a__a__a__a__a_
            970            980            990            1000           1010           1020
            GCC GCT CTG TCC AGC GAC GGG AGA ATC TTC ACC GGT GTG AAC GTC TAC CAC TTT ACA GGC
             A   A   L   S   S   D   G   R   I   F   T   G   V   N   V   Y   H   F   T   G>
             _a__a__a__a__a__a__a____"BLASTICIDIN"_a__a__a__a__a__a__a__a___>
            1030           1040           1050           1060           1070           1080
            GGA CCA TGC GCA GAG CTG GTG GTC CTG GGG ACT GCA GCC GCT GCA GCC GCT GGT AAT CTG
             G   P   C   A   E   L   V   V   L   G   T   A   A   A   A   A   G   N   L>
             _a__a__a__a__a__a__a____"BLASTICIDIN"_a__a__a__a__a__a__a__a_
            1090           1100           1110           1120           1130           1140
            ACC TGT ATC GTG GCC ATT GGC AAC GAA AAT AGG GGC ATC CTG TCC CCA TGC GGC AGG TGT
             T   C   I   V   A   I   G   N   E   N   R   G   I   L   S   P   C   G   R   C>
             _a__a__a__a__a__a__a____"BLASTICIDIN"_a__a__a__a__a__a__a__a_
            1150           1160           1170           1180           1190           1200
            CGG CAG GTG CTG CTG GAT CTG CAT CCT GGC ATC AAG GCA ATT GTC AAA GAC TCT GAT GGA
             R   Q   V   L   L   D   L   H   P   G   I   K   A   I   V   K   D   S   D   G>
             _a__a__a__a__a__a__a____"BLASTICIDIN"_a__a__a__a__a__a__a__a_
            1210           1220           1230           1240           1250           1260
            CAG CCT ACC GCC GTC GGT ATC CGT GAA CTG CTG CCT AGC GGC TAT GTC TGG GAG GGA TAA
             Q   P   T   A   V   G   I   R   E   L   L   P   S   G   Y   V   W   E   G   *>
             _a__a__a__a__a__a__a____"BLASTICIDIN"_a__a__a__a__a__a__a__a_
```

>"SV40_poly_A"
```
                 1270     |     1280           1290           1300           1310           1320
            TGA GC TTG GCT TCG AAA TGA CCG ACC AAG CGA CGC CCA ACC TGC CAT CAC GAG ATT TCG
                 1330           1340           1350           1360           1370           1380
            ATT CCA CCG CCG CCT TCT ATG AAA GGT TGG GCT TCG GAA TCG TTT TCC GGG ACG CCG GCT
                 1390           1400           1410           1420           1430           1440
            GGA TGA TCC TCC AGC GCG GGG ATC TCA TGC TGG AGT TCT TCG CCC ACC CCA ACT TGT TTA
                 1450           1460           1470           1480           1490           1500
            TTG CAG CTT ATA ATG GTT ACA AAT AAA GCA ATA GCA TCA CAA ATT TCA CAA ATA AAG CAT
```

>"PacI"   ex-MfeI/EcoR1
```
                 1510           1520          |1530          |1540
            TTT TTT CAC TGC ATT CTA GTT GTG GTT TAA TTA AGT CAA TTC
```

Fig. 3 (continued)

←D1.3 ANTIBODY EXPRESSION CASSETTE→

```
        6887       loxP site                    BstZ17I  AscI         AAVS1_right_HA
TGGCCCGGGCATG ATAACTTCGTATAATGTATGCTATACGAAGTTATG TATAC GGCGCGCCC ACTAGGGACAGGATTGGTGACA 6960         6970       6980       6990        7000        7010
     GAA AAG CCC CAT CCT TAG GCC TCC TCC TTC CTA GTC TCC TGA TAT TGG GTC TAA CCC CCA
     CCT CCT GTT AGG CAG ATT CCT TAT CTG GTG ACA CAC CCC CAT TTC CTG GAG CCA TCT CTC
     TCC TTG CCA GAA CCT CTA AGG TTT GCT TAC GAT GGA GCC AGA GAG GAT CCT GGG AGG GAG
     AGC TTG GCA GGG GGT GGG AGG GAA GGG GGG GAT GCG TGA CCT GCC CGG TTC TCA GTG GCC
     ACC CTG CGC TAC CCT CTC CCA GAA CCT GAG CTG CTC TGA CGC GGC TGT CTG GTG CGT TTC
     ACT GAT CCT GGT GCT GCA GCT TCC TTA CAC TTC CCA AGA GGA GAA GCA GTT TGG AAA AAC
     AAA ATC AGA ATA AGT TGG TCC TGA GTT CTA ACT TTG GCT CTT CAC CTT TCT AGT CCC CAA
     TTT ATA TTG TTC CTC CGT GCG TCA GTT TTA CCT GTG AGA TAA GGC CAG TAG CCA GCC CCG
     TCC TGG CAG GGC TGT GGT GAG GAG GGG GGT GTC CGT GTG GAA AAC TCC CTT TGT GAG AAT
     GGT GCG TCC TAG GTG TTC ACC AGG TCG TGG CCG CCT CTA CTC CCT TTC TCT TTC TCC ATC
     CTT CTT TCC TTA AAG AGT CCC CAG TGC TAT CTG GGA CAT ATT CCT CCG CCC AGA GCA GGG
     TCC CGC TTC CCT AAG GCC CTG CTC TGG GCT TCT GGG TTT GAG TCC TTG GCA AGC CCA GGA
     GAG GCG CTC AGG CTT CCC TGT CCC CCT TCC TCG TCC ACC ATC TCA TGC CCC TGG CTC TCC 7740      7750 End AAVS1 right Homol Arm   MluI   BstZ1  7790
     TGC CCC TTC CCT ACA GGG GTT CCT GGC TCT GCT CTG ACG CGT GTATAC TCG ATC TTT CCG
```

Fig. 3 (continued)

a
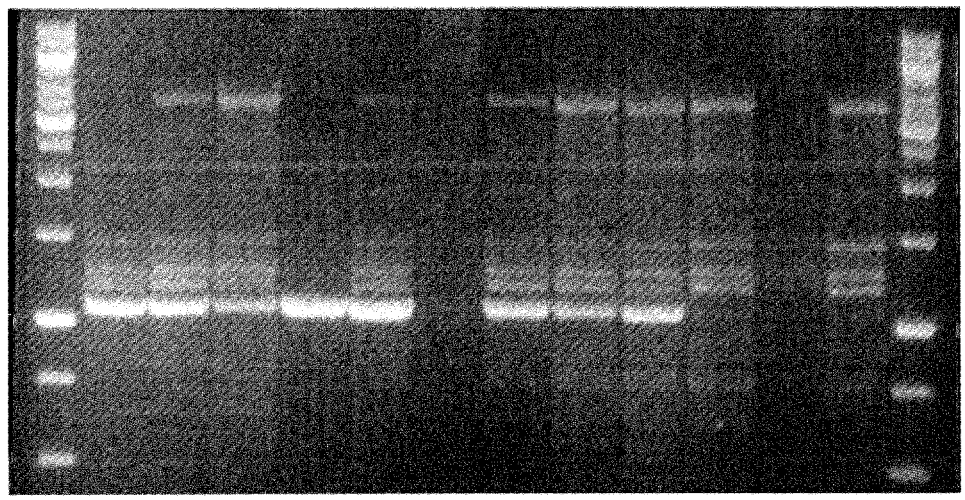
b
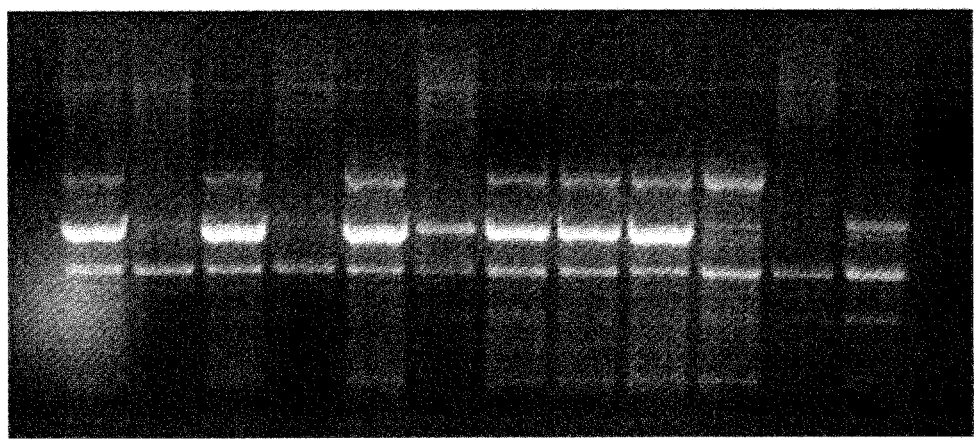
Fig. 7

```
            Acc65I"    EcoRI"       AAVS1_left_homology_arm"→
              |        |  10       20        30        40        50        60
                    GGT ACC GAA TTC GCC CTT TGC TTT CTC TGA CCT GCA TTC TCT CCC CTG GGC CTG TGC CGC
                                                                                                   822
             ←----AAVS left homology arm--→TTC TGG GTA CTT TTA TCT GTC CCC TCC ACC CCA CAG TGG GGC
                  Nsi1   832          FRT site
              AAG ATG CAT    GAAGTTCCTATTCCGAAGTTCCTATTCTCTAGAAAGTATAGGAACTTC GACC
                  lox_2272                       I-SceI_meganuclease
              ATAACTTCGTATAAAGTATCCTATACGAAGTTAT    GCGATCGCTCGCGCG    TAGGGATAACAGGGTAATAAG
                  eGFP Left TALEN    spacer     eGFP_right_TALEN
                  TCCACCGGTCGCCA CCATGGTGAGCAAGGG CGAGGAGCTGTTCA       CTTCTGACCTCTTCTCTTCCTCC
          >"Splice_acceptor_site"
               | 1030        1040|       1050         1060         1070         1080
              CACAG  GGC CTA GAG AGA TCT GGC AGC GGA GAG GGC AGA GGA AGT CTT CTA ACA TGC GGT GAC GTG
                          G   S   G   E   G   R   G   S   L   L   T   C   G   D   V>
                         _b__b__b__b__b__b_"T2A"__b__b__b__b__b__b__>
                     1090         1100         1110         1120         1130
                    GAG GAG AAT CCC GGA CCG ATG GTG AGC AAG GGA GAA GAA CTC TTC ACC GGG GTG
                     E   E   N   P   G   P   M   V   S   K   G   E   E   L   F   T   G   V>
                    _b__b_"T2A"___b__II __c__c__c__c__c_"EGFP "_c__c__c__c
             1140         1150         1160         1170         1180         1190
              GTG CCC ATC CTG GTC GAG CTG GAC GGC GAC GTG AAC GGC CAC AAG TTC AGC GTG TCC GGC
               V   P   I   L   V   E   L   D   G   D   V   N   G   H   K   F   S   V   S   G>
              _c__c__c__c__c__c__c__c____"EGFP "_c__c__c__c__c__c__c__c__c__>
              GAG GGC GAG GGC GAT GCC ACC TAC GGC AAG CTG ACC CTG AAG TTC ATC TGC ACC ACC GGC
              AAG CTG CCC GTG CCC TGG CCC ACC CTC GTG ACC ACC CTG ACC TAC GGC GTG CAG TGC TTC
              AGC CGC TAC CCC GAC CAC ATG AAG CAG CAC GAC TTC TTC AAG TCC GCC ATG CCC GAA GGC
              TAC GTC CAG GAG CGC ACC ATC TTC TTC AAG GAC GAC GGC AAC TAC AAG ACC CGC GCC GAG
              GTG AAG TTC GAG GGC GAC ACC CTG GTG AAC CGC ATC GAG CTG AAG GGC ATC GAC TTC AAG
              GAG GAC GGC AAC ATC CTG GGG CAC AAG CTG GAG TAC AAC TAC AAC AGC CAC AAC GTC TAT
              ATC ATG GCC GAC AAG CAG AAG AAC GGC ATC AAG GTG AAC TTC AAG ATC CGC CAC AAC ATC
              GAG GAC GGC AGC GTG CAG CTC GCC GAC CAC TAC CAG CAG AAC ACC CCC ATC GGC GAC GGC
              CCC GTG CTG CTG CCC GAC AAC CAC TAC CTG AGC ACC CAG TCC GCC CTG AGC AAA GAC CCC
                  1740         1750         1760         1770         1780         1790
                AAC GAG AAG CGC GAT CAC ATG GTC CTG CTG GAG TTC GTG ACC GCC GCC GGG ATC ACT CAC
                 N   E   K   R   D   H   M   V   L   L   E   F   V   T   A   A   G   I   T   H>
                _c__c__c__c__c__c__c__c____"EGFP "_c__c__c__c__c__c__c__c__c__>
             1800         1810         1820         1830         1840 MreI   1850
              GGC ATG GAC GAG CTG TAC AAG AAG CTG AGC CAC GGC TTC CCG CCG GCG GTG GCG GCG CAG
               G   M   D   E   L   Y   K   K   L   S   H   G   F   P   P   A   V   A   A   Q>
              ←---------------------EGFP_____--> II→MU ORNITHINE DECARBOXYLASE PEST SEQUENCE
             1860         1870         1880         1890         1900         1910
              GAT GAT GGC ACG CTG CCC ATG TCT TGT GCC CAG GAG AGC GGG ATG GAC CGT CAC CCT GCA
               D   D   G   T   L   P   M   S   C   A   Q   E   S   G   M   D   R   H   P   A>
              <_____ MU ORNITHINE DECARBOXYLASE PEST SEQUENCE_____>
                                           >"bGH_polyA"
             1920         1930         1940         1950 |       1960         1970         1980
              GCC TGT GCT TCT GCT AGG ATC AAT GTG TAG G TGA TCA GCC TCG ACT GTG CCT TCT AGT TGC
               A   C   A   S   A   R   I   N   V   *>
              MU ORNITHINE DECARBOXYLASE PEST SEQUENCE>
                          1990         2000         2010         2020         2030         2040
                    CAG CCA TCT GTT GTT TGC CCC TCC CCC GTG CCT TCC TTG ACC CTG GAA GGT GCC ACT CCC
                          2050         2060         2070         2080         2090         2100
                    ACT GTC CTT TCC TAA TAA AAT GAG GAA ATT GCA TCG CAT TGT CTG AGT AGG TGT CAT TCT
                          2110         2120         2130         2140         2150         2160
                    ATT CTG GGG GGT GGG GTG GGG CAG GAC AGC AAG GGG GAG GAT TGG GAA GAC AAT AGC AGG
```

Fig. 13

```
                              PGK_promoter→
              2170        2180        2190        2200        2210        2220
          CAT GCT GGG GAT GGC CCA ATT CTA CCG GGT AGG GGA GGC GCT TTT CCC AAG GCA GTC TGG
          AGC ATG CGC TTT AGC AGC CCC GCT GGG CAC TTG GCG CTA CAC AAG TGG CCT CTG GCC TCG
          CAC ACA TTC CAC ATC CAC CGG TAG GCG CCA ACC GGC TCC GTT CTT TGG TGG CCC CTT CGC
          GCC ACC TTC TAC TCC TCC CCT AGT CAG GAA GTT CCC CCC CGC CCC GCA GCT CGC GTC GTG
          CAG GAC GTG ACA AAT GGA AGT AGC ACG TCT CAC TAG TCT CGT GCA GAT GGA CAG CAC CGC
          TGA GCA ATG GAA GCG GGT AGG CCT TTG GGG CAG CGG CCA ATA GCA GCT TTG CTC CTT CGC
          TTT CTG GGC TCA GAG GCT GGG AAG GGG TGG GTC GGG GCG GCT CAG GGG CGG GCT CAG
          GGG CGG GGC GGG CGC CCG AAG GTC CTC CGG AGG CCC GGC ATT CTG CAC GCT TCA AAA GCG
              2650        2660       |2670        2680        2690        2700
          CAC GTC TGC CGC GCT GTT CTC CTC TTC CTC ATC TCC GGG CCT TTC GAC CTG CAG CCA ACG
              2710        2720        2730        2740        2750
          CCA CC ATG GGG ACC GAG TAC AAG CCC ACG GTG CGC CTC GCC ACC CGC GAC GAC GTC CCC
                 M   G   T   E   Y   K   P   T   V   R   L   A   T   R   D   D   V   P>
              ___c___c___c___c___c___c____"PURO_DELTATK"_c___c___c___c___c___c___>
              2760        2770        2780        2790        2800        2810
          CGG GCC GTA CGC ACC CTC GCC GCC GCG TTC GCC GAC TAC CCC GCC ACG CGC CAC ACC GTC
          GAC CCG GAC CGC CAC ATC GAG CGG GTC ACC GAG CTG CAA GAA CTC TTC CTC ACG CGC GTC
          GGG CTC GAC ATC GGC AAG GTG TGG GTC GCG GAC GAC GGC GCC GCG GTG GCG GTC TGG ACC
          ACG CCG GAG AGC GTC GAA GCG GGG GCG GTG TTC GCC GAG ATC GGC CCG CGC ATG GCC GAG
          TTG AGC GGT TCC CGG CTG GCC GCG CAG CAA CAG ATG GAA GGC CTC CTG GCG CCG CAC CGG
          CCC AAG GAG CCC GCG TGG TTC CTG GCC ACC GTC GGC GTC TCG CCC GAC CAC AGG GGC AAG
          GGT CTG GGC AGC GCC GTC GTG CTC CCC GGA GTG GAG GCG GCC GAG CGC GCC GGG GTG CCC
          GCC TTC CTG GAG ACC TCC GCG CCC CGC AAC CTC CCC TTC TAC GAG CGG CTC GGC TTC ACC
          GTC ACC GCC GAC GTC GAG GTG CCC GAA GGA CCG CGC ACC TGG TGC ATG ACC CGC AAG CCC
          GGT GCC GGA TCC ATG CCC ACG CTA CTG CGG GTT TAT ATA GAC GGT CCT CAC GGG ATG GGG
          AAA ACC ACC ACC ACG CAA CTG CTG GTG GCC CTG GGT TCG CGC GAC GAT ATC GTC TAC GTA
          CCC GAG CCG ATG ACT TAC TGG CAG GTG CTG GGG GCT TCC GAG ACA ATC GCG AAC ATC TAC
          ACC ACA CAA CAC CGC CTC GAC CAG GGT GAG ATA TCG GCC GGG GAC GCG GCG GTG GTA ATG
          ACA AGC GCC CAG ATA ACA ATG GGC ATG CCT TAT GCC GTG ACC GAC GCC GTT CTG GCT CCT
          CAT ATC GGG GGG GAG GCT GGG AGC TCA CAT GCC CCG CCC CCG GCC CTC ACC CTC ATC TTC
          GAC CGC CAT CCC ATC GCC GCC CTC CTG TGC TAC CCG GCC GCG CGA TAC CTT ATG GGC AGC
          ATG ACC CCC CAG GCC GTG CTG GCG TTC GTG GCC CTC ATC CCG CCG ACC TTG CCC GGC ACA
          AAC ATC GTG TTG GGG GCC CTT CCG GAG GAC AGA CAC ATC GAC CGC CTG GCC AAA CGC CAG
          CGC CCC GGC GAG CGG CTT GAC CTG GCT ATG CTG GCC GCG ATT CGC CGC GTT TAC GGG CTG
          CTT GCC AAT ACG GTG CGG TAT CTG CAG GGC GGC GGG TCG TGG CGG GAG GAT TGG GGA CAG
          CTT TCG GGG ACG GCC GTG CCG CCC CAG GGT GCC GAG CCC CAG AGC AAC GCG GGC CCA CGA
          CCC CAT ATC GGG GAC ACG TTA TTT ACC CTG TTT CGG GCC CCC GAG TTG CTG GCC CCC AAC
          GGC GAC CTG TAC AAC GTG TTT GCC TGG GCC TTG GAC GTC TTG GCC AAA CGC CTC CGT CCC
          ATG CAC GTC TTT ATC CTG GAT TAC GAC CAA TCG CCC GCC GGC TGC CGG GAC GCC CTG CTG
          CAA CTT ACC TCC GGG ATG GTC CAG ACC CAC GTC ACC ACC CCC GGC TCC ATA CCG ACG ATC
4260          4270        4280        4290        4300        4310        4320
          TGC GAC CTG GCG CGC ACG TTT GCC CGG GAG ATG GGG GAG GCT AAC TGA G CTC TAG AGC TCG
           C   D   L   A   R   T   F   A   R   E   M   G   E   A   N   *>
              ___c___c___c___c___c____"PURO_DELTATK"_c___c___c___c___c___c___>
                 >"bGH_pA"
              4330    |   4340        4350        4360        4370        4380
          CTG ATC AGC CTC GAC TGT GCC TTC TAG TTG CCA GCC ATC TGT TGT TTG CCC CTC CCC CGT
              4390        4400        4410        4420        4430        4440
          GCC TTC CTT GAC CCT GGA AGG TGC CAC TCC CAC TGT CCT TTC CTA ATA AAA TGA GGA AAT
              4450        4460        4470        4480        4490        4500
          TGC ATC GCA TTG TCT GAG TAG GTG TCA TTC TAT TCT GGG GGG TGG GGT GGG GCA GGA CAG
              4510        4520        4530        4540        4550        4560
          CAA GGG GGA GGA TTG GGA AGA CAA TAG CAG GCA TGC TGG GGA TGC GGT GGG CTC TAT GGC
              4570        4580        4590        4600        4610        4620
          TTC TGA GGC GGA AAG AAC CAG CTG GGG CTC GAG ATC ACT AG TTC TAG CCT CGA GGC TAG
                                                                                 Hpa1
              4630           loxP                                        4680
          AGC GGC CGG CCCT ATAACTTCGTATAATGTATGCTATACGAAGTTAT CAGGTAA GTT AAC AGGGCGCGCCC
              4692                                              5528           Bstz17I
          ACTAGGGACAGGATTGGTGACA ←AAVS1_right_homology_arm"→ TCTGCTCT GACGCGTGTATA
```

Fig. 13 (continued)

```
>"Acc65I"  >"EcoR1"   |_____AAVS1_Left_homology_arm_____>>
|       |  10        |   20         30         40         50         60
GGT ACC GAA TTC CTA GCT CTT CCA GCC CCC TGT CAT GGC ATC TTC CAG GGG TCC GAG AGC
         70         80         90        100        110        120
TCA GCT AGT CTT CTT CCT CCA ACC CGG GCC CCT ATG TCC ACT TCA GGA CAG CAT GTT TGC
        130        140        150        160        170        180
TGC CTC CAG GGA TCC TGT GTC CCC GAG CTG GGA CCA CCT TAT ATT CCC AGG GCC GGT TAA
        190        200        210 |      220        230        240
TGT GGC TCT GGT TCT GGG TAC TTT TAT CTG TCC CCT CCA CCC CAC AGT GGG GC Nsi1            FRT_site
AAGATGCAT       GAAGTTCCTATTCCGAAGTTCCTATTCTCTAGAAAGTATAGGAACTTC GACC Lox 2272                              I-SceI meganuclease
ATAACTTCGTATAAAGTATCCTATACGAAGTTAT GCGATCGCTCGCGCG TAGGGATAACAGGGTAAT AAG >"EGFP_left_TALEN"                              >"Splice_acceptor"
             |                                               |
             |   370        380        390        400        | 410
       TCCACCGGTCGCC ACCATGGT CT TCT GAC CTC TTC TCT TCC TCC CA CAG GGC ATG
                                                                    G   M 420        430        440        450        460        470
 GCA AAA CCT CTG AGC CAG GAA GAA AGC ACA CTG ATT GAA AGA GCA ACC GCT ACT ATC AAC
  A   K   P   L   S   Q   E   E   S   T   L   I   E   R   A   T   A   T   I   N>
 ___a___a___a___a___a___a___a____"BLASTICIDIN"__a___a___a___a___a___a___a___a___>

480        490        500        510        520        530
 AGC ATC CCC ATC TCC GAA GAC TAT TCT GTG GCT AGT GCC GCT CTG TCC AGC GAC GGG AGA
  S   I   P   I   S   E   D   Y   S   V   A   S   A   A   L   S   S   D   G   R>
 ___a___a___a___a___a___a___a____"BLASTICIDIN"__a___a___a___a___a___a___a___a___>

540        550        560        570        580        590
 ATC TTC ACC GGT GTG AAC GTC TAC CAC TTT ACA GGC GGA CCA TGC GCA GAG CTG GTG GTC
  I   F   T   G   V   N   V   Y   H   F   T   G   G   P   C   A   E   L   V   V>
 ___a___a___a___a___a___a___a____"BLASTICIDIN"__a___a___a___a___a___a___a___a___>

600        610        620        630        640        650
 CTG GGG ACT GCA GCC GCT GCA GCC GCT GGT AAT CTG ACC TGT ATC GTG GCC ATT GGC AAC
  L   G   T   A   A   A   A   A   G   N   L   T   C   I   V   A   I   G   N>
 ___a___a___a___a___a___a___a____"BLASTICIDIN"__a___a___a___a___a___a___a___a___>

660        670        680        690        700        710
 GAA AAT AGG GGC ATC CTG TCC CCA TGC GGC AGG TGT CGG CAG GTG CTG CTG GAT CTG CAT
  E   N   R   G   I   L   S   P   C   G   R   C   R   Q   V   L   L   D   L   H>
 ___a___a___a___a___a___a___a____"BLASTICIDIN"__a___a___a___a___a___a___a___a___>

720        730        740        750        760        770
 CCT GGC ATC AAG GCA ATT GTC AAA GAC TCT GAT GGA CAG CCT ACC GCC GTC GGT ATC CGT
  P   G   I   K   A   I   V   K   D   S   D   G   Q   P   T   A   V   G   I   R>
 ___a___a___a___a___a___a___a____"BLASTICIDIN"__a___a___a___a___a___a___a___a___>
```

Fig. 15

```
                                                         >"SV40_poly_A"
                                                              |
 780        790        800        810        820        830  |    840
 GAA CTG CTG CCT AGC GGC TAT GTC TGG GAG GGA TAA TGA A TGA GCT TGG CTT CGA AAT GAC
  E   L   L   P   S   G   Y   V   W   E   G   *   *>
___a___a___a___a__"BLASTICIDIN"____a___a___a___a___>

850        860        870        880        890        900
 CGA CCA AGC GAC GCC CAA CCT GCC ATC ACG AGA TTT CGA TTC CAC CGC CGC CTT CTA TGA 910        920        930        940        950        960
 AAG GTT GGG CTT CGG AAT CGT TTT CCG GGA CGC CGG CTG GAT GAT CCT CCA GCG CGG GGA 970        980        990       1000       1010       1020
 TCT CAT GCT GGA GTT CTT CGC CCA CCC CAA CTT GTT TAT TGC AGC TTA TAA TGG TTA CAA 1030       1040       1050       1060       1070       1080
 ATA AAG CAA TAG CAT CAC AAA TTT CAC AAA TAA AGC ATT TTT TTC ACT GCA TTC TAG TTG

PacI         →←D1.3 ANTIBODY EXPRESSION CASSETTE→
 TGG TTT AAT TAA CAA TTC

End polyA              6443 lox P recombination      BstZ17I

CAGGCATGCTGGGGA    TGGCCCGGGCATG ATAACTTCGTATAATGTATGCTATACGAAGTTATG TATAC

AscI           EGFP_right_TALEN     6510
               GGCGCGCCC GAGCAAGGG CGAGGAGCTGTTCA    CTTCTGACCTCTTCTCTTCCTCCCACCTG >"T2A"
  splice accceptor     6559 Start of T2a/GFP homology arm (6559-7332)
        |   6550       6560       6570       6580       6590       6600
      AGC CTA GAG AGA TCT GGC AGC GGA GAG GGC AGA GGA AGT CTT CTA ACA TGC GGT GAC
      GTG GAG GAG AAT CCC GGA CCG TGA GTG AGC AAG GGA GAA GAA CTC TTC ACC GGG GTG GTG
      CCC ATC CTG GTC GAG CTG GAC GGC GAC GTG AAC GGC CAC AAG TTC AGC GTG TCC GGC GAG
      GGC GAG GGC GAT GCC ACC TAC GGC AAG CTG ACC CTG AAG TTC ATC TGC ACC ACC GGC AAG
      CTG CCC GTG CCC TGG CCC ACC CTC GTG ACC ACC CTG ACC TAC GGC GTG CAG TGC TTC AGC
      CGC TAC CCC GAC CAC ATG AAG CAG CAC GAC TTC TTC AAG TCC GCC ATG CCC GAA GGC TAC
      GTC CAG GAG CGC ACC ATC TTC TTC AAG GAC GAC GGC AAC TAC AAG ACC CGC GCC GAG GTG
      AAG TTC GAG GGC GAC ACC CTG GTG AAC CGC ATC GAG CTG AAG GGC ATC GAC TTC AAG GAG
      GAC GGC AAC ATC CTG GGG CAC AAG CTG GAG TAC AAC TAC AAC AGC CAC AAC GTC TAT ATC
      ATG GCC GAC AAG CAG AAG AAC GGC ATC AAG GTG AAC TTC AAG ATC CGC CAC AAC ATC GAG
      GAC GGC AGC GTG CAG CTC GCC GAC CAC TAC CAG CAG AAC ACC CCC ATC GGC GAC GGC CCC
      GTG CTG CTG CCC GAC AAC CAC TAC CTG AGC ACC CAG TCC GCC CTG AGC AAA GAC CCC AAC
      GAG AAG CGC GAT CAC ATG GTC CTG CTG GAG TTC GTG ACC GCC GCC GGG ATC ACT CAC GGC
          7330      MluI BstZ17I
      ATG GAC GAG CCT GACGCGT GTATAC
```

Fig. 15 (continued)

```
     Ncol    10          20          30          40          50          60
CC ATG GGC TAT CCT TAC GAT GTC CCT GAT TAC GCC AAC AGT CCT GGT ATC CCT GGT ATG
   M   G   Y   P   Y   D   V   P   D   Y   A   N   S   P   G   I   P   G   M>
           b___b___b_"HA TAG"_b___b___b___>
     70          80          90         100         110         120
GGT CCT AAA AAG AAG CGA AAA GTG GGT AGA CTG GAA CCC GGC ATG AAG AAC ATT AAG AAA
 G   P   K   K   K   R   K   V   G   R   L   E   P   G   M   K   N   I   K   K>
    __c___c__"NLS"_c___c___c___>                        __d___d_"I-SCE1"_d___d__>
     130         140         150         160         170         180
AAT CAG GTG ATG AAC CTG GGA CCT AAT TCC AAG CTG CTG AAA GAG TAC AAG TCT CAG CTG
 N   Q   V   M   N   L   G   P   N   S   K   L   L   K   E   Y   K   S   Q   L>
    __d___d___d___d___d___d___d___d_"I-SCE1"_d___d___d___d___d___d___d___d__>
     190         200         210         220         230         240
ATC GAA CTG AAC ATT GAG CAG TTT GAA GCA GGG ATC GGT CTG ATT CTG GGG GAC GCC TAC
 I   E   L   N   I   E   Q   F   E   A   G   I   G   L   I   L   G   D   A   Y>
    __d___d___d___d___d___d___d___d_"I-SCE1"_d___d___d___d___d___d___d___d__>
     250         260         270         280         290         300
ATC CGG AGC AGG GAT GAG GGC AAG ACT TAT TGC ATG CAG TTC GAA TGG AAG AAT AAG GCC
 I   R   S   R   D   E   G   K   T   Y   C   M   Q   F   E   W   K   N   K   A>
    __d___d___d___d___d___d___d___d_"I-SCE1"_d___d___d___d___d___d___d___d__>
     310         320         330         340         350         360
TAC ATG GAC CAC GTG TGT CTG CTG TAT GAT CAG TGG GTC CTG TCT CCC CCT CAC AAG AAA
 Y   M   D   H   V   C   L   L   Y   D   Q   W   V   L   S   P   P   H   K   K>
    __d___d___d___d___d___d___d___d_"I-SCE1"_d___d___d___d___d___d___d___d__>
     370         380         390         400         410         420
GAG AGA GTG AAC CAT CTG GGC AAT CTG GTC ATT ACT TGG GGA GCA CAG ACC TTC AAG CAT
 E   R   V   N   H   L   G   N   L   V   I   T   W   G   A   Q   T   F   K   H>
    __d___d___d___d___d___d___d___d_"I-SCE1"_d___d___d___d___d___d___d___d__>
     430         440         450         460         470         480
CAG GCC TTT AAC AAA CTG GCT AAC CTG TTC ATC GTG AAC AAC AAG AAA ACC ATC CCT AAC
 Q   A   F   N   K   L   A   N   L   F   I   V   N   N   K   K   T   I   P   N>
    __d___d___d___d___d___d___d___d_"I-SCE1"_d___d___d___d___d___d___d___d__>
     490         500         510         520         530         540
AAT CTG GTC GAA AAC TAC CTG ACA CCA ATG AGT CTG GCC TAT TGG TTC ATG GAC GAT GGC
 N   L   V   E   N   Y   L   T   P   M   S   L   A   Y   W   F   M   D   D   G>
    __d___d___d___d___d___d___d___d_"I-SCE1"_d___d___d___d___d___d___d___d__>
     550         560         570         580         590         600
GGA AAA TGG GAC TAC AAC AAG AAC AGC ACA AAC AAA AGC ATC GTG CTG AAT ACC CAG TCC
 G   K   W   D   Y   N   K   N   S   T   N   K   S   I   V   L   N   T   Q   S>
    __d___d___d___d___d___d___d___d_"I-SCE1"_d___d___d___d___d___d___d___d__>
     610         620         630         640         650         660
TTC ACA TTT GAG GAA GTG GAG TAT CTG GTC AAG GGC CTG CGG AAC AAA TTC CAG CTG AAC
 F   T   F   E   E   V   E   Y   L   V   K   G   L   R   N   K   F   Q   L   N>
    __d___d___d___d___d___d___d___d_"I-SCE1"_d___d___d___d___d___d___d___d__>
     670         680         690         700         710         720
TGC TAC GTG AAG ATC AAC AAG AAC AAG CCA ATC ATC TAC ATC GAT TCT ATG AGT TAC CTG
 C   Y   V   K   I   N   K   N   K   P   I   I   Y   I   D   S   M   S   Y   L>
    __d___d___d___d___d___d___d___d_"I-SCE1"_d___d___d___d___d___d___d___d__>
     730         740         750         760         770         780
ATC TTT TAT AAC CTG ATT AAG CCA TAC CTG ATC CCC CAG ATG ATG TAT AAA CTG CCC AAT
 I   F   Y   N   L   I   K   P   Y   L   I   P   Q   M   M   Y   K   L   P   N>
    __d___d___d___d___d___d___d___d_"I-SCE1"_d___d___d___d___d___d___d___d__>
     790         800       Xbal
ACA ATC AGC TCC GAG ACT TTC CTG AAG GTCTAGA
 T   I   S   S   E   T   F   L   K   V>
    __d___d___d__"I-SCE1"___d___d___d__>
```

```
gctagcaagcaggaagtgactcagatcccagccgctctgagcgtgcctgagggagaaaac
Nhe1  K  Q  E  V  T  Q  I  P  A  A  L  S  V  P  E  G  E  N
ctggtcctgaattgcagtttcaccgactcagccatctataacctgcagtggtttcgccag
    L  V  L  N  C  S  F  T  D  S  A  I  Y  N  L  Q  W  F  R  Q
gatccaggcaagggactgacctccctgctgctgattcagagctcccagagggaacagaca
    D  P  G  K  G  L  T  S  L  L  L  I  Q  S  S  Q  R  E  Q  T
tctggcagactgaatgctagtctggacaaatctagtggacggtctaccctgtacatcgca
    S  G  R  L  N  A  S  L  D  K  S  S  G  R  S  T  L  Y  I  A
gccagccagcctggagattccgcaacatatctgtgcgccgtgcgcccacttacaggcgga
    A  S  Q  P  G  D  S  A  T  Y  L  C  A  V  R  P  L  T  G  G
agctacattcccaccttcgggcgaggtacaagcctgatcgtgcacccagacatccagaat
    S  Y  I  P  T  F  G  R  G  T  S  L  I  V  H  P  D  I  Q  N
ccggagcccgccgtataccagctgaaggaccccagaagccaggacagcaccctgtgcctg
    P  E  P  A  V  Y  Q  L  K  D  P  R  S  Q  D  S  T  L  C  L
ttcaccgacttcgacagccagatcaacgtgcccaagacaatggaaagcggcaccttcatc
    F  T  D  F  D  S  Q  I  N  V  P  K  T  M  E  S  G  T  F  I
accgacaagaccgtgctggacatgaaggctatggacagcaagagcaacggcgccattgcc
    T  D  K  T  V  L  D  M  K  A  M  D  S  K  S  N  G  A  I  A
tggtccaaccagaccagcttcacatgccaggacatcttcaaagagacaaacgccacctac
    W  S  N  Q  T  S  F  T  C  Q  D  I  F  K  E  T  N  A  T  Y
cccagcagcgacgtgccctgtgatgccaccctgaccgagaagtccttcgagacagacatg
    P  S  S  D  V  P  C  D  A  T  L  T  E  K  S  F  E  T  D  M
Aacctgaacttccagaacctgtccgcggccgcaggcctgctggatcccaagctgtgctac
                           Not1
    N  L  N  F  Q  N  L  S  A  A  A  G  L  L  D  P  K  L  C  Y
ctgctggacgggatcctgttcatctacggtgtgatcctgactgccctgttcctgcgagtc
    L  L  D  G  I  L  F  I  Y  G  V  I  L  T  A  L  F  L  R  V
aaatttctcggagtgccgacgctcctgcataccagcaggggcagaaccagctgtataac
    K  F  S  R  S  A  D  A  P  A  Y  Q  Q  G  Q  N  Q  L  Y  N
gagctgaatctgggtcggagggaggaatatgacgtgctggataagagacgcggcagggat
    E  L  N  L  G  R  R  E  E  Y  D  V  L  D  K  R  R  G  R  D
ccagaaatggggggcaagccccagcgacggaaaaaccctcaggagggactgtataatgaa
    P  E  M  G  G  K  P  Q  R  R  K  N  P  Q  E  G  L  Y  N  E
ctgcagaaggacaaaatggccgaggcttactctgaaattgggatgaagggcgagaggaga
    L  Q  K  D  K  M  A  E  A  Y  S  E  I  G  M  K  G  E  R  R
cgcggcaaaggacacgatggcctgtaccagggactgagcactgctaccaaggacacatat
    R  G  K  G  H  D  G  L  Y  Q  G  L  S  T  A  T  K  D  T  Y
gatgctctgcatatgcaggcactgccccctagataataaggtacc
    D  A  L  H  M  Q  A  L  P  P  R  -  -  Acc65I
```

Fig. 25 d
```
ccatggccaacgctggagtgactcagacccctaagttccaggtcctgaaaactgggcag
Nco M  A  N  A  G  V  T  Q  T  P  K  F  Q  V  L  K  T  G  Q
agtatgaccctgcagtgcgcacaggacatgaatcacgagtacatgtcatggtatcggcag
    S  M  T  L  Q  C  A  Q  D  M  N  H  E  Y  M  S  W  Y  R  Q
gatccagggatgggtctgaggctgatccattacagcgtgggcgctggaactaccgaccag
    D  P  G  M  G  L  R  L  I  H  Y  S  V  G  A  G  T  T  D  Q
ggcgaggtgcccaacggatataatgtctcaagaagcaccacagaagatttcccactgcga
    G  E  V  P  N  G  Y  N  V  S  R  S  T  T  E  D  F  P  L  R
ctgctgagcgccgctcctagccagacatccgtgtactttgcgccagctccaatgtcggg
    L  L  S  A  A  P  S  Q  T  S  V  Y  F  A  S  S  N  V  G
aacaccggcgagctgttctttggggaaggttcccgcctgacagtgctcgaggacctgaga
    N  T  G  E  L  F  F  G  E  G  S  R  L  T  V  L  E  D  L  R
                                                 Xho1
aacgtgaccccccccaaggtgtccctgttcgagcctagcaaggccgagatcgccaacaag
    N  V  T  P  P  K  V  S  L  F  E  P  S  K  A  E  I  A  N  K
cagaaagccaccctcgtgtgcctggccagaggcttcttccccgaccacgtggaactgtct
    Q  K  A  T  L  V  C  L  A  R  G  F  F  P  D  H  V  E  L  S
tggtgggtcaacggcaaagaggtgcacagcggcgtgtccaccgatccccaggcctacaaa
    W  W  V  N  G  K  E  V  H  S  G  V  S  T  D  P  Q  A  Y  K
gagagcaactacagctactgcctgagcagcagactgcgggtgtccgccaccttctggcac
    E  S  N  Y  S  Y  C  L  S  S  R  L  R  V  S  A  T  F  W  H
aaccccggaaccacttcagatgccaggtgcagtttcacggcctgagcgaagaggacaag
    N  P  R  N  H  F  R  C  Q  V  Q  F  H  G  L  S  E  E  D  K
tggcccgagggcagccctaagcccgtgacccagaatatctctgccgaagcctggggcaga
    W  P  E  G  S  P  K  P  V  T  Q  N  I  S  A  E  A  W  G  R
gccgactgtggcattaccagcgccagctaccagcagggcgtgctgtctgccaccatcctg
    A  D  C  G  I  T  S  A  S  Y  Q  Q  G  V  L  S  A  T  I  L
tacgaggtcgcgagcggactgctggacccaaagctgtgctacctgctggatgggatcctg
    Y  E  V  A  S  G  L  L  D  P  K  L  C  Y  L  L  D  G  I  L
ttcatctacggtgtgattctgacagccctgttcctgcgagtcaagttcagccggagcgcc
    F  I  Y  G  V  I  L  T  A  L  F  L  R  V  K  F  S  R  S  A
gacgcaccagcataccagcaggggcagaatcagctgtataacgagctgaatctgggtcgg
    D  A  P  A  Y  Q  Q  G  Q  N  Q  L  Y  N  E  L  N  L  G  R
agggaggaatacgacgtgctggataagagacgcggcagggatcccgaaatgggcggaaag
    R  E  E  Y  D  V  L  D  K  R  R  G  R  D  P  E  M  G  G  K
cctcagcgacggaaaaacccacaggagggactgtacaatgaactgcagaaggacaaaatg
    P  Q  R  R  K  N  P  Q  E  G  L  Y  N  E  L  Q  K  D  K  M
gctgaggcatattctgaaatcggcatgaaggggagagaggagacgcggcaaggacacgat
    A  E  A  Y  S  E  I  G  M  K  G  E  R  R  R  G  K  G  H  D
gggctgtaccagggtctgagtacagccactaaggacacctatgatgccctgcatatgcag
    G  L  Y  Q  G  L  S  T  A  T  K  D  T  Y  D  A  L  H  M  Q
gctctgccacccagataataaaagctt
    A  L  P  P  R  -  -  Hind 3
```

```
gctagccagaaagaggtggaacagaacagcggccctctgagcgtgccagaaggcgctatc
Nhel  Q  K  E  V  E  Q  N  S  G  P  L  S  V  P  E  G  A  I
gccagcctgaactgcacctacagctttctgggcagccagagcttcttctggtacagacag
 A  S  L  N  C  T  Y  S  F  L  G  S  Q  S  F  F  W  Y  R  Q
tacagcggcaagagccccgagctgatcatgttcacctacagagagggcgacaaagaggac
 Y  S  G  K  S  P  E  L  I  M  F  T  Y  R  E  G  D  K  E  D
ggcagattcaccgcccagctgaacaaggccagccagcacgtgtccctgctgatcagagac
 G  R  F  T  A  Q  L  N  K  A  S  Q  H  V  S  L  L  I  R  D
agccagcctagcgacagcgccacctacctgtgcgccgtgaatgatggcggcagactgacc
 S  Q  P  S  D  S  A  T  Y  L  C  A  V  N  D  G  G  R  L  T
tttggcgacggcaccacccctgaccgtgaagcctgacatccagaatccggagcccgccgta
 F  G  D  G  T  T  L  T  V  K  P  D  I  Q  N  P  E  P  A  V
taccagctgaaggaccccagaagccaggacagcaccctgtgcctgttcaccgacttcgac
 Y  Q  L  K  D  P  R  S  Q  D  S  T  L  C  L  F  T  D  F  D
agccagatcaacgtgcccaagacaatggaaagcggcaccttcatcaccgacaagaccgtg
 S  Q  I  N  V  P  K  T  M  E  S  G  T  F  I  T  D  K  T  V
ctggacatgaaggctatggacagcaagagcaacggcgccattgcctggtccaaccagacc
 L  D  M  K  A  M  D  S  K  S  N  G  A  I  A  W  S  N  Q  T
agcttcacatgccaggacatcttcaaagagacaaacgccacctaccccagcagcgacgtg
 S  F  T  C  Q  D  I  F  K  E  T  N  A  T  Y  P  S  S  D  V
ccctgtgatgccacccctgaccgagaagtccttcgagacagacatgaacctgaacttccag
 P  C  D  A  T  L  T  E  K  S  F  E  T  D  M  N  L  N  F  Q
aacctgtccgcggccgc
 N  L  S    Not1
``` f

```
Nco1
ccatggccagccagaccatccatcagtggcctgccaccctggtgcagcctgtgggatct
      M  A  S  Q  T  I  H  Q  W  P  A  T  L  V  Q  P  V  G  S
cctctgagcctggaatgcaccgtggaaggcaccagcaaccccaacctgtactggtacaga
 P  L  S  L  E  C  T  V  E  G  T  S  N  P  N  L  Y  W  Y  R
caggccgctggcagaggcccccagctgctgttttactggggcccctttggccagatcagc
 Q  A  A  G  R  G  P  Q  L  L  F  Y  W  G  P  F  G  Q  I  S
agcgaggtgccccagaacctgagcgccagcagaccccaggaccggcagtttatcctgagc
 S  E  V  P  Q  N  L  S  A  S  R  P  Q  D  R  Q  F  I  L  S
agcaagaagctgctgctgagcgacagcggcttctacctgtgcgcttggagcgagacaggc
 S  K  K  L  L  L  S  D  S  G  F  Y  L  C  A  W  S  E  T  G
ctgggcatgggcggatggcagtttggcgagggcagcagactgacagtgctcgag
 L  G  M  G  G  W  Q  F  G  E  G  S  R  L  T  V  L  E
                                                    Xho1
```

```
5' C ACG CGG CAC GCG GGT GAA NNS NNS CCT WCN ATG TAA GGG TGG AAG CCC GCTC
  C ACG CGG CAC GCG GGT GAA NNS NNS CCT WGN ATG TAA GGG TGG AAG CCC GCTC 5'
      C   A   V   R   P   L   X   X   G  S/T  Y   I   P   T   F   G   R
                              -----------CDR3"-----------------------
``` h

```
5' G TAC TTT TGC GCC AGC TCC NNS STC GGG NNS ACC GGC GAG CTG TTC TTTG
   C ATG AAA ACG CGG TCG AGG NNS SAG CCC NNS TGG CCG CTC GAC AAG AAAC 5'
       Y   F   C   A   S   S   N  V/L  G   N   T   G   E   L   F   F
                              ---------------CDR3-----------------
```

Leader Nco1           Not1
ggcg<u>ccatgg</u>cccaggtc<u>gcggccgc</u>aagcggactgctggacccaaagctgtgctacctg
 G  A  M  A              S  G  L  L  D  P  K  L  C  Y  L
ctggatgggatcctgttcatctacggtgtgattctgacagccctgttcctgcgagtcaag
 L  D  G  I  L  F  I  Y  G  V  I  L  T  A  L  F  L  R  V  K
ttcagccggagcgccgacgcaccagcataccagcaggggcagaatcagctgtataacgag
 F  S  R  S  A  D  A  P  A  Y  Q  Q  G  Q  N  Q  L  Y  N  E
ctgaatctgggtcggagggaggaatacgacgtgctggataagagacgcggcagggatccc
 L  N  L  G  R  R  E  E  Y  D  V  L  D  K  R  R  G  R  D  P
gaaatgggcggaaagcctcagcgacggaaaaacccacaggagggactgtacaatgaactg
 E  M  G  G  K  P  Q  R  R  K  N  P  Q  E  G  L  Y  N  E  L
cagaaggacaaaatggctgaggcatattctgaaatcggcatgaagggagagaggagacgc
 Q  K  D  K  M  A  E  A  Y  S  E  I  G  M  K  G  E  R  R  R
ggcaaaggacacgatgggctgtaccagggtctgagtacagccactaaggacacctatgat
 G  K  G  H  D  G  L  Y  Q  G  L  S  T  A  T  K  D  T  Y  D
                                              Hind3
gccctgcatatgcaggctctgccacccagataataa<u>aagctt</u>
 A  L  H  M  Q  A  L  P  P  R  -  -

```
Leader Nco1         Not1    I---CD8 hinge/Transmembrane→
gccatggcc caggtcgcggccgca acaacaaccccagcccccagacctcctacccct
 A  M  A                    T  T  T  P  A  P  R  P  P  T  P
gccctacaattgccagccagcctctgagcctgaggcccgaggcttgtagaccagctgct
 A  P  T  I  A  S  Q  P  L  S  L  R  P  E  A  C  R  P  A  A
ggcggagccgtgcacaccagaggactggatttcgcctgcgacatctacatctgggcccct
 G  G  A  V  H  T  R  G  L  D  F  A  C  D  I  Y  I  W  A  P ←---CD8 hinge transmembrane---II 4-1BB→
ctggccggcacatgtggcgtgctgctgctgagcctcgtgatcaccctgtactgc aagcgg
 L  A  G  T  C  G  V  L  L  L  S  L  V  I  T  L  Y  C   K  R
ggcagaaagaaactgctgtacatctttaagcagcccttcatgcggcccgtgcagaccacc
 G  R  K  K  L  L  Y  I  F  K  Q  P  F  M  R  P  V  Q  T  T ←-- 4-1BB--I
caggaagaggacggctgctcctgcagattccccgaggaagaagaaggc ggctgcgagctg
 Q  E  E  D  G  C  S  C  R  F  P  E  E  E  E  G   G  C  E  L I---CD3ζ→
agagtgaagttcagcagatccgccgacgcccctgcctacaagcagggccagaaccagctg
 R  V  K  F  S  R  S  A  D  A  P  A  Y  K  Q  G  Q  N  Q  L
tacaacgagctgaacctgggcagacgggaagagtacgacgtgctggacaagcggagaggc
 Y  N  E  L  N  L  G  R  R  E  E  Y  D  V  L  D  K  R  R  G
cgggacccagagatgggcggaaagcccagaagaaagaaccccaggaaggcctgtataac
 R  D  P  E  M  G  G  K  P  R  R  K  N  P  Q  E  G  L  Y  N
gaactgcagaaagacaaaatggccgaggcctacagcgagatcggaatgaagggcgagcgg
 E  L  Q  K  D  K  M  A  E  A  Y  S  E  I  G  M  K  G  E  R
agaagaggcaaggggcacgatggcctgtaccagggcctgagcaccgccaccaaggacacc
 R  R  G  K  G  H  D  G  L  Y  Q  G  L  S  T  A  T  K  D  T
tatgacgccctgcacatgcaggccctgccccctagataataaaagctt
 Y  D  A  L  H  M  Q  A  L  P  P  R  -  -  Hind 3
```

NcoI
```
gccatggccgaagtgaaactgcaggagtctggaccggcctggtggcccatctcagtct
 A  M  A  E  V  K  L  Q  E  S  G  P  G  L  V  A  P  S  Q  S
ctgagcgtgacctgtaccgtgtccggcgtgtccctgcctgactatggcgtgtcctggatc
 L  S  V  T  C  T  V  S  G  V  S  L  P  D  Y  G  V  S  W  I
agacagccccccagaaagggcctggaatggctgggagtgatctggggcagcgaaaccacc
 R  Q  P  P  R  K  G  L  E  W  L  G  V  I  W  G  S  E  T  T
tactacaacagcgccctgaagtcccggctgaccatcatcaaggacaactccaagagccag
 Y  Y  N  S  A  L  K  S  R  L  T  I  I  K  D  N  S  K  S  Q
gtgttcctgaagatgaacagcctgcagaccgacgacaccgccatctactactgcgccaag
 V  F  L  K  M  N  S  L  Q  T  D  D  T  A  I  Y  Y  C  A  K
cactactactacggcggcagctacgctatggactactggggccagggcacctcggtcacc
 H  Y  Y  Y  G  G  S  Y  A  M  D  Y  W  G  Q  G  T  S  V  T
gtctcgagtggtggaggcggttcaggcggaggtggctctggcggtggcgctagcgacatc
 V  S  S  G  G  G  G  S  G  G  G  G  S  G  G  A  S  D  I
cagatgacccagaccaccagcagcctgagcgccagcctgggcgatagagtgaccatcagc
 Q  M  T  Q  T  T  S  S  L  S  A  S  L  G  D  R  V  T  I  S
tgcagagccagccaggacatcagcaagtacctgaactggtatcagcagaaacccgacggc
 C  R  A  S  Q  D  I  S  K  Y  L  N  W  Y  Q  Q  K  P  D  G
accgtgaagctgctgatctaccacaccagcagactgcacagcggcgtgcccagcagattt
 T  V  K  L  L  I  Y  H  T  S  R  L  H  S  G  V  P  S  R  F
tccggctctggcagcggcaccgactacagcctgaccatctccaacctggaacaggaagat
 S  G  S  G  S  G  T  D  Y  S  L  T  I  S  N  L  E  Q  E  D
atcgctacctacttctgtcagcaaggcaacaccctgccctacaccttcggcggagggacc
 I  A  T  Y  F  C  Q  Q  G  N  T  L  P  Y  T  F  G  G  T
aagctggagatcaaacgtaccgcggccgca
 K  L  E  I  K  R  T  A  A  A
                              NotI
``` a

NcoI
gccatggctgctacaggcgtgcgggctgtgcccggcaatgagaacagcctggaaatcgag
 A  M  A  A  T  G  V  R  A  V  P  G  N  E  N  S  L  E  I  E
gaactggccagattcgccgtggacgagcacaacaagaaagagaacgccctgctggaattc
 E  L  A  R  F  A  V  D  E  H  N  K  K  E  N  A  L  L  E  F
gtgcgggtcgtgaaggccaaagagcagtggagcgaggccgacaacgactggcacaccatg
 V  R  V  V  K  A  K  E  Q  W  S  E  A  D  N  D  W  H  T  M
tactacctgaccctggaagccaaggacggcggcaagaagaagctgtacgaggccaaagtg
 Y  Y  L  T  L  E  A  K  D  G  G  K  K  K  L  Y  E  A  K  V
tgggtcaagctggacctggaaaccctggcagcacttcaacttcaaagagctccaggaattc
 W  V  K  L  D  L  E  T  W  Q  H  F  N  F  K  E  L  Q  E  F
aagcccgtgggcgacgctgcggccgcg
 K  P  V  G  D  A  A  A  A
                        NotI b

NcoI
gccatggctgctacaggcgtgcgggctgtgcccggcaatgagaacagcctggaaatcgag
 A  M  A  A  T  G  V  R  A  V  P  G  N  E  N  S  L  E  I  E
gaactggccagattcgccgtggacgagcacaacaagaaagagaacgccctgctggaattc
 E  L  A  R  F  A  V  D  E  H  N  K  K  E  N  A  L  L  E  F
gtgcgggtcgtgaaggccaaagagcaggaacagcccatcggcgagcaccccgtgaacgac
 V  R  V  V  K  A  K  E  Q  E  Q  P  I  G  E  H  P  V  N  D
accatgtactacctgaccctggaagccaaggacggcggcaagaagaagctgtacgaggcc
 T  M  Y  Y  L  T  L  E  A  K  D  G  G  K  K  K  L  Y  E  A
aaagtgtgggtcaagcggtggctgcggttcaccgagatctacaacttcaaagagctccag
 K  V  W  V  K  R  W  L  R  F  T  E  I  Y  N  F  K  E  L  Q
gaattcaagcccgtgggcgacgctgcggccgcg
 E  F  K  P  V  G  D  A  A  A  A
                              NotI

Adhiron_mut1

5' CAGGGTCAGGTAGTACATGGTSNNSNNSNN(SNN)$_n$ CTGCTCTTTGGCCTTCACGAC

Adhiron_mut2

CTGGAGCTCTTTGAAGTTSNNSNNSNN(SNN)$_n$ CTTGACCCACACTTTGGC

```
GTC GTG AAG GCC AAA GAG CAG (NNS)_n NNS NNS NNS ACC ATG TAC TAC CTG ACC CTG
CAG CAC TTC CGG TTT CTC GTC (NNS)_n NNS NNS NNS TGG TAC ATG ATG GAC TGG GAC
 V   V   K   A   K   E   Q    X      X   X   X   T   M   Y   Y   L   T   L

GCC AAA GTG TGG GTC AAG (NNS)_n NNS NNS NNS AAC TTC AAA GAG CTC CAG
CGG TTT CAC ACC CAG TTC (NNS)_n NNS NNS NNS TTG AAG TTT CTC GAG GTC
 A   K   V   W   V   K    X      X   X   X   N   F   K   E   L   Q
```

Nco1
gccatggccggtgtgtgccccaagatcttgaaaaagtgccgccgtgacagcgattgt
 A  M  A  G  V  C  P  K  I  L  K  K  C  R  R  D  S  D  C
cccggcgcctgcatctgccgcggcaatggctattgcggagcggccgca
 P  G  A  C  I  C  R  G  N  G  Y  C  G  Not 1 e

GGT GTG TGC VNS VNS VNS VNS VNS VNS VNS VNS VNS TGC CGC CGT
CCA CAC ACG BNS BNS BNS BNS BNS BNS BNS BNS BNS ACG GCG GCA
 G   V   C   X   X   X   X   X   X   X   X   X   C   R   R

GAC AGC GAT TGT CCC GGC GCC TGC ATC TGC CGC GGC AAT GGC TAT TGC GGA
CTG TCG CTA ACA GGG CCG CGG ACG TAG ACG GCG CCG TTA CCG ATA ACG CCT
 D   S   D   C   P   G   A   C   I   C   R   G   N   G   Y   C   G

```
   EcoR1                          Nsi1
     | 10         20         30     | 40         50         60
G  GTA CCG AAT TCT AGG GAT AAC AGG GTA ATA TGC ATC TTC TGA CCT CTT CTC TTC CTC CCA 70         80         90        100        110        120
     CAG GGC ATG GCA AAA CCT CTG AGC CAG GAA GAA AGC ACA CTG ATT GAA AGA GCA ACC GCT
              M   A   K   P   L   S   Q   E   E   S   T   L   I   E   R   A   T   A  >
                                     "BLASTICIDIN "                                    >
``` b

```
   EcoR1
     | 10         20         30         40         50         60
   GGT ACC GAA TTC TTT TCT GTC ACC AAT CCT GGG GCC ACT AGG GAC ACT GTG GGG TGG AGG

AAVS_TALE_Right_binding            AAVS_TALE_Left_binding

Nsi1
     | 70         80         90        100        110        120
   AAA TGC ATC TTC TGA CCT CTT CTC TTC CTC CCA CAG GGC ATG GCA AAA CCT CTG AGC CAG
                                                          M   A   K   P   L   S   Q  >
                                                              "BLASTICIDIN          >
```

Fig. 30 a

```
    Primer J60>
GCGATCGCGCTGATTGGCTTCTTTTCCTCCCGCCGTGTGTGAAAACACAAATGGCGTGTTTT
GGTTGGCGTAAGGCGCCTGTCAGTTAACGGCAGCCGGAGTGCGCAGCCGCCGGCAGCCTCGC
TCTGCCCACTGGGTGGGGCGGGAGGTAGGTGGGGTGAGGCGAGCTGGACGTGCGGGCGCGGT
CGGCCTCTGGCGGGGCGGGGGAGGGGAGGGAGGGTCAGCGAAAGTAGCTCGCGCGCGAGCGG
CCGCCCACCCTCCCCTTCCTCTGGGGGAGTCGTTTTACCCGCCGCCGGCCGGGCCTCGTCGT
CTGATTGGCTCTCGGGGCCCAGAAAACTGGCCCTTGCCATTGGCTCGTGTTCGTGCAAGTTG
AGTCCATCCGCCGGCCAGCGGGGGCGGCGAGGAGGCGCTCCCAGGTTCCGGCCCTCCCCTCG
GCCCCGCGCCGCAGAGTCTGGCCGCGCGCCCCTGCGCAACGTGGCAGGAAGCGCGCGCTGGG
GGCGGGGACGGGCAGTAGGGCTGAGCGGCTGCGGGGCGGGTGCAAGCACGTTTCCGACTTGA
GTTGCCTCAAGAGGGGCGTGCTGAGCCAGACCTCCATCGCGCACTCCGGGGAGTGGAGGGAA
GGAGCGAGGGCTCAGTTGGGCTGTTTTGGAGGCAGGAAGCACTTGCTCTCCCAAAGTCGCTC
TGAGTTGTTATCAGTAAGGGAGCTGCAGTGGAGTAGGCGGGGAGAAGGCCGCACCCTTCTCC
GGAGGGGGGAGGGGAGTGTTGCAATACCTTTCTGGGAGTTCTCTGCTGCCTCCTGGCTTCTG
AGGACCGCCCTGGGCCTGGGAGAATCCCTTCCCCCTCTTCCCTCGTGATCTGCAACTCCAGT
CTTTCTAGAATGCATTAAGGGATCTGTAGGGCGCAGTAGTCCAGGGTTTCCTTGATGATGTC
< 2706    NsiI    2709>

ATACTTATCCTGTCCCTTTTTTTCCACAGCTCGCGGTTGAGGACAAACTCTTCGCGGTCTT
TCCAGTGGGGATCGACGGTATCGTAGAGTCGAGGCCGCTCTAGGAATTCACGCCGCCACC
                                            <-Primer 2710
ATG ACC GAG
 M   T   E
   Puromycin>
``` b

```
 BstZ17I  Primer J61>
GTATACGGGAATTGAACAGGTGTAAAATTGGAGGGACAAGACTTCCCACAGATTTTCGGTTT
TGTCGGGAAGTTTTTTAATAGGGGCAAATAAGGAAATGGGAGGATAGGTAGTCATCTGGGG
TTTTATGCAGCAAAACTACAGGTTATTATTGCTTGTGATCCGCCTCGGAGTATTTTCCATCG
AGGTAGATTAAAGACATGCTCACCCGAGTTTTATACTCTCCTGCTTGAGATCCTTACTACAG
TATGAAATTACAGTGTCGCGAGTTAGACTATGTAAGCAGAATTTAATCATTTTTAAAGAGC
CCAGTACTTCATATCCATTTCTCCCGCTCCTTCTGCAGCCTTATCAAAGGTATTTTAGAAC
ACTCATTTTAGCCCCATTTTCATTATTATACTGGCTTATCCAACCCCTAGACAGAGCATTG
GCATTTTCCCTTTCCTGATCTTAGAAGTCTGATGACTCATGAAACCAGACAGATTAGTTACA
TACACCACAAATCGAGGCTGTAGCTGGGCCTCAACACTGCAGTTCTTTTATAACTCCTTAG
TACACTTTTTGTTGATCCTTTGCCTTGATCCTTAATTTTCAGTGTCTATCACCTCTCCCGTC
AGGTGGTGTTCCACATTTGGGCCTATTCTCAGTCCAGGGAGTTTTACAACAATAGATGTATT
GAGAATCCAACCTCCTGCAGG
   <-Primer J62 SbfI
```

Fig. 31

PREPARATION OF LIBRARIES OF PROTEIN VARIANTS EXPRESSED IN EUKARYOTIC CELLS AND USE FOR SELECTING BINDING MOLECULES

RELATED APPLICATIONS

This application claims priority to Great Britain Application Number 1407852.1 that was filed on May 2, 2014.

SEQUENCE LISTING

The instant application contains a Sequence Listing which has been submitted in ASCII format via EFS-Web and is hereby incorporated by reference in its entirety. Said ASCII copy, created on Oct. 31, 2016, is named 00130_003US1_SL.txt and is 92.9 kilobytes in size.

FIELD OF THE INVENTION

This invention relates to methods of producing eukaryotic (e.g., mammalian) cell libraries for screening and/or selection of binding molecules such as antibodies. Libraries can be used to contain and display a diverse repertoire of binders, allowing binders to be screened to select one or more binders having a desired property such as specificity for a target molecule. The invention especially relates to methods of introducing donor DNA encoding the binders into eukaryotic cells to provide a cell library in which a desired number of donor DNA molecules are faithfully integrated at a desired locus or loci in the cells.

INTRODUCTION

Protein engineering techniques permit creation of large diverse populations of related molecules (e.g., antibodies, proteins, peptides) from which individual variants with novel or improved binding or catalytic properties can be isolated. The ability to construct large populations of eukaryotic cells, particularly mammalian cells, where each cell expresses an individual antibody, peptide or engineered protein would have great value in identifying binders with desired properties.

The basic principle of display technology relies on the linkage of a binding molecule to the genetic information encoding that molecule. The binding properties of the binding molecule are used to isolate the gene which encodes it. This same underlying principles applies to all forms of display technology including, bacteriophage display, bacterial display, retroviral display, baculoviral display, ribosome display, yeast display and display on higher eukaryotes such as mammalian cells [1, 2, 3, 4].

Display technology has best been exemplified by display of antibodies on filamentous bacteriophage (antibody phage display) which over the last 24 years has provided important tools for discovery and engineering of novel binding molecules including the generation of human therapeutic antibodies. Using phage display antibody molecules are presented on the surface of filamentous bacteriophage particles by cloning the gene encoding an antibody or antibody fragment in-frame with the gene encoding a phage coat protein. The antibody genes are initially cloned into *E. coli* such that each bacterium encodes a single antibody. Generation of bacteriophage from the bacteria using standard methods results in the generation of bacteriophage particles displaying an antibody fragment on their surface and encapsulating the encoding antibody gene within the bacteriophage. The collection of bacteria or the bacteriophage derived from them is referred to as an "antibody library". Using antibody phage display, antibodies and their associated genes can be enriched within the population by exposing antibody-presenting bacteriophage to a target molecule of interest.

To allow recovery of bacteriophage displaying a binder recognising a target of interest, the target molecule needs to be immobilised onto the surface of a selection vessel or needs to be recoverable from solution by secondary reagents, e.g., biotinylated target protein, recovered from solution using streptavidin-coated beads. Following incubation of the library of binder-displaying bacteriophage with the target molecule, unbound phage are removed. This involves washing the matrix to which the target (and associated bacteriophage) is attached to remove unbound bacteriophage. Bound bacteriophage with their associated antibody gene can be recovered and/or infected into host bacterial cells. Using the approach outlined above it becomes possible to enrich a subset of bacteriophage clones capable of binding a target molecule of choice. Phage display libraries have been shown to provide a rich source of antibody diversity, providing hundreds of unique antibodies to a single target [5,6,7].

Historically, display systems for isolating novel antibody binding specificities have been based in prokaryotic systems and in particular on display of single chain Fvs (scFv) and to a lesser extent as Fabs on bacteriophage. Display of binders on the surface of bacteria has been described but has not been widely used and applications have largely been limited to peptide display or display of antibody fragments pre-enriched for binders through immunisation [8]. Despite the power of prokaryotic display systems including phage display there are limitations. Following selection by phage or ribosome display the genes encoding individual binding molecules are identified by introducing the selected gene population into bacteria, plating the bacterial populations, picking colonies, expressing binding molecules into the supernatant or periplasm and identifying positive clones in binding assays such as enzyme or fluorescence linked immunosorbent assays (ELISA). Although binding molecules are identified this approach does not resolved information on the extent of expression and the binding affinity of the resultant clones. Thus although it is possible to generate potentially thousands of binders, the ability to screen the output is limited by the need for colony picking, liquid handling etc., coupled with limited primary information on relative expression level and affinity.

Display of binding molecules on the surface of eukaryotic cells has the potential to overcome some of these problems. In conjunction with flow cytometry, eukaryotic display allows rapid, high throughput selection. It becomes possible to survey millions of cellular clones expressing different binding molecules on their surface. Cell surface display has best been exemplified for the display of antibody fragments formatted as scFvs on the surface of yeast cells. A commonly used modality for yeast surface display makes use of the yeast agglutinin proteins (Aga1p and Aga2p). As described by Chao et al. [9], genes encoding a repertoire of scFvs are genetically fused with the yeast agglutinin Aga2p subunit. The Aga2p subunit then attaches to the Aga1p subunit present in the cell wall via disulphide bonds. Yeast cells expressing a target-specific binding molecule can be identified by flow cytometry using directly or indirectly labelled target molecule. For example biotinylated target can be added to cells and binding to the cell surface can be detected with streptavidin-phycoerythrin. Within a population it becomes possible, using limiting target concentrations, to distinguish those clones which express higher affinity binding molecules since these clones will capture more target molecules and will therefore exhibit brighter fluorescence. Typically, each yeast cell will display 10,000 to 100,000 copies of a single scFv on the surface of the cell. To control for variation in scFv surface expression in different cells Chao et al used a fluorescently labelled anti-tag antibody to measure antibody expression level on the surface of each cell allowing normalisation for variation in expression level. This approach therefore allows yeast cells displaying high affinity binding molecules to be differentiated from those cells expressing high levels of a lower affinity antibody. Thus using fluorescence activated cell sorting (FACS) it is possible to separate cell clones according to the affinity and/or expression level of the encoded binding molecule.

Eukaryotic systems have also proven to be more effective than prokaryotic systems for the display of multi-chain antibody fragments and in particular with larger fragments such as full IgGs, FAbs or fusions of scFv with Fc domains (scFv-Fc fusions). Bead-based or flow sorting-based methods as described above for yeast cells could also be used to select antibodies from display libraries based on higher eukaryotes such as mammalian cells. The ability to format display libraries and select directly as IgGs, Fabs or as scFv-Fc fusions in mammalian cells would be a further advantage over yeast display. The glycosylation, expression and secretion machinery of bacterial and yeast cells is different from higher eukaryotes giving rise to antibodies with different post-translational modifications than those produced in mammalian cells. Since the manufacture of antibodies for research, diagnostic and therapeutic application is typically carried out in mammalian cells, display on mammalian cells (or other higher eukaryotic cells such as invertebrate, avian or plant cell lines) could give a better indication of potential issues or benefits for downstream manufacturing, e.g., identifying clones with optimal expression properties. In addition, antibodies discovered within the context of display on higher eukaryotes and particularly mammalian cells could be applied directly into cell-based reporter assays without extensive purification and without the complicating effect of contaminants from bacteria and yeast cells. Further, libraries of binders could be expressed directly in eukaryotic reporter cells such as mammalian cells to identify clones which directly affect cellular phenotype.

Despite the above advantages promised by eukaryotic display libraries, there remain significant problems with creation of libraries of binders in eukaryotic cells, especially higher eukaryotic cells. Introduction of a repertoire of exogenous genes ("transgenes") for expression in higher eukaryotes is more difficult than in yeast and bacteria. The cells of higher eukaryotes are more difficult to handle and scale up and transformation efficiencies are lower. Typical library sizes achieved are much smaller. In addition, introduced DNA integrates randomly within the genome leading to position effect variegation. Further, donor DNA introduced into mammalian cells by standard transfection or electroporation methods integrates as a linear array with variable copy number of the transfected transgene. The introduction of DNA encoding a repertoire of antibody genes therefore has the potential to introduce multiple antibody genes into each cell resulting in expression of multiple distinct antibodies per cell. In addition the presence of multiple antibody genes will reduce the relative expression of any given antibody and will lead to the isolation of many passenger antibody genes reducing the rate of enrichment of specific clones.

Although display of a library of binders on the surface of higher eukaryotes is more challenging, some examples have previously been described. In an early publication using mammalian display of IgGs derived from human immunisation, 3 rounds of selection (involving transient transfection, cell sorting, DNA recovery and re-transfection) were required to achieve a 450 fold enrichment of antigen-specific cells, averaging 7.6 fold enrichment per round [10]. Similarly transient expression from immunised libraries expressed within episomally-replicating vectors has also been described with antibodies formatted as scFvs [11, 12] or IgGs [13].

A number of approaches have been described to introduce a single or limited number of antibody genes into each cell. This includes dilution of DNA or mixing with carrier DNA [13] but this is a relatively uncontrolled method for managing copy number of introduced genes and reducing DNA input will have a detrimental effect on library size. Introduction of antibody genes by viral vectors has provided another solution to control the introduction of multiple antibody genes per cell. A cell surface display library has been generated in this way from several hundred human B lymphocytes generated by immunization and further enriched by flow sorting of antigen-specific B cells [14]. The antibody genes from this enriched pool were formatted as scFvs, cloned into a Sindbis alphavirus expression system and introduced into BHK cells using a low multiplicity of infection.

Breous-Nystrom et al. [15] used sequential retroviral infection to introduce a limited repertoire of 91 V kappa antibody genes followed by a heavy chain genes repertoire from 6 healthy donors into a murine pre-B cell line (1624-5). Infectious retrovirus was generated using the V-Pack system based on Moloney Murine Leukemia Virus (Stratagene). In order to bias towards single copy insertions, a multiplicity of infection was chose which led to infection of approximately 5% of cells. A major disadvantage of these approaches is that integration within the genome is random, leading to potential variation in transcription level based on the transcriptional activity of the site of integration. Another disadvantage in all these cases is that the integration of the antibody genes is controlled by limited infection or transfection which impacts on library size.

Site-specific integration of transgenes directed by recombinases has previously been described. Recombinases are enzymes that catalyse exchange reactions between DNA molecules containing enzyme-specific recognition sequences. For example Cre recombinase (derived from the site specific recombination system of *E. coli*) or Flp recombinase (utilising a recombination system of *Saccharomyces cerevisiae*) act on their specific 34 bp loxP recognition sites and 34 bp Flp Recombination Target (FRT) site respectively [16]. Recombinases have mainly been used in cellular engineering to catalyse site-specific integration. A number of studies from the work of Chen Zhou [17, 18, U.S. Pat. No. 7,884,054] have described the recombinase-mediated site-specific integration of antibody genes into the genome of mammalian cells using Flp recombinase within the "Flp-In" system, (http://tools.lifetechnologies.com/content/sfs/manuals/flpinsystem_man.pdf). The Flp-ln system utilises a variety of cell lines which have previously had a single FRT site introduced within their genome. By expressing the enzyme Flp recombinase it is possible to direct integration of expression plasmids, incorporating a FRT recombination site, into this pre-integrated FRT site in target cells.

Using the Flp-In system Zhou et al. [17] introduced an incoming antibody expression plasmid containing a FRT site into Chinese Hamster Ovary (CHO) cell line incorporating a FRT site (CHOF cells). Their work describes construction of a display library where 4 residues within an existing anti-OX40 ligand antibody were mutagenised. The library was screened using FACS to identify antibodies with anti-ligand affinity on the cell surface. The overall success in generating improved antibodies was limited to the isolation of a single improved antibody. The number of unique mammalian cell clones achieved was not reported.

A follow-on paper by Li et al. in 2012 [18] utilised lymphocytes from a hepatitis B patient to construct an antibody display library. Separate libraries were produced with the heavy and light chain genes obtained from a donor who had been immunised with HBsAg, individually reported to be libraries of size $1.02 \times 10^6$ and $1.78 \times 10^5$, respectively. A secondary library was then produced including both the heavy and light chains which reportedly had a size of $4.32 \times 10^5$. FACS analysis reportedly indicated that about 40% of the cells displayed detectable full-length antibodies on the cell surface. FACS screening of the library identified antibodies binding to HBsAg. Of a sample of 8 selected library members which bound to the antigen, six were found to have the same antibody, so in total three unique anti-HBsAg clones were identified.

The rather limited success of this work may be due to the fact that the Flp-In system is designed for accurate integration in a limited number of clones rather than large library construction. There is therefore a potential conflict between achieving fidelity of integration versus achieving maximal library size. The Flp-In system utilises a mutant Flp recombinase in the plasmid pOG44 which possesses only 10% of the activity at 37° C. of the native Flp recombinase [19]. A variant of Flp recombinase (Flpe) with better thermostability and higher activity than wild type has been identified [19, 20]. This was further improved by codon optimization to create $Flp_o$ encoded within plasmid cCAGGS-$Flp_o$ (Genebridges Cat. A203) According to the Flp-In manual however:

"When generating Flp-In™ expression cell lines, it is important to remember that you are selecting for a relatively rare recombination event since you want recombination and integration of your pcDNA™5/FRT construct to occur only through the FRT site and for a limited time. In this case, using a highly inefficient Flp recombinase is beneficial and may decrease the occurrence of other undesirable recombination events . . . .
. . . To increase the likelihood of obtaining single integrants, you will need to lower the transfection efficiency by limiting the amount of plasmid DNA that you transfect"

This is echoed by Buchholz et al., 1996 [19]:

"FLP may be particularly useful for applications that do not rely on efficiency but depend on tight regulation".

In model experiments and using "instructions described in the manual", Zhou et al. (2010) [17] indeed demonstrated that single copy insertions occurred in >90% of clones. In library construction however relatively high amounts of expression plasmid (2.5-3.2 µg per $10^6$ cells) and a donor excess over pOG44 recombinase-encoding plasmid was used [17, 18]. The Flp-In system recommends using a ratio of at least 9:1 in favour of the recombinase encoding plasmid versus the expression plasmid. However, when seeking to increase library size by transfecting larger amounts of DNA there is the potential for random integration of the incoming plasmid [21]. In all studies the accuracy of integration and the number of integrants per cell under "library construction" conditions was not reported.

In nuclease-directed integration of genes a site-specific nuclease is used to cleave cellular DNA at a specific location. It has previously been shown that this enhances the rate of homologous recombination by at least 40,000 fold and also allows repair by non-homologous end-joining mechanisms. This enhancement of site-specific integration has not previously been used or contemplated to solve the problems associated with creating libraries of binders.

US20100212035 describes methods for generation of rodents capable of expressing exogenous antibody by targeting the immunoglobulin locus of a mammalian embryo with a meganuclease to direct integration of a donor DNA. The potential to create variant libraries of meganucleases to create new DNA cleavage specificities is described but it his does not contemplate the use of meganucleases towards the generation of libraries of binders.

WO 2013/190032 A1 describes integration of genes into a specific locus (Fer1L4) previously modified with exogenous DNA ("a site specific integration" SSI host cell) to incorporate recombinase sites, such as loxP and FRT sites for recombinase-mediated site-specific gene introduction. Nuclease-directed library generation is not described.

WO 2012/167192 A2 describes targeting genes to a locus that can then be selected for amplification. Nuclease-directed methods are employed to target the locus. Nuclease-directed library generation is not described.

US 2009/0263900A1 describes DNA molecules comprising homology arms and their use in methods of homologous recombination. Nuclease-directed library generation is not described.

WO 2011/100058 describes methods for integration of nucleic acid into a genome that avoids the need for long homology arms and instead relies on microhomology or "sticky ends" on the genome and donor to help direct integration. Nuclease-directed library generation is not described.

WO 2011/090804 describes methods for integration of multiple genes or multiple copies of the same gene using different zinc finger nucleases (ZFNs) in sequential rounds. Nuclease-directed library generation is not described.

WO2014/039872 describes methods for engineering plant cells, incorporating a "landing site" into which donor DNA is integrated by homologous recombination or non-homologous end joining using site-directed nucleases. Bacterial artificial chromosome (BAC) libraries are used for initial cloning of donor DNA. Libraries are mentioned in relation to Illumina sequencing methods. Nuclease-directed library generation is not described.

WO2007/047859 A2 describes methods for engineering specificity of meganucleases and their used to target genomic loci. Libraries of mutant meganucleases that may contain meganucleases with new nuclease specificity are described. Nuclease-directed library generation is not described.

US2014/0113375 A1 describes a transient expression system for generation single-stranded DNA sequences homologous to a target genomic sequence, which can be transported to the nucleus to alter the genetic information of the target genomic sequence via DNA repair pathways or homologous recombination. It is suggested that a "library" of mutations could be created by low fidelity reverse transcription of the introduced (non-library) DNA. Mammalian display and selection of molecules with binding activity is not described.

US2012/0277120 describes methods and compositions for the simultaneous integration of a plurality of exogenous nucleic acids is in a single transformation reaction using the native homologous recombination machinery in yeast, which recombination may be further enhanced by inducing targeted double-strand breaks in the host cell's genome at the intended sites of integration. The methods are intended to overcome the need for multiple rounds of engineering to integrate multiple DNA assemblies, for example, for the construction of functional metabolic pathways in industrial microbes, such as yeast. The display or expression of libraries of binding molecules, the use of higher eukaryotes and the selection of molecules with binding activity is not described.

To fully realize the potential for antibody display on mammalian cells and other higher eukaryotes there is a need for a system to create large libraries which combine accurate integration into a pre-defined site with an efficiency that allows construction of large libraries.

SUMMARY OF THE INVENTION

We have overcome the problem of creating large libraries of binders encompassing one or two binder genes per cell by using nuclease-directed integration of populations of genes encoding binders. The invention thus allows preparation of populations of eukaryotic cells wherein a repertoire of binder-encoding is integrated into a fixed locus in the genome allowing expression of the encoded binding molecule, thereby creating a population of cells expressing different binders.

The present invention relates to methods of producing eukaryotic cell libraries encoding a repertoire of binding molecules ("binders"), wherein the methods use a site-specific nuclease for targeted cleavage of cellular DNA to enhance site-specific integration of binder genes through endogenous cellular repair mechanisms. Site-specific nucleases permit the accurate introduction of donor DNA encoding binder molecules into one or more defined loci within the eukaryotic genome or other eukaryotic cell DNA. The invention provides methods of preparing populations of eukaryotic cells in which a repertoire of genes encoding binders are integrated into a desired locus in cellular DNA (e.g., a genomic locus) allowing expression of the encoded binding molecule, thereby creating a population of cells expressing different binders.

Construction of libraries of binders within eukaryotic cells according to the present invention has advantages over recombinase-directed approaches for site-directed incorporation of expression constructs. The present invention uses cellular DNA cleavage by site-specific nucleases to solve problems previously associated with construction of large repertoires of binder genes in eukaryotic cells and particularly higher eukaryotes. This invention allows the efficient creation of large populations of cell clones each expressing individual binders integrated at a fixed locus in cellular DNA. From these libraries of cellular clones it becomes possible to isolate genes encoding novel binding or function-modifying proteins and peptides.

Rather than recombinase-directed exchange of DNA, the approach of the present invention utilises site-specific cleavage of cellular (e.g., genomic) DNA followed by the use of natural repair mechanisms to integrate binder-encoding donor DNA. Following cleavage of the cellular DNA at a sequence recognised by the site-specific nuclease ("recognition sequence"), breaks in the cellular DNA are repaired using mechanisms such as homologous recombination or non-homologous end joining (NHEJ). Creation of site-specific breaks in the cellular DNA enhances incorporation of exogenous donor DNA allowing the construction of large populations of cells with binder genes integrated at a fixed locus.

To date, site-specific nucleases such as meganucleases, ZFNs, TALE nucleases and CRISPR/Cas systems have been directed towards the efficient creation of cells with modifications to endogenous genes or for introduction of reporter genes for the study of cell function. There are also instances where nuclease-directed genomic targeting has been used to integrate genes encoding single secreted antibodies for antibody production (by purification from culture medium) [21, 22,].

The invention simplifies construction of large libraries while directing integration to a single or limited number of defined genetic loci. Integration of donor DNA at one or more fixed loci normalises transcription compared with random integration of variable numbers of transgenes, and allows selection of antibody clones on the basis of translational and stability properties of the binder itself. Faithful integration of donor DNA at a pre-determined location or locations in the cellular DNA results in relatively uniform levels of transcription of binders in the library, and high efficiency of donor DNA introduction, make cell populations created by the methods of the invention particularly useful as libraries for display and selection of binders. Methods of the invention thus produce high quality libraries of binders in eukaryotic cells, which can be screened to identify cells encoding and expressing a specific binder for a target of interest.

In various aspects the invention relates to new and improved methods of preparing eukaryotic cell libraries, the libraries themselves, isolation of desired binders, encoding nucleic acid and cells from the libraries, and uses of the libraries such as for expression and screening of binding molecules and for screening for the effects of binding molecules. Various methods will be described for producing libraries in vitro and using libraries in vitro or in vivo.

The invention provides a method of producing a library of eukaryotic cell clones containing DNA encoding a diverse repertoire of binders, the method comprising using a site-specific nuclease to target cleavage of eukaryotic cell DNA to enhance site-specific integration of binder genes into the cellular DNA through endogenous cellular DNA repair mechanisms.

A method of producing a library of eukaryotic cell clones containing DNA encoding a diverse repertoire of binders may comprise:

providing donor DNA molecules encoding the binders, and eukaryotic cells, introducing the donor DNA into the cells and providing a site-specific nuclease within the cells, wherein the nuclease cleaves cellular DNA to create an integration site at which the donor DNA becomes integrated into the cellular DNA, integration occurring through DNA repair mechanisms endogenous to the cells.

For multimeric binders comprising at least a first and second subunit (i.e., separate polypeptide chains, such as antibody VH and VL domains presented within a Fab or IgG format), the multiple subunits may be encoded on the same molecule of donor DNA. However, it may be desirable to integrate the different subunits into separate loci, in which case the subunits can be provided on separate donor DNA molecules. These could be integrated within the same cycle of nuclease-directed integration or they may be integrated sequentially using nuclease-directed integration for one or both integration steps.

Methods of producing libraries of eukaryotic cell clones encoding multimeric binders may comprise:

providing eukaryotic cells containing DNA encoding the first subunit, and providing donor DNA molecules encoding the second binder subunit, introducing the donor DNA into the cells and providing a site-specific nuclease within the cells, wherein the nuclease cleaves a recognition sequence in cellular DNA to create an integration site at which the donor DNA becomes integrated into the cellular DNA, integration occurring through DNA repair mechanisms endogenous to the cells, thereby creating recombinant cells which contain donor DNA integrated in the cellular DNA. These recombinant cells will contain DNA encoding the first and second subunits of the multimeric binder, and may be cultured to express both subunits. Multimeric binders are obtained by expression and assembly of the separately encoded subunits.

In the above example, nuclease-directed integration is used to integrate DNA encoding a second subunit into cells already containing DNA encoding a first subunit. The first subunit could be previously introduced using the techniques of the present invention or any other suitable DNA integration method. An alternative approach is to use nuclease-directed integration in a first cycle of introducing donor DNA, to integrate a first subunit, followed by introducing the second subunit either by the same approach or any other suitable method. If the nuclease-directed approach is used in multiple cycles of integration, different site-specific nucleases may optionally be used to drive nuclease-directed donor DNA integration at different recognition sites. A method of generating the library may comprise:

providing first donor DNA molecules encoding the first subunit, and providing eukaryotic cells, introducing the first donor DNA into the cells and providing a site-specific nuclease within the cells, wherein the nuclease cleaves a recognition sequence in cellular DNA to create an integration site at which the donor DNA becomes integrated into the cellular DNA, integration occurring through DNA repair mechanisms endogenous to the cells, thereby creating a first set of recombinant cells containing first donor DNA integrated in the cellular DNA, culturing the first set of recombinant cells to produce a first set of clones containing DNA encoding the first subunit, introducing second donor DNA molecules encoding the second subunit into cells of the first set of clones, wherein the second donor DNA is integrated into cellular DNA of the first set of clones, thereby creating a second set of recombinant cells containing first and second donor DNA integrated into the cellular DNA, and culturing the second set of recombinant cells to produce a second set of clones, these clones containing DNA encoding the first and second subunits of the multimeric binder, thereby providing a library of eukaryotic cell clones containing donor DNA encoding the repertoire of multimeric binders.

Site-specific integration of donor DNA into cellular DNA creates recombinant cells, which can be cultured to produce clones. Individual recombinant cells into which the donor DNA has been integrated are thus replicated to generate clonal populations of cells—"clones"—each clone being derived from one original recombinant cell. Thus, the method generates a number of clones corresponding to the number of cells into which the donor DNA was successfully integrated. The collection of clones form a library encoding the repertoire of binders (or, at an intermediate stage where binder subunits are integrated in separate rounds, the clones may encode a set of binder subunits). Methods of the invention can thus provide a library of eukaryotic cell clones containing donor DNA encoding the repertoire of binders.

Methods of the invention can generate libraries of clones containing donor DNA integrated at a fixed locus, or at multiple fixed loci, in the cellular DNA. By "fixed" it is meant that the locus is the same between cells. Cells used for creation of the library may therefore contain a nuclease recognition sequence at a fixed locus, representing a universal landing site in the cellular DNA at which the donor DNA can integrate. The recognition sequence for the site-specific nuclease may be present at one or more than one position in the cellular DNA.

Libraries produced according to the present invention may be employed in a variety of ways. A library may be cultured to express the binders, thereby producing a diverse repertoire of binders. A library may be screened for a cell of a desired phenotype, wherein the phenotype results from expression of a binder by a cell. Phenotype screening is possible in which library cells are cultured to express the binders, followed by detecting whether the desired phenotype is exhibited in clones of the library. Cellular read-outs can be based on alteration in cell behaviour such as altered expression of endogenous or exogenous reporter genes, differentiation status, proliferation, survival, cell size, metabolism or altered interactions with other cells. When the desired phenotype is detected, cells of a clone that exhibits the desired phenotype may then be recovered. Optionally, DNA encoding the binder is then isolated from the recovered clone, providing DNA encoding a binder which produces the desired phenotype when expressed in the cell.

A key purpose for which eukaryotic cell libraries have been used is in methods of screening for binders that recognise a target of interest. In such methods a library is cultured to express the binders, and the binders are exposed to the target to allow recognition of the target by one or more cognate binders, if present, and detecting whether the target is recognised by a cognate binder. In such methods, binders may be displayed on the cell surface and those clones of the library that display binders with desired properties can be isolated. Thus cells incorporating genes encoding binders with desired functional or binding characteristics could be identified within the library. The genes can be recovered and used for production of the binder or used for further engineering to create derivative libraries of binders to yield binders with improved properties.

The present invention offers advantages over previous approaches for construction of libraries in higher eukaryotes. Some studies have used lentiviral infection to introduce antibody genes into mammalian reporter cells [106]. This has the advantage that large libraries can be generated but there is no control over the site of integration and copy number is controlled by using a low multiplicity of infection (as discussed above). In an alternative approach antibody genes were introduced via homologous recombination, without the benefit of nuclease-directed integration and using homology arms of 10 kb but the efficiency of targeting was relatively low meaning that the potential library size was limited [105]. In contrast the use of sequence-directed nucleases retains the benefits of targeted integration to one or a few loci of choice while allowing efficient construction of large libraries. Nuclease-directed integration has the advantage that transgenes are targeted to a fixed locus or fixed loci within the cellular DNA. This means that promoter activity driving transcription of binder genes in all clones will be the same and the functionality of each binder will be a reflection of its inherent potency, translational efficiency and stability rather than being due to variation related to the integration site. Targeting to a single or limited number of loci will also enable better control of expression if required e.g., using inducible promoters.

Various features of the invention are further described below. It is noted that headings used throughout this specification are to assist navigation only and should not be interpreted as definitive, and that embodiments described in different sections may be combined as appropriate.

DETAILED DESCRIPTION

Eukaryotic Cells

The potential of populations of eukaryotic cells expressing a diverse repertoire of binders is exemplified and discussed in the Examples herein in relation to expression of antibody repertoires on the surface of mammalian cells. The benefits of the invention are not limited to mammalian cells and include all eukaryotes.

Yeast (e.g., *Saccharomyces cerevisiae*) has a smaller genome than mammalian cells and homologous recombination directed by homology arms (in the absence of nuclease-directed cleavage) is an effective way of introducing foreign DNA compared to higher eukaryotes. Thus, a particular benefit of nuclease-directed integration of the present invention relates to integration of binder genes into higher eukaryotic cells with larger genomes where homologous recombination in the absence of nuclease cleavage is less effective. Nuclease-directed integration has been used in yeast cells to solve the problem of efficient integration of multiple genes into individual yeast cells, e.g., for engineering of metabolic pathways (US2012/0277120), but this work does not incorporate introduction of libraries of binders nor does it address the problems of library construction in higher eukaryotes.

Libraries of eukaryotic cells according to the present invention are preferably higher eukaryotic cells, defined here as cells with a genome greater than that of *Saccharomyces cerevisiae* which has a genome size of $12 \times 10^6$ base pairs (bp). The higher eukaryotic cells may for example have a genome size of greater than $2 \times 10^7$ base pairs. This includes, for example, mammalian, avian, insect or plant cells. Preferably the cells are mammalian cells, e.g., mouse or human. The cells may be primary cells or may be cell lines. Chinese hamster ovary (CHO) cells are commonly used for antibody and protein expression but any alternative stable cell line may be used in the invention. HEK293 cells are used in Examples herein. Methods are available for efficient introduction of foreign DNA into primary cells allowing these to be used (e.g., by electroporation where efficiencies and viabilities up to 95% have been achieved http://www.maxcyte.com/technology/primary-cells-stem-cells.php).

T lymphocyte lineage cells (e.g., primary T cells or a T cell line) or B lymphocyte lineage cells are among the preferred cell types. Of particular interest are primary T-cells or T cell derived cell lines for use in TCR libraries including cell lines which lack TCR expression [23, 24, 25]. Examples of B lymphocyte lineage cells include B cells, pre-B cells or pro-B cells and cell lines derived from any of these.

Construction of libraries in primary B cells or B cell lines would be of particular value for construction of antibody libraries. Breous-Nystrom et al. [15] have generated libraries in a murine pre-B cell line (1624-5). The chicken B cell derived cell line DT40 (ATCC CRL-2111) has particular promise for construction of libraries of binders. DT40 is a small cell line with a relatively rapid rate of cell division. Repertoires of binders could be targeted to specific loci using ZFNs, TALE nucleases or CRISPR/Cas9 targeted to endogenous sequences or by targeting pre-integrated heterologous sites which could include meganuclease recognition sites. DT40 cells express antibodies and so it will be advantageous to target antibody genes within the antibody locus either with or without disruption of the endogenous chicken antibody variable domains. DT40 cells have also been used as the basis of an in vitro system for generation of chicken IgMs termed the Autonomously Diversifying Library system (ADLib system) which takes advantage of intrinsic diversification occurring at the chicken antibody locus. As a result of this endogenous diversification it is possible to generate novel specificities. The nuclease-directed approach described here could be used in combination with ADLib to combine diverse libraries of binders from heterologous sources (e.g., human antibody variable region repertoires or synthetically derived alternative scaffolds) with the potential for further diversification with the chicken IgG locus. Similar benefits could apply to human B cell lines such as Nalm6 [26]. Other B lineage cell lines of interest include lines such as the murine pre-B cell line 1624-5 and the pro-B cell line Ba/F3. Ba/F3 is dependent on IL-3 [27] and its use is discussed elsewhere herein. Finally a number of human cell lines could be used including those listed in the "Cancer Cell Line Encyclopaedia" [28] or "COSMIC catalogue of somatic mutations in cancer" [29].

Typically the library will be composed of a single type of cells, produced by introduction of donor DNA into a population of clonal eukaryotic cells, for example by introduction of donor DNA into cells of a particular cell line. The main significant difference between the different library clones will then be due to integration of the donor DNA.

Eukaryotic Viral Systems

The advantages of the system in creation of libraries of binders in eukaryotic cells could be applied to viral display systems based around eukaryotic expression systems, e.g., baculoviral display or retroviral display [1, 2, 3, 4]. In this approach each cell will encode a binder capable of being incorporated into a viral particle. In the case of retroviral systems the encoding mRNA would be packaged and the encoded binder would be presented on the cell surface. In the case of baculoviral systems, genes encoding the binder would need to be encapsulated into the baculoviral particle to maintain an association between the gene and the encoded protein. This could be achieved using host cells carrying episomal copies of the baculoviral genome. Alternatively integrated copies could be liberated following the action of a specific nuclease (distinct from the one used to drive site-specific integration). In the case of multimeric binder molecules some partners could be encoded within the cellular DNA with the genes for one or more partners being packaged within the virus.

Site-Specific Nuclease

The invention involves use of a site-specific nuclease for targeted cleavage of cellular DNA in the construction of a library of eukaryotic cells containing DNA encoding a repertoire of binders, wherein nuclease-mediated DNA cleavage enhances site-specific integration of binder genes through endogenous cellular DNA repair mechanisms. The site-specific nuclease cleaves cellular DNA following specific binding to a recognition sequence, thereby creating an integration site for donor DNA. The nuclease may create a double strand break or a single strand break (a nick). Cells used for creation of the library may contain endogenous sequences recognised by the site-specific nuclease or the recognition sequence may be engineered into the cellular DNA.

The site-specific nuclease may be exogenous to the cells, i.e., not occurring naturally in cells of the chosen type.

The site-specific nuclease can be introduced before, after or simultaneously with introduction of the donor DNA encoding the binder. It may be convenient for the donor DNA to encode the nuclease in addition to the binder, or on separate nucleic acid which is co-transfected or otherwise introduced at the same time as the donor DNA. Clones of a library may optionally retain nucleic acid encoding the site-specific nuclease, or such nucleic acid may be only transiently transfected into the cells.

Any suitable site-specific nuclease may be used with the invention. It may be a naturally occurring enzyme or an engineered variant. There are a number of known nucleases that are especially suitable, such as those which recognise, or can be engineered to recognise, sequences that occur only rarely in cellular DNA. Nuclease cleavage at only one or two sites is advantageous since this should ensure that only one or two molecules of donor DNA are integrated per cell. Rarity of the sequence recognised by the site-specific nuclease is more likely if the recognition sequence is relatively long. The sequence specifically recognised by the nuclease may for example be a sequence of at least 10, 15, 20, 25 or 30 nucleotides.

Examples of suitable nucleases include meganucleases, zinc finger nucleases (ZFNs), TALE nucleases, and nucleic acid-guided (e.g., RNA-guided) nucleases such as the CRISPR/Cas system. Each of these produces double strand breaks although engineered forms are known which generate single strand breaks.

Meganucleases (also known as homing endonucleases) are nucleases which occur across all the kingdoms of life and recognise relatively long sequences (12-40 bp). Given the long recognition sequence they are either absent or occur relatively infrequently in eukaryotic genomes. Meganucleases are grouped into 5 families based on sequence/structure. (LAGLIDADG, GIY-YIG, HNH, His-Cys box and PD-(D/E)XK). The best studied family is the LAGLIDADG family which includes the well characterised I-SceI meganuclease from *Saccharomyces cerevisiae*. I-SceI recognises and cleaves an 18 bp recognition sequence (5' TAGGGATAACAGGGTAAT) leaving a 4 bp 3' overhang. Another commonly used example is I-Cre1 which originates from the chloroplast of the unicellular green algae of *Chlamydomonas reinhardtii*, and recognizes a 22 bp sequence [30]. A number of engineered variants have been created with altered recognition sequences [31]. Meganucleases represent the first example of the use of site-specific nucleases in genome engineering [49, 50]. As with recombinase-based approaches, use of I-Sce1 and other meganucleases requires prior insertion of an appropriate recognition site to be targeted within the genome or engineering of meganucleases to recognize endogenous sites [30]. By this approach targeting efficiency in HEK293 cells (as judged by homology-directed "repair" of an integrated defective GFP gene) was achieved in 10-20% of cells through the use of I-Sce1 [32].

A preferred class of meganucleases for use in the present invention is the LAGLIDADG endonucleases. These include I-Sce I, I-Chu I, I-Cre I, Csm I, PI-Sce I, PI-Tli I, PI-Mtu I, I-Ceu I, I-Sce II, I-Sce III, HO, Pi-Civ I, PI-Ctr I, PI-Aae I, PI-Bsu I, PI-Dha I, PI-Dra I, PI-May I, PI-Mch I, PI-Mfu PI-Mfl I, PI-Mga I, PI-Mgo I, PI-Min I, PI-Mka I, PI-Mle I, PI-Mma I, PI-Msh I, PI-Msm I, PI-Mth I, PI-Mtu PI-Mxe I, PI-Npu I, PI-Pfu I, PI-Rma I, PI-Spb I, PI-Ssp I, PI-Fac I, PI-Mja I, PI-Pho I, Pi-Tag I, PI-Thy I, PI-Tko I, I-MsoI, and PI-Tsp I; preferably, I-Sce I, I-Cre I, I-Chu I, I-Dmo I, I-Csm I, PI-Sce I, PI-Pfu I, PI-Tli I, PI-Mtu I, and I-Ceu I.

In recent years a number of methods have been developed which allow the design of novel sequence-specific nucleases by fusing sequence-specific DNA binding domains to non-specific nucleases to create designed sequence-specific nucleases directed through bespoke DNA binding domains. Binding specificity can be directed by engineered binding domains such as zinc finger domains. These are small modular domains, stabilized by Zinc ions, which are involved in molecular recognition and are used in nature to recognize DNA sequences. Arrays of zinc finger domains have been engineered for sequence specific binding and have been linked to the non-specific DNA cleavage domain of the type II restriction enzyme Fok1 to create zinc finger nucleases (ZFNs). ZFNs can be used to create double stranded break at specific sites within the genome. Fok1 is an obligate dimer and requires two ZFNs to bind in close proximity to effect cleavage. The specificity of engineered nucleases has been enhanced and their toxicity reduced by creating two different Fok1 variants which are engineering to only form heterodimers with each other [33]. Such obligate heterodimer ZFNs have been shown to achieve homology-directed integration in 5-18% of target cells without the need for drug selection [21, 34, 35]. Incorporation of inserts up to 8 kb with frequencies of >5% have been demonstrated in the absence of selection.

It has recently been shown that single-stranded 5' overhangs created by nucleases such as ZFNs help drive efficient integration of transgenes to the sites of cleavage [45]. This has been extended to show that in vivo cleavage of donor DNA (through inclusion of a specific nuclease recognition site within the donor plasmid) enhances the efficiency on non-homologous integration. The mechanism is not entirely clear but it is possible that reduced exposure to cellular nucleases through in vivo linearisation may have contributed to the enhancement [45]. It is also possible that matches in the 5' overhangs of donor and acceptor DNA, generated by the nucleases drive ligation. Examination of sequences at the junctions however showed the occurrence of deletions. It is possible that perfectly matched junctions continue to act as substrate for the site-directed nucleases until deletion of the recognition sequence occurs. To overcome this potential problem, Maresca et al. [36] have inverted the recognition sites of left and right ZFNs within the donor DNA such that ligation of donor DNA into the genomic locus will lead to duplication of two left hand ZFNs on one flank of the integration and duplication of two right hand ZFNs at the other flank. The use of obligate heterodimer nucleases (as described for Fok1) means that neither of these newly created flanking sequences can be cleaved by the targeted nuclease.

The ability to engineer DNA binding domains of defined specificity has been further simplified by the discovery in *Xanathomonas* bacteria of Transcription activator-like effectors (TALE) molecules. These TALE molecules consist of arrays of monomers of 33-35 amino acids with each monomer recognising a single base within a target sequence [37]. This modular 1:1 relationship has made it relatively easy to design engineered TALE molecules to bind any DNA target of interest. By coupling these designed TALEs to Fok1 it has been possible to create novel sequence-specific TALE-nucleases. TALE nucleases, also known as TALENs, have now been designed to a large number of sites and exhibit high success rate for efficient gene modification activity [38]. In examples herein we demonstrate the enhanced integration of donor DNA through the use of TALE nucleases. Other variations and enhancements of TALE nuclease technology have been developed and could be used for the generation of libraries of binders through nuclease-directed integration. These included "mega-TALENs" where a TALE nuclease binding domain is fused to a meganuclease [39] and "compact TALENs" where a single TALE nuclease recognition domain is used to effect cleavage [40].

In recent years another system for directing double- or single-stranded breaks to specific sequences in the genome has been described. This system called "Clustered Regularly Interspaced Short Palindromic Repeats (CRISPR) and CRISPR Associated (Cas)" system is based on a bacterial defence mechanism [41]. The CRISPR/Cas system targets DNA for cleavage via a short, complementary single-stranded RNA (CRISPR RNA or crRNA) adjoined to a short palindromic repeat. In the commonly used "Type II" system, the processing of the targeting RNA is dependent on the presence of a trans-activating crRNA (tracrRNA) that has sequence complementary to the palindromic repeat. Hybridization of the tracrRNA to the palindromic repeat sequence triggers processing. The processed RNA activates the Cas9 domain and directs its activity to the complementary sequence within DNA. The system has been simplified to direct Cas9 cleavage from a single RNA transcript and has been directed to many different sequences within the genome [42, 43]. This approach to genome cleavage has the advantage of being directed via a short RNA sequence making it relatively simple to engineer cleavage specificity. Thus there are a number of different ways to achieve site-specific cleavage of genomic DNA. As described above this enhances the rate of integration of a donor plasmid through endogenous cellular DNA repair mechanisms.

Use of meganucleases, ZFNs, TALE nuclease or nucleic acid guided systems such as the CRISPR/Cas9 systems will enable targeting of endogenous loci within the genome. In the Examples herein we have demonstrated targeting to the AAVS locus but alternative loci could be targeted. For example the Type I collagen gene locus has been used for efficient transgene expression [44].

Alternatively heterologous recognition sites for targeted nucleases, including meganucleases, ZFNs and TALE nucleases could be introduced in advance for subsequent library targeting. In Examples herein, we describe the use of a TALE nuclease recognising a sequence within the AAVS locus to introduce by homologous recombination, an I-Sce1 meganuclease recognition sequence and heterologous TALE nuclease recognition sites within the AAVS locus. Nuclease-directed targeting could be used to drive insertion of target sequences by homologous recombination or NHEJ using vector DNA or even double stranded oligonucleotides [45]. As an alternative, non-specific targeting methods could be used to introduce targeting sites through the use of transposon-directed integration [46] to introduce recognition sites for site-specific nucleases. Viral-based systems, such as lentivirus, applied at low titre could also be used to introduce targeting sites. Transfection of DNA coupled with screening for single copy insertion has also been used to identify unique integration sites [17]. Such non-specific approaches would be particularly useful in the case of cells which do not have an obvious site to target or for genomes which have not been sequenced or for genomes for which no existing TALE nucleases, ZFNs or Cas9/CRISPR systems are available. Once a cell line has been established following random insertion of a nuclease recognition site, the cell line can be used subsequently to create libraries of binders where all clones of the library contain the transgene at the fixed locus using nuclease-directed integration.

In the Examples presented, three different plasmids are used encompassing pairs of TALE nucleases or ZFNs on individual plasmids with a separate plasmid for donor DNA. In the case of meganuclease the site-specific nuclease is encoded by a single gene and this is introduced on one plasmid with the donor DNA present on a second plasmid. Of course, combinations could be used incorporating two or more of these elements on the same plasmid and this could enhance the efficiency of targeting by reducing the number of number of plasmids to be introduced. In addition it may be possible to pre-integrate the nuclease(s) which could also be inducible to allow temporal control of nuclease activity as has been demonstrated for transposases [46]. Finally the nuclease could be introduced as recombinant protein or protein:RNA complex (for example in the case of an RNA directed nuclease such as CRISPR:Cas9).

Locus

A recognition sequence for the site-specific nuclease may be present in genomic DNA, or episomal DNA which is stably inherited in the cells. Donor DNA may therefore be integrated at a genomic or episomal locus in the cellular DNA.

In its simplest form a single gene encoding a binder (binder gene) is targeted to a single site within the eukaryotic genome. Identification of a cell demonstrating a particular binding activity or cellular phenotype will allow direct isolation of the gene encoding the desired property (e.g., by PCR from mRNA or genomic DNA). This is facilitated by using a unique recognition sequence for the site-specific nuclease, occurring once in the cellular DNA. Cells used for creation of the library may thus contain a nuclease recognition sequence at a single fixed locus, i.e., one identical locus in all cells. Libraries produced from such cells will contain donor DNA integrated at the fixed locus, i.e., occurring at the same locus in cellular DNA of all clones in the library.

Optionally, recognition sequences may occur multiple times in cellular DNA, so that the cells have more than one potential integration site for donor DNA. This would be a typical situation for diploid or polyploid cells where the recognition sequence is present at corresponding positions in a pair of chromosomes, i.e., replicate loci. Libraries produced from such cells may contain donor DNA integrated at replicate fixed loci. For example libraries produced from diploid cells may have donor DNA integrated at duplicate fixed loci and libraries produced from triploid cells may have donor DNA integrated at triplicate fixed loci. Many suitable mammalian cells are diploid, and clones of mammalian cell libraries according to the invention may have donor DNA integrated at duplicate fixed loci.

The sequence recognised by the site-specific nuclease may occur at more than one independent locus in the cellular DNA. Donor DNA may therefore integrate at multiple independent loci. Libraries of diploid or polyploid cells may comprise donor DNA integrated at multiple independent fixed loci and/or at replicate fixed loci.

In cells containing recognition sequences at multiple loci (whether replicate or independent loci), each locus represents a potential integration site for a molecule of donor DNA. Introduction of donor DNA into the cells may result in integration at the full number of nuclease recognition sequences present in the cell, or the donor DNA may integrate at some but not all of these potential sites. For example, when producing a library from diploid cells containing recognition sequences at first and second fixed loci (e.g., duplicate fixed loci), the resulting library may comprise clones in which donor DNA is integrated at the first fixed locus, clones in which donor DNA is integrated at the second fixed locus, and clones in which donor DNA is integrated at both the first and second fixed loci.

Methods of producing libraries may therefore involve site-specific nuclease cleavage of multiple fixed loci in a cell, and integration of donor DNA at the multiple fixed loci. As noted above, in cases where there are multiple copies of the same recognition sequence (e.g., as occurs when targeting endogenous loci in diploid or polyploid cells) it is possible that two binder genes will be integrated, particularly when an efficient targeting mechanisms is used, with only one gene being specific to the target. This can be resolved during subsequent screening once binder genes have been isolated.

In some instances it may be desirable to introduce more than one binder per cell. For example bi-specific binders could be generated from two different antibodies coming together and these may have properties absent in the individual binders [47]. This could be achieved by introducing different antibody genes into both alleles at duplicate fixed loci or by targeting different antibody populations into independent fixed loci using the methods described herein. Furthermore a binder may itself be composed of multiple chains (e.g., antibody VH and VL domains presented within a Fab or IgG format). In this case it may be desirable to integrate the different sub-units into different loci. These could be integrated within the same cycle of nuclease-directed integration, they could be integrated sequentially using nuclease-directed integration for one or both integration steps.

Introduction of Donor DNA

Numerous methods have been described for introducing donor DNA into eukaryotic cells, including transfection, infection or electroporation. Transfection of large numbers of cells is possible by standard methods including polyethyleneimine-mediated transfection as described herein. In addition methods are available for highly efficient electroporation of $10^{10}$ cells in 5 minutes, e.g., http://www.maxcyte.com.

Combinatorial libraries could be created wherein members of multimeric binding pairs (e.g., VH and VL genes of antibody genes) or even different parts of the same binder molecule are introduced on different plasmids. Introduction of separate donor DNA molecules encoding separate binders or binder subunits may be done simultaneously or sequentially. For example an antibody light chain could be introduced by transfection or infection, the cells grown up and selected if necessary. Other components could then be introduced in a subsequent infection or transfection step. One or both steps could involve nuclease-directed integration to specific genomic loci.

Integration of Donor DNA

The donor DNA is integrated into the cellular DNA, forming recombinant DNA having a contiguous DNA sequence in which the donor DNA is inserted at the integration site. In the present invention, integration is mediated by the natural DNA repair mechanisms that are endogenous to the cell. Thus, integration can be allowed to occur simply by introducing the donor DNA into a cell, allowing the site-specific nuclease to create an integration site, and allowing the donor DNA to be integrated. Cells may be kept in culture for sufficient time for the DNA to be integrated. This will usually result in a mixed population of cells, including (i) recombinant cells into which the donor DNA has integrated at the integration site created by the site-specific nuclease, and optionally (ii) cells in which donor DNA has integrated at sites other than the desired integration site and/or optionally (iii) cells that into which donor DNA has not integrated. The desired recombinant cells and the resulting clones of the library may thus be provided in a mixed population of other eukaryotic cells. Selection methods described elsewhere herein may be used to enrich for cells of the library.

Endogenous DNA repair mechanisms in eukaryotic cells include homologous recombination, non-homologous end joining (NHEJ) and microhomology-directed end joining. The efficiency of DNA modification by such processes can be increased by the introduction of double stranded breaks (DSBs) in the DNA and efficiency gains of 40,000 fold have been reported using rare cutting endonucleases (meganucleases) such as I-SceI [48, 49, 50].

Unlike the site-specific recombination involved in systems such as the Flp-In system [16], the present invention does not require exogenous recombinases or engineered recombinase recognition sites. Therefore, optionally the present invention does not include a step of recombinase-mediated DNA integration in creating the library, and/or optionally the eukaryotic cells into which the donor DNA is introduced lack a recombination site for a site-specific recombinase. The mechanisms and practicalities of directed insertion of donor DNA into cellular DNA by recombinases and nucleases are very distinct. As discussed by Jasin 1996 [50]:

" . . . the reaction catalyzed by site-specific recombinases is quite distinct from cellular repair of DSBs. Site-specific recombinases, such as cre, synapse two recognition sites and create single-strand breaks within the sites, thus forming Holliday intermediates. The intermediates are resolved to produce deletions, inversions and insertions (cointegrants), all of which restore the two recognition sites. The reaction is absolutely precise and, hence, reversible. The breaks are never exposed to the cellular repair machinery."

In contrast site-specific nuclease act to create breaks or nicks within the cellular DNA (e.g., genomic or episomal), which are exposed to and repaired by endogenous cellular repair mechanisms such as homologous recombination or NHEJ. Recombinase-based approaches have an absolute requirement for pre-integration of their recognition sites, so such methods require engineering of the "hot spot" integration site into the cellular DNA as a preliminary step. With nuclease-directed integration it is possible to engineer nucleases or direct via guide RNA in the case of CRISPR:Cas9 to recognise endogenous loci, i.e., nucleic acid sequences occurring naturally in the cellular DNA. Finally, at a practical level nuclease-directed approaches are more efficient for direct integration of transgenes at the levels required to make large libraries of binders.

The DNA repair mechanism by which the donor DNA is integrated in methods of the invention can be pre-determined or biased to some extent by design of the donor DNA and/or choice of site-specific nuclease.

Homologous recombination is a natural mechanism used by cells to repair double stranded breaks using homologous sequence (e.g., from another allele) as a template for repair. Homologous recombination has been utilised in cellular engineering to introduce insertions (including transgenes), deletions and point mutations into the genome. Homologous recombination is promoted by providing homology arms on the donor DNA. The original approach to engineering higher eukaryotic cells typically used homology arms of 5-10 kb within a donor plasmid to increase efficiency of targeted integration into the site of interest. Despite this, homologous recombination driven purely by long homology arms, is less efficient than Flp and Cre directed recombination particularly in higher eukaryotes with large genomes. Homologous recombination is particularly suitable for eukaryotes such as yeast, which has a genome size of only 12.5×10$^6$ bp, where it is more effective compared with higher eukaryotes with larger genomes e.g., mammalian cells with 3000×10$^6$ bp.

Homologous recombination can also be directed through [52] nicks in genomic DNA and this could also serve as a route for nuclease-directed integration into genomic DNA. Two distinct pathways have been shown to promote homologous recombination at nicked DNA. One is essentially similar to repair at double strand breaks, utilizing Rad51/Brca2, while the other is inhibited by Rad51/Brca2 and preferentially uses single-stranded DNA or nicked double stranded donor DNA [51].

Non homologous end-joining (NHEJ) is an alternative mechanism to repair double stranded breaks in the genome where the ends of DNA are directly re-ligated without the need for a homologous template. Nuclease-directed cleavage of genomic DNA can also enhance transgene integration via non-homology based mechanisms. This approach to DNA repair is less accurate and can lead to insertions or deletions. NHEJ nonetheless provides a simple means of integrating in-frame exons into intron or allows integration of promoter:gene cassettes into the genome. Use of non-homologous methods allows the use of donor vectors which lack homology arms thereby simplifying the construction of donor DNA.

It has been pointed out that short regions of terminal homology are used to re-join DNA ends and it was hypothesized that 4 bp of microhomology might be utilized for directing repairing at double strand breaks, referred to as microhomology-directed end joining [50].

Donor DNA

The donor DNA will usually be circularised DNA, and may be provided as a plasmid or vector. Linear DNA is another possibility. Donor DNA molecules may comprise regions that do not integrate into the cellular DNA, in addition to one or more donor DNA sequences that integrate into the cellular DNA. The DNA is typically double-stranded, although single-stranded DNA may be used in some cases. The donor DNA contains one or more transgenes encoding a binder, for example it may comprise a promoter:gene cassette.

In the simplest format double-stranded, circular plasmid DNA can be used to drive homologous recombination. This requires regions of DNA flanking the transgenes which are homologous to DNA sequence flanking the cleavage site in genomic DNA. Linearised double-stranded plasmid DNA or PCR product or synthetic genes could be used to drive both homologous recombination and NHEJ repair pathways. As an alternative to double-stranded DNA it is possible to use single-stranded DNA to drive homologous recombination [52]. A common approach to generating single-stranded DNA is to include a single-stranded origin of replication from a filamentous bacteriophage into the plasmid.

Single-stranded DNA viruses such as adeno-associated virus (AAV) have been used to drive efficient homologous recombination where the efficiency has been shown to be improved by several orders of magnitude [53, 54]. Systems such as the AAV systems could be used in conjunction with nuclease-directed cleavage for the construction of large libraries of binders. The benefits of both systems could be applied to targeting of libraries of binders. The packaging limit of AAV vectors is 4.7 kb but the use of nuclease digestion of target genomic DNA will reduce this allowing larger transgene constructs to be incorporated.

A molecule of donor DNA may encode a single binder or multiple binders. Optionally, multiple subunits of a binder may be encoded per molecule of donor DNA. In some embodiments, donor DNA encodes a subunit of a multimeric binder.

Promoters and Genetic Elements for Selection

Transcription of the binder from the encoding donor DNA will usually be achieved by placing the sequence encoding the binder under control of a promoter and optionally one or more enhancer elements for transcription. A promoter (and optionally other genetic control elements) may be included in the donor DNA molecule itself. Alternatively, the sequence encoding the binder may lack a promoter on the donor DNA, and instead may be placed in operable linkage with a promoter on the cellular DNA, e.g., an endogenous promoter or a pre-integrated exogenous promoter, as a result of its insertion at the integration site created by the site-specific nuclease.

Donor DNA may further comprise one or more further coding sequences, such as genetic elements enabling selection of cells containing or expressing the donor DNA. As with the sequence encoding the binder, discussed above, such elements may be associated with a promoter on the donor DNA or may be placed under control of a promoter as a result of integration of the donor DNA at a fixed locus. The latter arrangement provides a convenient means of selecting specifically for those cells which have integrated the donor DNA at the desired site, since these cells should express the genetic element for selection. This may be, for example, a gene conferring resistance to a negative selection agent such as blasticidin or puromycin. One or more selection steps may be applied to remove unwanted cells, such as cells that lack the donor DNA or which have not integrated the donor DNA at the correct position. Alternatively these cells may be permitted to remain mixed with clones of the library.

The expression of a membrane anchored binder could itself be used as a form of selectable marker. For example if a library of antibody genes, formatted as IgG or scFv-Fc fusions are introduced, then cells which express the antibody can be selected using secondary reagents which recognise the surface expressed Fc using methods described herein. Upon initial transfection with donor DNA encoding the transgene under the control of an exogenous promoter, transient expression (and cell surface expression) of the binder will occur and it will be necessary to wait for transient expression to abate (to achieve targeted integration of e.g., 1-2 antibody genes/cell).

As an alternative a construct encoding a membrane tethering element (e.g., the Fc domain of the present example fused to the PDGF receptor transmembrane domain) could be pre-integrated before the library of binders is introduced. If this membrane-tethering element lacks a promoter or is encoded within an exon which is out of frame with the preceding exon then surface expression will be compromised. Targeted integration of an incoming donor molecule can then correct this defect (e.g., by targeting a promoter or an "in-frame" exon into the intron which is upstream of the defective tethering element). If the frame "correcting exon" also encodes a binder then a fusion will be produced between the binder and the membrane tethering element resulting in surface expression of both. Thus correctly targeted integration will result in-frame expression of the membrane tethering element alone or as part of a fusion with the incoming binder. Furthermore if the incoming library of binders lack a membrane tethering element and these are incorrectly integrated they will not be selected. Thus expression of the binder itself on the cell surface can be used to select the population of cells with correctly targeted integration.

Number of Clones and Library Diversity

Yeast display libraries of $10^7$-$10^{10}$ have previously been constructed and demonstrated to yield binders in the absence of immunisation or pre-selection of the population [9, 55, 56, 57]. Many of the previously published mammalian display libraries used antibody genes derived from immunised donors or even enriched antigen-specific B lymphocytes, given the limitations of library size and variability when using cells from higher eukaryotes. Thanks to the efficiency of gene targeting described in the present invention large, naïve libraries can be constructed in higher eukaryotes such as mammalian cells, which match those described for simpler eukaryotes such as yeast.

Following integration of donor DNA into the cellular DNA, the resulting recombinant cells are cultured to allow their replication, generating a clone of cells from each initially-produced recombinant cell. Each clone is thus derived from one original cell into which donor DNA was integrated at an integration site created by the site-specific nuclease. Methods according to the present invention are associated with a high efficiency and high fidelity of donor DNA integration, and a library according to the present invention may contain at least 100, $10^3$, $10^4$, $10^5$, $10^6$, $10^7$, $10^8$, $10^9$ or $10^{10}$ clones.

Using nuclease-directed integration it is possible to target 10% or more of transfected mammalian cells. It is also practical to grow and transform $>10^{10}$ cells (e.g. from 5 litres of cells growing at $2\times10^6$ cells/ml). Transfection of such large numbers of cells could be done using standard methods including polyethyleneimine-mediated transfection as described herein. In addition methods are available for highly efficient electroporation of $10^{10}$ cells in 5 minutes e.g. http://www.maxcyte.com. Thus using the approach of the present invention it is possible to create libraries in excess of $10^9$ clones.

When the population of donor DNA molecules that is used to create the library contains multiple copies of the same sequence, two or more clones may be obtained that contain DNA encoding the same binder. It can also be the case that a clone may contain donor DNA encoding more than one different binder, for example if there is more than one recognition sequence for the site-specific nuclease, as detailed elsewhere herein. Thus, the diversity of the library, in terms of the number of different binders encoded or expressed, may be different from the number of clones obtained.

Clones in the library preferably contain donor DNA encoding one or two members of the repertoire of binders and/or preferably express only one or two members of the repertoire of binders. A limited number of different binders per cell is an advantage when it comes to identifying the clone and/or DNA encoding a particular binder identified when screening the library against a given target. This is simplest when clones encode a single member of the repertoire of binders. However it is also straightforward to identify the relevant encoding DNA for a desired binder if a clone selected from a library encodes a small number of different binders, for example a clone may encode two members of the repertoire of binders. As discussed elsewhere herein, clones encoding one or two binders are particularly convenient to generate by selecting a recognition sequence for the site-specific nuclease that occurs once per chromosomal copy in a diploid genome, as diploid cells contain duplicate fixed loci, one on each chromosomal copy, and the donor DNA may integrate at one or both fixed loci. Thus, clones of the library may each express only one or two members of the repertoire of binders.

Binders displayed on the surface of cells of the library may be identical to (having the same amino acid sequence as) other binders displayed on the same cell. The library may consist of clones of cells which each display a single member of the repertoire of binders, or of clones displaying a plurality of members of the repertoire of binders per cell. Alternatively a library may comprise some clones that display a single member of the repertoire of binders, and some clones that display a plurality of members (e.g., two) of the repertoire of binders.

Accordingly, a library according to the present invention may comprise clones encoding more than one member of the repertoire of binders, wherein the donor DNA is integrated at duplicate fixed loci or multiple independent fixed loci.

As noted above, it is easiest to identify the corresponding encoding DNA for a binder if the corresponding clone expresses only one binder. Typically, a molecule of donor DNA will encode a single binder. The binder may be multimeric so that a molecule of donor DNA includes multiple genes or open reading frames corresponding to the various subunits of the multimeric binder.

A library according to the present invention may encode at least 100, $10^3$, $10^4$, $10^5$ or $10^6$, $10^7$, $10^8$, $10^9$ or $10^{10}$ different binders. Where the binders are multimeric, diversity may be provided by one or more subunits of the binder. Multimeric binders may combine one or more variable subunits with one or more constant subunits, where the constant subunits are the same (or of more limited diversity) across all clones of the library. In generating libraries of multimeric binders, combinatorial diversity is possible where a first repertoire of binder subunits may pair with any of a second repertoire of binder subunits.

Binders

A "binder" in accordance with the present invention is a binding molecule, representing a specific binding partner for another molecule. Typical examples of specific binding partners are antibody-antigen and receptor-ligand.

The repertoire of binders encoded by a library will usually share a common structure and have one or more regions of diversity. The library therefore enables selection of a member of a desired structural class of molecules, such as a peptide or a scFv antibody molecule. For example, the binders may be polypeptides sharing a common structure and having one or more regions of amino acid sequence diversity.

This can be illustrated by considering a repertoire of antibody molecules. These may be antibody molecules of a common structural class, e.g., IgG, Fab, scFv-Fc or scFv, differing in one or more regions of their sequence. Antibody molecules typically have sequence variability in their complementarity determining regions (CDRs), which are the regions primarily involved in antigen recognition. A repertoire of binders in the present invention may be a repertoire of antibody molecules which differ in one or more CDRs, for example there may be sequence diversity in all six CDRs, or in one or more particular CDRs such as the heavy chain CDR3 and/or light chain CDR3.

Antibody molecules and other binders are described in more detail elsewhere herein. The potential of the present invention however extends beyond antibody display to include display of libraries of peptides or engineered proteins, including receptors, ligands, individual protein domains and alternative protein scaffolds [58, 59]. Nuclease-directed site-specific integration can be used to make libraries of other types of binders previously engineered using other display systems. Many of these involve monomeric binding domains such as DARPins and lipocalins, affibodies and adhirons [58, 59, 152]. Display on eukaryotes, particularly mammalian cells, also opens up the possibility of isolating and engineering binders or targets involving more complex, multimeric targets. For example T cell receptors (TCRs) are expressed on T cells and have evolved to recognise peptide presented in complex with MHC molecules on antigen presenting cells. Libraries encoding and expressing a repertoire of TCRs may be generated, and may be screened to identify binding to MHC peptide complexes as further described elsewhere herein.

For multimeric binders, donor DNA encoding the binder may be provided as one or more DNA molecules. For example, where individual antibody VH and VL domains are to be separately expressed, these may be encoded on separate molecules of donor DNA. The donor DNA integrates into the cellular DNA at multiple integration sites, e.g., the binder gene for the VH at one locus and the binder gene for the VL at a second locus. Methods of introducing donor DNA encoding separate binder subunits are described in more detail elsewhere herein. Alternatively, both subunits or parts of a multimeric binder may be encoded on the same molecule of donor DNA which integrates at a fixed locus.

A binder may be an antibody molecule or a non-antibody protein that comprises an antigen-binding site. An antigen binding site may be provided by means of arrangement of peptide loops on non-antibody protein scaffolds such as fibronectin or cytochrome B etc., or by randomising or mutating amino acid residues of a loop within a protein scaffold to confer binding to a desired target [60, 61, 62]. Protein scaffolds for antibody mimics are disclosed in WO/0034784 in which the inventors describe proteins (antibody mimics) that include a fibronectin type III domain having at least one randomised loop. A suitable scaffold into which to graft one or more peptide loops, e.g., a set of antibody VH CDR loops, may be provided by any domain member of the immunoglobulin gene superfamily. The scaffold may be a human or non-human protein.

Use of antigen binding sites in non-antibody protein scaffolds has been reviewed previously [63]. Typical are proteins having a stable backbone and one or more variable loops, in which the amino acid sequence of the loop or loops is specifically or randomly mutated to create an antigen-binding site having for binding the target antigen. Such proteins include the IgG-binding domains of protein A from *S. aureus*, transferrin, tetranectin, fibronectin (e.g. 10th fibronectin type III domain) and lipocalins. Other approaches include small constrained peptide e.g., based on "knottin" and cyclotides scaffolds [64]. Given their small size and complexity particularly in relation to correct formation of disulphide bond, there may be advantages to the use of eukaryotic cells for the selection of novel binders based on these scaffolds. Given the common functions of these peptides in nature, libraries of binders based on these scaffolds may be advantageous in generating small high affinity binders with particular application in blocking ion channels and proteases.

In addition to antibody sequences and/or an antigen-binding site, a binder may comprise other amino acids, e.g., forming a peptide or polypeptide, such as a folded domain, or to impart to the molecule another functional characteristic in addition to ability to bind antigen. A binder may carry a detectable label, or may be conjugated to a toxin or a targeting moiety or enzyme (e.g., via a peptidyl bond or linker). For example, a binder may comprise a catalytic site (e.g., in an enzyme domain) as well as an antigen binding site, wherein the antigen binding site binds to the antigen and thus targets the catalytic site to the antigen. The catalytic site may inhibit biological function of the antigen, e.g., by cleavage.

Antibody Molecules

Antibody molecules are preferred binders. Antibody molecules may be whole antibodies or immunoglobulins (Ig), which have four polypeptide chains—two identical heavy chains and two identical light chains. The heavy and light chains form pairs, each having a VH-VL domain pair that contains an antigen binding site. The heavy and light chains also comprise constant regions: light chain CL, and heavy chain CH1, CH2, CH3 and sometimes CH4 (the fifth domain CH4 is present in human IgM and IgE). The two heavy chains are joined by disulphide bridges at a flexible hinge region. An antibody molecule may comprise a VH and/or a VL domain.

The most common native format of an antibody molecule is an IgG which is a heterotetramer consisting of two identical heavy chains and two identical light chains. The heavy and light chains are made up of modular domains with a conserved secondary structure consisting of a four-stranded antiparallel beta-sheet and a three-stranded antiparallel beta-sheet, stabilised by a single disulphide bond. Antibody heavy chains each have an N terminal variable domain (VH) and 3 relatively conserved "constant" immunoglobulin domains (CH1, CH2, CH3) while the light chains have one N terminal variable domain (VL) and one constant domains (CL). Disulphide bonds stabilise individual domains and form covalent linkages to join the four chains in a stable complex. The VL and CL of the light chain associates with VH and CH1 of the heavy chain and these elements can be expressed alone to form a Fab fragment. The CH2 and CH3 domains (also called the "Fc domain") associate with another CH2:CH3 pair to give a tetrameric Y shaped molecule with the variable domains from the heavy and light chains at the tips of the "Y". The CH2 and CH3 domains are responsible for the interactions with effector cells and complement components within the immune system. Recombinant antibodies have previously been expressed in IgG format or as Fabs (consisting of a dimer of VH:CH1 and a light chain). In addition the artificial construct called a single chain Fv (scFv) could be used consisting of DNA encoding VH and VL fragments fused genetically with DNA encoding a flexible linker.

Binders may be human antibody molecules. Thus, where constant domains are present these are preferably human constant domains.

Binders may be antibody fragments or smaller antibody molecule formats, such as single chain antibody molecules. For example, the antibody molecules may be scFv molecules, consisting of a VH domain and a VL domain joined by a linker peptide. In the scFv molecule, the VH and VL domains form a VH-VL pair in which the complementarity determining regions of the VH and VL come together to form an antigen binding site.

Other antibody fragments that comprise an antibody antigen-binding site include, but are not limited to, (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [65, 66, 67], which consists of a VH or a VL domain; (v) isolated CDR regions; (vi) F(ab')2 fragments, a bivalent fragment comprising two linked Fab fragments (vii) scFv, wherein a VH domain and a VL domain are linked by a peptide linker which allows the two domains to associate to form an antigen binding site [68, 69]; (viii) bispecific single chain Fv dimers (PCT/US92/09965) and (ix) "diabodies", multivalent or multispecific fragments constructed by gene fusion (WO94/13804; [70]). Fv, scFv or diabody molecules may be stabilised by the incorporation of disulphide bridges linking the VH and VL domains [71].

Various other antibody molecules including one or more antibody antigen-binding sites have been engineered, including for example $Fab_2$, $Fab_3$, diabodies, triabodies, tetrabodies and minibodies (small immune proteins). Antibody molecules and methods for their construction and use have been described [72].

Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

A dAb (domain antibody) is a small monomeric antigen-binding fragment of an antibody, namely the variable region of an antibody heavy or light chain. VH dAbs occur naturally in camelids (e.g., camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "Nanobodies™".

Synthetic antibody molecules may be created by expression from genes generated by means of oligonucleotides synthesized and assembled within suitable expression vectors, for example as described by Knappik et al. [73] or Krebs et al. [74].

Bispecific or bifunctional antibodies form a second generation of monoclonal antibodies in which two different variable regions are combined in the same molecule [75]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways [76], e.g., prepared chemically or from hybrid hybridomas, or may be any of the bispecific antibody fragments mentioned above. These antibodies can be obtained by chemical methods [77, 78] or somatic methods [79, 80] but likewise and preferentially by genetic engineering techniques which allow the heterodimerisation to be forced and thus facilitate the process of purification of the antibody sought [81]. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful. Diabodies (and many other polypeptides, such as antibody fragments) of appropriate binding specificities can be readily selected. If one arm of the diabody is to be kept constant, for instance, with a specificity directed against an antigen of interest, then a library can be made where the other arm is varied and an antibody of appropriate specificity selected. Bispecific whole antibodies may be made by alternative engineering methods as described in Ridgeway et al., 1996 [82].

A library according to the invention may be used to select an antibody molecule that binds one or more antigens of interest. Selection from libraries is described in detail below. Following selection, the antibody molecule may then be engineered into a different format and/or to contain additional features. For example, the selected antibody molecule may be converted to a different format, such as one of the antibody formats described above. The selected antibody molecules, and antibody molecules comprising the VH and/or VL CDRs of the selected antibody molecules, are an aspect of the present invention. Antibody molecules and their encoding nucleic acid may be provided in isolated form.

Antibody fragments can be obtained starting from an antibody molecule by methods such as digestion by enzymes e.g. pepsin or papain and/or by cleavage of the disulphide bridges by chemical reduction. In another manner, the antibody fragments can be obtained by techniques of genetic recombination well known to the person skilled in the art or else by peptide synthesis by means of, for example, automatic peptide synthesisers, or by nucleic acid synthesis and expression.

It is possible to take monoclonal and other antibodies and use techniques of recombinant DNA technology to produce other antibodies or chimaeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature.

Antibody molecules may be selected from a library and then modified, for example the in vivo half-life of an antibody molecule can be increased by chemical modification, for example PEGylation, or by incorporation in a liposome.

Sources of Binder Genes

The traditional route for generation of monoclonal antibodies utilises the immune system of laboratory animals like mice and rabbits to generate a pool of high affinity antibodies which are then isolated by the use of hybridoma technology. The present invention provides an alternative route to identifying antibodies arising from immunisation. VH and VL genes could be amplified from the B cells of immunised animals and cloned into an appropriate vector for introduction into eukaryotic libraries followed by selection from these libraries. Phage display and ribosome display allows very large libraries ($>10^9$ clones) to be constructed enabling isolation of human antibodies without immunisation. The present invention could also be used in conjunction with such methods. Following rounds of phage display selection, the selected population of binders could be introduced into eukaryotic cells by nuclease-directed integration as described herein. This would allow the initial use of very large libraries based in other systems (e.g., phage display) to enrich a population of binders while allowing their efficient screening using eukaryotic cells as described above. Thus the invention can combine the best features of both phage display and eukaryotic display to give a high throughput system with quantitative screening and sorting.

Using phage display and yeast display it has previously been demonstrated that it is also possible to generate binders without resorting to immunisation, provided display libraries of sufficient size are used. For example multiple binders were generated from a non-immune antibody library of >$10^7$ clones [83]. This in turn allows generation of binders to targets which are difficult by traditional immunisation routes e.g., generation of antibodies to "self-antigens" or epitopes which are conserved between species. For example, human/mouse cross-reactive binders can be enriched by sequential selection on human and then mouse versions of the same target. Since it is not possible to specifically immunise humans to most targets of interest, this facility is particularly important in allowing the generation of human antibodies which are preferred for therapeutic approaches.

In examples of mammalian display to date, where library sizes and quality were limited, binders have only been generated using repertoires which were pre-enriched for binders, e.g., from immunisation or from engineering of pre-existing binders. The ability to make large libraries in eukaryotic cells and particularly higher eukaryotes creates the possibility of isolating binders direct from these libraries starting with non-immune binders or binders which have not previously been selected within another system. With the present invention it is possible to generate binders from non-immune sources. This in turn opens up the possibilities for using binder genes from multiple sources. Binder genes could come from PCR of natural sources such as antibody genes. Binder genes could also be re-cloned from existing libraries, such as antibody phage display libraries, and cloned into a suitable donor vector for nuclease-directed integration into target cells. Binders may be completely or partially synthetic in origin. Furthermore various types of binders are described elsewhere herein, for example binder genes could encode antibodies or could encode alternative scaffolds [58, 59], peptides or engineered proteins or protein domains.

Binder Display

To provide a repertoire of binders for screening against a target of interest, the library may be cultured to express the binders in either soluble secreted form or in transmembrane form. For cell surface display it is necessary to retain the expressed binder on the surface of the cell which encodes it. Binders may comprise or be linked to a membrane anchor, such as a transmembrane domain, for extracellular display of the binder at the cell surface. This may involve direct fusion of the binder to a membrane localisation signal such as a GPI recognition sequence or to a transmembrane domain such as the transmembrane domain of the PDGF receptor [84]. Retention of binders at the cell surface can also be done indirectly by association with another cell surface retained molecule expressed within the same cell. This associated molecule could itself be part of a heterodimeric binder, such as tethered antibody heavy chain in association with a light chain partner that is not directly tethered.

Although cell surface immobilisation facilitates selection of the binder, in many applications it is necessary to prepare cell-free, secreted binder. It will be possible to combine membrane tethering and soluble secretion using a recapture method of attaching the secreted binders to cell surface receptors. One approach is to format the library of binders as secreted molecules which can associate with a membrane anchored molecule expressed within the same cell which can function to capture a secreted binder. For example, in the case of antibodies or binder molecules fused to antibody Fc domains, a membrane tethered Fc can "sample" secreted binder molecules being expressed in the same cell resulting in display of a monomeric fraction of the binder molecules being expressed while the remainder is secreted in a bivalent form (U.S. Pat. No. 8,551,715). An alternative is to use a tethered IgG binding domain such as protein A.

Other methods for retaining secreted antibodies with the cells producing them are reviewed in Kumar at al. (2012) [85] and include encapsulation of cells within microdrops, matrix aided capture, affinity capture surface display (ACSD), secretion and capture technology (SECANT) and "cold capture" [85]. In examples given for ACSD and SECANT [85], biotinylation is used to facilitate immobilisation of streptavidin or a capture antibody on the cell surface. The captured molecule in turn captures secreted antibodies. In the example of SECANT in vivo biotinylated of the secreted molecule occurs. Using the "cold capture" technique secreted antibody can be detected on producer cells using antibodies directed to the secreted molecule. It has been proposed that this due to association of the secreted antibody with the glycocalyx of the cell [86]. Alternatively it has been suggested that the secreted product is trapped by staining antibodies on the cell surface before being endocytosed [87]. The above methods have been used to identify high expressing clones within a population but could potentially be adapted for identification of binding specificity, provided the association has sufficient longevity at the cell surface.

Even when the binder is directly tethered to the cell surface it is possible to generate a soluble product. For example the gene encoding the selected binder can be recovered and cloned into an expression vector lacking the membrane anchored sequence. Alternatively, and as demonstrated in the Examples, an expression construction can be used in which the transmembrane domain is encoded within an exon flanked by recombination sites, e.g., ROX recognition sites for Dre recombinase [88]. In this example the exon encoding the transmembrane domain can be removed by transfection with a gene encoding Dre recombinase to switch expression to a secreted form. As demonstrated herein, secreted antibody was produced by this method without the need for recombinase action. This is presumably as a result of alternative splicing [8 9].

Any of the above methods or other suitable approaches can be used to ensure that binders expressed by clones of a library are displayed on the surface of their expressing cells.

Screening to Identify Binders to a Target of Interest

As noted, the eukaryotic cell library may be used in a method of screening for a binder that recognises a target. Such a method may comprise:

providing a library as described herein, culturing cells of the library to express the binders, exposing the binders to the target, allowing recognition of the target by one or more cognate binders, if present, and detecting whether the target is recognised by a cognate binder.

Selections could be carried using a range of target molecule classes, e.g., protein, nucleic acid, carbohydrate, lipid, small molecules. The target may be provided in soluble form. The target may be labelled to facilitate detection, e.g., it may carry a fluorescent label or it may be biotinylated. Cells expressing a target-specific binder may be isolated using a directly or indirectly labelled target molecule, where the binder captures the labelled molecule. For example, cells that are bound, via the binder:target interaction, to a fluorescently labelled target can be detected and sorted by flow cytometry or FACS to isolate the desired cells. Selections involving cytometry require target molecules which are directly fluorescently labelled or are labelled with molecules which can be detected with secondary reagents, e.g., biotinylated target can be added to cells and binding to the cell surface can be detected with fluorescently labelled streptavidin such as streptavidin-phycoerythrin. A further possibility is to immobilise the target molecule or secondary reagents which bind to the target on a solid surface, such as magnetic beads or agarose beads, to allow enrichment of cells which bind the target. For example cells that bind, via the binder: target interaction, to a biotinylated target can be isolated on a substrate coated with streptavidin, e.g., streptavidin-coated beads.

In screening libraries it is preferable to over-sample, i.e., screen more clones than the number of independent clones present within the library to ensure effective representation of the library. Identifying binders from very large libraries provided by the present invention could be done by flow sorting but this would take several days, particularly if over-sampling the library. As an alternative initial selections could be based on the use of recoverable antigen, e.g., biotinylated antigen recovered on streptavidin-coated magnetic beads. Thus streptavidin-coated magnetic beads could be used to capture cells which have bound to biotinylated antigen. Selection with magnetic beads could be used as the only selection method or this could be done in conjunction with flow cytometry where better resolution can be achieved, e.g., differentiating between a clone with higher expression levels and one with a higher affinity [56, 57].

The in vitro nature of display technology approaches makes it is possible to control selection in a way that is not possible by immunisation, e.g., selecting on a particular conformational state of a target [90, 91]. Targets could be tagged through chemical modification (fluorescein, biotin) or by genetic fusion (e.g. protein fused to an epitope tag such as a FLAG tag or another protein domain or a whole protein). The tag could be nucleic acid (e.g., DNA, RNA or non-biological nucleic acids) where the tag is part fused to target nucleic acid or could be chemically attached to another type of molecule such as a protein. This could be through chemical conjugation or through enzymatic attachment [92]. Nucleic acid could be also fused to a target through a translational process such as ribosome display. The "tag" may be another modification occurring within the cell (e.g., glycosylation, phosphorylation, ubiqitinylation, alkylation, PASylation, SUMO-lation and others described at the Post-translational Database (db-PTM) at http://dbptm.mbc.nctu.edu.tw/statistics.php) which can be detected via secondary reagents. This would yield binders which bind an unknown target protein on the basis of a particular modification.

Targets could be detected using existing binders which bind to that target molecule, e.g., target specific antibodies. Use of existing binders for detection will have the added advantage of identifying binders within the library of binders which recognise an epitope distinct from the binder used for detection. In this way pairs of binders could be identified for use in applications such as sandwich ELISA. Where possible a purified target molecule would be preferred. Alternatively the target may be displayed on the surface of a population of target cells and the binders are displayed on the surface of the library cells, the method comprising exposing the binders to the target by bringing the library cells into contact with the target cells. Recovery of the cells expressing the target (e.g., using biotinylated cells expressing target) will allow enrichment of cells which express binders to them. This approach would be useful where low affinity interactions are involved since there is the potential for a strong avidity effect.

The target molecule could also be unpurified recombinant or unpurified native targets provided a detection molecule is available to identify cell binding (as described above). In addition binding of target molecules to the cell expressing the binder could be detected indirectly through the association of target molecule to another molecule which is being detected, e.g., a cell lysate containing a tagged molecule could be incubated with a library of binders to identify binders not only to the tagged molecule but also binders to its associated partner proteins. This would result in a panel of antibodies to these partners which could be used to detect or identify the partner (e.g., using mass spectrometry). Cellular fractionation could be used to enrich targets from particular sub-cellular locations. Alternatively differential biotinylation of surface or cytoplasmic fractions could be used in conjunction with streptavidin detection reagents for eukaryotic display [93,94]. The use of detergent solubilised target preparations is a particularly useful approach for intact membrane proteins such as GPCRs and ion channels which are otherwise difficult to prepare. The presence of detergents may have a detrimental effect on the eukaryotic cells displaying the binders requiring recovery of binder genes without additional growth of the selected cells.

Following detection of target recognition by a cognate binder, cells of a clone containing DNA encoding the cognate binder may be recovered. DNA encoding the binder may then be isolated (e.g., identified or amplified) from the recovered clone, thereby obtaining DNA encoding a binder that recognises the target.

Exemplary binders and targets are detailed elsewhere herein. A classic example is a library of antibody molecules, which may be screened for binding to a target antigen of interest. Other examples include screening a library of TCRs against a target MHC:peptide complex or screening a library of MHC:peptide complexes against a target TCR.

TCR: MHC and Other Receptor Interactions

T cell receptors (TCRs) are expressed on T cells and have evolved to recognise peptide presented in complex with MHC molecules on antigen presenting cells. TCRs are heterodimers consisting in 95% of cases of alpha and beta heterodimers and in 5% of cases of gamma and delta heterodimers. Both monomer units have an N terminal immunoglobulin domain which has 3 variable complementarity determining regions (CDRs) involved in driving interaction with target. The functional TCR is present within a complex of other sub-units and signalling is enhanced by co-stimulation with CD4 and CD8 molecules (specific for class I and class II MHC molecules respectively). On antigen presenting cells, proteins are processed, and presented on the cell surface in complex with MHC molecules which are themselves part of a multimeric protein complex. TCRs recognizing peptides originating from "self" are removed during development and the system is poised for recognition of foreign peptides presented on antigen presenting cells to effect an immune response. The outcome of recognition of a peptide:MHC complex depends on the identity of the T cell and the affinity of that interaction.

It would be valuable to identify the genes encoding TCRs or MHC:peptide complexes which drive interactions involved in pathological conditions, e.g., as occurs in autoimmune disease. In the case of autoimmune disease, identification of interacting partners, e.g., a TCR driving a pathogenic condition could pave the way to either specifically blocking such interactions or removing offending cytotoxic cells. It would be desirable to engineer TCRs for altered binding e.g. higher affinity to targets of interest, e.g., in re-targeting T cells in cancer or enhancing the effect of existing T cells [95]. Alternatively the behaviour of regulatory or suppressive T cells might be altered as a therapeutic modality, e.g., for directing or enhancing immunotherapy of cancer by introducing specific TCRs into T cells or by using expressed TCR protein as therapeutic entities [96].

Display of libraries of TCRs on surface of yeast cells and mammalian cells has previously been demonstrated. In the case of yeast cells it was necessary to engineer the TCR and present it in a single chain format. Since the affinity of interaction between TCR and peptide:MHC complex is low, the soluble component (e.g., peptide:MHC in this case) is usually presented in a multimeric format. TCR specificity has been engineered for peptides in complex with MHC class I [97] and MHC class II [98]. TCRs have also been expressed on the surface of a mutant mouse T cells (lacking TCR alpha and beta chains) and variant TCRs with improved binding properties have been isolated [99]. For example Chervin et al. introduced TCRs by retroviral infection and an effective library size of $10^4$ clones was generated [100]. Using nuclease-directed integration of binders as proposed here, a similar approach could be taken to engineering T cells. As well as selecting TCRs with altered recognition properties, display libraries could be used to screen libraries of peptide or of MHC variants for recognition by TCRs. For example peptide:MHC complexes have been displayed on insect cells and used to epitope map TCRs presented in a multimeric format [101].

As noted, screening methods may involve displaying the repertoire of binders on the cell surface and probing with a target presented as a soluble molecule, which may be a multimeric target. An alternative, which can be especially useful with multimeric targets, is to screen directly for cell:cell interactions, where binder and target are presented on the surface of different cells. For example if activation of a TCR of interest led to expression of a reporter gene this could be used to identify activating peptides or activating MHC molecules presented within a peptide:MHC library. In this particular example the reporter cell does not encode the library member but could be used to identify the cell which does encode it. The approach could potentially extend to a "library versus library" approach. For example extending the example described above, a TCR library could be screened against a peptide:MHC library. More broadly the example of screening a library of binders presented on one cell surface using a binding partner on another cell could be extended to other types of cell:cell interactions e.g., identification of binders which inhibit or activate signalling within the Notch or Wnt pathways. Thus the present invention could be used in alternative cell based screening system including recognition systems based on cell:cell interactions.

As an example, chimeric antigen receptors ("CARS") represent a fusion between an antibody binding domain (usually formatted as a scFv) and a signalling domain. These have been introduced into T cells with the aim of re-directing the T cell in vivo to attack tumour cells through antibody recognition and binding to tumour-specific antigens. A number of different factors could affect the success of this strategy including the combination of antibody specificity, format, antibody affinity, linker length, fused signalling module, expression level in T cells, T cell sub-type and interaction of the CAR with other signalling molecules [102, 103]. The ability to create large libraries of CARs in primary T cells incorporating individual or combinations of the above variables would allow a functional search for effective and optimal CAR construction. This functional "search" could be carried out in vitro or in vivo. For example Alonso-Camino (2009) have fused a scFv recognizing CEA to the ζ chain of the TCR:CD3 complex and introduced this genetic construct into a human Jurkat cell line [104]. Upon interaction with CEA present on either HeLa cells or tumour cells they showed upregulation of the early T cell activation marker CD69. This approach could be used to identify CAR fusion constructs with appropriate activation or inhibitory properties using cultured or primary cells.

Going one step further functionality of CAR constructs could be assessed in vivo. For example a library of CARs constructed in primary mouse T cells could be introduced into tumour bearing mice to identify T cell clones stimulated to proliferate through encounter with tumour. If necessary this T cell library could be pre-selected based on antigen binding specificity using the methods described above. In either case the incoming library of binders could be used to replace an existing binder molecule (e.g., MHC or TCR or antibody variable domain).

Phenotype Screens

Described here are various methods for selection of binders which modify cell signalling and cellular behaviour.

A library may be screened for altered cellular phenotype as a result of the action of the binder on its target.

Antibodies which modify cell signalling by binding to ligands or receptors have a proven track record in drug development and the demand for such therapeutic antibodies continues to grow. Such antibodies and other classes of functional binders also have potential in controlling cell behaviour in vivo and in vitro. The ability to control and direct cellular behaviour however relies on the availability of natural ligands which control specific signalling pathways. Unfortunately many natural ligands such as those controlling stem cell differentiation (e.g., members of FGF, TGF-beta, Wnt and Notch super-families) often exhibit promiscuous interactions and have limited availability due to their poor expression/stability profiles. With their exquisite specificity, antibodies have great potential in controlling cellular behaviour.

The identification of functional antibodies that modify cell signalling has historically been relatively laborious involving picking clones, expressing antibody, characterising according to sequence and binding properties, conversion to mammalian expression systems and addition to functional cell based assays. The eukaryotic display approach described herein will reduce this effort but there is still a requirement for production of antibody and addition to a separate reporter cell culture. Therefore, a preferred alternative may be to directly screen libraries of binders expressed in eukaryotic cells for the effect of binding on cell signalling or cell behaviour by using the production cell itself as a reporter cell. Following introduction of antibody genes, clones within the resulting population of cells showing alteration in reporter gene expression or altered phenotypes can be identified.

A number of recent publications have described the construction of antibody libraries by cloning repertoires of antibody genes into reporter cells [47, 105, 106]. These systems combine expression and reporting within one cell, and typically introduce a population of antibodies selected against a pre-defined target (e.g., using phage display).

A population of antibody genes may be introduced into reporter cells to produce a library by methods described herein, and clones within the population with an antibody-directed alteration in phenotype (e.g., altered gene expression or survival) can be identified. For this phenotypic-directed selection to work there is a requirement to retain a linkage between the antibody gene present within the expressing cell (genotype) and the consequence of antibody expression (phenotype). This has been achieved previously either through tethering the antibody to the cell surface [47] as described for antibody display or through the use of semi-solid medium to retain secreted antibodies in the vicinity of producing cells [105]. Alternatively antibodies and other binders can be retained inside the cell [107]. Binders retained on the cell surface or in the surrounding medium can interact with an endogenous or exogenous receptor on the cell surface causing activation of the receptor. This in turn can cause a change in expression of a reporter gene or a change in the phenotype of the cell. As an alternative the antibody can block the receptor or ligand to reduce receptor activation. The gene encoding the binder which causes the modified cellular behaviour can then be recovered for production or further engineering.

An alternative to this "target-directed" approach, it is possible to introduce a "naïve" antibody population which has not been pre-selected to a particular target [108]. The cellular reporting system is used to identify members of the population with altered behaviour. Since there is no prior knowledge of the target, this non-targeted approach has a particular requirement for a large antibody repertoire, since pre-enrichment of the antibody population to the target is not possible. This approach will benefit from using nuclease-directed transgene integration as described in the present invention.

The "functional selection" approach could be used on other applications involving libraries in eukaryotic cells, particularly higher eukaryotes such as mammalian cells. The antibody could be fused to a signalling domain such that binding to target causes activation of the receptor. Kawahara et al. have constructed chimeric receptors where an extracellular scFv targeting fluorescein was fused to a spacer domain (the D2 domain of the Epo receptor) and various intracellular cytokine receptor domain including the thrombopoeitin (Tpo) receptor, erythropoietin (Epo) receptor, gp130, IL-2 receptor and the EGF receptor [109, 110, 111]. These were introduced into an IL-3 dependent proB cell line (BaF3) [27], where chimaeric receptors were shown to exhibit antigen-dependent activation of the chimaeric receptor leading to IL-3 independent growth. This same approach was used in model experiments to demonstrate antigen mediated chemoattraction of BaF3 cells [110]. The approach was extended beyond stable culture cells to primary cells exemplified by the survival and growth of Tpo-responsive haematopoeitic stem cells [112] or IL2 dependant primary T cells where normal stimulation by Tpo and IL-2 respectively was replaced by fluorescein directed stimulation of scFv chimaeric receptors. Thus a system based on chimaeric antibody-receptor chimaeras can be used to drive target dependent gene expression or phenotypic changes in primary or stable reporter cells. This capacity could be used to identify fused binders which drive a signalling response or binders which inhibit the response.

In a modification of the above approach separate VH and VL domains from an anti-lysozyme antibody were fused to the Epo intracellular domain [113]. Cells grew in response to addition of lysozyme indicating an antigen induced dimerisation or stabilisation of the separate VH and VL fusion partners. Thus three interacting components come together for an optimal response in this system.

Although described here with reference to antibody molecules, the above methods may also be adapted and performed with libraries of other binders.

Protein fragment complementation represents an alternative system for studying and for selecting protein:protein interactions in mammalian cells [114, 115]. This involves restoring function of split reporter proteins through protein:protein interactions. Reporter proteins which have been used include ubiquitin, DNAE intein, beta-galactosidase, dihydrofolate reductase, GFP, firefly luciferase, beta-lactamase, TEV protease. For example a recent example of this approach is the mammalian membrane 2 hybrid (MaMTH) approach where association of a bait protein:split ubiquitin:transcription factor fusion with a partner protein:split ubiquitin restores ubiquitin recognition and liberates the transcription factor to effect reporter gene expression [116]. Again binders which interfere with or enhance this interaction could be identified through perturbed signalling.

Recovery and Reformatting of Binders and Encoding DNA

Following selection of a binder or clone of interest from the library, a common next step will be to isolate (e.g., identify or amplify) the DNA encoding the binder. Optionally, it may be desired to modify the nucleic acid encoding the binder, for example to restructure the binder and/or to insert the encoding sequence into a different vector.

Where the binder is an antibody molecule, a method may comprise isolating DNA encoding the antibody molecule from cells of a clone, amplifying DNA encoding at least one antibody variable region, preferably both the VH and VL domain, and inserting DNA into a vector to provide a vector encoding the antibody molecule. A multimeric antibody molecule bearing a constant domain may be converted to a single chain antibody molecule for expression in a soluble secreted form.

Antibodies may be presented in different formats but whatever format an antibody is selected in, once the antibody gene is isolated it is possible to reconfigure it in a number of different formats. Once VH or VL domains are isolated, they can be re-cloned into expression vectors encompassing the required partner domains (see Example 1 showing a dual promoter IgG expression cassette).

A reformatting step may comprise reformatting of binders composed of a pair of subunits (e.g., scFv molecules), to a different molecular binder format (e.g., Ig or Fab) in which the original pairing of the subunits is maintained. Such methods are described in more detail elsewhere herein and can be used for monoclonal, oligoclonal or polyclonal clone reformatting. The method can be used to convert "en masse" an entire output population from any of the commonly used display technologies including phage, yeast or ribosome display.

Display of scFvs on the Surface of Mammalian Cells Fused to Fc Domains.

Although many antibody phage display libraries are formatted to display scFvs, eukaryotic display systems will allow presentation in Fab or IgG format. To take full advantage of the potential for IgG/Fab expression, particularly when using scFvs from other display systems will be necessary to take selected linked VH and VL domains within a bacterial expression system and express them within a eukaryotic system fused to appropriate constant domains. Described here is a method to convert scFv populations to immunoglobulin (Ig) or fragment, antigen binding (Fab) format in such a way that original VH and VL chain pairings are maintained. In the present invention, conversion is possible using individual clones, oligoclonal mixes or whole populations formatted as scFv while retaining the original pairing of VH and VLs chains. The method proceeds via the generation of an intermediate non-replicative "mini-circle" DNA which brings in a new "stuffier" DNA fragment. The circular DNA is linearised (e.g., by restriction digestion or PCR) which alters the relative position of the original VH and VL fragments and places the "stuffier" DNA between them. Following linearization the product can be cloned into a vector of choice, e.g., a mammalian expression vector. In this way all of the elements apart from the VH and VL can be replaced. Elements for bacterial expression can be replaced with elements for mammalian expression and fusion to alternative partners. The complete conversion process only requires a single transformation step of *E. coli* bacteria to generate a population of bacterial colonies each harbouring a plasmid encoding a unique Ig or Fab formatted recombinant antibody. Extending beyond conversion of scFv to IgG/Fab, the method can be employed to reformat any two joined DNA elements to clone into a vector such that after re-formatting each DNA element is surrounded by different DNA control features whilst maintaining the original pairing. A previous method has been described wherein 2 sequential cloning steps are used [117] to replace these elements in contrast to the present method which proceeds via an intermediate non-replicative circular intermediate.

A method of restructuring a binder, or population of binders, may comprise converting scFv to Ig or a fragment thereof, e.g., Fab. The method may comprise converting nucleic acid encoding scFv to DNA encoding an immunoglobulin (Ig) or fragment thereof such as Fab format, in such a way that the original variable VH and VL chain pairings are maintained. Preferably the conversion proceeds via circular DNA intermediate which may be a non-replicative "mini-circle" DNA. The method requires a single transformation of *E. coli* for the direct generation of bacterial transformants harbouring plasmids encoding Ig or Fab DNA.

The method may be used for monoclonal, oligoclonal or polyclonal clone reformatting. The method may be used to convert "en masse" an entire output population from any of the commonly used display technologies including phage, yeast or ribosome display.

More generally, this aspect of the invention relates to a method that allows the reformatting of any two joined DNA elements into a vector where the DNA elements are cloned under the control of separate promoters, or separated by alternative control elements, but maintaining the original DNA pairing.

Examples 7 and 14 describe such methods in further detail.

Isolation, and optional restructuring, of DNA encoding binders may be followed by introduction of that DNA into further cells to create a derivative library as described elsewhere herein, or DNA encoding one or more particular binders of interest may be introduced into a host cell for expression. The host cell may be of a different type compared with the cells of the library from which it was obtained. Generally the DNA will be provided in a vector. DNA introduced into the host cell may integrate into cellular DNA of the host cell. Host cells expressing the secreted soluble antibody molecule can then be selected.

Host cells encoding one or more binders may be provided in culture medium and cultured to express the one or more binders.

Derivative Libraries

Following production of a library by the method of the invention, one or more library clones may be selected and used to produce a further, second generation library. When a library has been generated by introducing DNA into eukaryotic cells as described herein, the library may be cultured to express the binders, and one or more clones expressing binders of interest may be recovered, for example by selecting binders against a target as described elsewhere herein. These clones may subsequently be used to generate a derivative library containing DNA encoding a second repertoire of binders.

To generate the derivative library, donor DNA of the one or more recovered clones is mutated to provide the second repertoire of binders. Mutations may be addition, substitution or deletion of one or more nucleotides. Where the binder is a polypeptide, mutation will be to change the sequence of the encoded binder by addition, substitution or deletion of one or more amino acids. Mutation may be focused on one or more regions, such as one or more CDRs of an antibody molecule, providing a repertoire of binders of a common structural class which differ in one or more regions of diversity, as described elsewhere herein.

Generating the derivative library may comprise isolating donor DNA from the one or more recovered clones, introducing mutation into the DNA to provide a derivative population of donor DNA molecules encoding a second repertoire of binders, and introducing the derivative population of donor DNA molecules into cells to create a derivative library of cells containing DNA encoding the second repertoire of binders.

Isolation of the donor DNA may involve obtaining and/or identifying the DNA from the clone. Such methods may encompass amplifying the DNA encoding a binder from a recovered clone, e.g., by PCR and introducing mutations. DNA may be sequenced and mutated DNA synthesised.

Mutation may alternatively be introduced into the donor DNA in the one or more recovered clones by inducing mutation of the DNA within the clones. The derivative library may thus be created from one or more clones without requiring isolation of the DNA, e.g., through endogenous mutation in avian DT40 cells.

Antibody display lends itself especially well to the creation of derivative libraries. Once antibody genes are isolated, it is possible to use a variety of mutagenesis approaches (e.g., error prone PCR, oligonucleotide-directed mutagenesis, chain shuffling) to create display libraries of related clones from which improved variants can be selected. For example, with chain-shuffling the DNA encoding the population of selected VH clone, oligoclonal mix or population can be sub-cloned into a vector encoding a suitable antibody format and encoding a suitably formatted repertoire of VL chains [118]. Alternatively and again using the example of VHs, the VH clone, oligomix or population could be introduced into a population of eukaryotic cells which encode and express a population of appropriately formatted light chain partners (e.g., a VL-CL chain for association with an IgG or Fab formatted heavy chain). The VH population could arise from any of the sources discussed above including B cells of immunised animals or scFv genes from selected phage populations. In the latter example cloning of selected VHs into a repertoire of light chains could combine chain shuffling and re-formatting (e.g., into IgG format) in one step.

A particular advantage of display on eukaryotic cells is the ability to control the stringency of the selection/screening step. By reducing antigen concentration, cells expressing the highest affinity binders can be distinguished from lower affinity clones within the population. The visualisation and quantification of the affinity maturation process using flow cytometry is a major benefit of eukaryotic display as it gives an early indication of percentage positives in naïve library and allows a direct comparison between the affinity of the selected clones and the parental population during sorting. Following sorting, the affinity of individual clones can be determined by pre-incubating with a range of antigen concentrations and analysis in flow cytometry or with a homogenous Time Resolved Fluorescence (TRF) assay or using surface plasmon resonance (SPR) (Biacore).

Characteristics and Form of the Library

The present invention enables construction of eukaryotic cell libraries having many advantageous characteristics. The invention provides libraries having any one or more of the following features:

Diversity. A library may encode and/or express at least 100, $10^3$, $10^4$, $10^5$ $10^6$, $10^7$, $10^8$ or $10^9$ different binders.

Uniform integration. A library may consist of clones containing donor DNA integrated at a fixed locus, or at a limited number of fixed loci in the cellular DNA. Each clone in the library therefore contains donor DNA at the fixed locus or at least one of the fixed loci. Preferably clones contain donor DNA integrated at one or two fixed loci in the cellular DNA. As explained elsewhere herein, the integration site is at a recognition sequence for a site-specific nuclease. Integration of donor DNA to produce recombinant DNA is described in detail elsewhere herein and can generate different results depending on the number of integration sites. Where there is a single potential integration site in cells used to generate the library, the library will be a library of clones containing donor DNA integrated at the single fixed locus. All clones of the library therefore contain the binder genes at the same position in the cellular DNA. Alternatively where there are multiple potential integration sites, the library may be a library of clones containing donor DNA integrated at multiple and/or different fixed loci. Preferably, each clone of a library contains donor DNA integrated at a first and/or a second fixed locus. For example a library may comprise clones in which donor DNA is integrated at a first fixed locus, clones in which donor DNA is integrated at a second fixed locus, and clones in which donor DNA is integrated at both the first and second fixed loci. In preferred embodiments there are only one or two fixed loci in the clones in a library, although it is possible to integrate donor DNA at multiple loci if desired for particular applications. Therefore in some libraries each clone may contain donor DNA integrated at any one or more of several fixed loci, e.g., three, four, five or six fixed loci.

For libraries containing binder subunits integrated at separate sites, clones of the library may contain DNA encoding a first binder subunit integrated at a first fixed locus and DNA encoding a second binder subunit integrated at a second fixed locus, wherein the clones express multimeric binders comprising the first and second subunits.

Uniform transcription. Relative levels of transcription of the binders between different clones of the library is kept within controlled limits due to donor DNA being integrated at a controlled number of loci, and at the same locus in the different clones (fixed locus). Relatively uniform transcription of binder genes leads to comparable levels of expression of binders on or from clones in a library. Binders displayed on the surface of cells of the library may be identical to (having the same amino acid sequence as) other binders displayed on the same cell. The library may consist of clones of cells which each display a single member of the repertoire of binders, or of clones displaying a plurality of members of the repertoire of binders per cell. Alternatively a library may comprise some clones that display a single member of the repertoire of binders, and some clones that display a plurality of members (e.g., two) of the repertoire of binders. Preferably clones of a library express one or two members of the repertoire of binders.

For example, a library of eukaryotic cell clones according to the present invention may express a repertoire of at least $10^3$, $10^4$, $10^5$ $10^6$, $10^7$, $10^8$ or $10^9$ different binders, e.g., IgG, Fab, scFv or scFv-Fc antibody fragments, each cell containing donor DNA integrated at a fixed locus in the cellular DNA. The donor DNA encodes the binder and may further comprise a genetic element for selection of cells into which the donor DNA is integrated at the fixed locus. Cells of the library may contain DNA encoding an exogenous site-specific nuclease.

These and other features of libraries according to the present invention are further described elsewhere herein.

The present invention extends to the library either in pure form, as a population of library clones in the absence of other eukaryotic cells, or mixed with other eukaryotic cells. Other cells may be eukaryotic cells of the same type (e.g., the same cell line) or different cells. Further advantages may be obtained by combining two or more libraries according to the present invention, or combining a library according to the invention with a second library or second population of cells, either to facilitate or broaden screening or for other uses as are described herein or which will be apparent to the skilled person.

A library according to the invention, one or more clones obtained from the library, or host cells into which DNA encoding a binder from the library has been introduced, may be provided in a cell culture medium. The cells may be cultured and then concentrated to form a cell pellet for convenient transport or storage.

Libraries will usually be provided in vitro. The library may be in a container such as a cell culture flask containing cells of the library suspended in a culture medium, or a container comprising a pellet or concentrated suspension of eukaryotic cells comprising the library. The library may constitute at least 75%, 80%, 85% or 90% of the eukaryotic cells in the container.

BRIEF DESCRIPTION OF THE DRAWINGS

Embodiments of the invention will now be described in more detail, with reference to the accompanying drawings, which are as follows:

FIG. 2. Sequence of pD1 (SEQ ID NO: 1, 2, 3, 4 & 5): a dual promoter antibody expression cassette for surface expression.
Features:
pEF promoter 13-1180
BM40 leader 1193-1249
Humanised D1.3 VL 1250-1578
Human C kappa 1577-1891BGH poly A 1916-2130
CMV promoter 2146-2734

Mouse VH leader with intron 32832-3414
Humanised D1.3 VH 3419-3769
Optimised human IgG2 CH1-CH3

Figure 3:
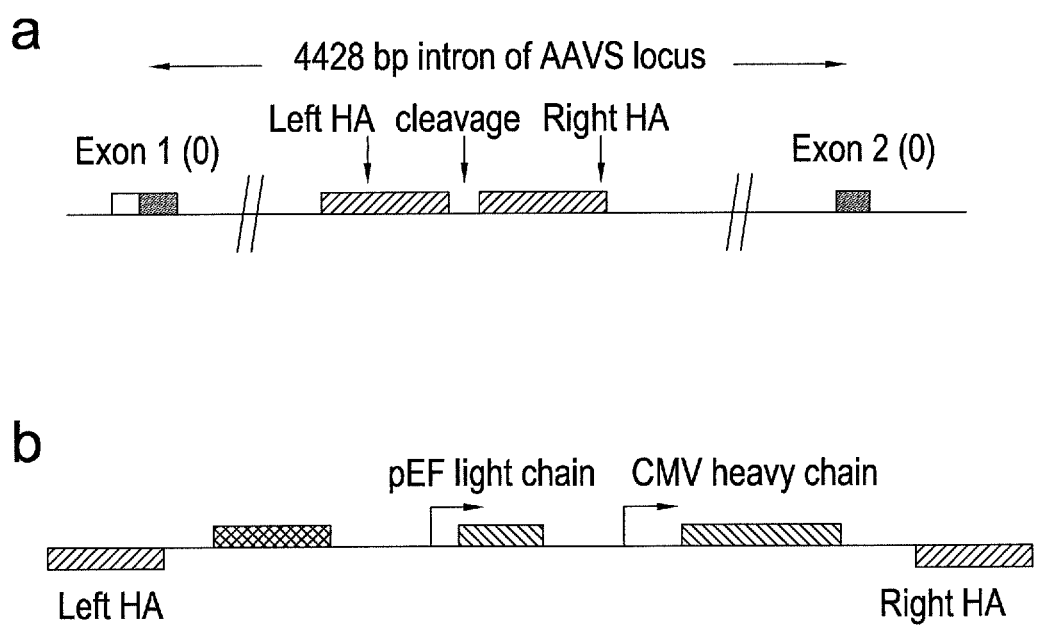

FIG. 3. Construction of AAVS Donor plasmid (pD2)

a. Representation of the human AAVS locus. Exon 1 and Exon 2 of the AAVS locus (encoding protein phosphatase 1, regulatory subunit 12C, PPP1R12C) are separated by an intron of 4428 bp. Splicing is in frame "0" i.e. splicing occurs between 2 intact codons from each exon. TALENs and CRISPR/Cas9 constructs are available to cleave within this intron. Hatched blocks represent the regions to the left and right of this cleavage site that are used within vector constructs to drive homologous recombination into this locus (AAVS homology arm left "Left HA" and AAVS homology arm right ("right HA").

b. Representation of the antibody encoding donor plasmid pD2. Left and right homology arms are shown at the ends of the construct representation. A synthetic Blasticidin gene is preceded by a splice acceptor which creates an "in-frame" fusion with AAVS exon 1. Also shown is the antibody expression cassette consisting of a D1.3 light chain and a D1.3 IgG2 heavy chain driven by pEF and CMV promoters respectively.

c. Sequence of donor construct pD1-huD1.3 (SEQ ID NO: 6, 7 & 8). AAVS homology arms are shown underlined and emboldened. For brevity antibody cassette (previously shown in FIG. 2) is not shown in detail. Restriction sites used in clone are shown emboldened. The sequence of the plasmid backbone is shown up to the ampicillin resistance gene.

Figure 4:
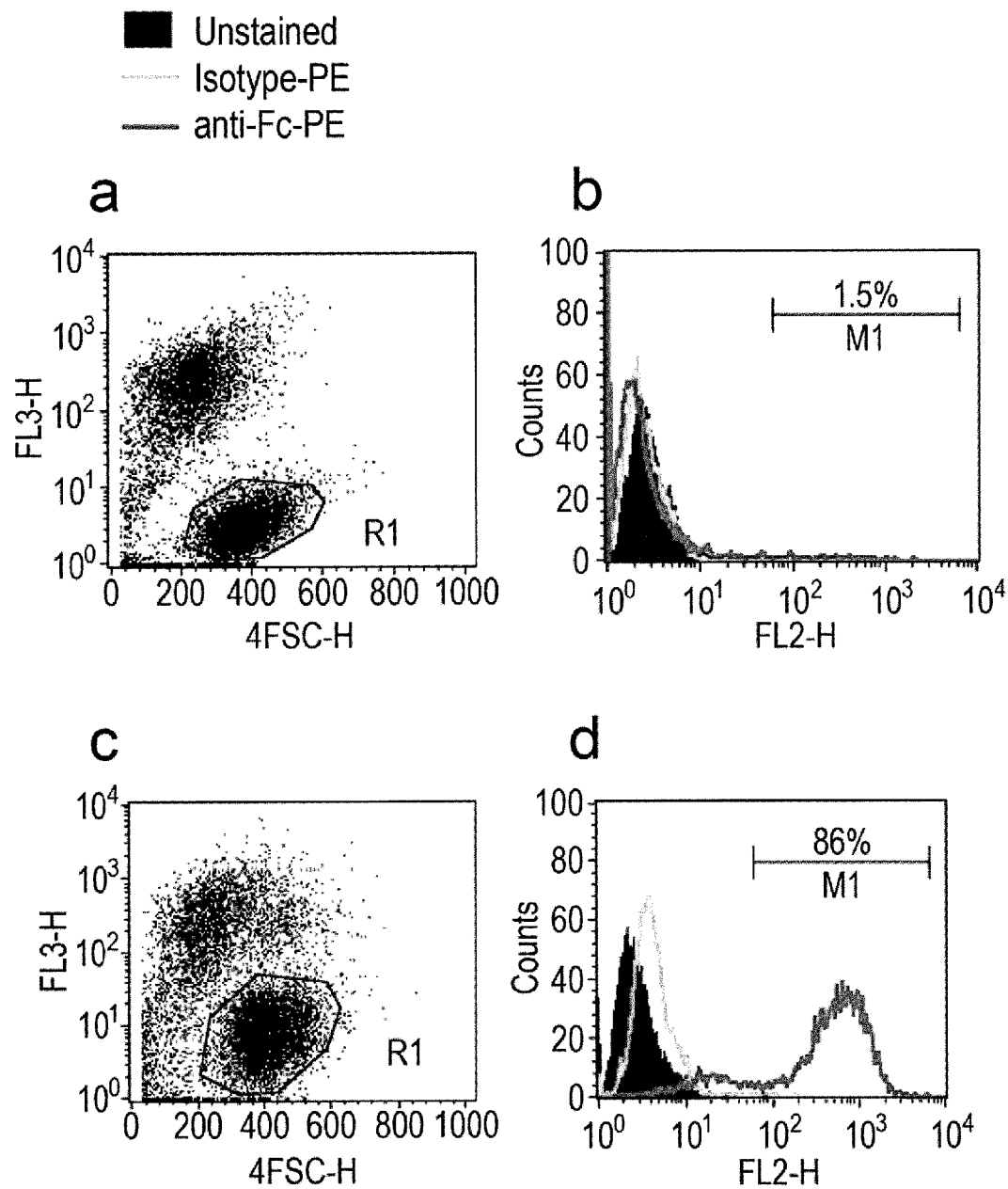

FIG. 4. Expression of IgG on cell surface a, c. Analysis was focused on viable cells using forward scatter and staining in the FL3 channel (a, c). Cells positive for staining in the FL3 channel (representing non-viable cells which took up 7-AAD) were excluded. All cells were transfected with pD2-D1.3 in absence (a, b) or presence (c.d) of the AAVS TALENs and were stained with anti-Fc antibody.

Figure 5:
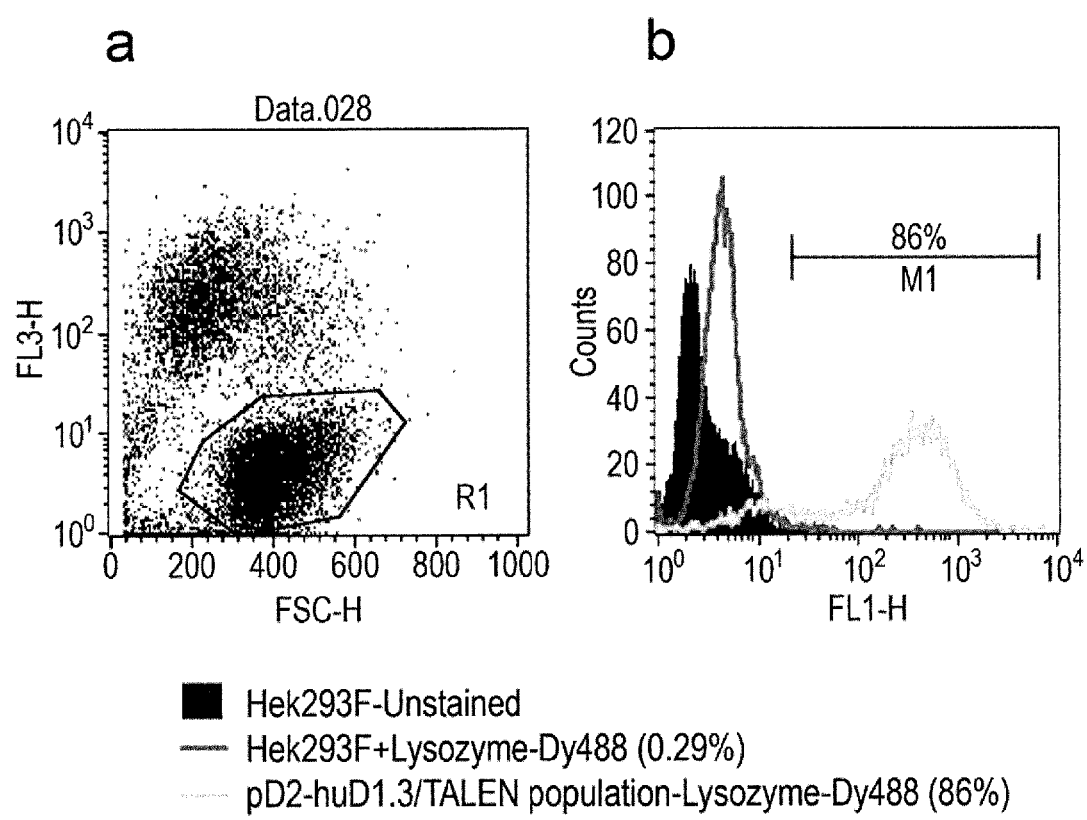

FIG. 5. Antibody binding of antigen on cell surface. Viable cells were selected on the basis of Forward Scatter and occlusion of 7AAD (a). Cells were incubated with fluorescently labelled hen egg lysozyme (b).

Figure 6:
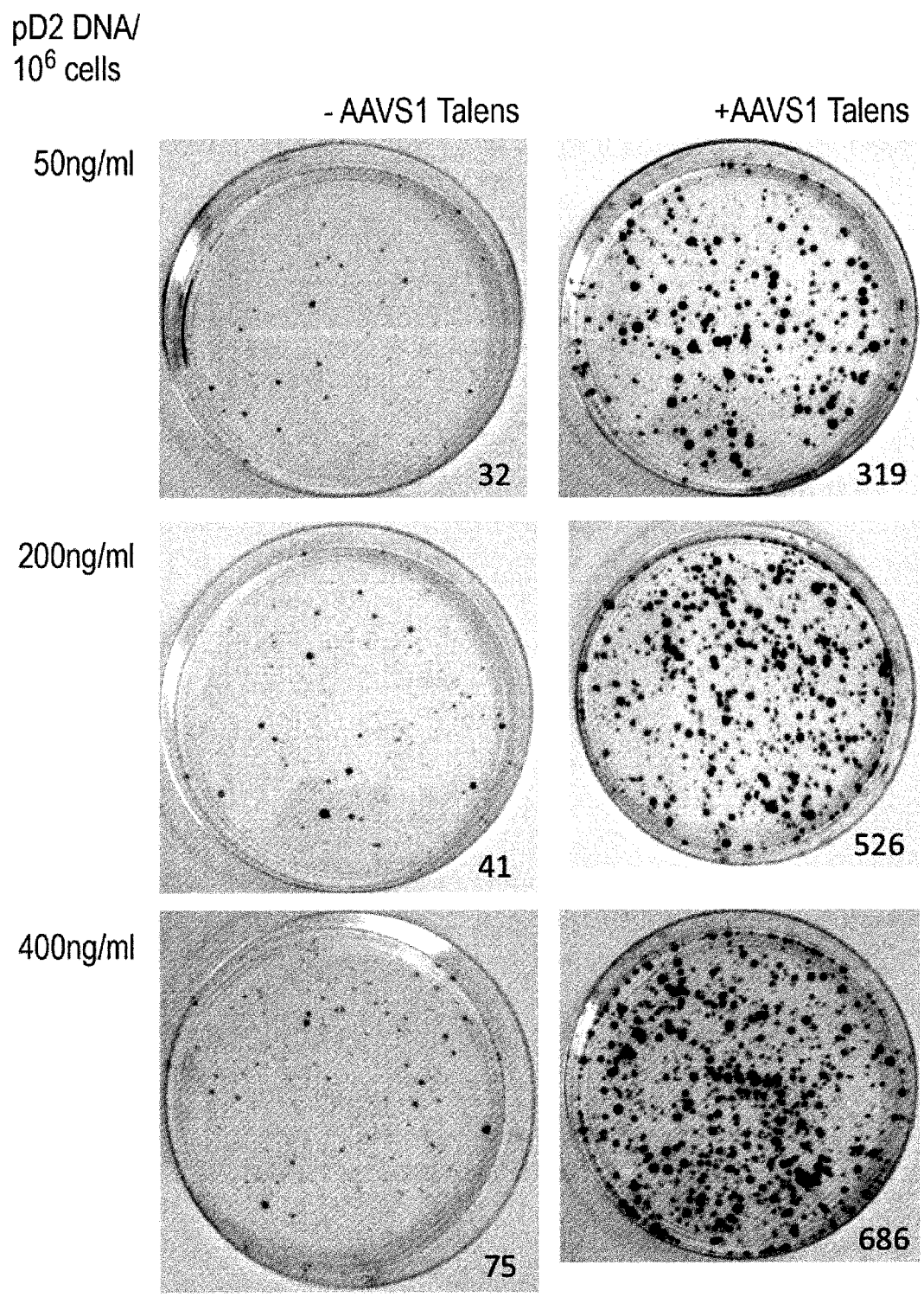

FIG. 6. Effect of TALEN-directed genomic cleavage on integration of blasticidin resistance gene. Figure shows number of colonies under the conditions described.

FIG. 7. Analysis of integration of pD2-D1.3 donor plasmid into AAVS locus.

Following transfection cells were selected in Blasticidin and genomic DNA was prepared. Samples 1-9 benefitted from addition of AAVS-directed TALE nucleases, samples 10-11 were from clones arising from cell transfected in the absence of TALE nuclease. Genomic DNA analysis carried out by PCR as described in text. a. Verification from 5' end of integration site. B. Verification from 3' end of integration site.

Figure 8:
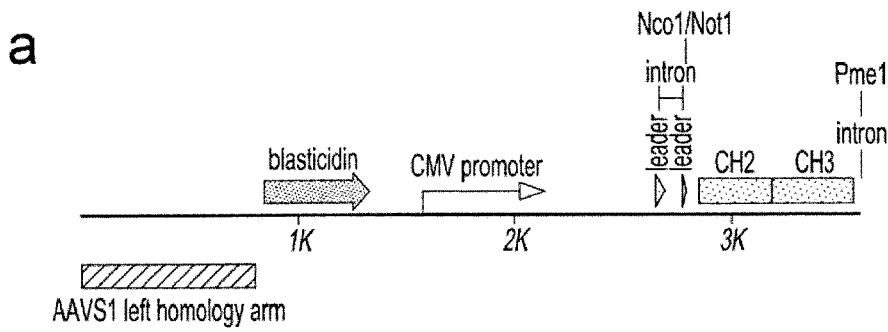

FIG. 8. Construction of the scFv-Fc expression vector pD6 a. Antibodies formatted as scFv are cloned into the Nco1/Not1 sites to create an "in-frame" fusion with the human Fc region of IgG2.

b. Sequence of pD6 from the Nco1 to Pme1 sites (SEQ ID NO: 9, 10 &11).

Figure 9:
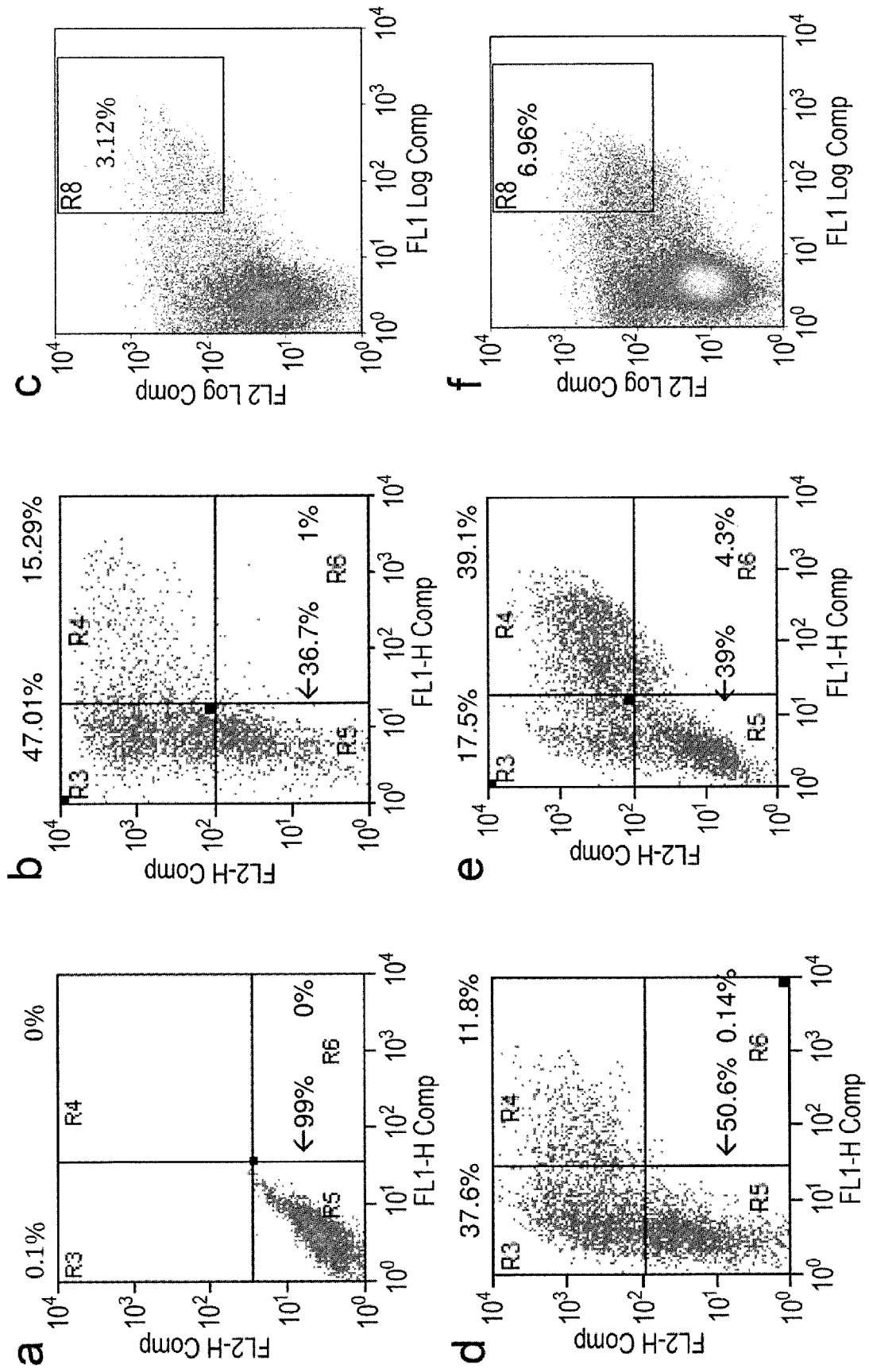
Figure 9:
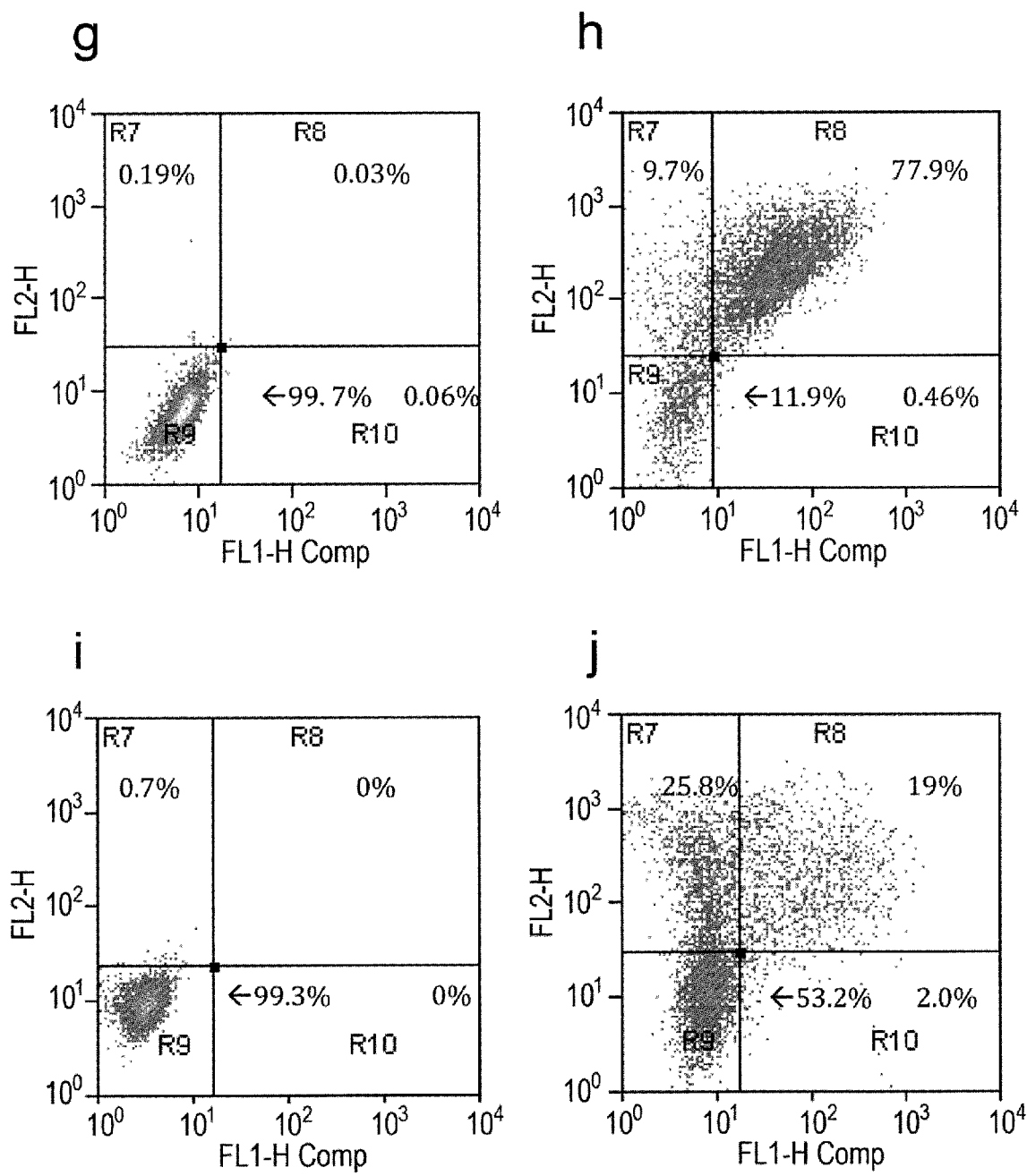

FIG. 9. Selection of binders from cell surface scFv-Fc library (from selected phage populations). Flow cytometry analysis is shown of cells with:

a-c. integrated anti-CD229 sFv-Fc population from 2 rounds of phage display selection on CD229 d. f integrated anti-β-galactosidase sFv-Fc population from 1 round of phage display selection on β-galactosidase (β-galR1 cells)

e. integrated anti-β-galactosidase sFv-Fc population from 2 rounds of phage display selection on β-galactosidase Sample (a) shows unstained cells and the rest were stained with human anti-Fc-phycoerythrin (in FL2) and 100 nM appropriate biotinylated antigen/streptavidin FITC (in FL1). Cells were analysed after 13 days (a,b, d, e). Examples c and f show cells stained after 20 days and the marked region shows cells collected by flow cytometry h. β-galR1 cells selected by flow cytometry (FIG. 6f) were grown for 22 days and re-analysed for scFv-Fc expression and antigen binding (using 100 nM antigen). g. show the unstained equivalent.

j. shows unsorted β-galR1 cells from the original population (as in d) which had been grown for 42 days after transfection (j). Unlabeled cells of each population are shown for comparison (g, i)

Figure 10:
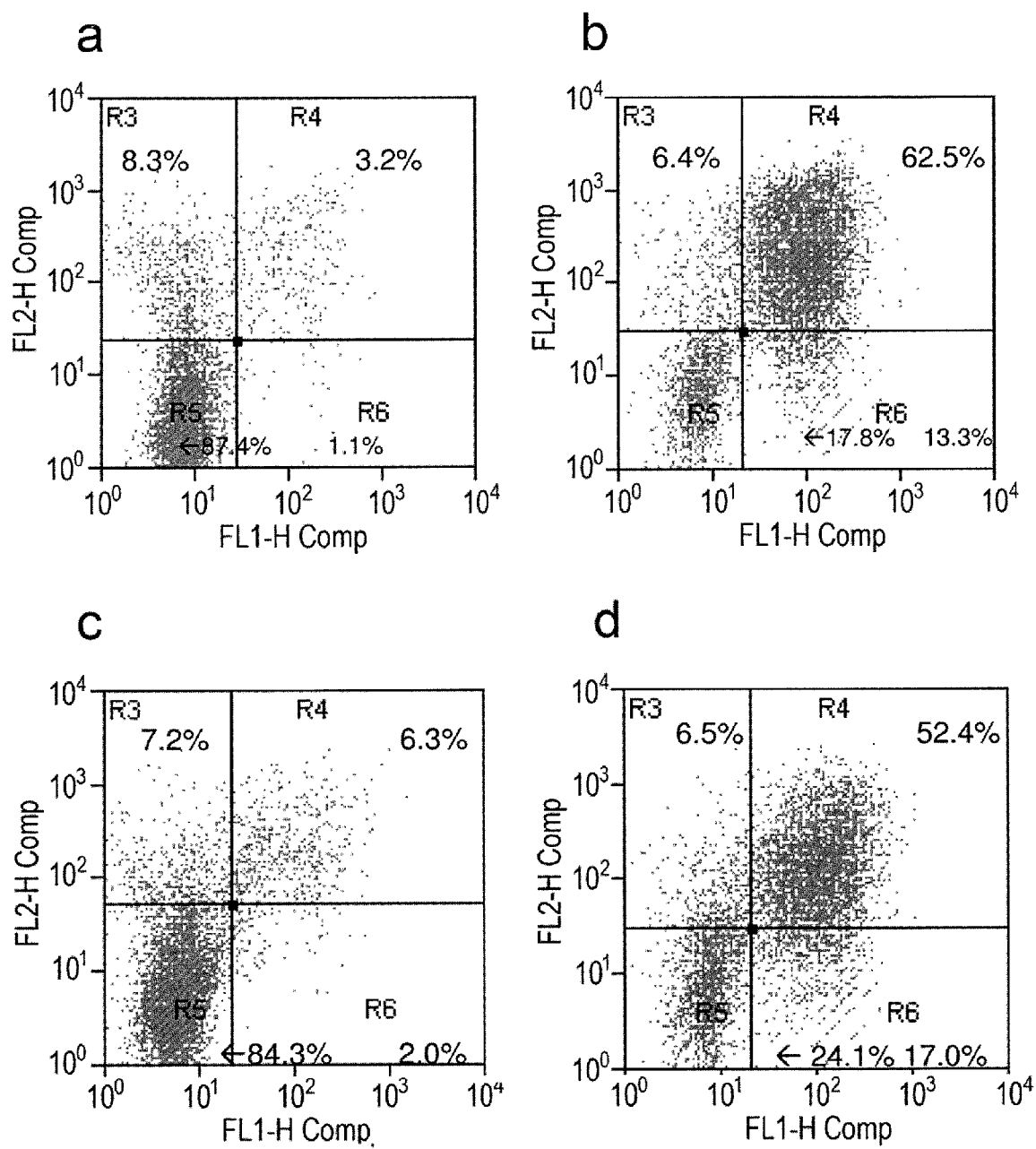

FIG. 10. Mammalian display and sorting of IgG formatted library.

A population of antibodies were selected on β-galactosidase using 1 or 2 rounds phage display, reformatted as IgG and targeted via nuclease-directed integration into the AAVS locus of HEK293 cells. Panels a, b show cells derived from the round 1phage population either a, unsorted (after 38 days growth) or b, sorted by flow cytometry and grown for 19 days. Panels c, d show cells derived from round 2 phage population either c, unsorted (after 38 days growth or d, sorted and grown for 19 days.

Figure 11:
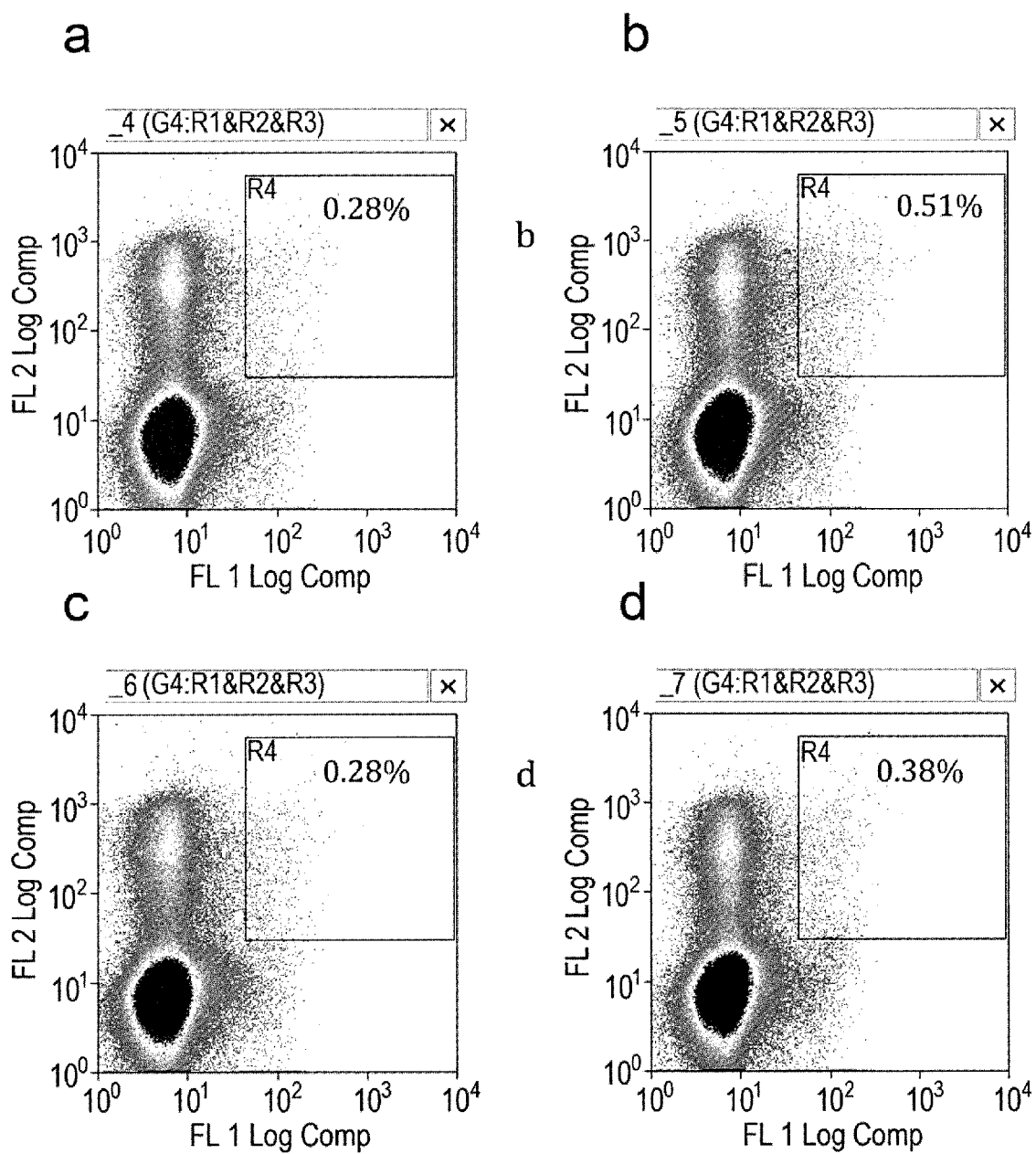

FIG. 11. Construction of large naïve scFv-Fc library and selection of binders

Cells from the naïve scFv-Fc library were stained with 500 nM biotinylated antigen and streptavidin-FITC along with phycoerythrin-labelled anti-Fc antibody as before. Region shows cells which were selected by flow sorting. Samples were labelled with biotinylated:

a. CD28
b. β-galactosidase
c. Thyroglobulin
d. EphB4

Figure 12:
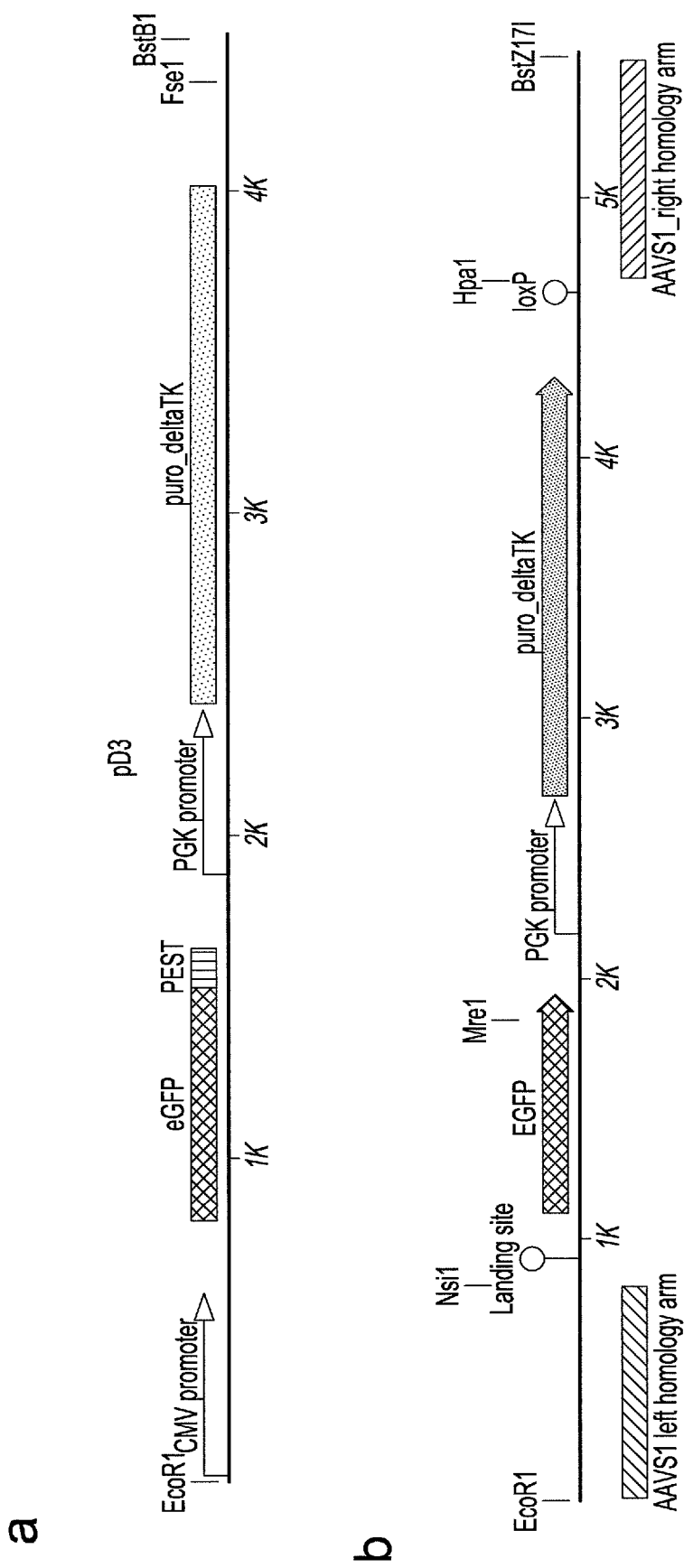

FIG. 12. Targeting vector to introduce intron containing "multiple landing" sites for comparison of integration methods.

a. Intermediate GFP expression plasmid (pD3)
b. AAVS1_directed targeting vector (pD4). "Landing site" incorporates elements for
directing integration which are FRT, lox 2272, I-Sce1 meganuclease and GFP TALEN Following integration of pD4 into the AAVS locus, multiple recombination or nuclease cleavage sites are present within the genome. The incoming pD5 plasmid (FIG. 15) has left and right homology arms equivalent to the sequence present on either side of the "landing site" to drive antibody insertion by homologous recombination.

FIG. 13. Sequence of pD4 (SEQ ID NO: 12, 13, 14, 15, 16, 17 & 18.).

Sequence features include:
AAVS Left homology 19-822
FRT site 832-879, Lox 2272 site 884-917, I-Sce1meganuclease site 933-950
GFP left TALEN binding 954-968, GFP right TALEN binding 984-997
T2A 1041-1103
GFP 1104-1949
PGK promoter 2178-2691

Puromycin delta thymidine kinase 2706-4307
loxP 4634-4667
AAVS right homology 4692-5528

Figure 14:
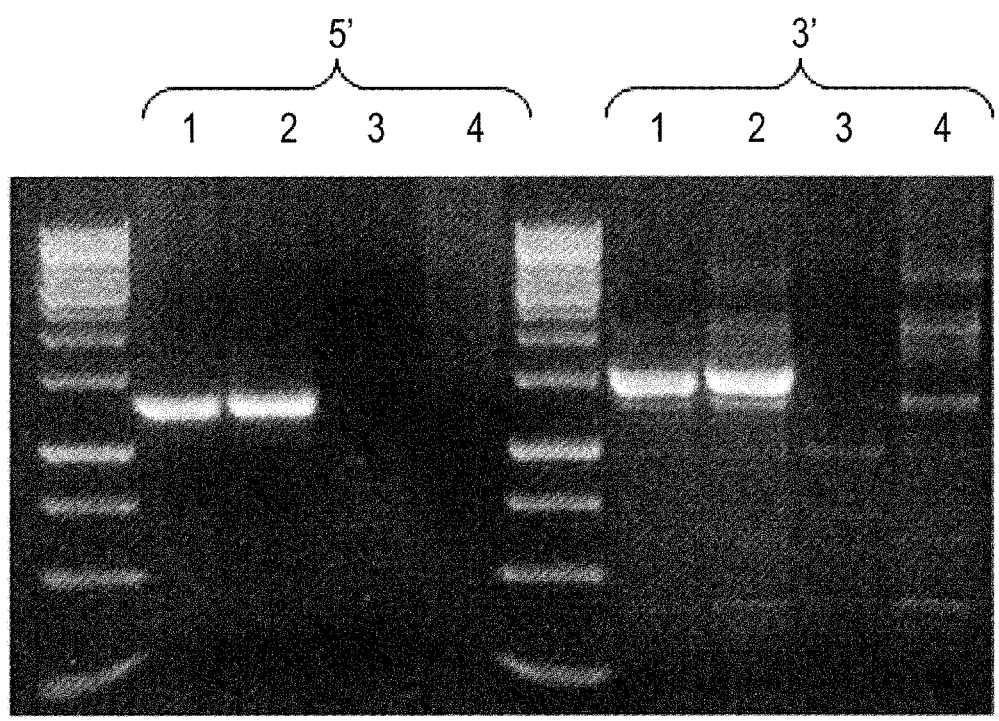

FIG. 14. Verification of integration of "multiple landing site" intron in clone 6F.

Following transfection cells were selected in puromycin and genomic DNA was prepared. Samples 1 represents the whole selected population. Sample 2 represents clone 6F, sample 3 is a clone transfected in the absence of TALENs and sample 4 is wild-type HEK293 cells. Primers and conditions described in text were used to verify by PCR the correct integration at the 5' and 3' ends of the genomic insertion. The major (correct sized) band is seen for the selected clone (6F) as well as the selected population.

FIG. 15. Sequence of donor plasmid for integration into Flp/GFP TALEN sites (pD5) (SEQ ID NO: 19, 20 & 21). Features include:
AAVS HA 13-233
FRT site 243-290
Lox2272 295-328
I-Sce1 344-361
Blasticidin resistance 417-818
Poly A 832-1070

FIG. 16. Sequence of I-Sce1 meganuclease construct (SEQ ID NO: 22 & 23)

Figure 17:
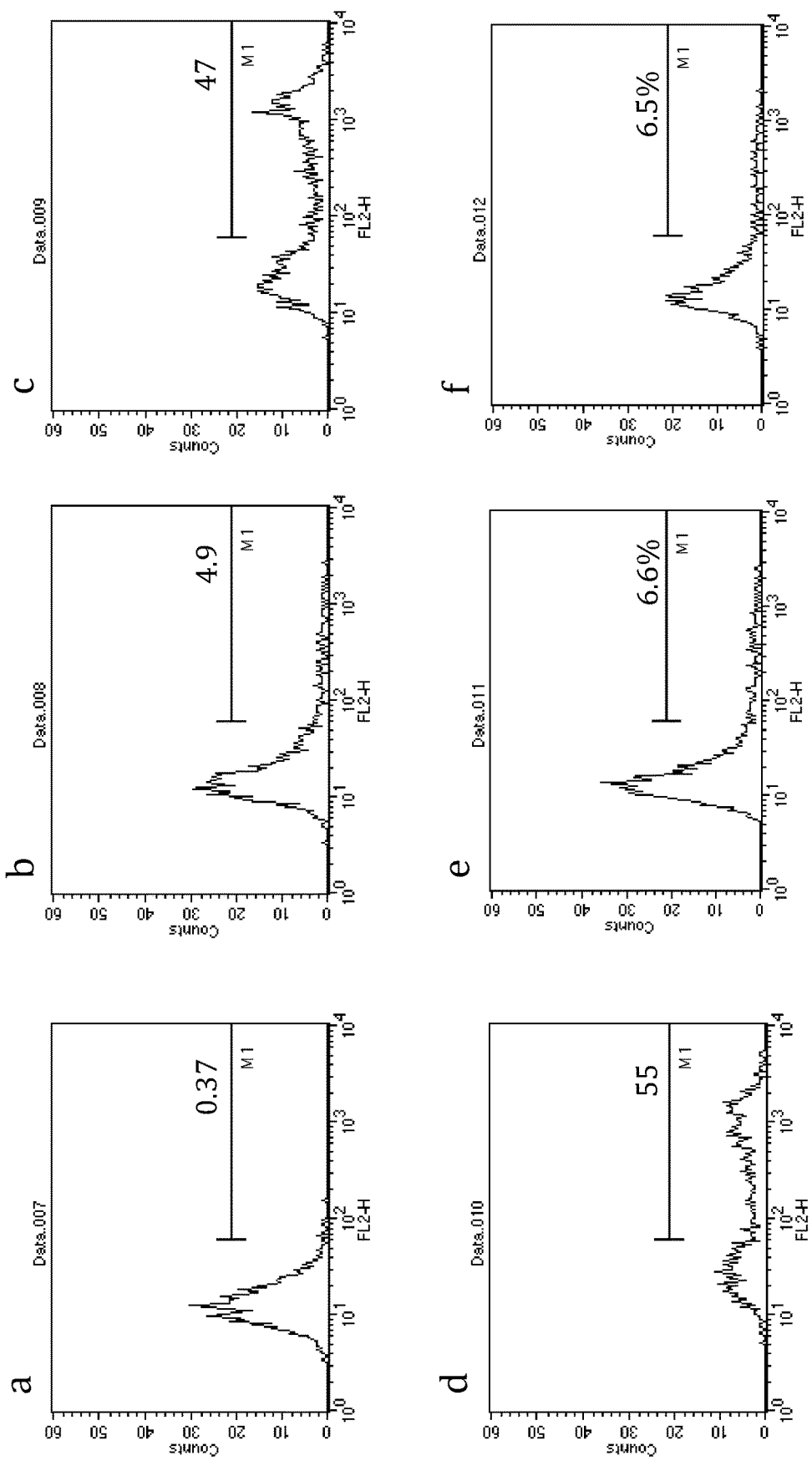

FIG. 17. Flow cytometry analysis comparing nuclease-directed integration using I-Sce1 meganuclease with recombinases.

Clone 6F cells were co-transfected with pD5-D1.3 and plasmids encoding the indicated nuclease/recombinase. Cells were selected with blasticidin and analysed 13 days after transfection using biotinylated anti-human Fc antibodies and streptavidin phycoerythrin. Percentage positive cells are indicated (also summarized in Table 5)
 a. Non-transfected, b Donor only c. I-Sce1, d, eGFP TALEN, e. Cre, f. Flp recombinase (encoded by pOG44 plasmid).

Figure 18:
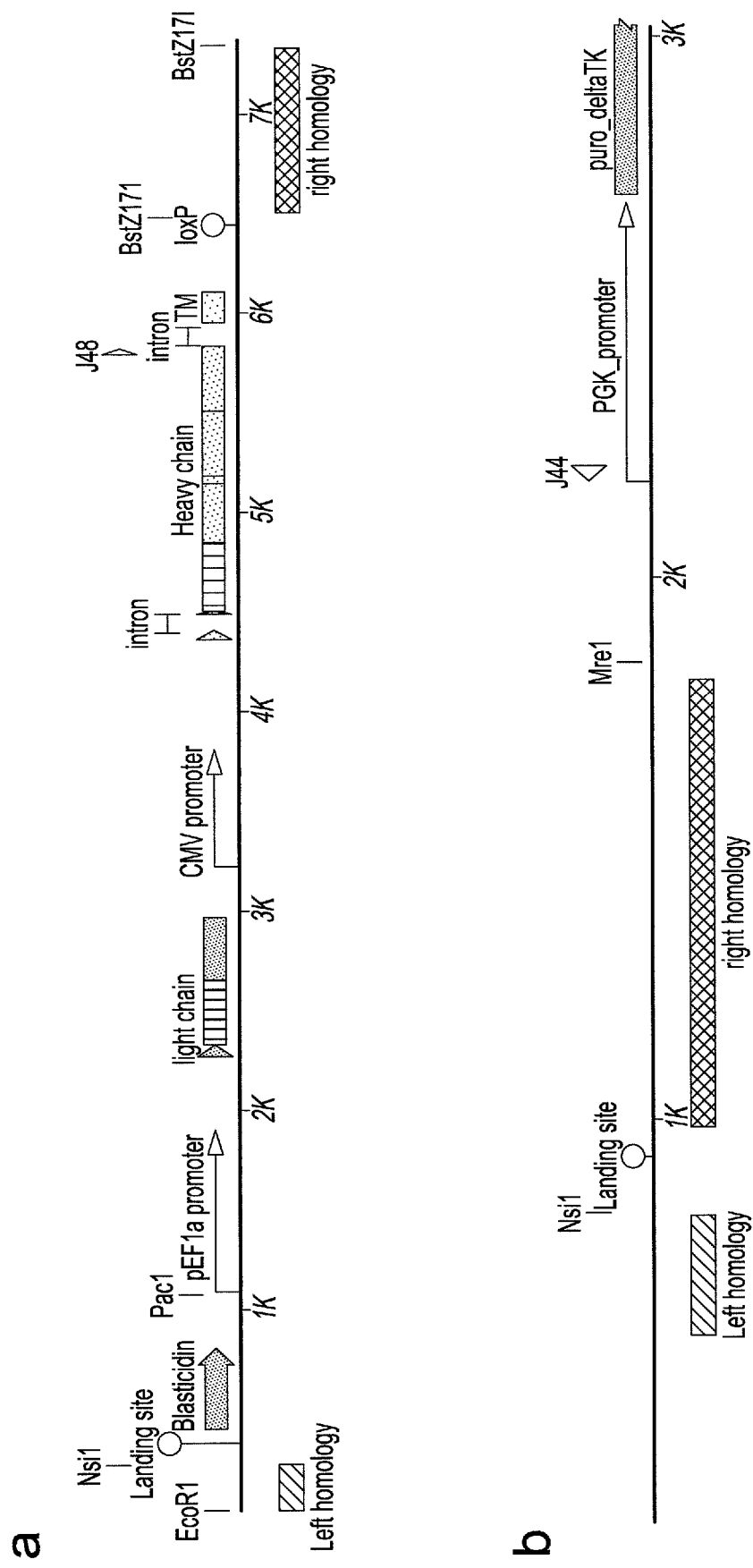
Figure 18:
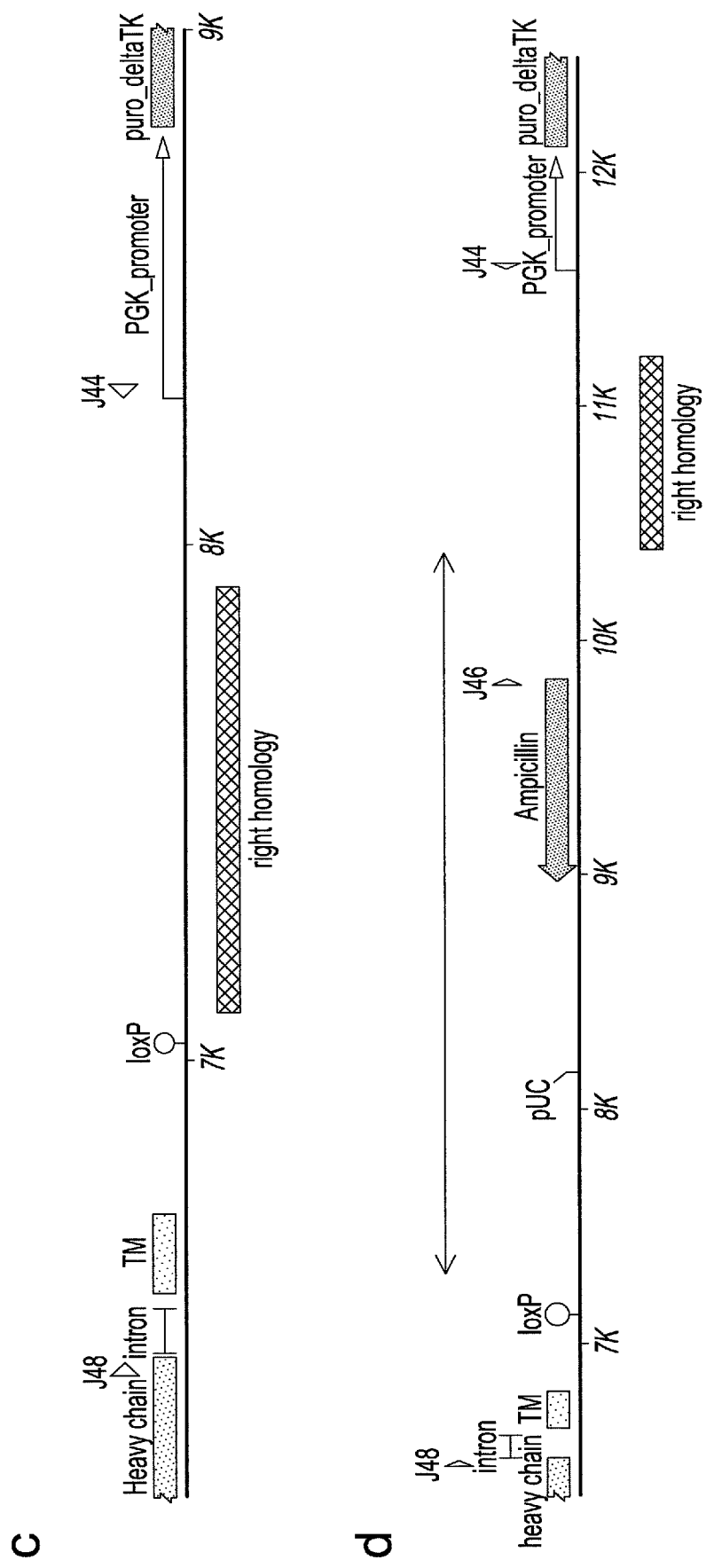
Figure 18:
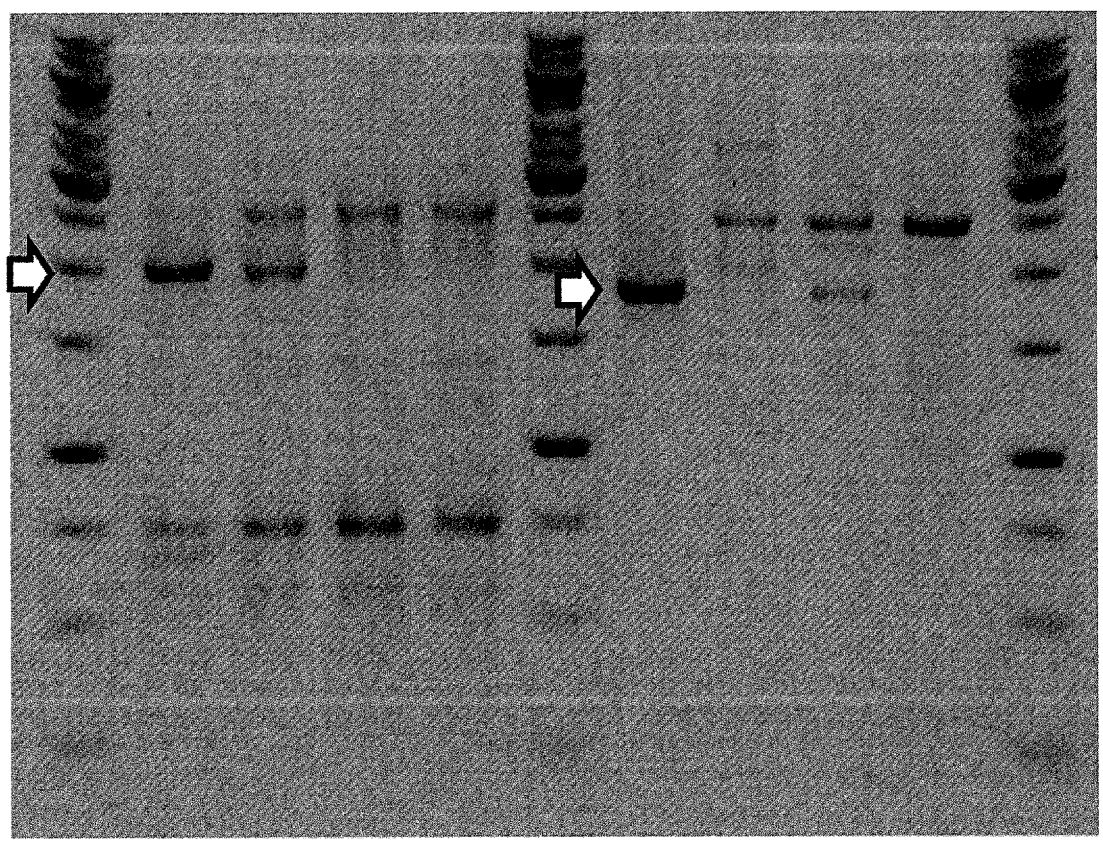

FIG. 18. Nuclease-directed integration drives homologous recombination and "non-homologous end joining" (NHEJ).
 a. Representation of structure of plasmid pD5 used to target the multiple "landing site" within the intron of "clone 6F cells showing position of primer J48. The "landing site" in this plasmid incorporates a FRT site, a lox2272 site and an I-Sce1 meganuclease site (but no GFP TALEN site).
 b. Representation of integration site within clone 6F (derived from pD4) showing position of primer J44. "Landing site" incorporates elements for directing integration which are FRT, lox 2272, I-Sce1 meganuclease and GFP TALEN.
 c. Representation of clone 6F integration site after homologous recombination of pD5, showing position of primers J44 and J48.
 d. Representation of integration site of clone 6F after NHEJ or Flp recombination of pD5, showing position of primers J44, J46 and reverse primer J44. The double headed arrow indicates the "extra" plasmid derived DNA incorporated by NHEJ or Flp-directed integration. Note in this example the incoming plasmid DNA (pD5) has homology arms (which direct homologous recombination but are not required for NHEJ). These sequences are retained after integration by NHEJ, causing a duplication of the sequence represented within the homology arms with one pair coming from the plasmid in this case and the other pair representing the endogenous genomic sequences. For simplicity the plasmid encoded homology arms are not shown, just their equivalent sequence within the genome.
 e. Primers 44 and 48 were used as PCR primers for samples i-iv where genomic DNA from cells transfected with the following nucleases/integrases were used:
  i. Sce1, ii. TALEN (GFP), iii. Flp (pOG44), iv. Donor only. Molecular weight markers were "GeneRuler 1 kb ladder (New England Biolabs). Primers J44 and J48 reveal homologous recombination has occurred producing a band of 1928 bp (indicated by arrow) in nuclease cleaved samples i and ii.

Primers 44 and 46 were used for samples v-viii where genomic DNA from the following samples was used. v. Sce1, vi. TALEN (GFP), vii. Flp (pOG44), viii. Donor only.

Primers J44 and J46 reveal that cleavage of donor and genomic DNA by I-Sce1 meganuclease has resulted in NHEJ (sample v.) producing a band of 1800 bp (indicated by arrow). As expected a similar sized band was achieved by Flp mediated integration (vii). NHEJ has not occurred with GFP TALEN since there was no cleavage site in the incoming plasmid.

Figure 19:
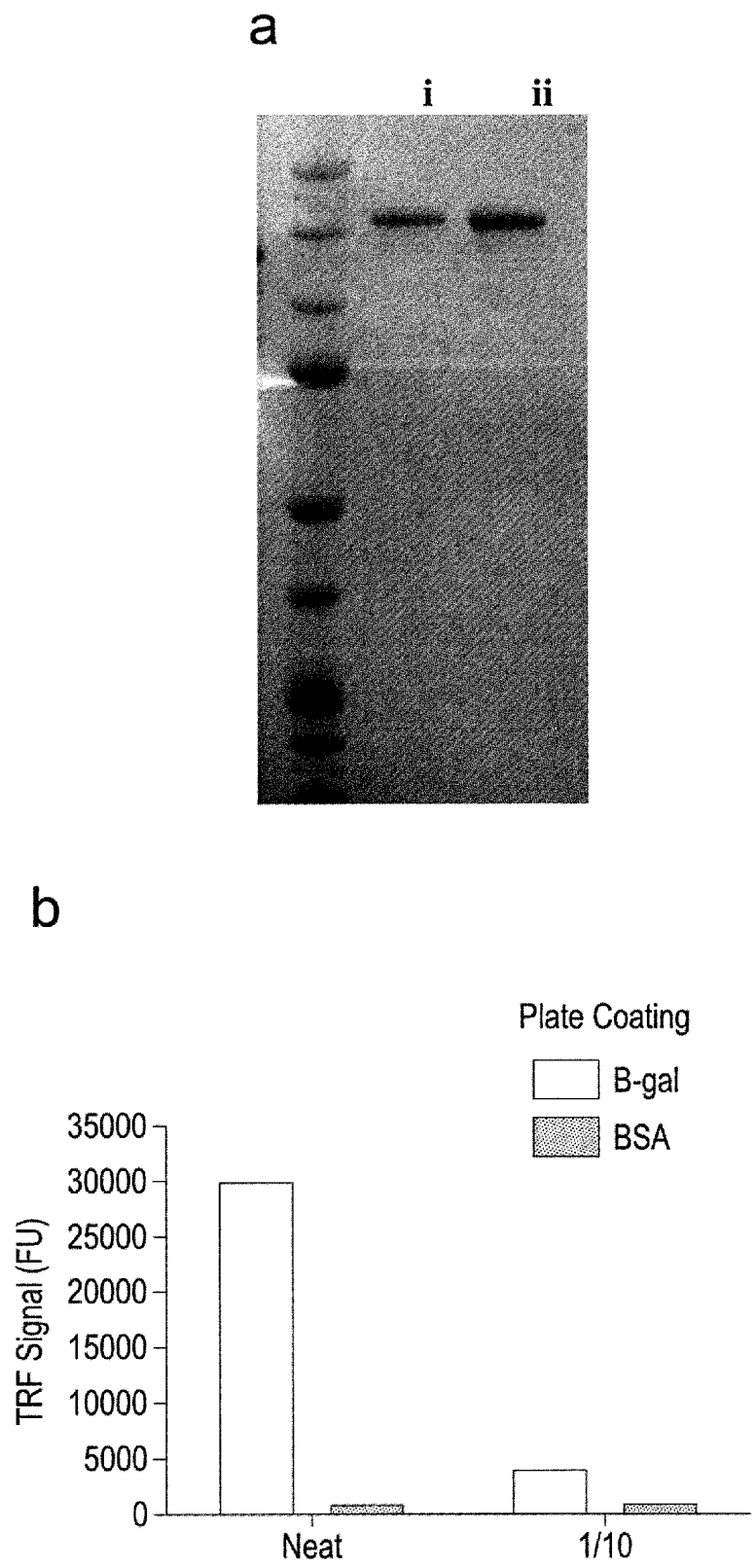

FIG. 19. Secretion of IgG antibodies into culture supernatant.
 a. Coomassie stained gel of protein A purified IgG from culture supernatants.
  i. IgG purified from supernatant of pD2-D1.3 cells without transfection of Dre recombinase gene.
  ii. IgG purified from supernatant of pD2-D1.3 cells transfected with Dre recombinase gene. Polyclonal ELISA of secreted antibodies. Sorted cells from the experiment shown in FIG. 9H (originally from antibody population cells selected by 1 round of phage display) were grown for 7 days post sorting and the culture supernatant collected. ELISA plates were coated with either β-galactosidase (10 ug/ml) or BSA (10 ug/ml) overnight. Culture supernatants were diluted down to 66% after mixing with a 33% volume of 6% Marvel-PBS (this is described above as the 'neat' sample). Supernatant was also diluted 1/10 in PBS and mixed with 6% MPBS in the same manner. Detection of bound scFv-Fc fusion was performed using anti-Human IgG-Eu (Perkin Elmer Cat 1244-330).

Figure 20:
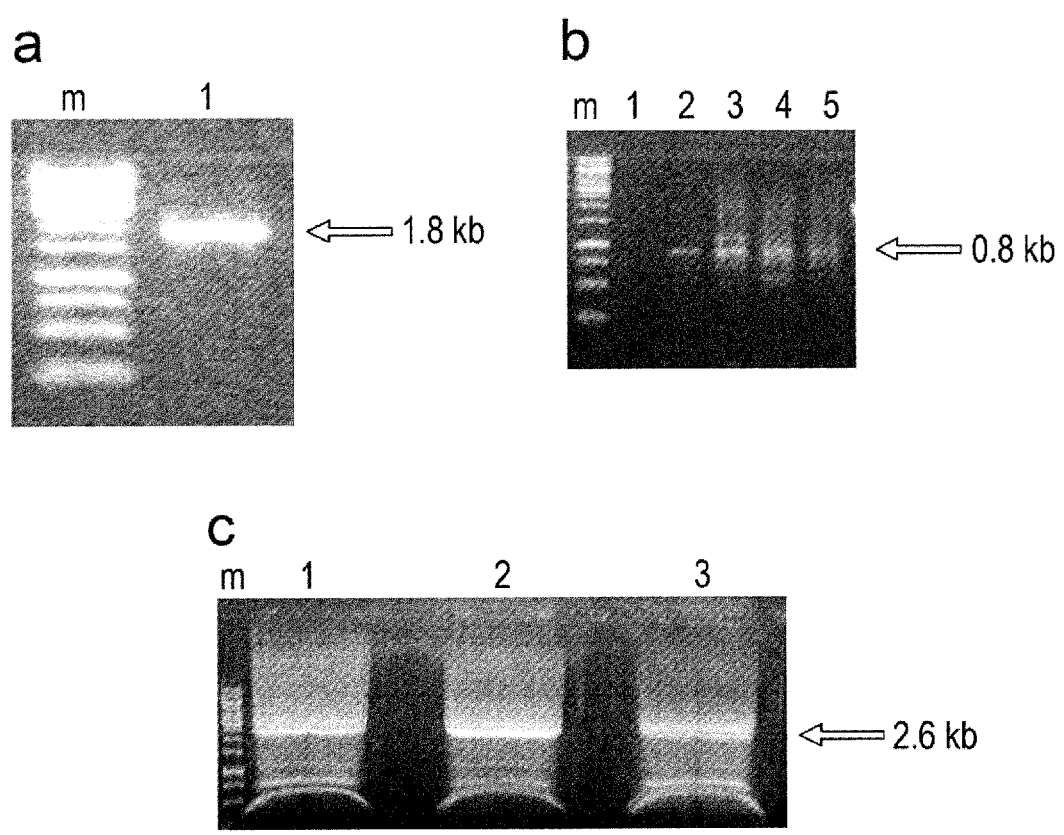
Figure 21:
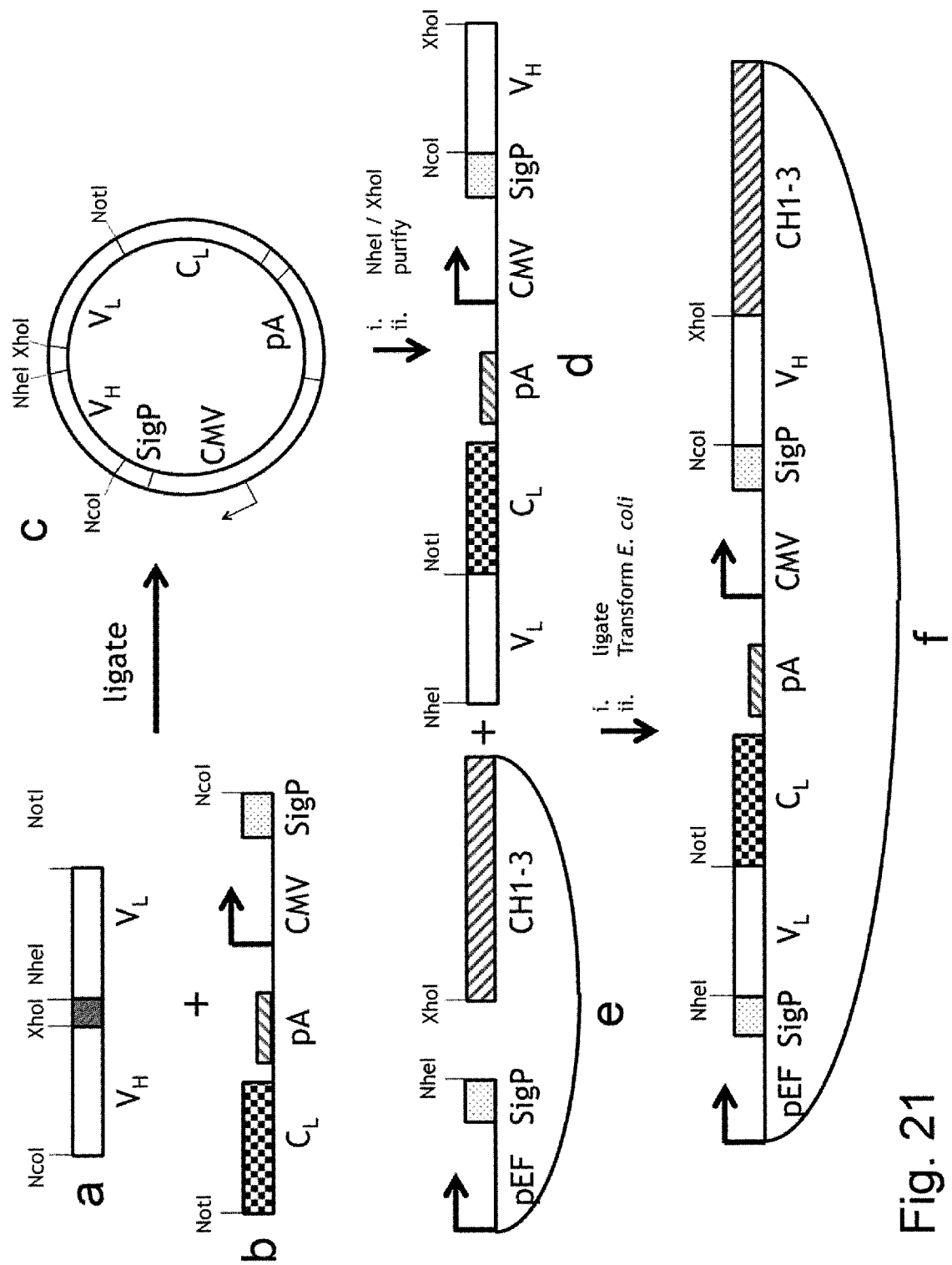

FIG. 20. Preparation of DNA fragments for the conversion of selected populations of scFv to IgG format. (a) Generation of CL-pA-CMV-Sigp DNA insert (as depicted in FIG. 21b). PCR amplification from plasmid pD2 with primers 2595 and 2597 and gel purified. Lane m, Generuler 1 kb ladder (Thermo, SM031 D), lane 1 CL-pA-CMV-Sigp DNA insert. (b) Generation of scFv DNA insert was as described in Example 6. Lane m, Generuler 1 kb ladder (Thermo, SM031 D), lane 1 blank, lane 2 purified scFv, lane 3 β-galactosidase round 1 output scFv population, lane 4 β-galactosidase round 2 output scFv population, lane 5 CD229 round 2 output scFv population. (c) Purification of NheI and XhoI digested "mini-circle" DNA. Ligations between NcoI/NotI digested DNA encoding scFv (FIG. 21, insert a) and DNA encoding constant light ($C_L$) chain, poly A (pA), CMV promoter and signal peptide (FIG. 21, insert b) to form "mini-circle" DNA (FIG. 21c) were spin column purified, digested with NheI and XhoI and purified by 1% agarose gel. Lanes are m, Generuler 1 kb ladder (Thermo, SM031 D), lane 1β-galactosidase round 1 output, lane 2 β-galactosidase round 2 output, lane 3 CD229 round 2 output. Linearised product at 2.6 kb, indicated by arrow, was excised and purified.

FIG. 21. Schematic representation of the conversion process from scFv to IgG format. A DNA insert (a) encoding the antibody VH and VL domains is ligated with DNA fragment (b) encoding a constant light (CL) chain, a polyadenylation sequence (pA) a cytomegalovirus (CMV) promoter and a signal peptide (SigP). The joining of DNA molecules a and b to create a non-replicative DNA "mini-circle" c is facilitated by a "sticky-end" ligation. After ligation, the "mini-circle" c is linearized with restriction enzymes NheI and XhoI. Linearized product d is then purified and ligated with the digested vector e. The vector e includes a pEF promoter and SigP sequence upstream of the NheI site and encodes the antibody constant heavy (CH) domains 1 to 3 downstream of the XhoI site. The product of ligation of insert d with vector e would result in plasmid f, which can be used to transform bacteria and growth with a suitable selectable marker would allow the production and purification of plasmid DNA by standard methods. Purified plasmid f can be introduced into mammalian cells [134] for heterologous Ig antibody expression. Alternatively DNA encoding CH1-3 in vector e, could be replaced with DNA encoding a single CH1 domain for Fab expression. VH and VL are antibody variable heavy and light chain respectively. DNA encoding an elongation factor promoter (pEF) an antibody constant light chain ($C_L$) and constant heavy domains 1 to 3 (CH1-3), a polyadenylation sequence (pA) a cytomegalovirus (CMV) promoter and a signal peptide (SigP) are depicted.

Figure 22:
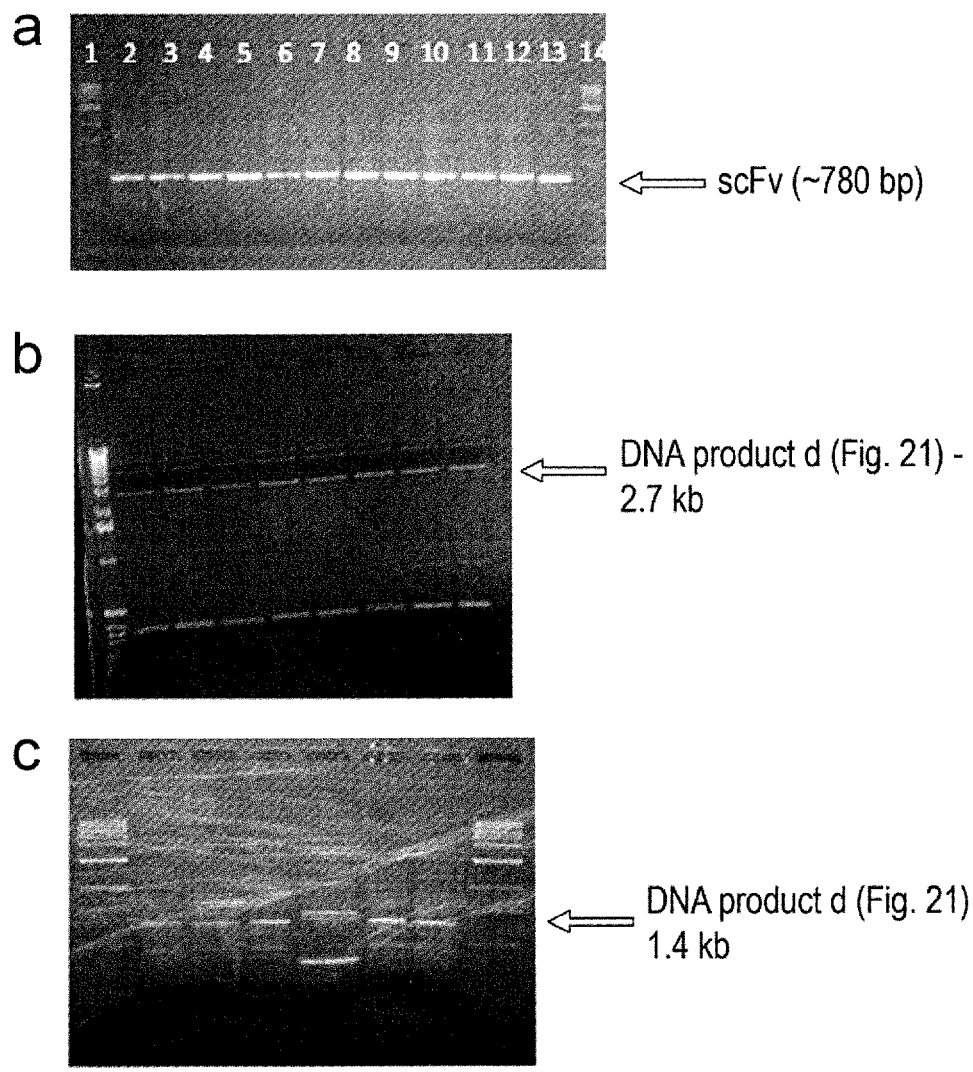

FIG. 22. Additional example of preparation of DNA fragments required for the conversion of scFv to IgG (a) scFv inserts generated as described in Example 14 were separated on a 1% agarose TBE gel. Lanes 1 and 14 is a 500 bp DNA ladder starting at 500 bp. Lanes 2 to 13 are scFv PCRs. (b) The purification of the linearised "mini-circle" d (FIG. 21) was performed by separation on a 1% agarose TBE gel. From left to right, the first lane is a DNA ladder (1 kb ladder, Lifetech, 15615-024) and remaining lanes linearised "mini-circle" d. (c) As (b) except the CMV promoter is replaced by a P2A sequence and the DNA ladder employed was Generuler 1 kb ladder (Thermo, SM031D).

Figure 23:
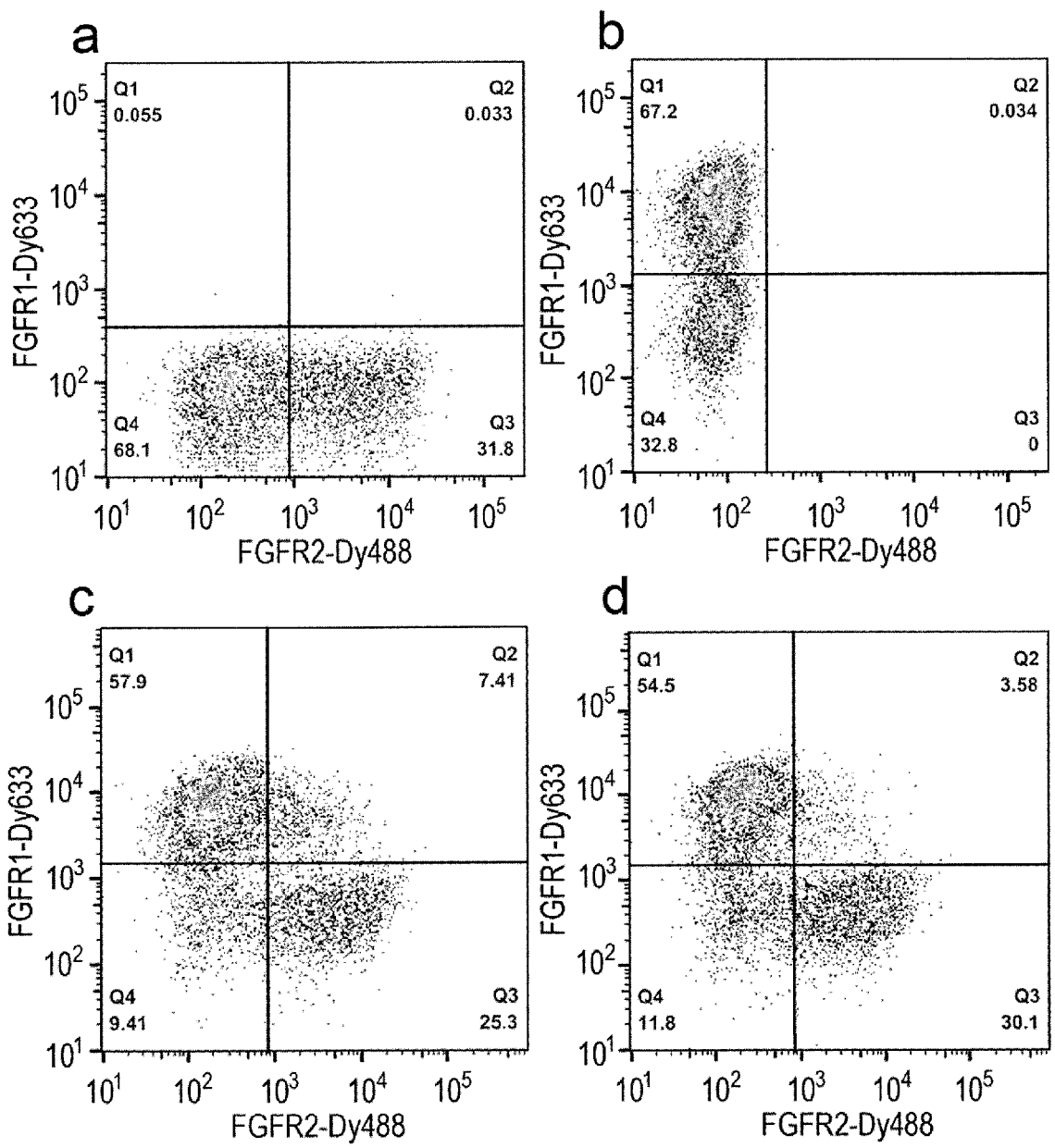

FIG. 23. Nuclease-directed integration of binder genes using flow electroporation systems. A 50:50 mix pD6 plasmids encoding either an anti-FGFR1 or an FGFR2 antibody was electroporated using a Flow electroporation system. After 13 days blasticidin selection cells were labelled with FGFR1-Fc labelled with Dyelight-633 (FGFR1-Dy633) or FGFR2-Fc labelled with Dyelight 488 (FGFR2-Dy488). Dot blots represent:
  a. Single staining FGFR2-488 (sample 1b from Table 7)
  b. single staining FGFR1-633 (sample 1 b from Table 7)
  c. Dual staining FGFR1-633/FGFR2-488 (sample 1b from Table 7)
  d. Dual staining FGFR1-633/FGFR2-488 (sample 3 from Table 7)

Figure 24:
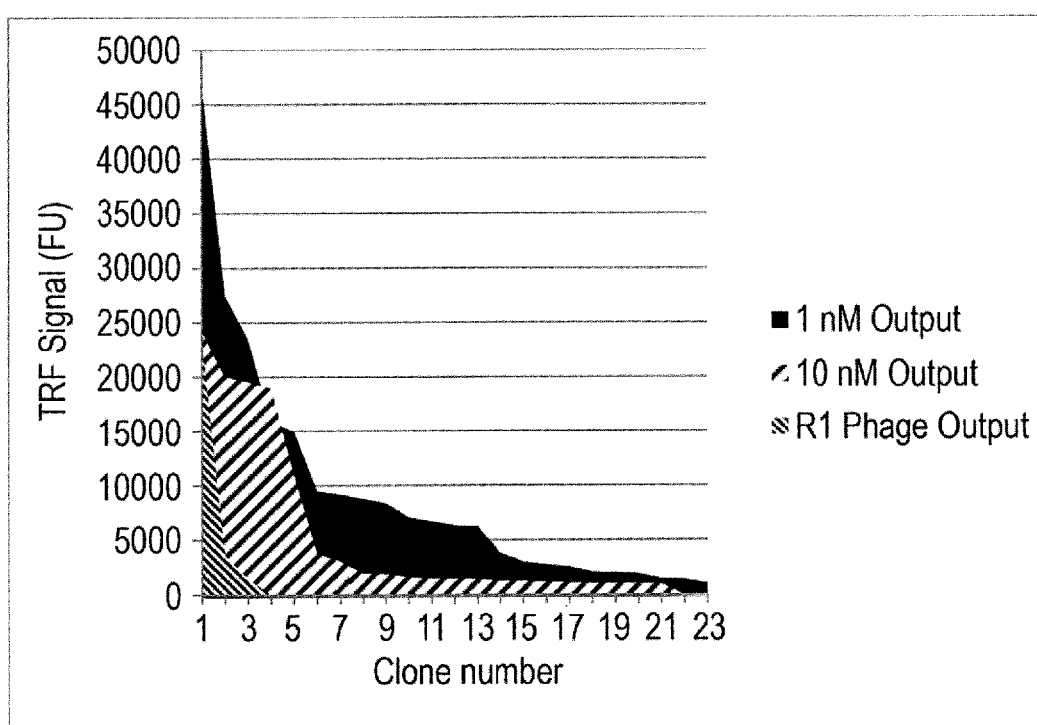

FIG. 24. Recovery of antibody genes after flow sorting.
A population of antibodies was selected by one round of phage display and a mammalian display library was created by Flow electroporation using the Maxcyte system. Cells were sorted using either 1 nM or 10 nM antigen and mRNA isolated directly. The antibody genes were recovered by PCR, cloned into a bacterial expression vector and the proportion of ELISA positives determined ("1 nM output", "10 nM output"). This was compared with the original round 1 output ("R1 phage output"). Plot shows the profile of ELISA signals obtained with each population.

Figure 25:
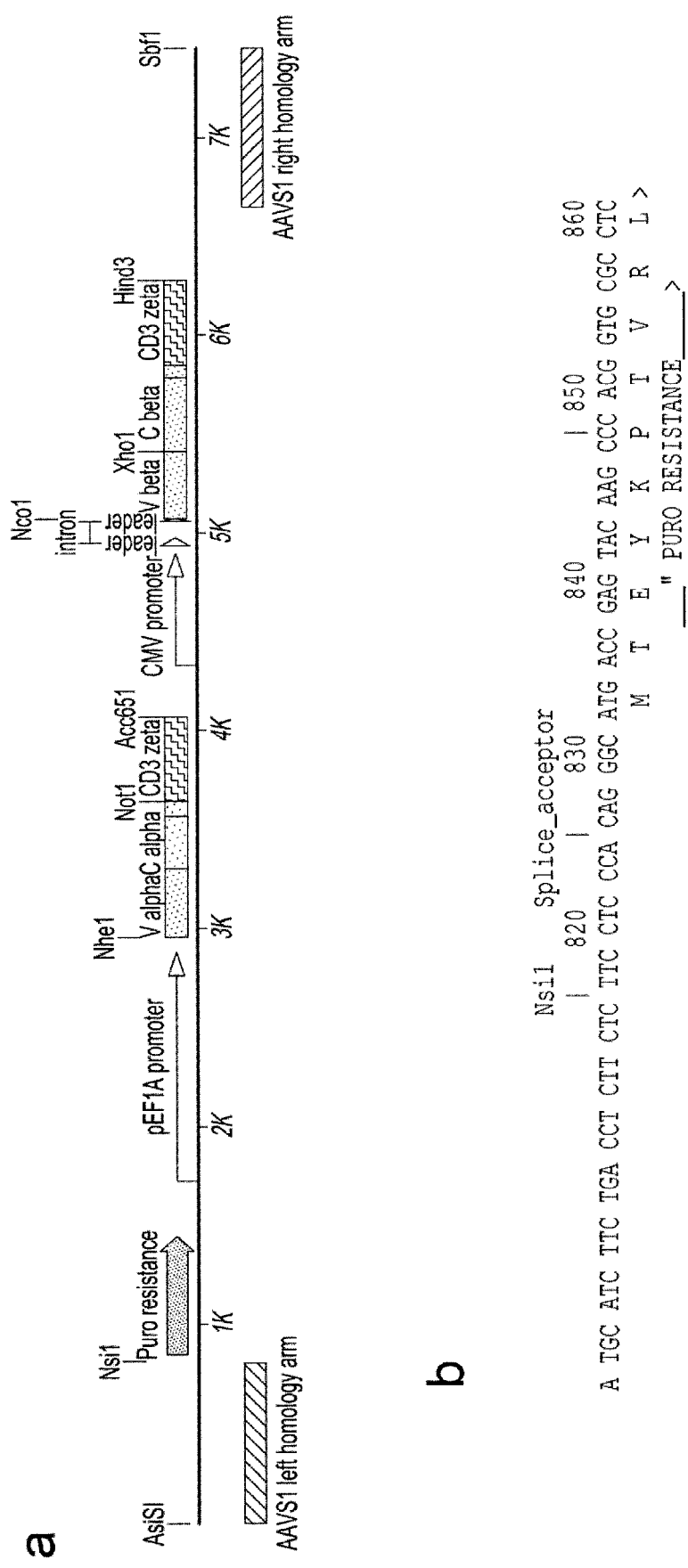

FIG. 25. pINT20 vector for expression of T Cell Receptors.
  a. Representation of the dual promoter plasmid pINT20 showing AAVS homology arms, puromycin selectable gene (with region around splice acceptor site shown below). Alpha chain (encompassing variable alpha, mouse alpha constant-CD3ζ) is flanked by Nhe1, Not1 and Acc65I restriction sites and is under the control of the pEF promoter. The beta chain (encompassing variable beta, mouse beta constant-CD3ζ) is flanked by Nco1, Xho1 and hind3 sites and is under the control of the CMV promoter.
  b. Sequence at the splice acceptor and beginning of puromycin gene (SEQ ID NO: 24 & 25)
  c. Sequence of T cell receptor clone c12/c2 alpha chain construct showing Nhe1, Not1 and Acc65I restriction sites (SEQ ID NO: 26 & 27).
  d. Sequence of T cell receptor clone c12/c2 beta chain construct showing Nco1. Xho1 and Hind 3 restriction sites (SEQ ID NO: 28 & 29).
  e. Sequence of T cell receptor clone 4JFH alpha chain construct showing Nhe1/Not1 restriction sites (SEQ ID NO: 30 & 31).
  f. Sequence of T cell receptor clone 4JFH beta chain construct showing Nco1/Xho1 restriction sites (SEQ ID NO: 32 & 33).
  g. Strategy and primer used to mutate CDR3 of c12/c2 TCR alpha chain (SEQ ID NO: 34, 35, 36 & 37).
  h. Strategy and primer used to mutate CDR3 of c12/c2 TCR beta chain (SEQ ID NO: 38, 39, 40 & 41).
  (N=A, C, G, T; S=C OR G; W=A OR T)

Figure 26:
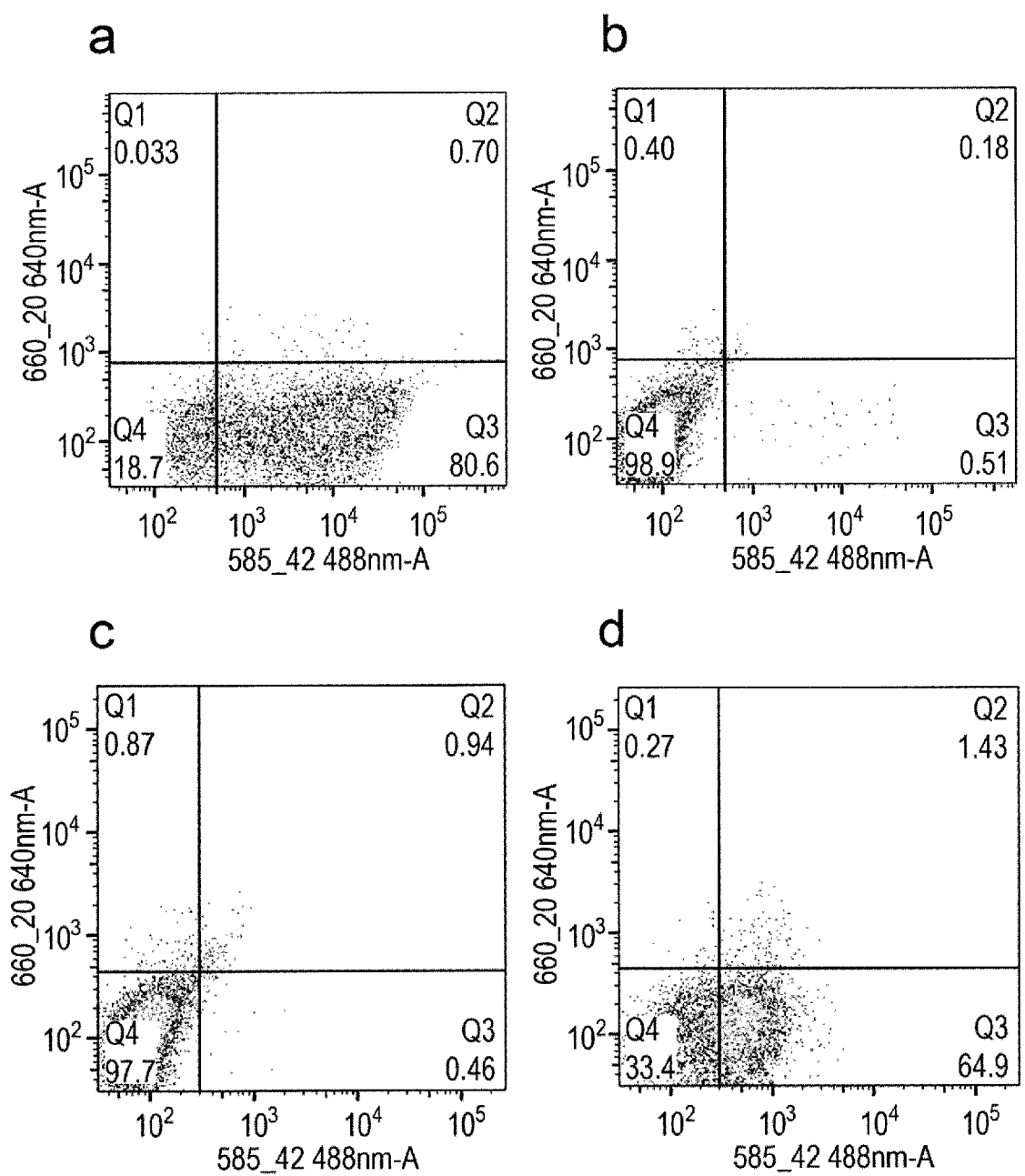
Figure 26:
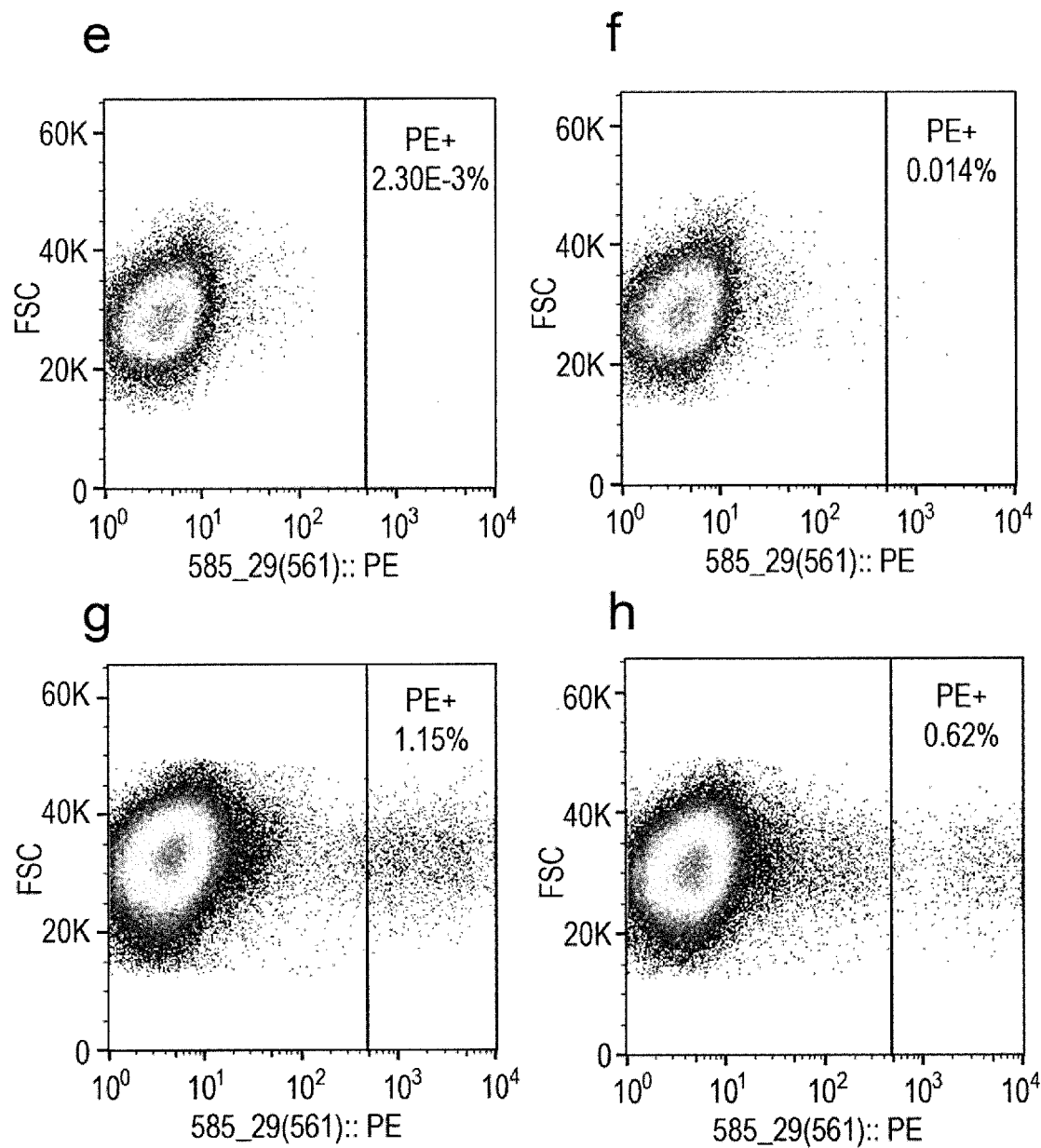
Figure 26:
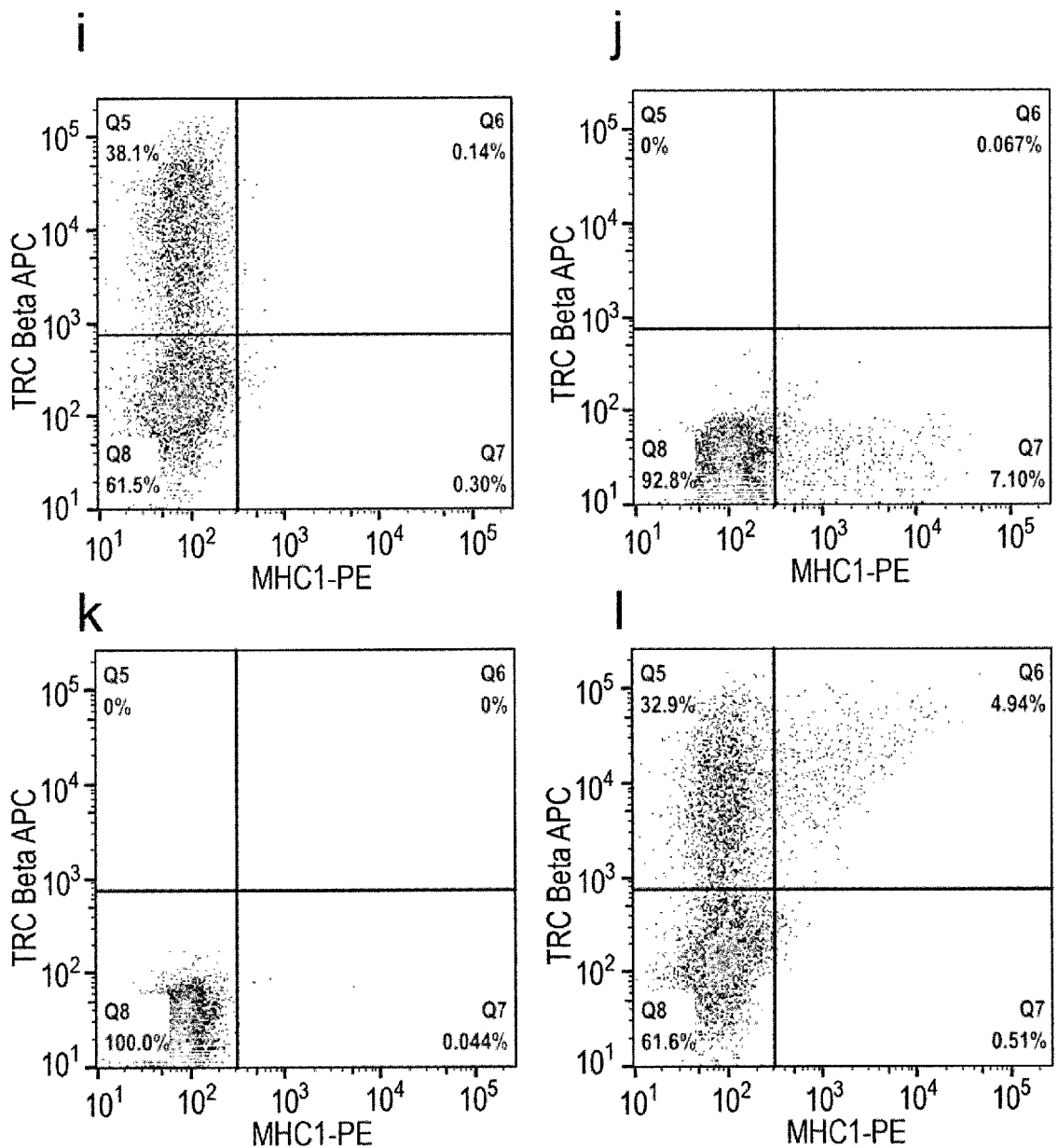
Figure 26:
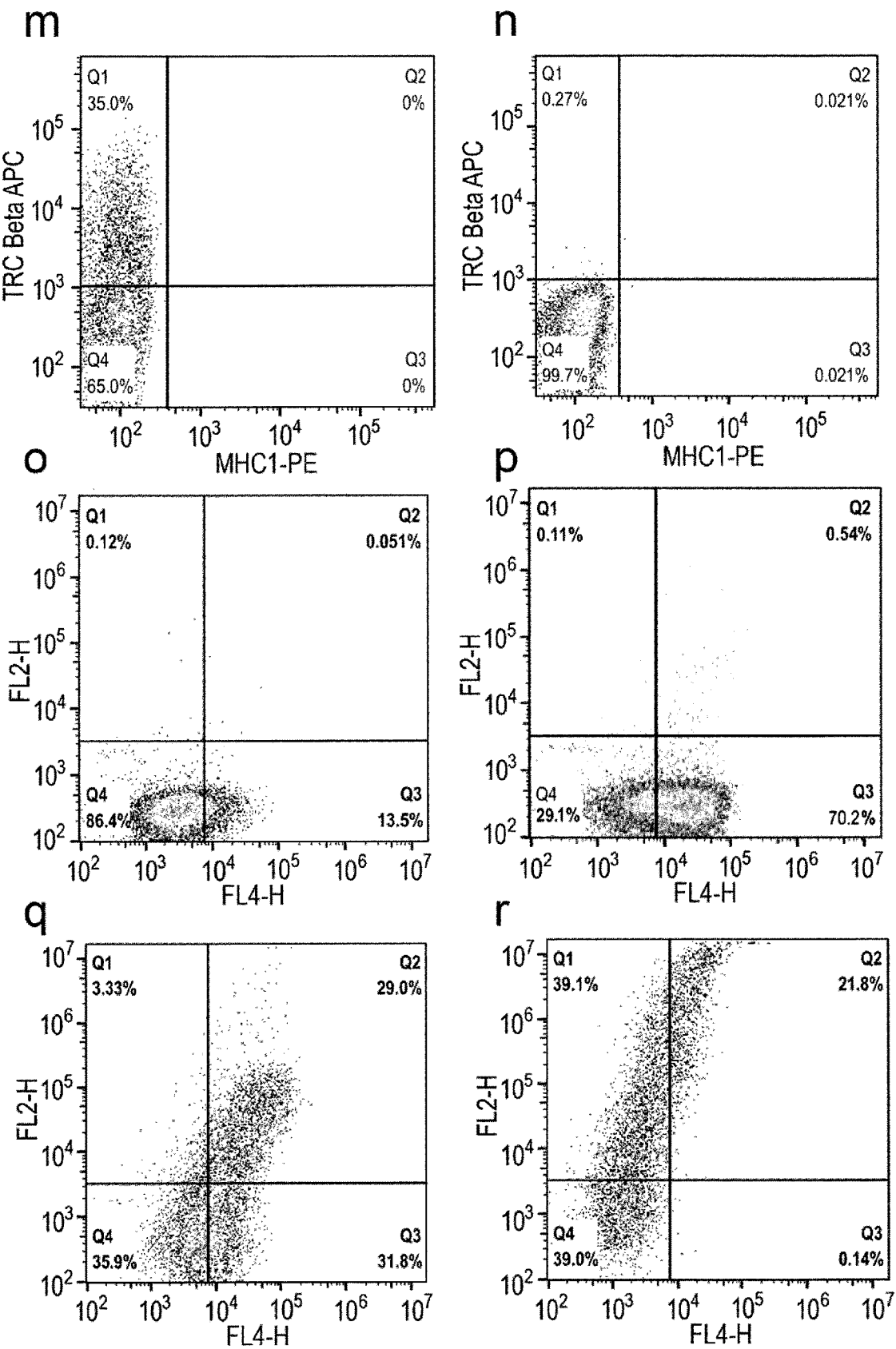

FIG. 26. Recognition of peptide;MHC complexes by T cell receptors introduced into mammalian cells by nuclease-directed integration.

TCR1 is TCR c12/c2 recognising peptide 1 (SLL-MWITQV) in the form of complex with phycoerythrin-labelled HLA-A2 (peptide 1). TCR2 is TCR 4JFH recognizing peptide 2 (ELAGIGILTV) in the form of complex with phycoerythrin-labelled HLA-A2 (peptide 2). Sample a and c show cells expressing TCR1 exposed to peptide 1 (a) or peptide 2 (c). Sample b and d show cells expressing TCR2 exposed to peptide 1 (a) or peptide 2 (c).

Samples e and f show non-transfected HEK293 cells labelled with peptide 1 (e) or peptide 2 (f).

g. Plasmid encoding TCR1 was mixed with 100 fold excess of TCR2 plasmid, introduced by nuclease-directed integration into HEK cells. 1.15% of cells and was labelled with peptide 1. 1.15% of cells were positive.
  h. Plasmid encoding TCR2 was mixed with 100 fold excess of TCR1plasmid, introduced by nuclease-directed integration and was labelled with peptide 2. 0.62% of cells were labelled. Positive cells collected by flow sorting and mRNA recovered for analysis of specific TCR enrichment.

Samples i-I illustrate expression of a T cell library in HEK293 cells. TCR library was introduced by Maxcyte electroporation and selected for 11 days in puromycin
  I. Shows cells labelled with an APC labeled anti-TCR antibody (y axis).
  j. Shows cells labelled with phycoerythrin-labelled peptide 1:MHC (x axis)
  k. Shows untransfected cells labelled with both anti-TCR antibody and peptide 1:MHC
  l. Shows TCR1 library transfected cells labelled with both anti-TCR antibody and peptide 1:MHC Samples m-n illustrate expression of TCRs in Jurkat cells. TCR1 was delivered by Amaxa electroporation and selected for 25 days in puromycin. Plasmid was transfected in presence (m) or absence (n) of TALE nuclease and was incubated with an APC labelled anti-TCR β chain antibody. Samples o-r illustrates T cell receptor activation of the same TCR1-transfected Jurkat cells. All cells are labelled with anti-CD69 antibody (y axis). Sample o was unstimulated and p was stimulated for 24 hours with an anti-CD3 antibody. Samples q and r were incubated for 24 hours with 2 ul and 6 ul respectively of PE labeled MHC:peptide 1. All cells were also exposed to CD28 antibody.

Figure 27:
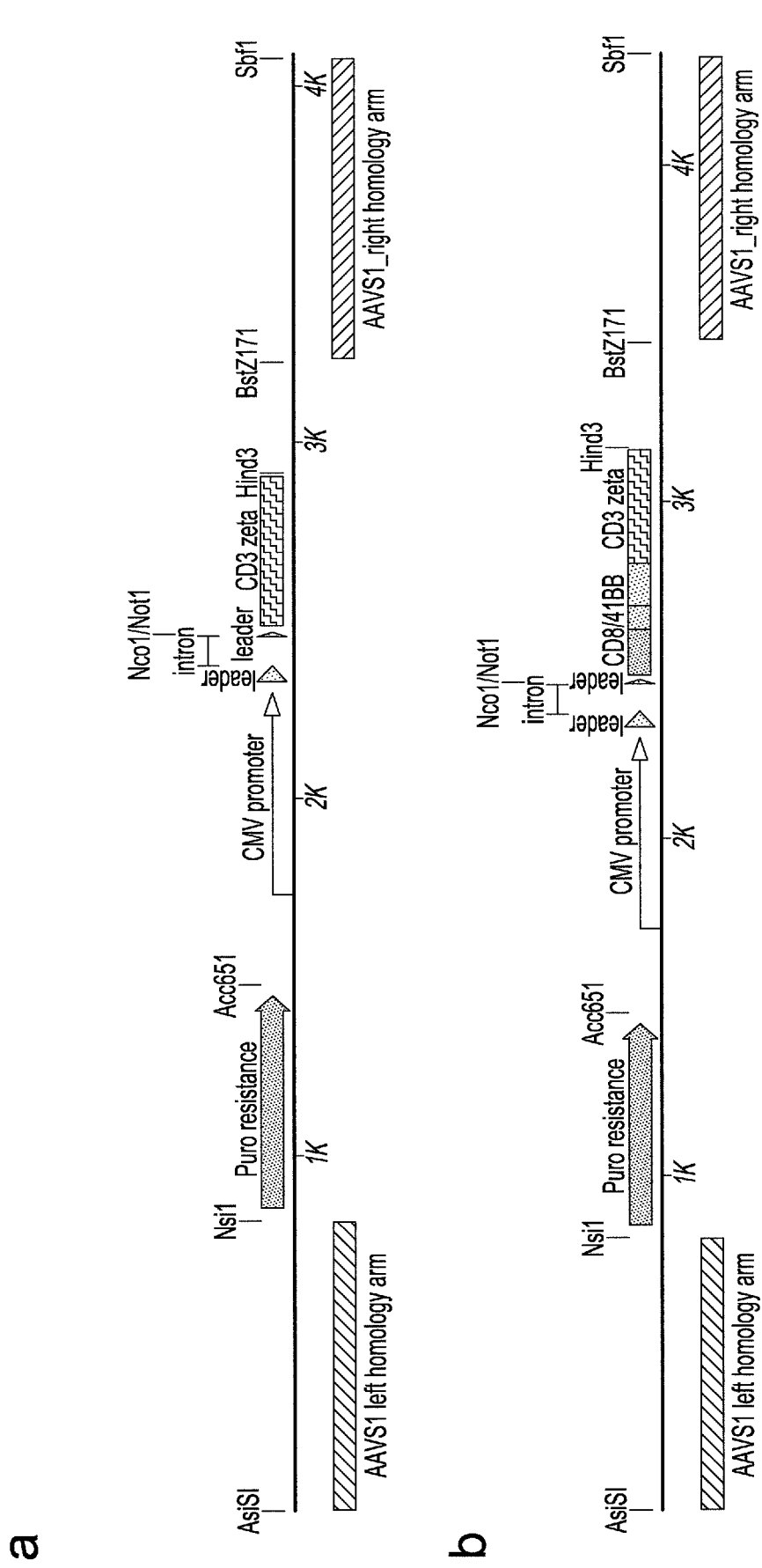

FIG. 27. pINT21 CAR1 and pINT21 CAR2 vectors for introduction of Chimeric Antigen Receptor (CAR) libraries into human cells.

Representation of the single promoter plasmid pINT21 showing AAVS homology arms, puromycin selectable gene, CMV promoter driving fusion of binder to CD3ζ signalling domain. Nco1 and Not 1 sites are sued for cloning the binder.
  a. pINT21 CAR1 fuses the binder to the juxtamembrane, transmembrane and signalling domain of CD3ζ.
  b. pINT21 CAR2 fuses the binder to CD8 hinge and transmembrane domain, 4-1 BB and CD3ζ activation domains
  c. Sequence of CD3ζ in pINT 21_CAR1 (SEQ ID NO: 42, 43 & 44)
  d. Sequence of CD8, 4-1 BB and CD3ζ in pINT 21_CAR2 (SEQ ID NO: 45 & 46)
  e. Sequence of FMC63 H-L (anti CD19 antibody) (SEQ ID NO: 47 & 48)

Figure 28:
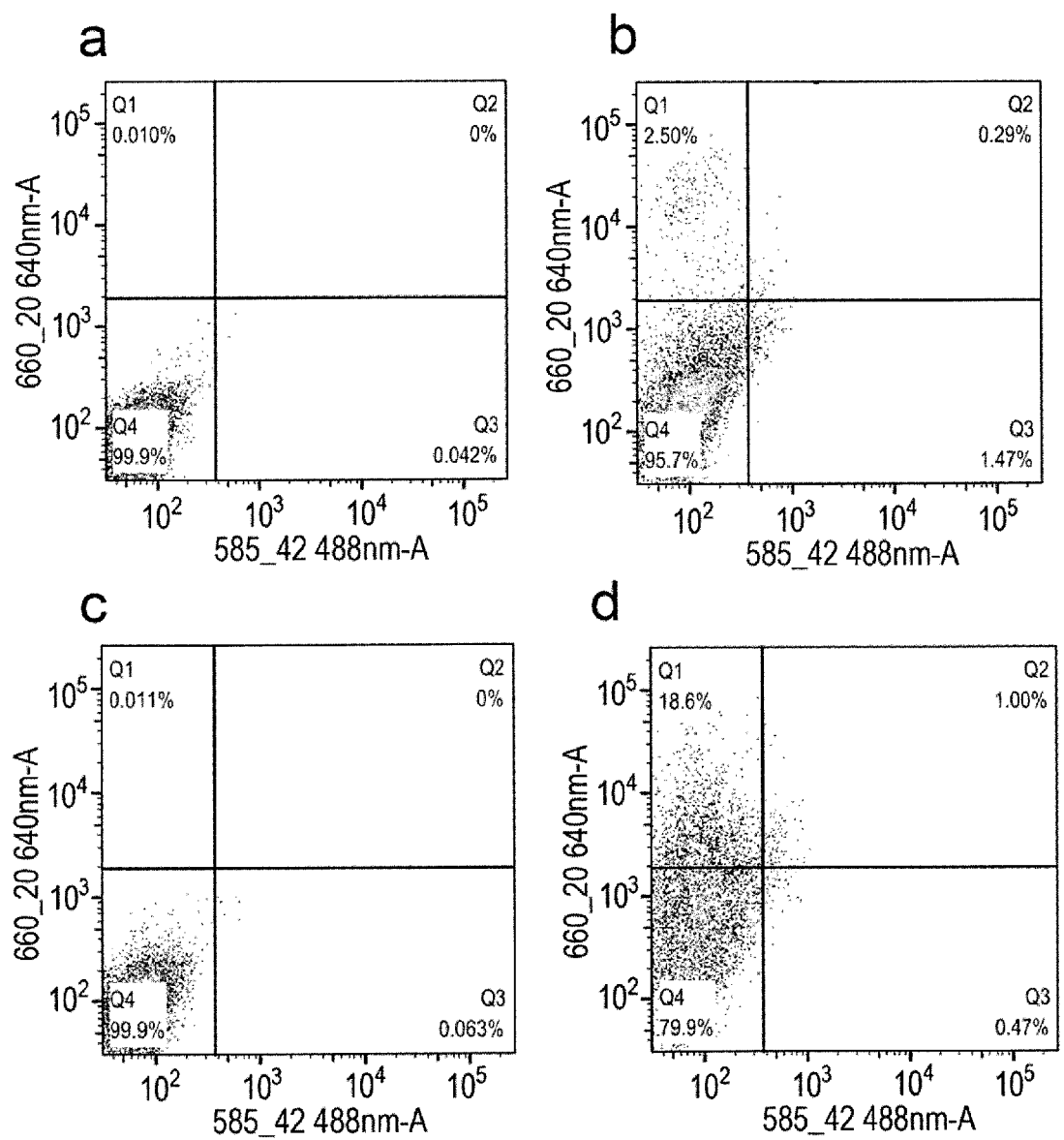
Figure 28:
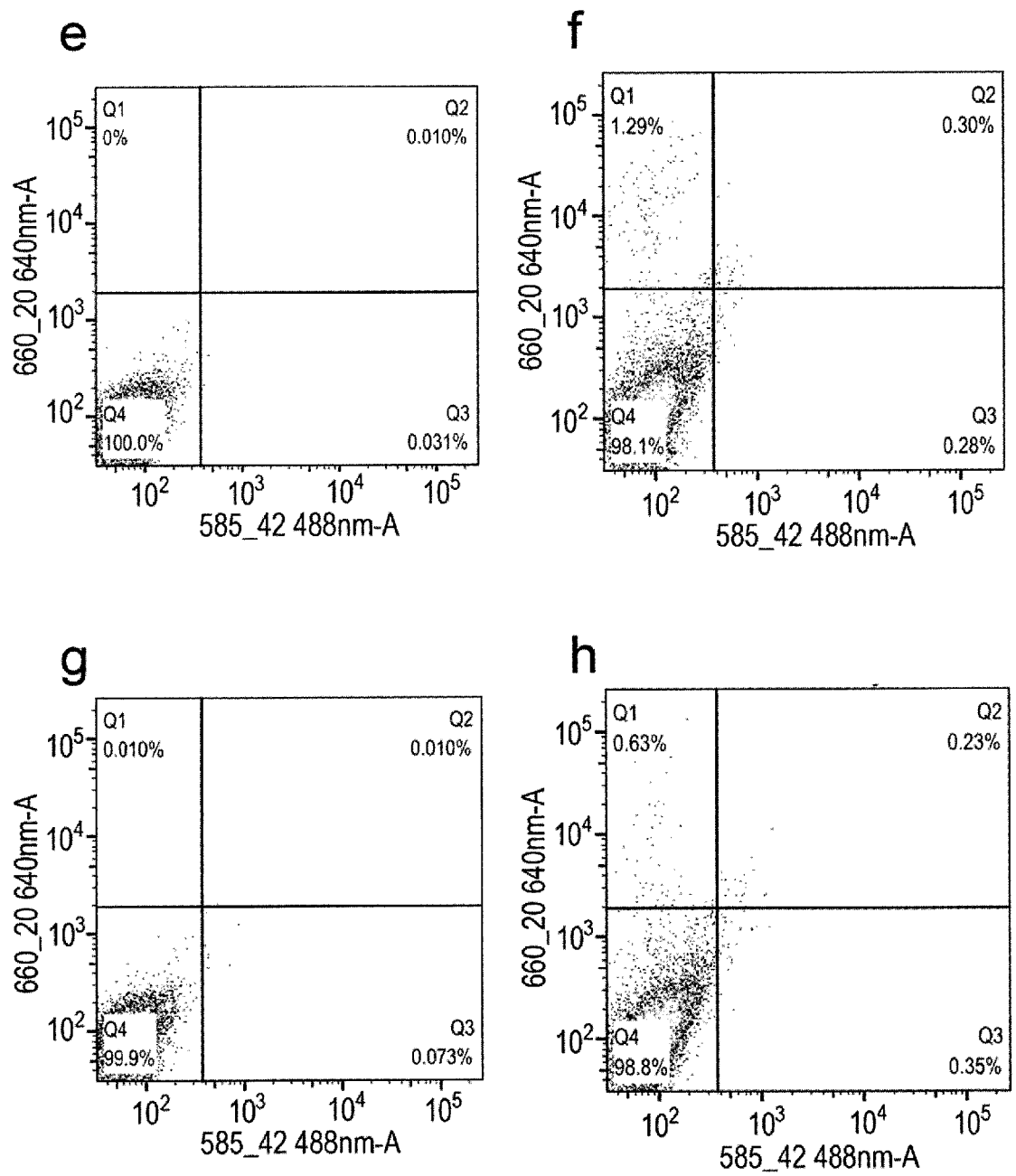

FIG. 28 Expression of scFv and alternative scaffold within chimeric antigen receptor construct introduced into human cells by nuclease-mediated integration.

HEK cells were transfected with anti-FGFR1 antibodies (b) or lox1 adhiron (c) and labelled with labelled FGFR1 and lox1 respectively. As control the same antigens were incubated with non-transfected HEK293 cells (a and c respectively).

Populations from phage display libraries selected on mesothelin and CD229 were introduced into HEK cells by nuclease-mediated integration (f and h respectively) and were selected in puromycin for 11 days. These cells or untransfected HEK293 cells were incubated with labelled mesothelin (e, f) or CD229 (g, h). e and h represent untransfected HEK293 cells.

FIG. 29. Sequence of alternative binder scaffolds for mammalian display Libraries of different binder formats can easily be introduced by nuclease-directed integration using vector described herein. By example Adhiron constructs were prepared with flanking Nco1 and Not 1 sites for introduction into CAR constructs or Fc fusion constructs.
  a. Sequence of lox1 binding Adhiron_lox1A (SEQ ID NO: 49 & 50)
  b. Sequence of lox1 binding Adhiron_lox1B (SEQ ID NO: 51 & 52)
  (Variable loops are shown emboldened and underlined on the protein sequence).
  c. Potential mutagenic primers for construction of library of binders within loop 1 (adhiron mut1) (SEQ ID NO: 53, 55 & 56) or loop 2 (adhiron mut2) (SEQ ID NO: 54, 57 & 58),
  Below is a representation of the region covered by the primers (lower strand) showing protein translation. n represents variable number of NNS codons giving rise to different loop lengths.
  d. Sequence of trypsin binding knottin MCoTI-II with flanking Nco1 and Not1 sites allowing knottin expression within vectors described herein. Sequence of first loop is underlined SEQ ID NO: 59 & 60).
  e. Strategy for creation of library of knottin mutants. In this example loop 1 is replaced by 10 randomised amino acids. In this example VNS codons are introduced (V=A, C or G) providing 24 codons encoding 17 amino acids. This sequence can be introduced into a clone encoding MCoTI-II using standard methods (SEQ ID NO: 61, 62 & 63).

FIG. 30. Example sequences for Nuclease mediated antibody gene insertion by ligation or microhomology-mediated end-joining (MMEJ).
  a. Sequence of pD7-Sce1 (nucleotides 1-120) (SEQ ID NO: 64, 65). The sequence is as pD6 (see FIG. 3c, 8) except the AAVS left arm between EcoR1 and Nsi1 has been replaced by the I-Sce1 meganuclease recognition (bold). Also the AAVS right arm between Asc1 and Mlu1 has been replaced by an insert encoded by primers 2723 and 2734 (not shown).
  b. Sequence of pD7-ObLiGaRe (nucleotides 1-120) (SEQ ID NO: 66, 67). The sequence is as pD6 (see FIG. 3c, 8) except the AAVS left arm between EcoR1 and Nsi1 has been replaced by the AAVS TALE right and left arm recognitions sites. Also the AAVS right arm between Asc1 and Mlu1 has been replaced by an insert encoded by primers 2723 and 2734 (not shown).

FIG. 31. Nuclease directed integration of binders into the ROSA 26 locus.
  a. Shows sequence of left homology arm up to the beginning of the puromycin gene showing primers and restriction sites mentioned in example 22 (SEQ ID NO: 68).
  b. Sequence of right homology arm for nuclease directed integration into the ROSA 26 locus showing primers and restriction sites mentioned in example 22 (SEQ ID NO: 69).

EXAMPLES

Example 1. Construction of Vectors for Expression of IgG Formatted Antibodies

To effect genetic selections of binders (e.g. antibody, protein or peptide) it is necessary to introduce a gene encoding this binder and to drive expression of this gene from an exogenous promoter, or by directing integration of the transgene downstream of a promoter pre-existing in the cellular DNA, e.g., an endogenous promoter. Antibodies represent the most commonly used class of binders and they can be formatted for expression in different forms. In examples below, we describe expression of a single gene format where a scFv is fused to a Fc domain (scFv-Fc). We also exemplify expression of antibodies formatted as human IgG2 molecules. To express IgG or FAb formatted antibodies in producer cells such as higher eukaryotes, it is necessary to express the separate heavy and light chains. This can be done by introducing separate plasmids encoding each chain or by introducing them on a single plasmid. Within a single plasmid the 2 chains can be expressed from a multicistronic single mRNA. Expression of distinct proteins from a single message requires elements such as an Internal Ribosome Entry (IRE) sequences which enables translation to initiate at a secondary downstream location. Alternatively, sequence elements promoting stalling/re-initation of translation such as viral 2A sequences could be used [119].

Figure 1:
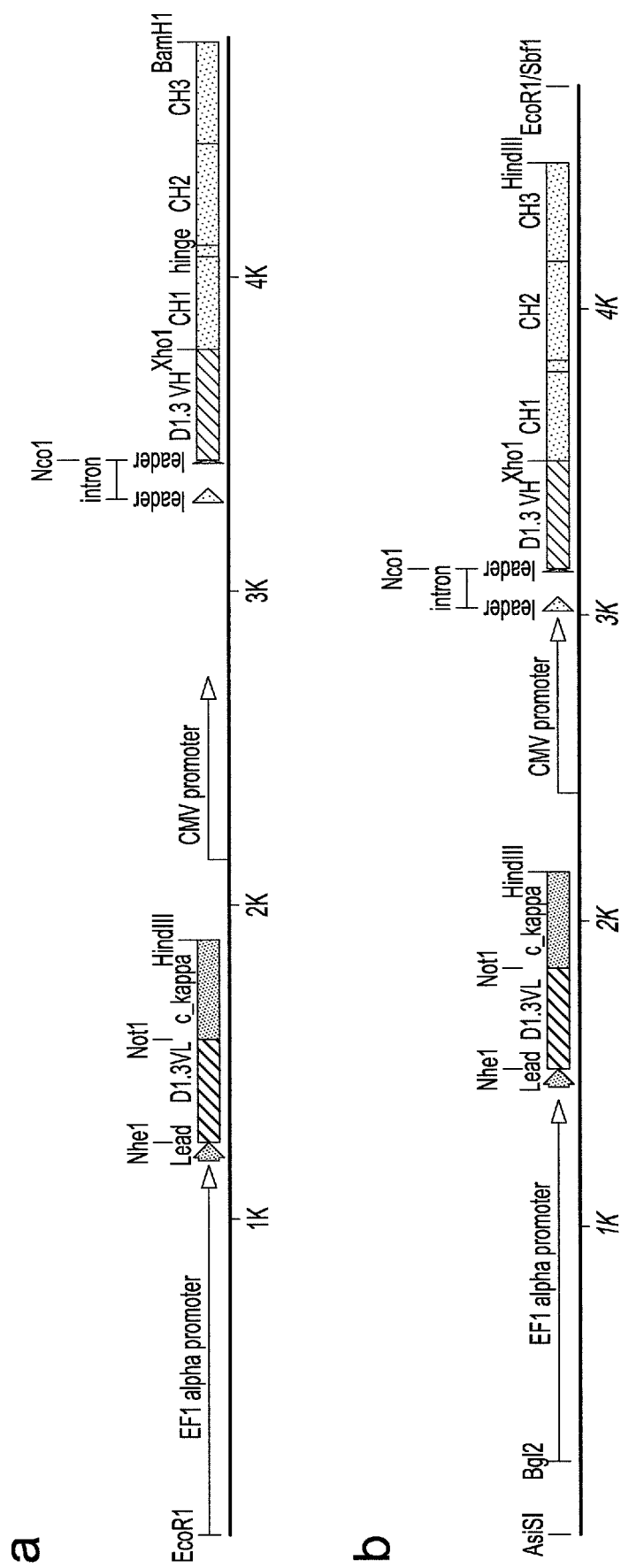
FIG. 1. Vector for expression of IgG formatted antibodies
a. pDUAL D1.3, a dual promoter expression vector for IgG secretion (in in "pCMV/myc/ER" vector backbone)
b. pINT3-D1.3, a dual promoter expression vector for IgG secretion (in "pSF-CMV-f1-Pac1" vector backbone)
c. pCMV/myc/ER vector backbone. ECoR1 site precedes CMV promoter. BstB1 and BstZ171 sites flank the SV40 poly A sites.
d. pSF-CMV-f1-Pac1 vector backbone (Oxford Genetics)
e. synthetic gene with exon encoding PDGFR transmembrane region (TM) and exon causing secretion (sec). Solid arrows represent Rox recombination sites.
Figure 1:
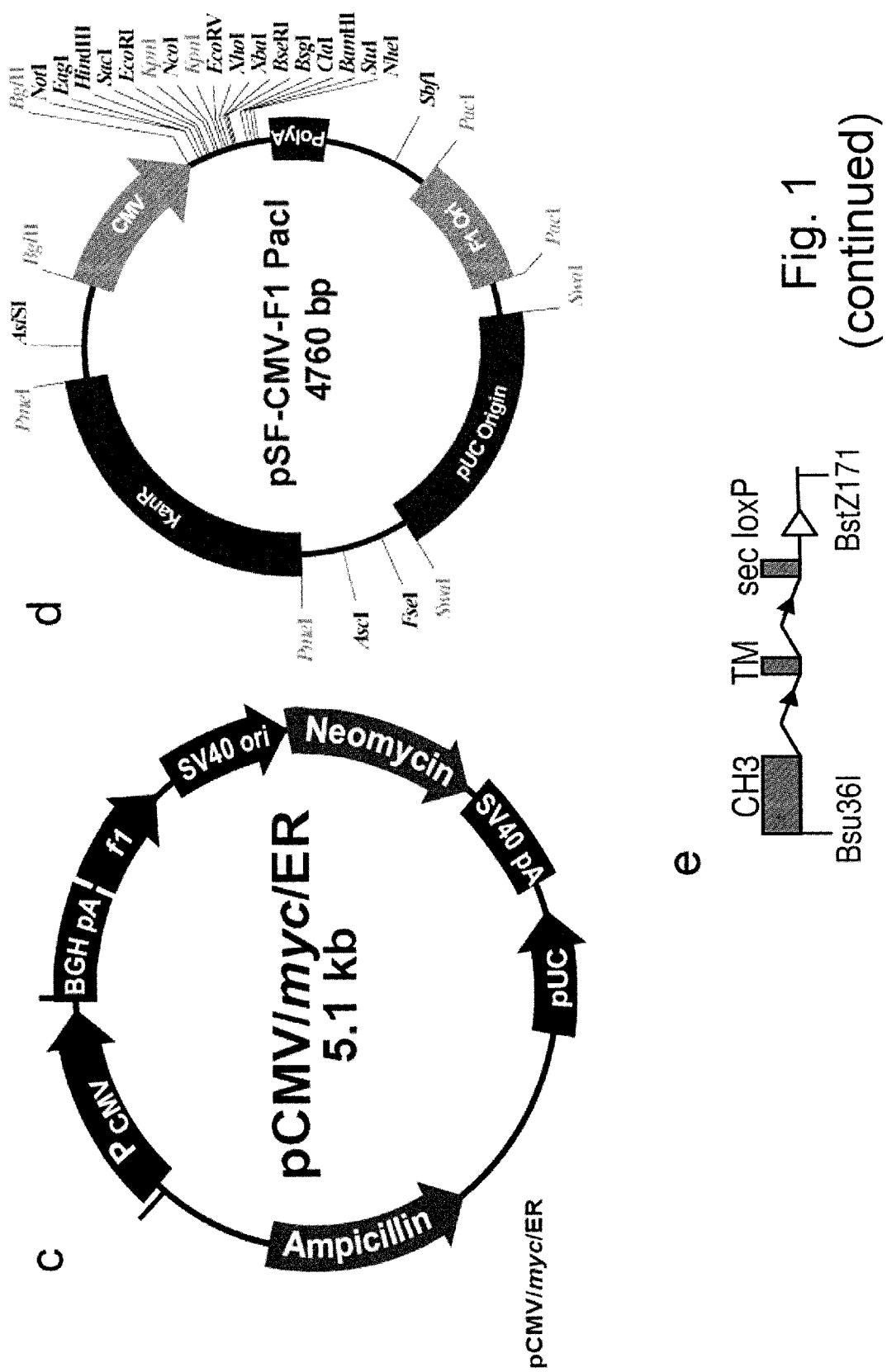

Alternatively, multiple distinct proteins can be expressed from a single plasmid using multiple promoters. FIGS. 1a and 1b show the organisation of 2 similar expression cassettes within different vector backbones (pDUAL and pINT3) which were developed for expression of secreted IgG formatted antibodies. These expression cassettes were created using a combination of gene synthesis and polymerase chain reaction amplification of standard elements such as promoters and poly A sequences. First separate plasmids were created within pCMV/myc/ER (FIG. 1c, Life Technologies) for expression of antibody heavy chain (pBIOCAM1-NewNot) and light chain (pBIOCAM2-pEF). The elements from pBIOCAM2-pEF (including pEF promoter, light chain gene and poly A site) were cloned into pBIOCAM1-NewNot to create pDUAL. The examples shown include VH and VL domains from a humanised anti-lysozyme antibody called D1.3 [120] and are referred to as pDUAL-D1.3 and pINT3-D1.3. The elements of pDUAL D1.3 represented in FIG. 1a are present between the EcoR1 and BGH polyA site of the plasmid backbone from pCMV/myc/ER (Life Technologies Cat V82320 FIG. 1c).

In a similar way separate light chain and heavy chain cassettes were introduced into pSF-pEF (Oxford Genetics OG43) and pSF-CMV-F1-Pac1 (Oxford Genetics OG111) respectively to create pINT1 and pINT2. These were combined by cloning the light chain cassette (including pEF promoter, light chain gene and poly A site) upstream of the CMV promoter in pINT2, to create pINT3. The elements of pINT3-D1.3 represented in FIG. 1b are cloned between the first Bgl2 and the Sbf1 represented within the plasmid pSF-CMV-F1-Pac1 (FIG. 1d, Oxford Genetics OG111).

The immediate early promoter of cytomegalovirus (CMV promoter) is a powerful promoter and was used to drive expression of heavy chains. pDUAL D1.3 also incorporates an adenovirus 2 tripartite leader (TPL) and enhanced major late promoter (enh MLP) immediately downstream of the CMV promoter [121]. Elongation factor-1 alpha protein is ubiquitously and abundantly expressed in most eukaryotic cells and its promoter (pEF promoter) is commonly used for driving transgene expression [122]. In pDUAL-D1.3 and pINT3-D1.3 the pEF promoter is used to drive antibody light chain expression. The polyadenylation sites originating in bovine growth hormone (BGH polyA) is present at the end of each expression cassette.

Secretion of the separate heavy and light chains in the endoplasmic reticulum (and ultimately culture supernatant) is directed by 2 different leader sequences. Light chain secretion is directed by a BM40 leader sequence [123]. This is followed by Nhe1 and Not1 cloning sites which allow in-frame cloning of VL genes which are in turn fused to a human C kappa gene. Secretion of the heavy chain is directed by a leader split by an intron originating from a mouse VH gene (as found in pCMV/myc/ER). The leader is followed by Nco1 and Xho1 sites allowing in frame cloning of antibody VH genes followed by a codon optimised IgG2 gene. The VL and VH genes of the humanised D1.3 antibody [120] were cloned into the Nhe1/Not1 and Nco1/Xho1 sites respectively within pDUAL-D1.3 and pINT3-D1.3.

Membrane anchored versions of these plasmids were created for mammalian display. Plasmid pD1 was created by digesting pDUAL-D1.3 with Bsu361 (which cuts in CH3 domain of the IgG2 heavy chain gene) and with BstZ171, which cuts in the backbone after the SV40 poly A region of the neomycin resistance cassette (FIG. 1c). This therefore removes most of the CH3 domain and the entire neomycin expression cassette. The CH3 domain is replaced by a synthetic insert with compatible Bsu361 and BstZ171 ends (represented in FIG. 1e). The synthetic insert was designed to replace the stop codon at the end of the antibody CH3 domain with a splice donor and intron which causes splicing of the CH3 terminus to an exon encoding the human PDGF receptor transmembrane domain [84] the first 5 intracellular residues, a stop codon and an additional splice donor. This is followed by an additional intron and splice acceptor followed by a codon for single amino acid then a stop codon (FIG. 1e). The 2 synthetic introns which flank the exon encoding the transmembrane domain were designed with ROX recognition sites located within them. ROX sites are recognized by Dre recombinase causing recombination between DNA containing these sites [88]. Inclusion of 2 ROX sites flanking the transmembrane domain-encoding exon creates the potential to remove this exon by the transfection of a gene encoding Rox recombinase. This would be anticipated to create a secreted antibody product.

FIG. 2 shows the sequence of the resulting dual promoter antibody expression plasmid expressing a humanised D1.3 anti-lysozyme antibody (hereafter referred to as pD1-D1.3 (SEQ ID NO: 1). Anti-lysozyme binding specificity is incorporated through inclusion of VH and VL sequences from D1.3 [120] between Nco/Xho1 and Nhe1/Not1 restriction sites respectively. The sequence is shown from the ECoR1 site to the BstZ171. The sequences beyond the ECoR1 and BstZ171 sites are from the vector backbone as represented in FIG. 1c.

Example 2. Construction of Vector (pD2) for Targeting an Antibody Cassette to the AAVS Locus Cleavage within the genome using site-specific nucleases facilitates the insertion of heterologous DNA through homologous recombination or non-homologous end joining (NHEJ). Human HEK293 cells were cleaved with nucleases targeting the first intron of the protein phosphatase 1, regulatory subunit 12C (PPP1R12C) gene. This locus was identified as a common integration site of adeno-associated virus and is referred to as the AAVS site (FIG. 3a). The AAVS site is considered a "safe harbour" locus for insertion and expression of heterologous genes in human cells [124].

Following site-specific cleavage within the genome it is possible to promote integration of a protein expressing cassette using homologous recombination. To do this it is necessary to flank the expression cassette with regions homologous to the sequences found on either side of the genomic cleavage site. To direct integration into the AAVS locus, an 804 bp section of the AAVS locus 5' to the intended cleavage site, was PCR amplified to create an EcoR1 and an Mfe 1 site at the 5' and 3' end respectively. This product, representing the left homology arm for targeting the antibody cassette, was cloned into the EcoR1 site of pD1 recreating the EcoR1 site at the 5' end. For the right homology arm an 836 bp section of the AAVS locus, 3' of the cleavage site, was PCR amplified to create Bstz171 sites at each terminus and this was cloned into the Bstz171 of pD1. The construct is represented in FIG. 3b and the sequence of the resulting construct (pD2) is shown in FIG. 3c.

During cloning of the AAVS left homology arm Nsi1 and Pac1 restriction sites were also inserted at the 3' end. These sites were subsequently used to clone a synthetic intron followed by a blasticidin gene with an accompanying poly A site. The blasticidin gene lacks a promoter but is preceded by a splice acceptor site that creates an in-frame fusion with the upstream exon from the AAVS locus (FIG. 3a, b). Integration into the AAVS locus causes expression of the promoter-less blasticidin gene. The sequence of this final construct, called pD2, is shown in FIG. 3c.

The sequence of the antibody cassette, encompassing the pEF promoter, D1.3 light chain, poly A region, CMV promoter, D1.3 heavy chain, alternative splice sites and poly A site, is shown in FIG. 2. To avoid duplication this sequence is represented in FIG. 3c as a block labelled "D1.3 ANTIBODY EXPRESSION CASSETTE".

Example 3. AAVS TALEN-Directed Integration of IgG Construct for Cell Surface Antibody Expression and Antigen Binding HEK293F cells (Life Technologies), grown in Freestyle medium were transfected with pD2-D1.3 DNA in the presence or absence of an AAVS directed TALEN vector pair. An AAVS TALEN pair ("AAVS original") was previously described [125] and recognises the sequence:

```
LEFT TALEN:
                                         (SEQ ID NO: 70)
5' (T)CCCCTCCACCCCACAGT

Spacer
                                         (SEQ ID NO: 71)
5' GGGGCCACTAGGGAC Right TALEN: complement of
                                         (SEQ ID NO: 72)
5' AGGATTGGTGACAGAAAA (i.e. 5' TTTTCTGTCACCAATCCT (SEQ ID NO: 73)
```

An alternative, more efficient AAVS targeted TALEN pair was identified and used in later experiments (pZT-AAVS1 L1 TALE-N and pZT-AAVS1 R1 TALE, Cat No GE601A-1 System Biosciences). This pair, which recognises the same site (but not the first "T" residue shown in brackets above), are referred to as the "AAVS-SBI" TALEN pair.

Cells were seeded at $0.5 \times 10^6$ cells/ml and transfected next day at $10^6$ cells/ml using DNA:polyethylene imine (PolyPlus) added at a ratio of 1:2 (w/w). Cells were transfected with 0.6 µg/ml of pD2 and were co-transfected with either pcDNA3.0 as a control (0.6 µg/ml) or the combined left and right "original AAVS" TALEN plasmids (0.3 µg each/ml). pD3 which expresses EGFP from the CMV promoter (see below) was included in the experiment as a transfection control and showed 35% transfection efficiency. Cells were selected in suspension culture using Freestyle medium (Life Technology) supplemented with 5 ug/ml blasticidin.

To determine whether antibody expression had occurred on the cell surface, cells were stained with an anti-human Fc antibody according to the following protocol:

1. 16 days after transfection, $0.5-1 \times 10^6$ cells from the populations selected with Blasticidin were centrifuged for 2 minutes (200-300×g) at 4° C.
2. Wash cells with 1 ml wash buffer (0.1% BSA in PBS Gibco #10010) and spin cells for 2 minutes (200-300×g) at 4° C.
3. Resuspend cells in 100 µl staining buffer (1% BSA in PBS) and add 5-10 ul of fluorochrome—conjugated antibodies. Antibodies were phycoerythrin-labelled anti-human IgG Fc (clone HP6017, Cat. No. 409304, Biolegend) or phycoerythrin-labelled mouse IgG2a, κ isotype control (Cat. No. 400214, Biolegend). Incubate for >30 min at 4° C. in the dark.
4. Wash twice with 1 ml wash buffer and resuspend in 500 ul wash buffer.
5. Add 5 ul of cell viability staining solution (#00-6993-50 eBioscience) containing 50 ug/ml 7-amino-actinomycin D (7-AAD) to identify dead cells.
6. Cells were analysed on a (Beckton Dickinson FACS II) flow cytometer.

FIG. 4 shows that there was a significantly higher population of antibody expressing cells when pD2-D1.3 is transfected in the presence of the AAVS targeted TALEN with 86% positive compared with pD2-D1.3 alone with 1.5% positive.

The functionality of the surface expressed anti-lysozyme antibody was determined by assessing binding to labelled antigen. Hen egg lysozyme (Sigma: L6876) was labelled using Lightning-Link Rapid conjugation system (Dylight 488, Innova Biosciences: 322-0010) as follows:

1. Add 10 ul LL-Rapid Modifier reagent to 100 ul lysozyme (200 ug dissolved in 100 ul PBS) and mix gently.
2. Add the mix to Lightning-Link® Rapid mix and resuspend gently by pipetting up and down.
3. Incubate the mix for 15-30 minutes in the dark at room temperature.
4. Add 10 ul LL-Rapid Quencher reagent to the reaction and mix gently.
5. Store at 4° C. Final concentration of lysosyme-Dy488 is 1.6 µg/µl.
6. Use 6 ul lysosyme-Dy488 (~10 ug) per staining.
7. Staining, washing and flow cytometry was as described above.

Analysis shows that 86% of cells transfected with pD2-huD1.3 bound labelled HEL (as judged by the M1 gate) compared with 0.29% for un-transfected cells (FIG. 5).

Example 4. Site-Specific Nucleases (AAVS Directed TALENs) Enhance Donor DNA Integration Transfected cells were also plated out and selected with blasticidin to determine the number of cells in which expression of the promoterless blasticidin gene was activated. 24 hours after transfection cells were plated at $0.25 \times 10^6$ cells/10 cm petri dish (tissue culture treated) and were grown in 10% foetal bovine serum ($10270-10^6$, Gibco) and 1% Minimal Essential medium non-essential amino acid (MEM_NEAA #11140-035 Life Technologies). 5 ug/ml blasticidin was added after another 24 hours and medium was changed every 2 days. After 9 days cells which did not receive pD2 plasmid were all dead. After 12 days plates were stained with 2% methylene blue (in 50% methanol). Colony density was too high for accurate quantitation but showed an increased number of blasticidin resistant colonies in the presence of the AAVS TALENs suggesting targeted integration into the AAVS locus. A reduced amount of DNA was introduced for more accurate quantitation.

Transfections were carried out as described earlier using either 50, 200 or 400 ng pD2-D1.3/$10^6$ cells in presence or absence of the AAVS TALENs (0.3 ug/ml of each TALEN where present, Table 1A). The total DNA input was adjusted to 1.2 ug DNA per $10^6$ cells with control plasmid pcDNA3.0. After 24 hrs of transfection, $0.25 \times 10^6$ cells were plated in a 10 cm dish and 7.5 ug/ml blasticidin was added after 24 hrs of plating. 10 days after blasticidin selection the colonies are stained with 2% methylene blue (in 50% methanol). Results are shown in FIG. 6 and summarised in Table 1A. This shows that co-transfection of DNA encoding AAVS-directed TALENs increases the number of blasticidin resistant colonies achieved by approximately 10 fold.

A comparison was carried out between "AAVS original" and the "AAVS SBI" TALEN pairs targeting the AAVS locus. Table 1B shows an increased number of blasticidin resistant colonies using the "AAVS SBI" TALEN pair.

Table 1. Quantitation of blasticidin-resistant colonies from transfection of pD2-D1.3

A.

| Enzyme plasmid | pD2-D1.3 donor (ng/10$^6$ cells) | With AAVS TALEN | Without AAVS TALEN |
|---|---|---|---|
| AAVS original | 50 | 319 | 32 |
| AAVS original | 200 | 526 | 41 |
| AAVS original | 400 | 686 | 75 |

B.

| Enzyme plasmid | pD2-D1.3 donor (ng/10$^6$ cells) | With AAVS TALEN | Without AAVS TALEN (Control pcDNA3.0) |
|---|---|---|---|
| AAVS original | 300 | 1420 | 111 |
| AAVS original | 1000 | 1080 | 127 |
| AAVS original | 3000 | 560 | 70 |
| AAVS-SBI | 300 | 2800 | 111 |
| AAVS-SBI | 1000 | 1630 | 127 |
| AAVS-SBI | 3000 | 870 | 70 |

Here we have compared the effect of TALEN nuclease addition using either cell surface antibody expression (Example 3) or activation of a promoter-less blasticidin gene (Example 4). The benefit of nuclease-directed integration is more obvious when measuring antibody expression compared to effect on blasticidin-resistant colonies. One likely explanation is that the levels of expression required to effect survival in the presence of blasticidin may be significantly less than the expression levels required to detect IgG2 expression on the surface. Thus misincorporation/splicing of the promoter-less blasticidin gene could lead to a low level expression of the blasticidin resistance gene causing a higher background of blasticidin resistant colonies in the absence of significant antibody expression.

Example 5. Determination of Accuracy of Integration Using AAVS TALEN

To investigate the accuracy of integration, colonies were picked from the experiment in Example 4/Table 1A (from duplicate, unstained plates), expanded and genomic DNA from these cells was used as template in PCR. For preparation of genomic DNA, cells were harvested and were re-suspended in 700 μL of lysis buffer (10 mM Tris.Cl, pH=8.0, 50 mM EDTA, 200 mM NaCl, 0.5% SDS, supplemented with 0.5 mg/mL of Proteinase K (added just before lysis). The cell re-suspension in lysis buffer was then transferred to a microfuge tube and kept at 60° C. for about 18 hours. Next day, 700 μL of isopropanol was added to the lysate in order to precipitate genomic DNA. The microfuge tube was spun at 13,000 rpm for 20 minutes. The genomic DNA pellet was then washed with 70% ethanol, and spun at 13,000 rpm for another 10 minutes. After spinning, the supernatant was carefully separated taking care not to touch the genomic DNA pellet. The genomic DNA pellet was then re-suspended in 100 μL buffer containing 10 mM Tris (pH 8.0), and 1 mM EDTA and kept at 60° C. for 30 minutes keeping the lid open in order to get rid of traces of ethanol. To this 100 μL solution, RNAse A was added (final concentration of 20 μg/mL), and incubated at 60° C. for about one hour. Genomic DNA concentration was measured using nanodrop spectrophotometer (Nanodrop).

To identify correct integration, PCR primers were designed which hybridise in the AAVS genomic locus beyond the left and right homology arms. These were paired up with insert specific primers. At the 5' end the primers were:

```
AAVS-Left-arm-junction-PCR-Forw (9625)
                                      (SEQ ID NO: 74)
5' CCGGAACTCTGCCCTCTAAC BSD_Junction PCR-rev (9626):
                                      (SEQ ID NO: 75)
5' TAGCCACAGAATAGTCTTCGGAG
```

These give a product of 1.1 kb where correct integration occurs. 8/9 clones arising from AAVS directed integration gave a band of correct size (FIG. 7a, b). 2 blasticidin resistant clones derived without TALENs did not give a product (FIG. 11a) indicative of random integration. At the 3' end primers were:

```
Donor_plasmid_seq_PDGFRTM-2 Forw
                                      (SEQ ID NO: 76)
5' ACACGCAGGAGGCCATCGTGG AAVS1_right arm_junction_PCR_rev
                                      (SEQ ID NO: 77)
5' TCCTGGGATACCCCGAAGAG
```

These give a product of 1.5 kb with correct integration. 7/9 clones arising from AAVS directed integration gave a band of correct size. 2 blasticidin resistant clones derived without TALENs did not give a product (FIG. 11b). Thus the majority of blasticidin resistant cells arise from correct integration into the AAVS locus whereas blasticidin resistant colonies arising in the absence of TALENs are not correctly integrated.

Example 6. Construction of an scFv Display Library from a Selected Population from Phage Display and Selection Via Mammalian Display scFv formatted soluble antibodies have previously been expressed from the vector pBIOCAM5-3F where expression is driven by the CMV promoter and the vector provides a C-terminal fusion partner, consisting of human Fc, His6 and 3xFLAG, to the antibody gene [105, 126]. This was modified to create the vector pBIOCAM5newNot where the Not1 site was embedded within the Fc region of the antibody (as shown in FIG. 8). This was used as a starting point to create the vector pD6 (FIG. 8) for expression of scFv-Fc fusions tethered to the cell surface. Primers (2598 and 2619) were designed to allow amplification of the CMV promoter-scFv-Fc expression cassette from pBIOCAM5newNotPrimer 2598 hybridises upstream of the CMV promoter and places a PacI site (underlined) at the end.

```
2598:
                                      (SEQ ID NO: 78)
TTTTTTTTAATTAA GATTATTGACTAGTTATTAATAGTAATCAATTACG
GGGTC
```

Primer 2619 hybridises near the end of the Fc domain and introduces a slice donor site and Pme1 site (underlined) at the beginning of the intron.

2619:
(SEQ ID NO: 79)
TTTTTTGTTTAAACTTACCTTGGATCCCTTGCCGGGGCTCAGGCTCAGGG
AC

The resulting PCR product is compatible with the Pac1 and Pme1 sites of pD2 (FIG. 3).

Digestion of pD2 with Pac1 and Pme1 removes: pEF promoter-leader-light chain-CMV promoter-leader-heavy chain Cloning of the Pac1/Pme1 cut PCR product insets: CMV promoter-leader-Nco1/Not1 sites-human Fc.

Cloning in this way positions the scFv-Fc cassette appropriately for splicing to the downstream trans-membrane domain previously described for IgG presentation on the cell surface in pD2. The final vector pD6 is shown in FIG. 8, the sequence of D6 from Nco1 to Pme1 sites is shown.

Phage display selections were carried out using the McCafferty phage display library [7] using beta-galactosidase (Rockland, Cat B000-17) and CD229 (R and D Systems, Cat 898-CD-050) as antigens. Methods for selection and sub-cloning were essentially as described previously [6, 7, 118, 127]. scFv genes from populations arising from one or two rounds of selection on beta-galactosidase and two rounds of selection on CD229 were recovered by PCR. Primers M13Leadseq hybridises within the bacterial leader sequence preceding the scFv gene and Notmycseq hybridises in the myc tag following the scFv gene in the phage display vector [127].

M13Leadseq
(SEQ ID NO: 80)
AAA TTA TTA TTC GCA ATT CCT TTG GTT GTT CCT

Notmycseq
(SEQ ID NO: 81)
GGC CCC ATT CAG ATC CTC TTC TGA GAT GAG

PCR product was digested with Nco1 and Not1, the digested insert was gel purified. The digested product was ligated into the Nco1 and Not 1 sites of the bacterial expression plasmid pSANG10-3F and antibody expressed and screened as described [127]. After 2 rounds of selection on beta-galactosidase and CD229, 40/190 (21%) and 35/190 (18%) clones were found to be positive by ELISA.

550 ng of Nco/Not cut insert was also ligated into the Nco1 and Not 1 sites of pD6 (2.4 µg) to create a construct expressing a fusion between the scFv and the Fc region of human IgG2. Ligated DNA was transformed into electrocompetent NEB5alpha cells (New England Biolabs, Cat C2989) which generated a library size of 2-3×10⁷ clones for each population. DNA was prepared and was co-transfected into 100 mls HEK293 cells grown in Freestyle medium as described above using 0.3 µg donor DNA (pD6-library) per $10^6$ cells. Cells were co-transfected with 0.5 µg each of "AAVS-SBI" TALENs (pZT-AAVS1 L1 TALE-N and pZT-AAVS1 R1 TALE, Cat No GE601A-1 System Biosciences).

24 hours after transfection the volume of the bulk culture was doubled and 24 hours later blasticidin (10 µg/ml) was added. Medium was refreshed every 3-4 days and after 6 days blasticidin concentration was increased to 20 µg/ml.

In order to determine the library size, 20,000 cells were plated in a 10 cm petri dish (tissue culture treated) 24 hours after transfection and were grown in 10% foetal bovine serum (10270-106, Gibco) and 1% Minimal Essential medium non-essential amino acid (MEM_NEAA #11140-035 Life Technologies). 10 µg/ml blasticidin was added after another 24 hours and medium was changed every 2 days. After 8 days plates were stained with 2% methylene blue (in 50% methanol). Results are shown in Table 2. This shows that libraries of around 3×10⁶ clones (representing 3% of transfected cells) were obtained for the 3 populations.

TABLE 2

Determination of scFv-Fc library size.

| Sample | No colonies/ 20,000 cells | No colonies/ $10^6$ cells | Library size |
| --- | --- | --- | --- |
| β-galactosidase Rd1 | 546 | 27,300 | 2.7 × 10⁶ |
| β-galactosidase Rd2 | 654 | 32,700 | 3.2 × 10⁶ |
| CD229 Rd2 | 556 | 27,800 | 2.8 × 10⁶ |

The protocol for labelling and flow sorting 10-20×10⁶ cells is shown below. Initial analysis was carried out 13 days post-transfection using only $10^6$ cells/sample and with reduced incubation volumes (reagent volumes that are 1/10th of those shown).

FIG. 9 shows that at 13 days post-transfection at least 43-46% of cells express scFv-Fc fusion on the cell surface and this can be detected using either FITC or phycoerythrin-labelled anti-Fc antibodies. Binding of biotinylated beta-galactosidase is also detected within this population using either FITC or phycoerythrin-labelled streptavidin. Using streptavidin-FITC 11.8% and 39% of the cell were positive for both antibody expression and antigen binding using libraries derived from output populations arising from 1 or 2 rounds of phage display selection respectively. For CD229 derived from 2 rounds of phage display, 66% of cells were positive for scFv-Fc and 24% of these were positive for CD229 binding (15% of the total population).

At 20 days after transfection cells were labelled according to the protocol below (using biotinylated antigen/phycoerythrin-labelled streptavidin and FITC-labelled anti human Fc).

1. Harvest, wash and adjust cells in 15-20×10⁶ cells per sample. Spin down cells at 250 g for 4', RT, wash cells with 1 ml PBS+0.1% BSA (4° C.), spin down cells at 250 g for 4', RT, resuspend in 1 ml PBS+1% BSA
2. Add biotinylated antigen to a final conc. 100 nM and incubate 30' at 4° C.
3. Wash the cells 2 times 1 ml of 0.1% BSA by centrifugation at 1500 rpm for 5 minutes
4. Add either:
   10 µl of FITC-labelled streptavidin (1 µg/ml, Sigma Cat S3762) and 20 µl of phycoerythrin-labelled anti human Fc (200 µg/ml, BioLegend Cat. 409304), or:
   20 µl phycoerythrin-labelled streptavidin (200 µg/ml, Biolegend Cat 405203) and 20 µl of FITC-labelled anti human Fc (200 µg/ml, Biolegend Cat 409310) PBS+1% BSA, for 15 at 4° C. in the dark
5. Wash the cells 2 times 1 ml of 0.1% BSA by centrifugation at 1500 rpm for 5 minutes
6. resuspend them in 500 µl ice cold PBS+1% BSA
7. Add 20 ul of 7AAD/vial for viability staining For sorting cells were gated on the basis of cell size, granularity, pulse width and viability (via 7-AAD staining, forward scatter and side scatter. Results are shown in FIGS. 9c and f. In total 10 million cells were sorted and 3.1% and 7% of doubly positive cells were collected for libraries derived from output populations arising from 2 rounds of CD229 (CD229 R2) selection and 1 round of β-galactosidase selection (β-galR1) respectively.

Selected cells from the β-galR1-derived cells were grown for a further 20 days and re-analysed (FIG. 9h). This shows that the majority of cells now express scFv-Fc and bind β-galactosidase. This figure also shows that the proportion of double positive cells within the unselected population has not diminished 42 days after transfection (FIG. 9k).

Genomic DNA was prepared from 150,000-10$^6$ sorted cells. Genomic DNA was prepared using method described earlier or using a GenElute mammalian genomic DNA miniprep kit (Sigma G1N10).

scFv genes were PCR amplified from genomic DNA using the following primers:

```
2623
                                           (SEQ ID NO: 82)
TAAAGTAGGCGGTCTTGAGACG 2624
                                           (SEQ ID NO: 83)
GAAGGTGCTGTTGAACTGTTCC
```

PCR reactions were carried out using Phusion polymerase (NEB Cat M0532S) in manufacturer's buffer containing 0.3 uM of each primer and 3% DMSO. 100-1000 ng of genomic DNA was used as template in a 50 ul reaction. 30 cycles were carried out at 98° C. for 10 secs, 55° C. for 25 secs, 72° C. for 45 secs. This gave a product of 1.4 kB which was digested with Nco1 and Not1. A band of approximately 750-800 bp was generated and gel purified before cloning into pSANG10. Ligated DNA was transformed into BL21 cells (Edge Bio Ultra BL21 (DE3) competent cells, Cat. 45363). In this way scFv fragments derived from the sorted population can be expressed in bacteria as described previously [7, 127].

As an alternative to isolating the antibody gene and expressing in an alternative vector/host combination, it is possible to derive secreted antibody directly from the selected cells either following single cell cloning or using a sorted population to generate a polyclonal antibody mix. To exemplify this culture supernatant was taken from sorted cells (from βgalR1 cells) after 7 days in culture. This was shown to be positive in ELISA using plates coated with βgalactosidase (see Example 13 and FIG. 19b).

Example 7. Construction and Selection from an IgG Display Library from a Selected Population from Phage Display DNA fragments encoding scFv, representing the round 1 and 2 antibody phage display outputs of selections against β-galactosidase and CD229, were generated as described in Example 6. The scFv populations were converted to IgG format according to Example 14 and as detailed in the method below.

A DNA insert encoding the human kappa light chain constant domain ($C_L$), polyadenylation sequence (pA), CMV promoter and signal peptide from murine $V_H$ chain (represented between the Not1 and Nco1 sites of pD2 shown in FIG. 21b) was PCR amplified from plasmid pD2 with primers 2595 (GAGGGCTCTGGCAGCTAGC) (SEQ ID NO: 84) and 2597 (TCGAGACTGTGACGAGGCTG) (SEQ ID NO: 85). PCR reactions were carried out using KOD hot start polymerase (Novagen Cat 71086-4) in manufacturer's buffer containing 0.25 μM of each primer. 10 ng of pD2 plasmid DNA was used as template in a 50 ul reaction. 25 cycles were carried out at 98° C. for 10 secs, 55° C. for 25 secs, 72° C. for 40 secs. This gave a product of 1.8 kB which was digested with Nco1 and Not1 and gel purified (FIG. 20a represented as $C_L$-pA-CMV-SigP insert in FIG. 21b).

DNA fragments encoding scFv, representing the round 1 and 2 antibody phage display outputs of selections against β-galactosidase and CD229, were generated as described in Example 6. FIG. 20b shows scFv populations selected against β-galactosidase and CD229 separated by 1 agarose gel electrophoresis.

Ligations between scFv insert and $C_L$-pA-CMV-SigP insert were performed by incubating NcoI/NotI digested scFv insert (1 μg) with NcoI/NotI digested $C_L$-pA-CMV-SigP insert (1 μg) with T4 DNA ligase (1.5 μl, Roche, 10-481-220-001) in manufacturer's buffer in a total volume of 40 μl to form the "mini-circle" depicted in FIG. 21c. Ligations were incubated at 16° C. for 16 hours, purified by spin column, digested with NheI and XhoI and the 2.6 kb product (depicted in FIG. 21d) purified by electrophoretic separation on 1% agarose gel (FIG. 20c).

The DNA insert depicted in FIG. 21d encoding VL-CL-pA-CMV-SigP-$V_H$ (0.5 μg) was ligated with NheI/XhoI digested, gel purified vector pD2 (0.7 μg) (FIG. 21e) with T4 DNA ligase (1.5 μl, Roche, 10-481-220-001) in manufacturer's buffer in a total volume of 40 μl to produce the targeting vector depicted in FIG. 21f. This encodes populations of antibodies formatted as IgGs, originating from first or second round antibody phage display selections to β-galactosidase or CD229. Ligations were incubated at 16° C. for 16 hours, purified by spin column and eluted with HPLC grade water.

Ligated DNA was transformed into electro-competent NEB5alpha cells (New England Biolabs, Cat C2989) which generated a library size of 1-4×10$^5$ clones for each population. DNA was prepared and was co-transfected into 100 mls HEK293 cells grown in Freestyle medium as described above using 0.3 μg donor DNA (pD6-library) per 10$^6$ cells. Cells were co-transfected with 0.5 μg each of "AAVS-SBI" TALENs (pZT-AAVS1 L1 TALE-N and pZT-AAVS1 R1 TALE, Cat No GE601A-1 System Biosciences).

24 hours after transfection the volume of the bulk culture was doubled and 24 hours later blasticidin (10 μg/ml) was added. Medium was refreshed every 3-4 days and after 6 days blasticidin concentration was increased to 20 μg/ml.

In order to determine the library size, 250,000 cells were plated in a 10 cm petri dish (tissue culture treated) 24 hours after transfection and were grown in 10% foetal bovine serum (10270-106, Gibco) and 1% Minimal Essential medium non-essential amino acid (MEM_NEAA #11140-035 Life Technologies). 10 μg/ml blasticidin was added after another 24 hours and medium was changed every 2 days. After 8 days plates were stained with 2% methylene blue (in 50% methanol). Results are shown in Table 3. This shows that libraries of between 5×10$^5$ and 9×10$^5$ clones (representing 0.5% to 0.9% of transfected cells) were obtained for the 3 populations.

TABLE 3

Determination of size of mammalian display libraries formatted as IgG.

| Sample | No. colonies/ 0.25 × 10$^6$ cells | No. colonies/ 10$^6$ cells | Library size (×10$^5$) |
|---|---|---|---|
| β-galactosidase Rd1 | 1337 | 5348 | 5.3 |
| β-galactosidase Rd2 | 1972 | 7888 | 7.9 |
| CD229 Rd2 | 2175 | 8700 | 8.7 |

The bulk of the population of cells transfected with the outputs from 1 or 2 rounds of selection on β-galactosidase were selected in blasticidin containing medium as described earlier. After 19 days 10-20×10$^6$ cells were labelled and flow sorting carried out as described in example 6. Sorted cells were grown for 17 days and re-analysed by flow cytometry (FIG. 10). This showed that the majority of cells were now double positive for IgG expression and binding to β-galactosidase.

Genomic DNA was prepared from the sorted cells and DNA encoding the IgG insert was isolated by PCR. The IgG-encoding insert was amplified using KOD polymerase (Merck, cat. no. 71086-3), with annealing temperature of 60° C. and employing 30 cycles. Manufacturer provided buffer with 5% DMSO was used with 0.3 µM of primers 2597 (SEQ ID NO: 54) and 2598 (SEQ ID NO: 47). The product of desired size was gel purified. The gel purified product was then used for nested PCR using KOD polymerase (Merck, cat. no. 71086-3) in manufacturer's buffer with 5% DMSO using 0.3 µM of primer 2625 (SEQ ID NO: 55) in combination with either primer 1999 (SEQ ID NO: 56) (for R1 sample), or 2595 (SEQ ID NO: 53) (for 4R1 and 5R1), using annealing temperature of 60° C. employing 30 cycles. These nested PCR products were gel purified and subjected to double digestion with NheI-HF (NEB, cat. no. R3131S) and XhoI (NEB, cat. no. R0146S) in order to ligate them with similarly double digested pINT3 (FIG. 1) for expression of soluble IgG formatted binders. Primer sequences are:

2597:
(SEQ ID NO: 85)
AGGGGTTTTATGCGATGGAGTT

2598:
(SEQ ID NO: 78)
GTTACAGGTGTAGGTCTGGGTG

2625:
(SEQ ID NO: 86)
CCTTGGTGCTGGCACTCGA

1999:
(SEQ ID NO: 87)
AAAAAGCAGGCTACCATGAGGGCCTGGATCTTCTTTCTCC

2595:
(SEQ ID NO: 84)
GAGGGCTCTGGCAGCTAGC

Example 8. Construction and Selection from a Naïve scFv Library

Schofield et al. [7] describe the construction of a phage display library (McCafferty library") wherein antibody genes from the B-lymphocytes of a number of human donors were first cloned into an "intermediate library" before re-cloning into the final functional phage display library. This same intermediated library and the same methodology was used to generate a new library (IONTAS library) of 4×10$^{10}$ clones. Plasmid DNA was prepared from this library taking care to ensure sufficient representation of the library within the bacterial inoculation. A number of PCR reactions were set up using a total of 2 ug of DNA template. The PCR product was digested with Nco1 and Not 1 gel purified and ligated as described in Example 6. 9.3 ug of pD6 and 0.93 ug of PCR insert were ligated overnight, the ligation reaction cleaned up using phenol chloroform extraction and the DNA electroporated into DH5alpha cells as described previously [7]. As a result a library of 2.4×10$^8$ clones was created within the scFv-Fc display vector. DNA was prepared from this "naïve library" cloned in pD6 and transfected into 1 litre of HEK293F cells (Life Technologies) grown in Freestyle medium (as described above). 0.3 ug pD6-library DNA, 0.5 ug of each "AAVS-SBI" TALEN pair. 24 hours after transfection the culture volume was doubled and 48 hour after transfection Blasticidin selection was commenced as described above. The library size was determined by plating aliquots of the culture 24 hours after transformation and selecting on blasticidin as described above. A library of 0.9×10$^7$ clones was created.

A number of antigens were biotinylated using EZ-Link Sulfo-NHS-LC-Biotin kit (Pierce Cat. No. 21327) according to manufacturer's instructions. Antigens were bovine thyroglobulin (Calbiochem Cat. 609310), human CD28-Fc chimera (R and D Systems, Cat 342-CD-200) and mouse EphB4-Fc chimera (R and D Systems, Cat. 446-B4-200). Biotinylated β-galactosidase (Rockland Cat. B000-17) was also used.

Transfected cells were selected in blasticidin in liquid culture as described above for 17 days. Cells were harvested, washed and adjusted to 15-20×10$^6$ cells per sample. Cells were prepared as described and biotinylated antigen added to a concentration of 500 nM. Labelling and flow sorting a as described above. Using control cells incubated with only the phycoerythrin-labelled anti-Fc antibody a "gate" was created which included 0.05% of these cells. Using the same gate for labelled cells between 0.28-0.51% of cells were included (FIG. 11). These were collected and grown to allow additional rounds of sorting and amplification of scFv genes from the naïve library.

Example 9. Creation of a Cell Line with Multiple "Landing Sites" to Compare Nuclease and Recombinase-Directed Approaches to Genomic Integration To allow comparison of integration methods based on either genomic cleavage or recombinase-mediated integration an AAVS-directed targeting vector (pD4) was constructed which introduces an intron with multiple "landing sites" (Example 3). These include an FRT site recognized by Flp recombinase and a pair of a lox2272/loxP sites recognized by Cre recombinase. To allow targeted cleavage, pD4 also includes a sequence from GFP for which a TALEN pair have been designed [128] and an I-Sce 1 meganuclease site to allow endonuclease-directed integration. A compatible incoming donor plasmid was constructed (pD5) with appropriate recognition sites such that nuclease or recombinase directed integration causes activation of a promoter-less blasticidin gene and integration an antibody expression cassette.

The organisation of the plasmid and the sequence of pD4 is shown in FIG. 12b. An intermediate plasmid pD3 was first created which encompasses a GFP gene under the control of the CMV promoter followed by a puromycin/Thymidine kinase gene fusion under the control of the PGK promoter (FIG. 12a). This was created by digesting pBIOCAM1-newNot with Sac1 (at the end of the CMV promoter) and BstB1 (between the Neo gene and the poly A site, FIG. 1a). This removed the neomycin expression cassette and allows replacement with a synthetic insert encompassing an enhanced Green Fluorescent Protein (EGFP) gene under the control of the CMV promoter. This GFP construct was fused at the C terminus to residues 422-461 of a mutated mouse ornithine decarboxylase PEST sequence. This PEST sequence is incorporated in plasmid pZsGreen1-DR (Clontech) and has been shown to reduce the half-life of the fused GFP to 1 hour. A cassette encoding a PGK promoter, Puromycin/Thymidine kinase gene fusion (Puro deltaTK) and polyA cassette was excised from the plasmid pFLEX-IBLE [129] using Xmn1 and Fse1 and was cloned into Sma1 and Fse1 sites present in the original synthetic insert. The resultant plasmid (called pD3) encodes a CMV-driven GFP gene and a puromycin resistance gene driven from a PGK promoter.

To create the final targeting vector pD4, the CMV promoter was removed and AAVS homology arms were inserted. An 850 bp section of the AAVS locus was PCR amplified to create an AAVS left homology arm flanked by an EcoR1 at the 5' end and an Mre1 at the 3' end. This was cloned into the ECoR1/Mre1 site of pD3 thereby removing the CMV promoter. An Nsi1 site was also incorporated at the 3' end of this AAVS left homology arm. The neighbouring Mre1 and Nsi1 sites were used to introduce a synthetic fragment fusing an intron to the EGFP gene as shown in FIG. 13. The synthetic intron preceding the EGFP gene incorporates:

a FRT recognition site for Flp recombinase
a lox 2272 recombination site
an I-Sce1 meganuclease site
GFP TALEN recognition site
a T2A ribosomal stalling sequence [130]

The AAVS right homology arm was generated by PCR to create a Hpa1 and BstZ171 sites at 5' and 3' ends. This fragment was cloned into the Hpa1 and BstZ171 sites of pD3. The resulting plasmid pD4, encodes a puromycin resistance cassette ("Puro deltaTK") and can be used to introduce a "landing sites" into the AAVS locus incorporating various nuclease and recombinase sites for comparison. The sequence of pD4 is shown in FIG. 13 (SEQ ID NO: 5, SEQ ID NO: 6 and SEQ ID NO: 7). The AAVS left and right targeting arms are shown in detail in FIG. 3 and are therefore abbreviated in FIG. 13.

The intron introduced into pD4 contains a TALEN recognition sites originating from GFP [128]. The eGFP directed TALEN pair (eGFP-TALEN-18-Left and eGFP-TALEN-18-right) recognise the sequence shown below (all sequences and primers are presented in a 5' to 3' direction) where capitals represent the recognition site of left and right TALENs and the lower case shows the spacer sequence. The right hand TALEN recognises the complement of the sequence shown. The first base pair is equivalent of the minus16 position of the sequence relative to the initiating ATG sequence of GFP (shown underlined in the spacer).

```
                                       (SEQ ID NO: 88)
TCCACCGGTCGCCAccatggtgagcaagggCGAGGAGCTG
TTCA
```

The plasmid pD4 also incorporates an I-Sce1 meganuclease site and an FRT site recognised by Flp recombinase. Finally pD4 incorporates lox 2272 and loxP (which are mutually incompatible) flanking the GFP and puromycin expression cassettes. Incorporation of these same 2 loxP sites flanking the donor plasmid (pD5 below) affords an opportunity to substitute the integrated cassette (including the PGK puro delta TK cassette) replacing it with an incoming cassette driving expression of blasticidin and antibodies via recombinase mediated cassette exchange.

Creation of a Cell Line by Transfection of pD4.

HEK293F cells were resuspended at $10^6$ cells/ml and DNA:polyethylene imine (PolyPlus) added at a ratio of 1:2 (w/w). Cells were transfected with 0.6 µg/ml of pD4 and were co-transfected with either the "original AAVS" TALEN pair or pcDNA3.0 as a control (0.6 µg/ml). pD3 which expresses EGFP from the CMV promoter was included in the experiment as a transfection control and showed 35% transfection efficiency. After 24 hours transfected cells were plated at $0.5 \times 10^6$ cells/10 cm petri dish (tissue culture treated) and were grown in 10% foetal bovine serum (10270-106, Gibco) and 1% Minimal Essential medium non-essential amino acid (MEM_NEAA #11140-035 Life Technologies). 5 µg/ml puromycin was added after another 24 hours and medium was changed every 2 days. After 5 days untransfected cells or cells transfected with pD3 only were dead. After 12 days there were approximately 200 colonies on cells transfected with pD4 only and approximately 400 colonies on cells transfected with pD4 and the AAVS TALEN pair.

The puromycin resistant population arising from transfection with pD4 and the AAVS TALEN pair was analysed for correct integration. In addition a single colony was picked from this population (clone 6F) and compared with a colony from the puromycin resistant population arising from pD4 transfection in the absence of the AAVS TALEN pair. To identify correct integration, PCR primers were designed which hybridise in the AAVS genomic locus beyond the left and right homology arms. These were paired up with insert specific primers. At the 5' end the primers were:

```
AAVS1_HA-L_Nested_Forw1
                                       (SEQ ID NO: 89)
GTGCCCTTGCTGTGCCGCCGGAACTCTGCCCTC EGFP_Synthetic_gene_Rev_Assembly
                                       (SEQ ID NO: 90)
TTCACGTCGCCGTCCAGCTCGAC Purotk_seq_fow2
                                       (SEQ ID NO: 91)
TCCATACCGACGATCTGCGAC AAVS1_Right_arm_Junction_PCR_Rev
                                       (SEQ ID NO: 77)
TCCTGGGATACCCCGAAGAG
```

FIG. 14 shows that clone 6F and the population are correct at both left and right ends but the clone picked from the non-AAVS directed population is negative. Thus PCR analysis indicates that the accuracy of integration of the donor cassette is greater when directed by AAVS TALEN cleavage of genomic DNA.

pD4 introduces a promoter-less, in-frame GFP gene driven from the AAVS promoter. Flow cytometry of the puromycin resistant population showed an absence of GFP expression. This failure to express could be due to the combination of a short half-life (from the murine ornithine decarboxylase PEST sequence element) combined with reduced expression arising from the use of the T2A promoter. In fact it was found that addition of the T2A element in front of a promoterless blasticidin element (as described for pD2) reduced the number of blasticidin resistant colonies by 4 fold. Despite the absence of GFP expression, the integration of multiple landing sites still affords an opportunity for comparison of recombinase-directed versus DNA cleavage directed genomic integration.

Example 10. Construction of a Vector for Inserting an Antibody Cassette (pD5) into the "Multiple Landing" Site Following introduction of the "multiple landing site" intron into the AAVS locus, it is possible to introduce an antibody cassette via nuclease-directed or recombinase-directed means. To do this a donor plasmid pD5 was created where the expression cassette is flanked by left and right homology arms which are equivalent to the sequences flanking the GFP TALEN cleavage site introduced into pD4. pD5 does not itself incorporate an intact GFP TALEN recognition site and integration is driven by homologous recombination. Homology-directed integration of the donor plasmid will lead to introduction of a blasticidin gene which lacks a promoter but is preceded by a splice acceptor site that creates an in-frame fusion with the upstream exon from the AAVS locus as described earlier. Integration into the AAVS locus will cause expression of the promoter-less blasticidin gene. The inserted cassette also encodes an IgG formatted antibody heavy and light chains under the control of pEF and CMV promoters respectively as described above. pD5 incorporates an I-Sce1 meganuclease site which can lead to cleavage of the incoming donor affording an opportunity for NHEJ (see Example 12). An FRT site is also incorporated into the donor plasmid pD5 allowing recombinase-directed incorporation of the promoter-less blasticidin gene and antibody expression cassettes at the same locus. As discussed above Cre recombinase will act on the loxP sites in donor and genomic DNA to direct recombinase-mediated cassette exchange.

The sequence of pD5 is shown in FIG. 15. The sequence at the 5' end of the GFP TALEN site is from the AAVS locus. A 267 bp section of the AAVS locus upstream of the TALEN cleavage site was generated by PCR. Primers were used which created an EcoR1 and an Mfe 1 site at the 5' and 3' end and the product was cloned into the ECoR1 site of pD1-D1.3. The EcoR1 site is re-created at the 5' end. During cloning of the left homology arm an Nsi1 and Pac1 was also inserted at the 3' end. A right homology arm, incorporating approximately 700 bp equivalent to the sequence 3' of the GFP TALEN was created by PCR assembly. PCR primers introduce BstZ171 sites at 5' and at the 3' end of the assembled fragment and this was cloned into the BstZ171 site of pD1-D1.3. The PCR primers also introduced a Hpa1 site at the 5' end.

A PCR fragment encompassing the intron (which incorporates recognition sites for GFP TALEN, I-Sce1endonuclease, Flp recombinase and Cre recombinase), a splice acceptor region, a Blasticidin resistance gene and poly A site (described above) was created with Nsi1 site at the 5' end and a Pac1 site at the 3' end. This was cloned into the Nsi1 and Pac1 site of the plasmid described above to create pD5-D1.3 (sequence shown in FIG. 15 and plasmid structure shown in FIG. 18a).

Example 11. Comparison of Nuclease-Directed and Flp-Directed Integration of an Antibody Expression Cassette The Flp-In system which has previously been used for recombinase-mediated integration of antibody expression cassettes [18] uses a mutant Flp recombinase (in the plasmid pOG44) which possesses only 10% of the activity at 3TC of the native Flp recombinase [19]. A variant of Flp recombinase (Flpe) with better thermostability and activity at 3TC than wild type has been identified [19, 20]. This was further improved by codon optimization to create Flpo encoded within plasmid cCAGGS-Flpo (Genebridges Cat. A203). The effect of both variants of Flp recombinase (encoded within pOG44 and cCAGGS-Flpo) was compared. Recombination directed by Cre recombinase was also examined by co-transfecting cells with a plasmid which encodes Cre recombinase [132] (pCAGGS-Cre, Genebridges Cat. A204). In each vector the recombinase is expressed under the control of the chicken-β-actin promoter and a CMV immediate early enhancer. An SV40 Large T nuclear localization sequence is used for nuclear localisation [20]. In the original vectors (cCAGGS-Flpo and pCAGGS-Cre) recombinase expression was linked to a puromycin resistance gene by an internal ribosomal entry site (IRES) which was removed using standard molecular biology techniques.

An experiment was carried out to compare the efficiencies of genomic cleavage-directed versus recombinase directed integration of an antibody cassette. The outcome was assessed in 2 ways:
1. Measuring the number of blasticidin-resistant colonies arising from integration of a promoter-less blasticidin gene
2. Assessing the extent of antibody expression achieved by the different approaches.

As described in Example 9, the recognition sites for Cre recombinase (lox2272 and loxP) and Flp recombinase (FRT) were previously integrated into the AAVS locus within clone 6F. In addition recognition sites for a GFP TALEN pair and for the meganuclease I-Sce1 are also present within the same intron. The donor plasmid pD5-D1.3 carries the same recognition sites (apart from GFP TALEN) within an intron upstream of a promoter-less blasticidin gene. Correct integration will lead to activation of the blasticidin gene. pD5-D1.3 also encodes an IgG formatted D1.3 antibody gene which will be expressed on the cell surface.

Co-transfection of pD5-D1.3 with pOG44 or pCAGGS-Flpo (encoding 2 variants of Flp recombinase) should result in integration of the entire pD5 plasmid into the FRT site of clone 6F. The donor plasmid pD5-D1.3 also has lox2272 site within the synthetic intron upstream of the blasticidin gene and a loxP site at the end of the antibody expression cassette. Under the action of Cre recombinase expressed from pCAGGS-Cre, recombinase-mediated cassette exchange should result in the integration of the blasticidin and antibody expression cassettes into the lox2722 and loxP sites within clone 6F.

The efficiency of vector integration using recombinase-directed approaches with genomic cleavage-directed approaches was compared using a pair of TALENs (eGFP-TALEN-18-Left and eGFP-TALEN-18-right) directed towards a sequence from GFP (Reyon et al., 2012). In the case of GFP TALENs the element between the left and right homology arms will be integrated following genomic cleavage by TALENs.

To allow comparison with I-Sce1 meganuclease a codon optimised gene encoding I-Sce1 was constructed (FIG. 16). This gene has an N terminal HA epitope tag/SV40 nuclear localisation signal (NLS) at the N terminus and is flanked by Nco1 and Xba1 sites at the 5' and 3' termini. The gene was cloned into the vector pSF-CMV-F1-Pac1 (Oxford Genetics OG111) where expression is driven from the CMV promoter.

Transfections were carried out using the clone 6F with a correctly integrated "multiple landing site". Cells were suspended at $10^6$/ml and transfected with 50 ng of pD5-D1.3 donor plasmid/$10^6$ cells along with enzyme encoding plasmids (Table 4A).

After 24 hours transfected cells were plated at $0.5 \times 10^6$ cells/10 cm petri dish (tissue culture treated) and were grown in 10% foetal bovine serum (10270-106, Gibco) and 1% Minimal Essential medium non-essential amino acid (MEM_NEAA #11140-035 Life Technologies). 5 ug/ml blasticidin was added after another 24 hours and medium was changed every 2 days. After 12 days plates were stained with 2% methylene blue (in 50% methanol) and colony numbers counted (Table 2). In a direct comparison between Flp recombinase, Cre recombinase and TALEN, the greatest number of colonies were obtained through use of the GFP TALEN where there was a 9-fold increase compared with "donor only" (Table 4A). It also appears that the use of the optimised Flpo gene actually resulted in a reduction of the number of blasticidin resistant colonies compared to "donor only" control, presumably through toxicity of the enhanced activity Flp recombinase. There was also an increase in colony number using pCAGGS-Cre compared to the donor only control.

A second experiment was carried out comparing GFP TALEN with both enhanced Flp (from cCAGGS-Flpo) as well as the low activity Flp enzyme encoded within pOG44 from the Flp-In system (as used by Zhou et al. [17, 18, U.S. Pat. No. 7,884,054]. These were compared with GFP TALEN and Cre recombinase (Table 4B). Cells were transfected with the amounts DNA shown per million cells. $0.25 \times 10^6$ cells were plated out and the number of blasticidin resistant colonies determined as described above. Cells were also selected for blasticidin resistance in liquid culture for 30 days before determining the proportion of cells which expressed surface IgG (as described above). Table 4B shows that the TALEN was superior to the other approaches in terms of number of resistant colonies. Again the use of optimised Flp within cCAGGS-Flpo actually caused a reduction in number of blasticidin resistant colonies compared to "donor only" controls. Cre recombinase again led to an increase in blasticidin colony count compared with control whereas the Flp gene within pOG44 showed only a marginal increase compared with control.

Table 4. Comparison of TALE nuclease-directed and recombinase-directed integration approaches.

A.

| Enzyme plasmid | Amount | pD5-D1.3 donor (ng/$10^6$ cells) | Blasticidin resistant colonies (colonies/$10^6$ cells) |
|---|---|---|---|
| GFP TALEN pair | 0.575 µg each | 50 | 152 (304) |
| pCAGGS-Flp$_o$ | 1.15 µg | 50 | 1 (2) |
| pCAGGS-Cre | 1.15 µg | 50 | 57 (114) |
| control (pCDNA3.0) | 1.15 µg | 50 | 17 (34) |

B.

| Sample 2 µg each per $10^6$ cells | pD5-D1.3 Donor µg/$10^6$ cells | Blasticidin colonies | Blasticidin colonies per $10^6$ cells (percentage blasticidin resistant) | Percentage positive in flow |
|---|---|---|---|---|
| GFP TALEN pair | 0.6 | 270 | 1080 (1.1%) | 95.6 |
| cCAGGS-Flp$_o$ | 0.6 | 35 | 140 (0.14% | Too few cells |
| pOG44 | 0.6 | 96 | 384 (0.38%) | 6.4 |
| pCAGGS-Cre | 0.6 | 180 | 720 (0.72%) | 4 |
| Control (PCDNA3.0) | 0.6 | 81 | 324 (0.32%) | 37.3 |

C.

| Sample 2 µg each per $10^6$ cells | pD5-D1.3 Donor µg/$10^6$ cells | Blasticidin colonies | Percentage positive in flow |
|---|---|---|---|
| GFP TALEN | 2 | 210 | 95.3 |
| GFP TALEN | 6 | 120 | 73.6 |
| cCAGGS- Flp$_o$ | 2 | 62 | Too few cells |
| cCAGGS- Flp$_o$ | 6 | 41 | Too few cells |
| pOG44 | 2 | 178 | 35.6 |
| pOG44 | 6 | 63 | 58.7 |
| pCAGGS-Cre | 2 | 84 | 40.9 |
| pCAGGS-Cre | 6 | 52 | Too few cells |
| Control (PCDNA3.0) | 2 | 340 | 65.6 |
| Control (PCDNA3.0) | 6 | 82 | 55.5 |

With the addition of more donor DNA (Table 4C) there was an increase in colony numbers at intermediate levels (2 µg/million cells) and a decline at higher levels across the board (6 µg/million cells). None of the other samples achieved levels of antibody display seen with the GFP TALEN directed integration.

Cells were also selected for blasticidin resistance in liquid culture and the cells stained for antibody expression as described above. TALEN-directed integration gave a significantly higher proportion of antibody-positive cells compared with the other approaches. Cells transfected with cCAGGS-Flpo and with high concentrations of pCAGGS-Cre were not healthy and there were insufficient numbers to carry out flow cytometry.

The comparison was extended to included I-Sce endonuclease. A synthetic gene encoding I-Sce1 was synthesised (FIG. 16) and cloned into the Nco1/Xba 1 site of pSF-CMV-f1-Pac1 (Oxford Genetics). Cells were suspended at $10^6$/ml and transfected for each ml of cells ($10^6$ cells/nil) with 300 ng of pD5-D1.3 donor plasmid along with plasmids encoding enzymes (1 ug/$10^6$ cells). Next day 0.05 ml of cells were plated and selected in blasticidin and stained after 14 days as described. Table 5 shows that the highest number of blasticidin resistant colonies came from I-Sce1 meganuclease followed by the eGFP TALEN pair. Both Cre and Flp recombinase (encoded within pOG44) gave numbers slightly higher than the "donor only" control. As before transfection with the Flpe encoding plasmids actually reduced colony numbers compared to "donor only".

TABLE 5

Comparison of meganuclease-directed and recombinase-directed integration approaches

| Sample 2 µg each per $10^6$ cells | pD5-D1.3 Donor µg/$10^6$ cells | Blasticidin colonies | Blasticidin colonies per $10^6$ cells (percentage blasticidin resistant) | Percentage positive in flow d 7 | Percentage positive in flow d 13 |
|---|---|---|---|---|---|
| GFP TALEN pair | 0.6 | 90 | 1800 | 27.6 | 55% |
| I-Sce1 meganuclease | | 150 | 3000 | 29.9 | 47% |
| pOG44 | 0.6 | 60 | 1200 | 2.79 | 6.5% |
| pCAGGS-Cre | 0.6 | 56 | 1120 | 2.95 | 6.6% |
| cCAGGS-Flp$_o$ | 0.6 | 4 | 80 | 5.9 (low cell nos) | Too few cells |
| Control (PCDNA3.0) | | 40 | 800 | 3.3 | 4.9% |

TABLE 5-continued

Comparison of meganuclease-directed and recombinase-directed integration approaches

| Sample 2 µg each per 10⁶ cells | pD5-D1.3 Donor µg/10⁶ cells | Blasticidin colonies | Blasticidin colonies per 10⁶ cells (percentage blasticidin resistant) | Percentage positive in flow d 7 | Percentage positive in flow d 13 |
|---|---|---|---|---|---|
| (SBI AAVS into WT HEKs | | 251 (x2) | 10040 (1%) | ND | ND |

After transfection the bulk of cells were selected for blasticidin resistance in liquid culture and after 7 and 13 days were stained with an anti-Fc phycoerythrin labelled antibody as described above. FIG. 17 (summarised in Table 5) shows significantly higher antibody expression was achieved for cells transfected with I-Sce1 endonuclease and eGFP TALEN (47% and 55% respectively) compared to "donor only" (4.9%). In contrast the percentage of antibody positive cells when cells were co-transfected with plasmids encoding Flp recombinase (pOG44) or Cre recombinase were 6.6 and 6.5% respectively. The proportion of antibody positive cells continues to increase with continued selection in blasticidin and achieves 85-90% antibody positive in the case of the I-Sce1 and EGFP TALEN transfected samples when assayed on day 19. Thus meganucleases provide an alternative approach to effect nuclease-directed integration of antibody-encoding transgenes.

Example 12. Nuclease-Directed Integration of an Antibody Cassette can Occur by Both Homologous Recombination and NHEJ The efficiency of integration of transgenes into cellular DNA can be enhanced by the introduction of double stranded breaks (DSBs). Endogenous DNA repair mechanisms in eukaryotic cells include homologous recombination non-homologous end joining (NHEJ) and variants of these. All provide a means for introducing genes encoding binders within a library. Homologous recombination provides a precise join between the regions of homology and the inserted transgene but require the provision of regions of homology in the donor plasmid. DNA for homologous recombination can be provided as linear or circular DNA. With NHEJ the ends of DNA are directly re-ligated without the need for a homologous template. This approach to DNA repair is less accurate and can lead to insertions or deletions. NHEJ nonetheless provides a simple means of integrating in-frame exons into intron or allows integration of promoter: gene cassettes into the genome. Use of non-homologous methods allows the use of donor vectors which lack homology arms thereby simplifying the construction of donor DNA.

Clone 6F has GFP TALEN and I-Sce1 nuclease recognition sites integrated into the genome and these will be cleaved when these nucleases are provided. The donor vector pD5 does not have a GFP TALE nuclease recognition site but has homology arms flanking the cleavage site and so is expected to integrate by homologous recombination only. Cleavage of genomic DNA at the neighbouring I-Sce1 meganuclease will also lead to integration of the pD5 elements by homologous recombination. pD5 however also has an I-Sce1 meganuclease site which can be cleaved in vivo when I-Sce1 is provided. This will create a linear DNA product which can potentially be integrated by NHEJ. As described earlier there may even be efficiency advantages using in vivo cleavage of donor DNA when NHEJ is used.

FIG. 18a represents the incoming pD5-D1.3 donor DNA and FIG. 18b represents the genomic locus of clone 6F cells incorporating the "multiple landing" site. FIG. 18c represents the consequence of homologous recombination between pD5-D1.3 (FIG. 18a) and the multiple landing site of clone 6F (FIG. 18b). FIG. 18d in contrast represents the consequence of NHEJ. In this case extra DNA from the backbone of the incoming plasmid is incorporated (represented by a double arrow). Flp mediated recombination at the "multiple landing" site will lead to a similar product. In order to determine which route is being used with the samples described in Example 11 (shown in FIG. 17) genomic DNA was prepared from the blasticidin selected population as described before. A reverse PCR primer (J44) was designed which hybridizes to the integrated PGK promoter. This was used in conjunction with either J48 which hybridises at the end of the IgG protein. Primers J44 and J48 were designed to reveal homologous recombination producing a band of 1928 bp when I-Sce1 is responsible for integration (indicated by arrow in FIG. 18e). (Potentially a band of 5131 bp could be produced by this primer pair when NHEJ has occurred but this longer product was not visible in the genomic PCRs of this experiment.)

Primer J46 was designed to hybridise within the β-lactamase gene within the vector backbone. Primers J44 and J46 are anticipated to produce a band of 1800 bp when NHEJ has occurred. A similar sized band is expected where Flp recombinase has led to recombinase-mediated integration.

```
J44:
                                    (SEQ ID NO: 92)
AAAAGCGCCTCCCCTACCCGGTAGAAT

J46:
                                    (SEQ ID NO: 93)
GGCGACACGGAAATGTTGAATACTCAT

J48:
                                    (SEQ ID NO: 94)
CACTACACCCAGAAGTCCCTGAGCCTG
```

FIG. 18e clearly reveals that homologous recombination occurs only with the samples treated with GFP TALEN and I-Sce1 meganuclease ((i and ii compared with iii and iv). In contrast NHEJ only occurs when cleavage is effected by I-Sce1 meganuclease (FIG. 18e v.) but not GFP TALEN (FIG. 18e vi). As expected a similar size band is found in the sample treated with Flp recombinase (FIG. 18e vii). Thus this experiment reveals nuclease-directed integration of an antibody cassette can occur by both homologous recombination and NHEJ.

Example 13. Generation of Secreted and Membrane Bound Antibody Fragments from the Same Cell As described above, mammalian display vectors pD2 and pD5 were constructed with an exon encoding a transmembrane domain flanked by two ROX recognition sites recognised by Dre recombinase [88]. In order to determine whether it was possible to convert from a membrane bound form to a secreted form, the blasticidin resistant population arising from transfection with pD2-D1.3/AAVS TALEN pair was re-transfected with the plasmid encoding Dre recombinase (pCAGGs-Dre). This was based on the plasmid pCAGGs-Dre-IRES puro [88] which drives the Dre recombinase gene from a CAGGs promoter (GeneBridges A205). The puromycin resistance gene was removed using standard molecular biology techniques. After 22 days of blasticidin selection, cells were set up at $0.5 \times 10^6$ cells/ml and transfected as described earlier with 0.5 µg pCAGGs-Dre per $10^6$ cells. After 6 days supernatants were collected, antibody purified using protein A and samples run on an SDS-PAGE gel and stained with Coomassie blue. FIG. 19a shows that secreted antibody was found in the supernatant even without transfection with the Dre recombinase gene. This may arise from alternative splicing where the exon encoding the transmembrane domain is skipped. Alternatively antibody in the culture supernatant could arise from cleavage of the membrane bound antibody. Transfection of Dre recombinase increased the level of secreted antibody (FIG. 19a).

Production of secreted scFv-Fc fusion was also demonstrated in the experiment describe in example 7 (FIG. 9h). Antibody scFv populations selected by 1 round of phage display on β-galactosidase were introduced into the pD6 vector and integrate into the AAVS locus of HEK293 cells using the AAVS TALEN. Antigen binding cells were sorted by flow sorting and selected cells were grown for 7 days post-sorting without a change of medium to allow antibody to accumulate. ELISA plates were coated with either β-galactosidase (10 ug/ml) or BSA (10 ug/ml) overnight. Culture supernatants from 7 day cultures were mixed with a 50% volume of 6% Marvel-PBS and the sample tested in triplicate. A 1/10 dilution was also tested. Detection of bound scFv-Fc fusion was performed using anti-Human IgG-Eu (Perkin Elmer Cat 1244-330). FIG. 19b shows that antibody binding can be detected directly from culture supernatants either neat or with a 1/10 dilution. This illustrates that both surface display and antibody secretion can be achieved within the same cells without additional steps. It will be possible to derive secreted antibody directly from the selected cells either following single cell cloning or using a sorted population as shown here generate a polyclonal antibody mix.

Example 14. A Simple Method for Conversion of scFvs to IgG or Fab Format

A novel method was invented to effect the conversion of antibodies formatted as scFv to an IgG format as described in Example 7. This conversion is a necessary process during antibody drug discovery projects employing scFv antibody phage display libraries where an IgG or Fab formatted antibody is required as the final format. Current methods are tedious and involve individual cloning of the variable heavy (VH) and variable light (VL) chains into suitable expression vectors. Furthermore conversion of a population of scFvs "en masse" is not possible because the link between the $V_H$ and $V_L$ chains is lost. This is a problem because both the VH and VL chains contribute to antigen binding specificity. The current inability to easily convert populations of scFv to Ig or Fab format limits the ability to screen large numbers of antibodies in the final format they will be used in the clinic. The ability to screen recombinant antibodies in Ig or Fab format for target binding, cell reporter screens and biophysical properties and function including aggregation state is a necessary step to choose candidate antibody drugs as clinical candidates. The greater number of antibodies tested at this stage, in IgG or Fab format, the greater the chance of selecting the best antibody drug candidate.

Described here is a method to convert single chain antibody (scFv) populations to immunoglobulin (Ig) or Fab format in such a way that the original variable heavy (VH) and variable light (VL) chain pairings are maintained. The method allows one to convert monoclonal, oligoclonal or polyclonal scFvs simultaneously to Ig or Fab format. Preferably, the method proceeds via the generation of a non-replicative "mini-circle" DNA. Preferably the complete conversion process entails a single transformation of bacteria such as E. coli to generate a population of bacterial colonies each harbouring a plasmid encoding a unique Ig or Fab formatted recombinant antibody. This is distinct from alternative methods requiring two separate cloning and transformation steps [117].

More broadly this aspect of the invention relates to a method of converting a genetic construct with 3 linked genetic elements A, B and C (represented by the $V_H$, linker and $V_L$ respectively in the case of an scFv) to a format where the order of the flanking elements (A and C) are reversed, in a single cloning step. The intermediate element could be retained but most usefully the method permits the replacement of this intermediate element by a new element D (to give C-D-A). In the example of conversion of a scFv to an IgG or Fab then C is an antibody VL domain and A is a VH domain. In this example element D encapsulate a light chain constant domain, poly A site, promoter and leader sequence fused to the VH (element A). In the process the product (C-D-A) is re-cloned allowing the flanking sequences to also be changed. In the scFv to IgG conversion example the VL element is preceded by a promoter and leader sequence and the VH is followed by a $C_{H1}$-$C_{H2}$-$C_{H3}$ domain in the case of IgG formatted antibodies and by a CH1 domain in the case of Fab formatted antibodies. The method could be applied more broadly where elements A and C (using above nomenclature) could represent other genetic elements, e.g., in construction of proteins with circularly permutation where the original N and C termini are fused and novel internal termini are engineered.

FIG. 21 illustrates the conversion process schematically using scFv to IgG conversion as an example. A DNA insert (a) encoding the antibody VH and VL domains is ligated with DNA fragment (b) encoding a constant light (CL) chain, a polyadenylation sequence (pA), a cytomegalovirus (CMV) promoter and a signal peptide (SigP). DNA fragment (b) could also encode any promoter in place of the CMV promoter. Also the pA-CMV cassette could be replaced by an internal ribosomal entry sites (IRES) [119] or a 2A type "self-cleaving" small peptide [130, 133]. The joining of DNA molecules (a) and (b) to create a non-replicative DNA "mini-circle" (c) is facilitated by a "sticky-end" ligation. In FIG. 21, NcoI and NotI sites are employed because these were used in the creation of the McCafferty phage display library [7] however any suitable restriction sites could be used to create the non-replicative "mini-circle" c. After ligation, the "mini-circle" c is linearized with restriction enzymes NheI and XhoI, the recognition sites of which flank the linker between the VH and VL domains. NheI and XhoI were chosen to illustrate this invention because they were used in the creation of the McCafferty phage display library [7], however any suitable restriction sites could be used.

Linearised product d is then purified and ligated with the digested vector (e). The vector (e) includes a CMV or pEF promoter and signal sequence upstream of the NheI site and encodes the antibody constant heavy (CH) domains 1 to 3 downstream of the XhoI site. The vector would also encode a bacterial origin or replication and antibiotic resistance marker (not shown) to enable selection and replication of the resultant plasmid DNA in bacteria. The product of ligation of insert (d) with vector (e) would result in plasmid f, which can be used to transform bacteria and growth with a suitable selectable marker would allow the production and purification of plasmid DNA by standard methods. Purified plasmid f can be introduced into mammalian cells [134] for heterologous Ig antibody expression. Alternatively DNA encoding $CH_{1-3}$ in vector (e), could be replaced with DNA encoding a single $C_{H1}$ domain for Fab expression.

In the detailed method description below used to illustrate this invention, the insert b contains either a CMV promoter or a P2A peptide which enables expression of the separate antibody light and heavy chains from a single messenger RNA (mRNA). The method is non-obvious and was refined after several experimental attempts. For example, initially linearisation of the DNA "mini-circle" (c) was attempted by PCR. However this resulted in the amplification of homo-dimer side-products, resulting in a low yield of the desired product (d). In contrast, direct digestion of the DNA "mini-circle" (c) provided sufficient material (d) to allow the method to be successfully implemented. Secondly, in an attempt to prevent undesired homo-dimer product, insert (a) was initially dephosphorylated. However, this required careful control to prevent "end" digestion resulting in product lacking the desired "sticky-ends" for ligation. The optimal method does not include dephosphorylation to maximise the proportion of ligation competent product. Lastly, careful control of the ratios used in the ligation of DNA inserts (a) and (b) was required to maximise the yield of the DNA "mini-circle" (c).

1. Preparation of PCR scFv Inserts

From a bacterial glycerol stock, harbouring plasmid DNA encoding scFv scrape into 50 ul of water. Dilute this 1 in 10. Use 5 ul of this for PCR reaction containing forward primer pSANG10peIB (CGCTGCCCAGCCGGCCATGG SEQ ID NO: 95) (2.5 µl, 5 µM), reverse primer 2097 (GATGGTGATGATGATGTGCGGATGCG SEQ ID NO: 96), (2.5 µl, 5 µM), 10×KOD buffer (KOD hot start kit from Merck, 71086-4), dNTPs (5 µl, 2 mM), MgSO4 (2 µl, 25 mM), KOD hot start polymerase (2.5 units) in a total volume of 50 µl. Cycling conditions were 94° C. for 2 min then 25 cycles of 94° C. 30 sec, 54° C. for 30 sec then 72° C. for 1 min. PCR clean up was performed by spin column (Qiagen or Fermentas) and the PCR reactions eluted in 90 µl. FIG. 22a shows 1 µl of PCR reaction loaded on a 1% agarose TBE gel. Purified scFv DNA (80 µl, 8 µg) was digested by the addition of buffer 4 (New England Biolabs), BSA (0.1 mg/ml) and 40 units of NcoI-HF and NotI-HF in a total volume of 100 µl and incubated for 2 hours at 37° C. Inserts were purified with a Qiagen PCR cleanup kit, eluted in 30 µl and the DNA concentration measured by measuring the absorbance at 260 nM with a nanodrop spectrophotometer (Thermo).

2. Ligation of DNA Inserts (FIGS. 21a and b)

A ligation reaction is performed to produce the DNA "mini-circle" (FIG. 21c). The ligation reaction contains insert b (125 ng), scFv insert a (FIG. 21) (125 ng), 10× ligation buffer (Roche T4 DNA ligase kit, 1.5 ul), T4 DNA ligase (1 unit) in a total volume of 15 µl. Incubate 1-2 hr 21° C. Water (35 µl) was added to the ligation mix and purified with a Qiagen PCR cleanup kit and eluted in 30 µl.

3. Digestion of DNA "Mini-Circle" (FIG. 21c) with Xho1/Nhe1

Purified ligation reaction (28 µl) is digested by the addition of buffer 4 (New England Biolabs, 3.5 µl), BSA (0.1 mg/ml) and 10 units of NcoI-HF and NotI-HF in a total volume of 35 µl and incubated at 37° C. This is then purified by separation on a 1% agarose TBE (FIG. 22b). Alternatively FIG. 22c shows a linearised "mini-circle" containing a P2A sequence in place of a CMV promoter. DNA band at 2.6 kb (FIG. 22b) is excised and purified with Qiagen gel extraction kit and eluted in 30 µl.

4. Ligation of Linearised DNA "Mini-Circle" d with pINT3 (XhoI/NheI Cut) Vector and Transformation of E. coli DH5α.

A standard ligation was set-up with pINT3 cut vector (50 ng), linearised "mini-circle" d (20 ng), 10× ligase buffer (Roche, 1.5 µl) and 1 unit of T4 DNA ligase (NEB) in a final volume of 15 µl. Incubation was at 21° C. for 2 hrs. Transformation of E. coli DH5alpha chemically competent cells, subcloning efficiency, (Invitrogen, cat. 18265017) was according to the manufacturer's instructions. 80 µl of chemically competent DH5a cells were added to 6 µl ligation mix, placed on ice for 1 hour and heat shocked at 42° C. 1 min, ice for 2 min and then transferred to a 14 ml polypropylene tube containing 900 µl SOC media and incubated at 3TC for 1 hour and plated on LB amp plates.

Example 15. Construction of Large Display Libraries in Mammalian Cells by Nuclease-Directed Integration Using Flow Electroporation Electroporation is an efficient way of introducing DNA, RNA and protein into cells and electroporation flow systems allow for efficient introduction of DNA into large numbers of mammalian cells. For example the "MaxCyte STX Scalable Transfection System" (Maxcyte) permits the electroporation of $10^{10}$ cells within 30 mins, creating the potential for transfecting up to $10^{11}$ cells in a day. Cells and DNA are mixed and passed from a reservoir to an electroporation chamber, electroporated, pumped out and the process repeated with a fresh aliquot of cells and DNA. The same method can be applied for introduction of DNA, RNA, protein or mixtures thereof into cultured cells (e.g., human HEK293 cells or Jurkat cells) or primary cells e.g. human lymphocytes [135]. Flow electroporation has been used to efficiently introduce DNA, RNA and protein into a large number of primary and cultured cells.

Here we exemplify the use of such a system to introduce donor DNA, encoding antibody genes, by co-transfecting with DNA encoding a pair of TALE nucleases targeted to the human AAVS locus of human HEK293 cells and Jurkat cells.

The distribution of the 2 different antibody specificities was determined by flow cytometry using fluorescently-labelled antigen. The generation of antibodies recognising the FGF receptors FGFR1 or FGFR2 has been described previously [105]. Clones α-FGFR1_A and α-FGFR2_A (described therein) were cloned into pD6 as described in example 6. In addition a population of scFv antibodies selected from the "McCafferty" phage display library [7] using one round of phage display on β-galactosidase (β-gal) were also cloned into this vector (as described in example 6).

HEK293 cells were centrifuged and re-suspended in a final volume of $10^8$ cells/ml in the manufacturer's electroporation buffer (Maxcyte Electroporation buffer, Thermo Fisher Scientific Cat. No. NC0856428)). An aliquot of $4 \times 10^7$ cells (0.4 ml) was added to the electroporation cuvette with 100 µg DNA (i.e., 2.5 µg/$10^6$ cells). The amounts of the different components used are shown below. Donor DNA encoding antibodies α-FGFR1_A and α-FGFR2_A was provided as an equimolar mix with the total amount per $10^6$ cells shown in Table 6 below. DNA encoding AAVS-SBI TALENs (pZT-AAVS1 L1 and pZT-AAVS R1 Systems Bioscience Cat. No. GE601A-1) was used as an equimolar mix with the total amount per $10^6$ cells shown in Table 6 below. In samples without added TALENs, the input DNA was brought to 2.5 μg/10⁶ cells using control plasmid pcDNA3.0.

The percentage transfection efficiency was calculated by counting the number of blasticidin colonies achieved for a given input of total cells. The fold difference compared to negative controls (i.e., no TALEN DNA added) is shown in brackets. Finally, the number of transformed colonies achievable by running a full cycle of the Maxcyte system, involving electroporation of $10^{10}$ cells is calculated in the last column. This represents a single cycle of approximately 30 minutes, giving the potential to run multiple cycles in a day. Thus, the daily output could be 5-10-fold higher. Large scale fermentation and culture systems such as Wavebag system (GE Healthcare) or the Celltainer system (Celltainer Biotech) can be used to generate cells for transfection and can be used to cultivate the resulting libraries.

TABLE 6

Electroporation of HEK293 cells

| Sample | αFGFR1_A/ αFGFR2_A ng donor DNA/ 10⁶ cells | ng TALEN DNA/10⁶ cells | % transfection | No clones per 10¹⁰ cells |
|---|---|---|---|---|
| 1 | 580 | 1920 | 5.1 (51x) | 5.1 × 10⁸ |
| 1b | 580 | 640 | 3.3 (33x) | 3.3 × 10⁸ |
| 2 | 580 | — | 0.1 | 0.1 × 10⁸ |
| 3 | 194 | 1920 | 2.7 (89x) | 2.7 × 10⁸ |
| 4 | 194 | — | 0.03 | 0.03 × 10⁸ |
| 5 | 1185 | 1315 | 5.8 (25x) | 5.8 × 10⁸ |
| 6 | 1185 | — | 0.23 | 0.23 × 10⁸ |
| 7 | 1825 | 675 | 6.1 (11x) | 6.1 × 10⁸ |
| 8 | 1825 | — | 0.57 | 0.57 × 10⁸ |
| 9 | 580 (FGFR1 alone) | 1920 | 5.3 | 5.3 × 10⁸ |
| 10 | 580 (FGFR2 alone) | 1920 | 5.3 | 5.3 × 10⁸ |

| Sample | β-galactosidase donor DNA/10⁶ cells | ng TALEN DNA/10⁶ cells | % transfection | No clones per 10¹⁰ cells |
|---|---|---|---|---|
| 11 | 580 | 1920 | 4.5 | 4.5 × 10⁸ |
| 12 | 580 | — | 0.21 | 0.21 × 10⁸ |
| 13 | 1185 | 1315 | 5.5 | 5.5 × 10⁸ |
| 14 | 1185 | — | 0.21 | 0.21 × 10⁸ |

This example demonstrates that it is possible to make very large libraries of cells with integrated antibody cassettes. The transfection efficiency ranged from 2.7 to 6.1%. In the case of the β-galactosidase selected population (sample 13) a library of 5.5×10⁸ clones can be created in a single flow electroporation session. With more than one session in a day, a library of 2-5×10⁹ clones can be generated.

After 13 days of blasticidin selection (10 μg/ml), cells were labelled with phycoerythrin labelled anti-Fc antibody (Biolegend, Cat. No. 409304) as described earlier. Of the antibody population selected on β-galactosidase, 34-36% of cells were positive for Fc expression and 11-13% were positive for binding of Dyelight-633-labelled antigen at 10 nM concentration.

Where FGFR binding clones were used, 98-99% of cells were positive for Fc expression. Use of a mixture of α-FGFR1_A and α-FGFR2_A antibodies affords an opportunity to examine the proportion of cells containing multiple integration events. For an individual cell with a correctly-integrated cassette (e.g., α-FGFR1_A) there is approximately a 50:50 chance that a second integration will be of the alternative specificity (i.e., α-FGFR2_A). If there are frequent multiple integrations, then the proportion of double-positive clones will be high, however, the proportion of double-positive clones was not found to be high, illustrating the fidelity of the nuclease-directed library integration system in generating one antibody gene/per cell. The ability of the surface displayed anti-FGFR antibodies to specifically bind their appropriate antigen was confirmed. Expression of antigen was from a plasmid pTT3DestrCD4 (d3+4)-His10 [134] encoding mouse Fgfr1 ectodomain (ENSMUSP00000063808). This was used to transfect HEK293 suspension cells and secreted Fgfr1-rCd4-His10 purified by immobilised metal affinity chromatography as described previously [134]. Mouse Fgfr2 ectodomain was PCR amplified from IMAGE clone 9088089 using primers:

2423
(SEQ ID NO: 97)
(TTTTTTCCATGGGCCGGCCCTCCTTCAGTTTAGTTGAG)
and 2437
(SEQ ID NO: 98)
(TTTTTTGCGGCCGCGGAAGCCGTGATCTCCTTCTCTCTC), digested with NcoI/NotI and cloned into expression plasmid pBIOCAM5 [126]. Fgfr2-Fc was expressed by transient transfection of HEK293 cells as described previously [134] and purified by affinity chromatography.

Transfected populations were probed for dual binding using both of the labelled antigens and the proportion of double positives was low. In this experiment the optimal balance of library size (2.7×10⁸ clones/per Maxcyte session) with low percentage of double positives (3.5%) was found using 197 ng donor DNA per 10⁶ cells (FIG. 23).

This proportion of double positives could represent misincorporation of a second antibody cassette but given the efficiency of nuclease-directed integration of the library it is also possible that both alleles (the AAVS locus in this example) could be targeted with incoming binders in a proportion of cells. The presence of two different antibody genes within a cell in itself does not prevent the isolation of binders or their encoding genes but this can be circumvented by first modifying the target cell at a single locus to introduce a single nuclease targeting site, e.g., a pre-integrated Sce1 meganuclease site as demonstrated in example 9.

Example 16. Recovery of Genes Encoding Binders from Sorted Library Populations

Phage display selections were carried on β-galactosidase (as described in example 6) and antibody populations from 1-2 rounds of selection were cloned into vector pD6 and introduced into the AAVS locus of HEK293 cells as described in example 6. β-galactosidase was labelled using Lightning Link Dyelight-633 (Innova Bioscience Cat. No 325-0010) according to manufacturer's instructions. Transfected cell populations were selected for 25 days in blasticidin (10 μg/ml) and were labelled with 10 nM Dyelight-633 labelled β-galactosidase and phycoerythrin-labelled anti-Fc (Biolegend Cat. No. 409304). Cells were incubated with antibodies for 30 minutes at 4° C., washed twice in PBS/ 0.1% BSA, re-suspended in PBS/0.1% BSA and double-positive cells sorted using a flow sorter.

Sorted cells were expanded and a second round of sorting was carried out using 10 nM antigen. Cells were grown and either genomic DNA or mRNA was isolated from the sorted, selected populations.

Where binders encompassing different chains (e.g., IgG formatted antibodies) are present on the same genomic sequence (e.g., by introduction on the same plasmid) but are transcribed into different mRNAs it may be optimal to recover the separate genes encoding the multimeric binder by amplification from genomic DNA. As an alternative, binders encompassing multiple protein chains can be encoded on the same mRNA through the use of "internal ribosome entry sequence" (IRES) elements or sequences such as viral P2A or T2A sequences that promote translational stalling/protein cleavage [133, 136]. In this case and in the case of binders encoded on a single protein chain it will also be possible to isolate the encoded genes from mRNA.

Genomic DNA was prepared using the "DNeasy blood and tissue kit" (QIAGEN Cat. No. 69504). mRNA was prepared using an "Isolate II RNA mini kit" (Bioline Bio-52072). For amplification from genomic DNA a PCR reaction was set up using Phusion polymerase with the "2×Phusion GC" mix according to manufacturer's instructions. Primers which flank the Nco1 and Not1 cloning sites, e.g., primers 2622 (GAACAGGAACACGGAAGGTC) (SEQ ID NO: 99) and 2623 (TAAAGTAGGCGGTCTTGAGACG) (SEQ ID NO: 82) were used to amplify the antibody cassette (98° C. 10 secs, 58° C. 20 secs, 72° C. 90 secs for 35 cycles.

Genes encoding selected scFv genes were amplified from mRNA. Total RNA was isolated from the sorted cells using the "Isolate II RNA mini kit" (Bioline Cat No Bio-52072). cDNA was synthesized from 2 µg RNA using Superscript II reverse transcriptase (Life Technologies, Cat no 180064-022). The selected scFv genes were then amplified from the cDNA by PCR using KOD Hot Start DNA polymerase (Merck Millipore Cat. No. 71086-3) using primers which flank the Nco1 and Not1 cloning sites. In this case, primers:

```
41679
                                        (SEQ ID NO: 100)
ATGAGTTGGAGCTGTATCATCC
and 2621
                                        (SEQ ID NO: 101)
GCATTCCACGGCGGCCGC
``` were used to amplify the antibody cassette (95° C. for 20 seconds, 60° C. for 10 seconds, 70° C. for 15 seconds, for 25 cycles). PCR products were digested with Nco1 and Not 1 before cloning into the Nco/Not1 site of bacterial antibody expression vector pSANG10. Construction of pSANG10, methods for bacterial expression and screening by ELISA are described in Martin et al 2006 [127].

ELISA screening of the population from 1 round of selection by phage display revealed that 0/90 of the clones were positive. In contrast, when this same population was further subjected to mammalian display and the scFv gene population was recovered and screened, 27/90 clones (30%) were positive in ELISA. This illustrates that it is possible to carry out mammalian display on a library and recover an enriched population of binders.

Example 15 describes the introduction of the population selected by 1 round of phage display on β-galactosidase into HEK cells using flow electroporation. The mammalian display cell population was selected in blasticidin as before and was subjected to flow sorting using 10 nM of labelled β-galactosidase. After 9 days growth 75% of cells were found by flow cytometry to be positive for β-galactosidase binding using 10 nM β-galactosidase). These were sorted and expanded further. To illustrate the potential to drive stringency, labelling was carried out using either 1 nM or 10 nM antigen concentrations. 20.3% and 55.9% of cells respectively were sorted from each population. After sorting, mRNA was prepared immediately from the sorted population without additional cell culture. Following cloning, expression in bacteria and ELISA screening (as before) it was found that the success rate in ELISA increased with increasing stringency during flow sorting. The clones displaying highest signal level came from this group and the number of positives clones was also improved (FIG. 24). This illustrates the ability to drive stringency of selection within display populations, reflected in the better performance of the resulting antibodies.

Example 17. Incorporation of T Cell Receptors (TCRs) Genes for Mammalian Library Production by Nuclease-Directed Integration The methods described herein have application beyond display of antibodies. To demonstrate the potential for screening libraries of T-cell receptors using nuclease-directed integration, a vector construct (pINT20) allowing expression of T-cell receptors was constructed.

pINT20 (FIG. 25a) is a dual promoter vector for targeting the human AAVS locus. It has left and right homology arms as presented in FIG. 3. The left AAVS homology arm is flanked by unique AsiSI and Nsi1 sites and is followed by a splice acceptor and a puromycin gene. The sequence between the end of the left homology arm and the splice acceptor is the same as previously described and the puromycin gene commences with an ATG in frame with the upstream exon ((FIG. 25B and as also shown for the blasticidin gene in FIG. 3). Correct nuclease-directed integration will lead to in-frame splicing of a puromycin gene which is spliced to an endogenous upstream exon which itself driven by the endogenous AAVS promoter allowing selection of clones with correct integration. The puromycin resistance gene is followed by an SV40 polyadenylation site. The right AAVS homology arm is flanked by unique BstZ171 and Sbf1 sites.

pINT20 is configured with a pEF promoter (from pSF-pEF, Oxford Genetics Cat. No. OG43), which allows genes of interest to be cloned into Nhe1/Kpn1 sites. The Nhe1 site is preceded by a secretion leader sequence and the Kpn1 site is followed by the polyadenylation signal of bovine growth hormone (bGH poly A) as shown previously in FIG. 2. Downstream is a CMV promoter (from pSF-CMV-f1-Pac1, Oxford Genetics Cat No OG111) allowing cloning via Nco and Not (as shown in FIG. 2) or Hind3. The Nco1 site is preceded by a secretion leader sequence and the cassette is followed by a bGH polyA site.

To exemplify display and enrichment of T cell receptors (TCRs) a TCR recognising a cancer marker described by Li et al. (2005) and later by Zhao et al. (2007)[137, 138] was used. This TCR called c12c2 recognises the peptide SLL-MWITQV (SE ID NO: 102) presented on HLA-A2 with an affinity of 450 nM. This peptide represents residues 157-165 from NY-ESO-1 (NY-ESO-1 157-165). This is an affinity-matured variant of a parental antibody called 1G4 with affinity of 32 µM.

A second TCR was used which recognises another cancer marker. The parental MEL5 TCR recognises the peptide MART-1 26-35 ("Melanoma antigen recognised by T cells-1") presented on HLA-A2 with peptide sequence ELA-GIGILTV (SEQ ID NO: 103). This TCR was affinity matured by phage display to give clone α24/β17 with 0.5 nM affinity described in Madura at al. (2013) [139]. The structure of the complex between TCR and MHC:peptide complex has been solved (pdb code 4JFH) and the clone is hereafter named as "4JFH". The same parental TCR has also been engineered based on design by Pierce et al. (2014) [140] and the structure of the complex solved.

According to Debets and colleagues the attachment of the CD3 ζ domain as shown tends to cause association of the heterologous gene even in the presence of native human TCRs [141, 142]. The CD3ζ element used is composed of an extracellular domain, a transmembrane domain and a complete cytoplasmic domain. In addition substitution of human constant domains by mouse constant domains in the heterologous genes also tends to drive their association over association with endogenous human constant domains [143]. Finally the use of mouse constant domains offers the option of detecting the heterologous TCR chains against a background of human TCRs. These elements were incorporated into the design of the TCR expression cassette.

Two synthetic genes were designed and synthesised giving rise to gene constructs with the following structure:
Human TCR Vα-mouse α constant-human CD3 ζ
Human TCR Vβ-mouse β constant-human CD3 ζ

The sequence of the synthetic gene incorporating the α chain and the β chain constructs incorporating the variable domains of c12/c2 is shown in FIGS. 25*c* and *d*. These are cloned into the Nhe1/Kpn1 sites and the Nco1/Hind3 sites of pINT20 respectively. The construct encoding this TCR is called pINT20-c12/c2. In the first instance the synthetic gene was designed to incorporate a Vα Cα domain (flanked by Nhe1 and Not 1 sites) and Vβ domain (flanked by Nco1/Xho1 sites encoding the TCR c12/c2). These elements can then be replaced by alternative TCRs using these restriction sites.

Two additional synthetic genes were made encoding the Vα and V β domains of 4JFH [139] (FIGS. 25*e* and *f*). The construct encoding this TCR is called pINT20-4JFH.

$10^7$ HEK293 cells were transfected using 3 µg of pINT20-c12/c2 and pINT20-4JHF as donor DNA (300 ng donor DNA per $10^6$ cells) in the ratios shown in Table 7. pINT20-c12/c2 is referred to as TCR1 and pINT20-4JHF is referred to as TCR2. 5 µg each of pZT-AAVS1 L1 and pZT-AAVS R1 TALENs were added to $10^7$ cells (500 ng each per $10^6$ cells) with the exception of sample 6 where this was replaced by 10 µg of control DNA (pcDNA3.0). DNA was introduced by polyethyleneimine transfection, as described above.

TABLE 7

| Sample | TCR1/TCR2 ratio |
|---|---|
| 1 | 1:100 |
| 2 | 100:1 |
| 3 | 50:50 |
| 4 | 100% TCR1 |
| 5 | 100% TCR2 |
| 6 | 50:50 (no TALE nuclease) |

Following 12 days in selection (0.25 µg/ml puromycin) cells were labelled with target antigen. The peptide:MHC complexes recognised by the TCRs described above are presented as a phycoerythrin labelled pentamer (Proimmune). c12/c2 recognises peptide SLLMWITQV presented on HLA-A2 representing NY-ESO-1 157-165 (Proimmune product code 390). 4JHF (also known as α24/β17) recognises peptide ELAGIGILTV presented on HLA-A2 representing MelanA/MART 26-35 (Proimmune product code 082). In each case the MHC:peptide complex was labelled with phycoerythrin and used according to manufacturer's instructions. FIG. 26 (*a-d*) shows that each TCR is specific for the expected MHC: peptide complex (a, d) and fails to bind to the non-cognate peptide in complex (FIG. 26*b, c*). DNA encoding each TCR was mixed with a 100-fold excess of DNA encoding the other (samples 1-2, Table 7). HEK293 cells were transfected and selected in puromycin. Sorting of antigen positive cells was performed after 14 days of puromycin selection (FIG. 26*g, h*).

In order to quantitate the level of enrichment within the flow-sorted output populations, the TCR genes were recovered by PCR amplification and the relative amounts of each TCR species determined following cloning. Total RNA was isolated from the sorted population. cDNA synthesis was performed as described in example 16. Primers to amplify the TCR alpha and beta chain were 1999/2782 and 41679/2789 respectively (Table 8). PCR amplification employed KOD hot start polymerase using the manufacturer's recommended protocol (EMD Millipore, 71086, EMD Millipore). PCR reaction conditions were 95° C. (2 mins) and 25 cycles of 95° C. (20 s), 60° C. (10 s), 70° C. (15 s) followed by 70° C. (5 mins). The amplified TCR alpha and beta chains were digested with NheI/NotI or NcoI/XhoI and sub-cloned into vectors with compatible sites (in this case pBIOCAM1-Tr-N NheI/NotI or pBIOCAM2-Tr-N(NcoI/XhoI) cut vectors respectively). PCR of individual clones were amplified with a c2c12 (TCR1) specific TCR alpha primer (2781) or a 4JFH (TCR2) specific TCR alpha primers (4JFH-Vα-F) and vector specific primers to assay for TCR clone identity. After sorting of the sample 1 (Table 7) where a ratio of 1:100 TCR1/TCR2 donor plasmid was employed (Table 7) with enrichment for TCR1 specific clones using peptide SLLMWITQV presented on HLA-A2 (Proimmune, product code 390), the proportion of TCR1 clones, as determined by colony PCR, increased to 11/15 (73%). Enrichment by sorting the sample 2 where a ratio of 100:1 TCR1/TCR2 donor plasmid was employed (Table 7), with peptide ELAGIGILTV presented on HLA-A2 (Proimmune product code 082) resulted in an increase of the proportion of TCR2 clones to 4/15 (27%), determined by colony PCR.

To demonstrate library selection using nuclease-directed integration, a mutant library based on c12/c2 was created by cloning a repertoire of genes encoding mutant TCR alpha chains along with a repertoire of genes encoding mutant TCR beta chains. Such a library could be created using oligonucleotide-directed mutagenesis approaches. e.g., methods based on Kunkel mutagenesis [144]. As an alternative and by way of example, a PCR assembly approach was used to create a mutant TCR alpha chain (as a Nhe1/Kpn1 fragment) and a mutant TCR beta chain (as a Kpn/Hind 3 fragment, including the CMV promoter) which is cloned into the Nhe1/Hind 3 site of pINT20. This was done using primers shown in Table 8.

TABLE 8

Primers used in library construction and clone recovery

| | |
|---|---|
| 4JFH-Vα-F (SEQ ID NO: 104) | ACACACGCTAGCCAGAAAGAGGTGGAACAG |
| 1999 (SEQ ID NO: 87) | AAAAAGCAGGCTACCATGAGGGCCTGGATCTTC TTTCTCC |
| 2770 (SEQ ID NO: 105) | CAAAGAACAGCTCGCCGGTSNNCCCGASSNNGG AGCTGGCGCAAAAGTAC |
| 2771 (SEQ ID NO: 106) | CTCGCCCGAAGGTGGGAATGTANGWTCCSNNSN NAAGTGGGCGCACGGCGCAC |

TABLE 8 -continued

Primers used in library construction and clone recovery

| | | |
|---|---|---|
| 2780 (SEQ ID NO: 107) | | CTGGCAGCTAGCAAGCAGGAAG |
| 2781 (SEQ ID NO: 108) | | TACATTCCCACCTTCGGGCGAG |
| 2782 (SEQ ID NO: 109) | | TTTTTTGCGGCCGCGGACAGGTTCTG |
| 2783 (SEQ ID NO: 110) | | CGTAAGCTGGTACCTTATTATCTAGGG |
| 2785 (SEQ ID NO: 111) | | CCCTAGATAATAAGGTACCAGCTTACG |
| 2787 (SEQ ID NO: 112) | | ACCGGCGAGCTGTTCTTTG |
| 2788 (SEQ ID NO: 113) | | AGTGACAAGCTTTTATTATCTGGGTG |
| 2789 (SEQ ID NO: 114) | | CAGGTCCTCGAGCACTGTC |
| 41679 (SEQ ID NO: 100) | | ATGAGTTGGAGCTGTATCATCC |

(N = A, C, G, T. S = C OR G, W = A OR T)

A mutant oligonucleotide was designed (primer 2771) which randomised 2 amino acid positions within CDR3 of the c12/c2 alpha chain and provide the option of either serine or threonine at another position (primer 2771 is also represented by the lower strand of FIG. 25g). Primer 2771 was used in conjunction with primer 2780 to create mutant TCR alpha repertoire going from the Nhe1 cloning site incorporating the region of CDR3 mutagenesis with an invariant sequence at the end. Primer 2781 is complementary to the invariant 5' end of primer 2771. PCR with primers 2781 and 2783 provided the remainder of the TCR alpha-CD3 zeta cassette up to the Kpn1 site. PCR assembly of the 2 PCR fragments is used to create the TCR alpha-CD3 zeta fragment which can be cloned into pINT20 following digestion with Nhe1 and Kpn1.

A second mutant oligonucleotide (primer 2770) was designed which randomised 2 amino acid positions within CDR3 of the c12/c2 beta chain and provide the option of either valine or leucine at another position (primer 2770 represented by the lower strand of FIG. 25h). Primer 2770 was used in conjunction with primer 2785 to create a mutant TCR beta repertoire from the Kpn1 cloning site incorporating the region of CDR3 mutagenesis with an invariant sequence at the end. Primer 2787 is complementary to the invariant 5' end of primer 2700. PCR with primers 2787 and 2788 provided the remainder of the TCR beta-CD3 zeta cassette up to the Hind 3 site. PCR assembly of these 2 PCR fragments is used to create a TCR beta-CD3 zeta fragment which can be cloned into pINT20. A complete repertoire incorporating mutations at both CDR 3 of alpha and beta chains was created by cloning of the Nhe1/Kpn fragment, the Kpn1/Hind3 fragment into Nhe1/Hind3 digested pINT20. Following ligation the library was cloned into electrocompetent DH10B cells. Plasmid DNA was prepared and the DNA transfected into HEK293 cells along with vectors encoding TALE nuclease as described earlier (an equimolar mix of pZT-AAVS1 L1 and pZT-AAVS R1 Systems Bioscience Cat. No. GE601A-1).

Following ligation of the mutant alpha and beta chains of the c12/c2 mutant library into pINT20, DNA was electroporated into DH10B cell, plasmid DNA was prepared and the library was co-transfected with TALE nuclease targeting the AAVS locus. Transfection was performed using Maxcyte electroporation. Growth and selection were as described above. Quantitation of the library size, by titration of transfected cells and plate-based selection in puromycin, indicated that a library size $5 \times 10^5$ was created. After puromycin selection for 11 days cells were labelled with an APC-labelled antibody specific to the β chain of the mouse TCR (Life Technologies Cat H57-957). FIG. 26 i-j shows 38% of clones in the population express a T cell receptor. Of this TCR positive population, 13% also bound peptide1 (5% of the total population). By this approach clones with improved expression or peptide:MHC binding activity can be isolated.

From FIG. 26 it can be seen that each T cell receptor recognised only its cognate antigen. Furthermore when a mixture of the two different specificities are used it is possible to distinguish each of them through the labelled antigen. This approach also allows TCR clones with improved affinity (or expression) to be distinguished within the mutant TCR library by identifying a subset of the library that was labelled to a greater extent than the parental clone T cell receptor genes were also introduced into Jurkat cells by electroporation. Jurkat cells were centrifuged and re-suspended in a final volume of $10^8$ cells/ml in the manufacturer's electroporation buffer (Maxcyte Electroporation buffer, Thermo Fisher Scientific Cat. no NC0856428)). An aliquot of $4 \times 10^7$ cells (0.4 ml) was added to the OC400 electroporation cuvette with 40 µg DNA (i.e., 1 µg/$10^6$ cells). DNA consisted of a mixture of donor plasmid DNA (pINT20-c12/c2 or pINT20-4JHF or pINT20-c12/c2 TCR library, 9.2 µg) and an equimolar mix of DNA (30.8 µg total) of DNA encoding the AAVS-SBI TALENs (pZT-AAVS1 L1 and pZT-AAVS R1 Systems Bioscience Cat No GE601A-1). In samples without added TALENs the input DNA was brought to 1 µg/$10^6$ cells using control plasmid pcDNA3.0. An alternative method of introducing T cell receptor genes into Jurkat cells used the 4D-Nucleofector (Lonza). Here, the transfection protocol followed the manufacturer's instructions according to the SE cell-line kit (Lonza, Cat. PBC1-02250). Briefly, 2 µg of DNA, consisting of a mixture of donor plasmid DNA (pINT20-c12/c2 or pINT20-4JHF or pINT20-c12/c2 TCR library, 0.46 µg) and an equimolar mix of DNA (1.54 µg total) of DNA encoding the AAVS-SBI TALENs (pZT-AAVS1 L1 and pZT-AAVS R1 Systems Bioscience Cat No GE601A-1) was transfected per $10^6$ Jurkat cells. The pulse code setting was CL120 and cell type programme was specific for Jurkat E6.1 (ATCC) cells.

FIG. 26 demonstrates that TCR expression was achieved and recognition of the appropriate peptide:MHC molecule was achieved. This was dependent on the use of TALE nuclease (compare FIGS. 26 m and n). Signalling through the introduced TCR was also achieved using the relevant peptide:MHC molecule.

pINT20-c12/c2 transfected Jurkat cells or untransfected Jurkat cells were plated in a 96-well plate at a density of $1 \times 10^6$/ml, 200 µl per well. Cells were stimulated with either 2 µl or 6 µl per well of PE labelled peptide 1-MHC pentamer (ProImmune) or 2 µg/ml anti-human CD3 (BD Pharmingen, Cat 555329) in the presence and absence of anti-human CD28 (BD Pharmingen Cat 555725) at 2 µg/ml. After a 24 hour incubation at 37° C. and 5% $CO_2$, the activation of Jurkat cells was detected by investigating CD69 expression.

Cells were stained with 50 µl PBS+1% BSA+0.5 µl of anti-human CD69-APC (Invitrogen, Cat. MHCD6905) per well for 45 minutes at 4° C.

FIG. 26 (sample o and p) demonstrates up-regulation of CD69 upon stimulation with CD3. The figure also shows the effect of adding 2 µl (q) or 6 µl (r) of peptide1:MHC. A population of double-positive cells which bind peptide:MHC and express CD69 is obvious. This example shows cells incubated in the presence of CD28 but the same effect was observed in the absence of CD28 (not shown).

This example demonstrates the potential of nuclease-directed integration of libraries of an alternative type of binder, i.e., T cell receptors. We demonstrate that it is possible to express and detect TCR expression on the cell surface using specific antibodies. We also demonstrate that these T cell receptors specifically recognise their respective targets. We have also constructed a mutant library allowing selection of improved binders. Finally we have demonstrated that library screening based on activation of TCR signalling in T cells is possible. Here we have used a cultured human T cell line. It is also possible to introduce DNA into primary T cells by Maxcyte electroporation. Methods for the isolation and preparation of primary T lymphocytes are known to those skilled in the art (e.g., Cribbs et al., 2013, Oelke et al. 2003 [145, 146]. Exposure of TCR transfected lymphocytes to multimeric peptide:MHC can then be used to achieve activation either through exposure to peptide:MHC multimers [146] or to antigen presenting cells loaded with the appropriate peptide [146, 147]. Activation can be detected either through expression of reporter genes or through up-regulation of endogenous genes such as CD69 [104, 148].

Example 18. Display of Libraries of Chimeric Antigen Receptors on Mammalian Cells Activation of T cells normally occurs through interaction of the T Cell Receptor (TCR) with specific peptide:MHC complexes. This in turn leads to signalling directed via CD3 and other T cell signalling molecules. As an alternative to target recognition directed by the TCR it has been shown that alternative binding molecules such as single chain Fvs can be presented on T cells as fusions to downstream signalling molecules in a way that re-directs T cell activation to the molecule recognised by the scFv (or alternative binder). In this way T cell activation is no longer limited to the molecular recognition directed towards peptide:MHC complexes by TCRs but can be directed to other cell surface molecules. This alternative format wherein a non-TCR binding entity is fused to a signalling component is referred to as a "chimeric antigen receptor" (CAR). In the case of T cells this has been shown to be an important and valuable means of re-directing T cell activation.

For any given target it is still not clear what the optimal epitope or affinity features should be for incorporation into a CAR [103]. Features of the CAR design such as linker length, or choice of transmembrane domain may in turn affect what constitutes an optimal epitope. The combination of antigen density on target and non-target cells together with the choice of signalling domain could affect the optimal affinity requirements. The ability to present libraries of chimeric antigen receptors on T cells affords an opportunity to identify optimal binding specificity, binder format, linker length/sequence, variants of fused signalling module, etc., either alone or in combination. Here we demonstrate the utility of nuclease-directed integration for construction of libraries of chimeric antigen receptors in mammalian cells.

The vector pINT21 (FIG. 27a) is a single CMV promoter vector for convenient expression and secretion of binders such as scFvs flanked by Nco1/Not1 restriction sites to allow in frame expression with an upstream leader sequence and a downstream fusion partner (as shown earlier in FIG. 8). The CAR expression cassette in pINT21 is flanked by AAVS homology arms as described earlier in FIG. 3.

The vector pINT21-CAR1 (FIG. 27a, c) fuses binders such as single chain Fvs to the transmembrane domain and intracellular domain of CD3 (FIG. 27c and as described for TCR expression in FIG. 25). This format is often referred to as a "first generation" chimeric antigen receptor. Signalling domains from other co-stimulatory molecules have also been used to provide additional signals and these have been shown to give improved signalling. These have been referred to as second and third generation chimeric antigen receptors. For example pINT21-CAR2 (FIG. 27 b, d) fuses the binder (conveniently cloned in this case as an Nco1/Not 1 fragment to a previously described second generation domain (WO 2012/079000 A1) consisting of:
The hinge and transmembrane domain from CD8
4-1BB signalling domain
CD3ζ signalling domain By way of example a number of different binder groups were cloned into the Nco/Not1 sites of pINT20-CAR1 and pINT20-CAR2. CD19 has previously been used in a number of different studies to target B-cell malignancies references in Sadelain et al. (2013) [103]. A previously described anti-CD19 antibody (WO 2012/079000 A1) (called FMC63) was prepared as a synthetic scFv gene in either a VH-linker-VL configuration or a VL-linker-VH configuration (FMC63 H-L or FMC L-H respectively, FIG. 27E shows the sequence of FMC63 H-L. FMC63 L-H was configured with the variable domains in VL-linker-VH configuration flanked by Nco1 and Not1 at 5' and 3' ends respectively.

As controls, scFvs with alternative binding specificities were also cloned into pINT20. These include anti-FGFR1_A [105] and an anti-desmin control antibody [7]. In addition, Adhirons [152] recognising lox1 (FIG. 29 a, b) were introduced as an example of an alternative format of binder configured as a CAR fusion (see example 19 for description).

To demonstrate the creation of libraries of binders presented in a CAR format, populations of scFv-formatted antibodies selected on mesothelin and CD229 were cloned. Mesothelin is a cell surface glycoprotein which is highly expressed in a number of cancers including mesothelioma. A number of antibody-based formats are under development and in clinical trial including CARs directed to mesothelin [149]. CD229 represents another potential tumour-associated antigen which could be targeted by immune therapy in cancers such as chronic lymphocytic leukaemia and multiple myeloma [150, 151].

A population of antibodies recognising either mesothelin or CD229 was created by selection using the "McCafferty" phage display library as described in example 6 and ref 7). Two rounds of selection were carried out and the scFv-encoding genes recovered using primers M13leadseq and Notmycseq (example 6). Products were cut with Nco1/Not 1, gel purified and cloned into pINT21-CAR2. These were directed into the AAVS locus of HEK293 cells by TALE nuclease cleavage to generate a library of $4.8 \times 10^5$ for CD229 and $6.4 \times 10^5$ for mesothelin (representing a 30× and 53× increase in library compared to samples transfected in the absence of TALE nuclease).

pINT20-CAR1 and pINT20-CAR2 were introduced into HEK293 cells by PEI transfection. Here donor plasmid DNA (pINT20-CAR1 or pINT20-CAR2, 6 µg was mixed with an equimolar mix of DNA (20 µg total) of DNA encoding the AAVS-SBI TALENs (pZT-AAVS1 L1 and pZT-AAVS R1 Systems Bioscience Cat No GE601A-1) in Freestyle 293 media (Lifetech, Cat. 12338-026), linear PEI (52 µl, 1 mg/ml, Polysciences Inc.) added and incubated at room temperature for 10 mins. The mixture is then added to 20 ml HEK293 suspension cells ($1 \times 10^6$ cell/ml) in a 125 ml vented Erlenmeyer flask. pINT20-CAR1 and pINT20-CAR2 were also introduced into Jurkat cells by electroporation. Jurkat cells were centrifuged and re-suspended in a final volume of $10^8$ cells/ml in the manufacturer's electroporation buffer (Maxcyte Electroporation buffer, Thermo Fisher Scientific Cat. no NC0856428)). An aliquot of $4 \times 10^7$ cells (0.4 ml) was added to the OC400 electroporation cuvette with 40 µg DNA (i.e., 1 µg/$10^6$ cells). DNA consisted of a mixture of donor plasmid DNA (pINT20-CAR1 and pINT20-CAR2, 9.2 µg) and an equimolar mix of DNA (30.8 µg total) of DNA encoding the AAVS-SBI TALENs (pZT-AAVS1 L1 and pZT-AAVS R1 Systems Bioscience Cat No GE601A-1). In samples without added TALENs, the input DNA was brought to 1 µg/$10^6$ cells using control plasmid pcDNA3.0

Fluorescent labelling of the various antigens was performed using Lightning-Link Rapid Dye-Light 633 conjugation kit (Innova Biosciences, cat. 325-0010). Preparation of FGFR1 and FGFR2 is described in example 15. Lox1 and CD229 were from R and D Systems (Cat. Nos. 1798-LX-050, and 898-CD050 respectively), CD19-Fc and mesothelin were from (AcroBiosystems Cat. No. CD9-H5259 and MSN-H526× respectively).

FIG. 28 b illustrates display of nuclease-directed anti-FGFR1 antibody [105] within a second generation CAR construct (pINT21-CAR2-FGFR1_A). FIG. 28d also illustrates display of an alternative scaffold molecule (an Adhiron ref [152]) as a fusion with a second generation chimeric antigen receptor (pINT21-CAR2-lox1). FIGS. 28 f and g also illustrate positive clones within a library of scFvs selected on mesothelin or CD229.

In this example CARs were introduced into HEK cells and Jurkat cells but this could equally be done by introducing the constructs into primary cells such as human T lymphocytes (e.g., as described by Sadelain et al. (2013) [103], for example using electroporation [135]. Expression constructs for CAR expression in lymphocytes may be further optimised, e.g. by optimising mRNA stability and translation through variation in 5' and 3'untranslated regions, poly A length etc., as has previously been described [135]. Signalling of CAR constructs introduced into primary T lymphocytes or T lymphocyte cell lines can be induced by exposure to cells expressing target antigen or using multimeric antigen, e.g. antigen immobilised on a surface or presented on beads [104, 148].

Example 19. Display of Libraries of Alternative Scaffolds Constructed in Mammalian Cells Via Nuclease-Directed Integration The method described for constructing libraries of binders can be employed beyond display of antibodies and T cell receptors. A number of alternative scaffolds have been described allowing construction of libraries of variants from which novel binding specificities have been isolated, e.g., Tiede et al. (2014) [152] and references therein. In the example described by Tiede et al. (2014) a stable, versatile scaffold based on a consensus sequence from plant-derived phytocystatins was used. This scaffold is referred to as an Adhiron and FIG. 29a shows a synthetic gene encoding an Adhiron which was selected to bind to lox1 (WO 2014125290 A1). FIG. 29 B shows an alternative lox1 binder (lox1B). Both were synthesised and cloned into the Nco1/Not1 site of pINT20_CAR2 to create a fusion with the downstream partner.

A library can be constructed by randomising loop residues (e.g., by Kunkel mutagenesis or PCR assembly as described above in example 17). By way of example, FIG. 29c shows the design of a mutant oligonucleotides useful to create a library following the same approach as described in example 17. In this case, randomisation is achieved by introducing a variable number of NNS residues, although alternative strategies known to those skilled in the art could be used.

As another example FIGS. 29 d and e demonstrates the means to create a library of binders by nuclease-directed integration based on a knottin scaffold [156]. Knottins are peptides of approximately 30 amino acids which are stabilised by three disulphide bonds, with one threaded through the other two to create a "knotted" structure. FIG. 29 d shows the trypsin binding knottin MCoTI-II with an Nco1 site at the 5' end and a Not site at the 3' end allowing in-frame expression with the vectors described herein. As an example for library construction the 6 amino acids of the first loop (underlined in FIG. 29d) can be mutated with variable number of amino acids. FIG. 29e illustrates a mutagenic strategy replacing the 6 amino acids of loop 1 with 10 randomised amino acids using the codons VNS (where V=A, C or G and S=C or G).

The VNS codon encompasses 24 codons encoding 17 amino acids which exclude cysteines. This strategy is for illustrative purposes and alternative mutagenic strategies will be known to those skilled in the art.

Example 20. Nuclease-Directed Introduction of Antibody Libraries Using CRISPR/Cas9

Nuclease-directed integration via CRISPR/Cas9 was demonstrated using the "Geneart CRISPR nuclease vector kit" (Lifetech A21175). In this system, a U6 RNA polymerase III promoter drives expression of a target complementary CRIPSR RNA (crRNA) which is linked to a trans-activating crRNA (tracrRNA). The crRNA and tracrRNA together make up a guide RNA which directs the cleavage specificity of a Cas9 protein encoded on the same "GeneArt CRISPR nuclease vector" (see manufacturer's instructions). The vector is provided as a linearised plasmid into which a short double-stranded oligonucleotide with appropriate 3' overhangs is cloned. Cleavage specificity is then determined by the sequence of the cloned segment. Two different targeting sequences were designed to direct cleavage to the human AAVS locus describe above.

The sequences were:

CRISPR1 double-stranded DNA insert:

(SEQ ID NO: 115)
5' GGGGCCACTAGGGACAGGATGTTTT (SEQ ID NO: 116)
3' GTGGCCCCCGGTGATCCCTGTCCTAC

CRISPR2 double-stranded DNA insert:

```
                                    (SEQ ID NO: 117)
5' GTCACCAATCCTGTCCCTAGGTTTT (SEQ ID NO: 118)
3' GTGGCCAGTGGTTAGGACAGGGATC
```

The resulting guide RNAs target cleavage within the same region of the AAVS locus as the TALE nucleases described above (with CRISPR2 being in the reverse orientation from CRISPR1). Thus the AAVS homology arms used previously to direct integration of the expression cassette can be used for integration directed by these CRISPR guide RNAs. Linearised vector and double stranded oligonucleotides were ligated and transformed into electrocompetent DH10B cells. Cloning of the correct insert was confirmed by sequencing and plasmid DNA was prepared. The Cas9/CRISPR2 construct (encompassing the CRISPR2 oligonucleotide) was transfected together with donor DNA encoding a β-galactosidase library selected by 1 round of phage display selection (example 15). These were transfected into HEK293 cells using Maxcyte electroporation system with the OC-400 assembly. $4 \times 10^7$ cells were transfected with 23.2 μg of donor DNA representing a population of scFv genes selected by one round of phage display on β-galactosidase cloned into pD6. Cells were co-transfected with either 77 μg of Cas9-CRISPR2 plasmid, or 77 μg TALEN plasmid (38.5 μg each of pZT-AAVS1 L1 and pZT-AAVS) or 77 μg control plasmid

TABLE 9

| Sample no | Nuclease used | Transfection efficiency % | Number of clones per $10^{10}$ cells |
|---|---|---|---|
| 1 | Cas9/CRISPR 2 | 10.53 (29x) | $10 \times 10^8$ |
| 2 | AAVS TALEN | 5.1 (14 x) | $5.1 \times 10^8$ |
| 3 | None (pCDNA3.0) | 0.36 | $0.36 \times 10^8$ |

Titration of the number of transformants formed by Cas9/CRISPR2 transfection (by measuring blasticidin resistance colonies) revealed that 1053 blasticidin resistant colonies were generated from plating 10,000 cells, equating to a transfection efficiency of 10.5% (Table 9). In the case of TALE nuclease-directed a transfection efficiency of 5.1% was achieved. In contrast, in the absence of the Cas9/CRISPR2 construct only 0.36% transfection efficiency was achieved.

As an alternative to transfection using plasmid DNA to introduce the Cas9 protein and guide RNA into cells it is also possible to directly introduce a nucleoprotein complex consisting of Cas9 protein (Toolgen, Inc.) and a guide RNA. Guide RNA was prepared by Toolgen, Inc. using in vitro transcription from a T7 promoter as a single transcript which included the TRACR sequence (underlined) preceded by sequence complimentary to the target DNA (in bold) as shown below.

CRISPR 1 RNA (SEQ ID NO: 119:
5' GGGGGGCCACUAGGGACAGGAUGUUUUAGAGCUAGAAAUAGCAAG

UUAAAAUAAGGCUAGUCCGUUAUCAACUUGAAAAAGUGGCACCGAGUC

GGUGCUUUU

CRISPR 2 RNA (SEQ ID NO: 120):
5' GGGUCACCAAUCCUGUCCCUAGGUUUUAGAGCUAGAAAUAGCAAG

UUAAAAUAAGGCUAGUCCGUUAUCAACUUGAAAAAGUGGCACCGAGUC

GGUGCUUUU 6.6 μg of Cs9 protein, 4.6 μg of RNA and 10 μg of donor DNA (encoding the anti-FGFR1_A antibody in pD6) were introduced into $10^7$ HEK293 cells by Maxcyte electroporation as described above. Transfection efficiencies of 2.2% and 2.9% were achieved for CRISPR 1 and CRISPR2 RNA respectively with 0.7% and 0.8% in the absence of added Cas9:RNA protein complex.

These guide RNAs target the same sequences encoded by CRISPR1 and CRISPR2. As an alternative, crRNA and tracrRNA can be made by chemical synthesis (e.g., GE Dharmacon).

Example 21. Nuclease Mediated Antibody Gene Insertion by Ligation or Microhomology-Mediated End-Joining (MMEJ)

Although homologous recombination (HR) is useful for the precise insertion of large DNA fragments, this requires the construction of large targeting vectors incorporating long homology arms. This can make the construction of large libraries more difficult due to the reduced transformation efficiency of larger DNA constructs. Alternatively, simple ligation reactions can occur between the chromosomal DNA and targeting vector, if a nuclease recognition sequence is incorporated into the targeting vector. The ligation reactions can either be "sticky-end" employing, for example, zinc finger nucleases (Orlando at al., 2010) [45] or TALENs (Cristea et al., 2013) [22] which can make double-strand breaks (DSBs) that leave 5' overhangs or "blunt-end" employing CRISP/Cas9 ribonucleoprotein. An example of nuclease gene integration by ligation using I-SceI meganuclease was shown by the construction of vector pD7-Sce1. pD7 is derived from pD6 (FIG. 8) but the left and right AAVS homology arms were replaced with short double stranded oligonucleotides. The left AAVS homology arm of the pD vector series is flanked by EcoR1 and Nsi1 restriction enzymes (see FIG. 3). To convert pD6 to pD7-Sce1, this was replaced by a double-stranded oligonucleotide insert formed by primers 2778 and 2779 encoding an I-SceI meganuclease recognition sequence with "sticky ends" compatible with the "sticky ends" formed by EcoRI/NsiI. The right hand AAVS homology arm is flanked by Asc1 and Mlu1 restriction sites (FIG. 3). The right homology arm was replaced by a double-stranded oligonucleotide insert with "sticky ends" compatible with the "sticky ends" formed by AscI/MluI digestion and is formed by primers 2723 and 2724.

TABLE 10

Primers for pD7 and pINT19 construction

| | |
|---|---|
| 2723 (SEQ ID NO: 121) | CGCGCCAGAAGTCTCACCAAGCCCA |
| 2724 (SEQ ID NO: 122) | CGCGTGGGCTTGGTGAGACTTCTGG |
| 2768 (SEQ ID NO: 123) | AATTCTCCCCTCCACCCCACAGTAGGGACAGTG GGGCCAGGATTGGTGACAGAAAATGCA |

TABLE 10 -continued

Primers for pD7 and pINT19 construction

| 2769 (SEQ ID NO: 124) | TTTTCTGTCACCAATCCTGGCCCCACTGTCCCT ACTGTGGGGTGGAGGGGAG |
| --- | --- |
| 2778 (SEQ ID NO: 125) | AATTCTAGGGATAACAGGGTAATATGCA |
| 2779 (SEQ ID NO: 126) | TATTACCCTGTTATCCCTAG |
| 2808 (SEQ ID NO: 127) | AATTCTTTTCTGTCACCAATCCTGGGGCCACTA GGGACACTGTGGGGTGGAGGGGATGCA |
| 2809 (SEQ ID NO: 128) | TCCCCTCCACCCCACAGTGTCCCTAGTGGCCCC AGGATTGGTGACAGAAAAGAATTG |

Antibodies recognising Fgfr1 and Fgfr2 (example 15) were cloned into pD7 to create pD7-SceI anti-Fgfr1 and pD7-SceI anti-Fgfr2 respectively. These were co-transfected with the I-Sce1 expression plasmid (example 11, FIG. 16) into the HEK293 clone 6F cell line (see example 11) which contains an integrated I-Sce1 recognition site.

Ligation of DSBs in the chromosome and targeting vector generated by zinc finger nuclease or TALE nucleases can also be achieved. By inverting the zinc finger nuclease or TALEN recognition sites on the targeting vector this can ensure that the product of the insertion is no longer a target for cleavage in a method termed "Obligate ligation-gated recombination" or ObLiGaRe (Maresca et al., 2013) [153]. pD7-ObLiGaRe vectors can be generated in the same way as described above for the creation of pD7-Sce1. In this case, the left hand homology arm is replaced by an oligonucleotide consisting of primers 2808 and 2809 encoding an inverted TALEN recognition site (shown in bold) and spacer region. The right hand homology arm is replaced with primers 2723 and 2809 as described above.

An alternative to simple ligation reactions between DSBs in the chromosome and targeting vector, mediated by non-homologous end joining (NHEJ) is microhomology-mediated end-joining (MMEJ). MMEJ is a DSB repair mechanism that uses microhomologous sequences between 5 to 25 bp for error-prone end joining (McVey and Lee, 2008) [154]. A strategy for precise gene integration has been devised where the genomic sequence and the targeting vector contain the same TALE nuclease pair recognition sequence, but a different vector spacer sequence in which the anterior and posterior half are switched. The genomic sequence and vector can be cut by the same TALEN pair and MMEJ takes place via the microhomologous DNA ends. The resultant integrated targeting vector is no longer a target for TALE nuclease because of the shortened spacer region which are not optimal for TALE nuclease cleavage (Nakade et al., 2014) [155].

The MMEJ AAVS targeting vector pD7-MMEJ can be generated in the same way as described above for the creation of pD7-Sce1. In this case the left hand homology arm is replaced by an oligonucleotide consisting of primers 2768 and 2769 encoding the TALEN recognition site (shown in bold) and switched spacer region (underlined). The right hand homology arm is replaced with primers 2723 and 2809 as described above.

Example 22. Design of Primers for Creation of Single (CMV) Promoter Cassette Flanked by ROSA26 Arms (pINT19-ROSA)

This example is intended to demonstrate that antibody or alternative binding molecule genes can be integrated into the genome of mammalian cells by nuclease directed methods and the resultant clones screened for a desired function by either reporter or phenotypic screening. An example of this was previously demonstrated where antibody genes were integrated into the chromosome of mouse embryonic stem (ES) cells and individual ES colonies screened for their ability to maintain pluripotency when subjected to differentiation conditions [105]. Antibody genes recovered from ES colonies which maintained a pluripotent phenotype were shown to block the FGFR1/FGF4 signaling pathway. A problem with this previously reported method is that homologous recombination can result in small library sizes, thus limiting its ability to directly screen for rare clones present in large binding molecule libraries. Nuclease-mediated gene integration methods for antibody and binding molecule gene integration are more efficient resulting in larger library size generation and thus more likely to generate mammalian cell libraries capable of identifying functional antibodies by phenotypic or reporter cell screening.

The donor targeting vector pINT19 is designed to integrate antibody genes into the mouse ROSA26 locus by nuclease directed methods for direct functional screening. pINT19 is a single CMV promoter vector for scFv-Fc fusion expression. The expression cassette is flanked by mouse ROSA26 arms. Since the upstream exon is untranslated, the puromycin gene is preceded by a splice acceptor and further down has a KOZAK sequence leading into the puromycin gene.

The AAVS left homology arm and puromycin resistance gene of pINT18 was replaced by a cassette encoding the ROSA26 left homology, splice acceptor, optimized kozak consensus sequence and puromycin resistance gene. The ROSA26 left homology arm was initially amplified from pGATOR (Melidoni et al., 2013 (105)) as two fragments which knocked out an internal NotI site. The two fragments, generated by primers J60/2716 and 2715/2706 were combined in an assembly PCR with primers J60 and 2706 and digested with AsiSI and NsiI. The splice acceptor was amplified from pGATOR using primers 2709 and 2710 and the puromycin resistance cassette amplified with primers 2745 (which included a region homologous to the splice acceptor and optimized Kozak consensus) and J59. The splice acceptor region and puromycin resistance cassette were combined in assembly PCR using primers 2709 and J59 and digested with Nsi1 and Bgl2. The ROSA26 left arm homology and splice acceptor-puromycin cassettes were ligated with pINT18 (AsiS1/Bgl2) vector.

To complete the ROSA targeting vector the right hand ROSA26 homology arm, downstream of CMV-scFv-Fc cassette, was introduced to replace the pINT18 AAVS right homology arm. This was performed by PCR of the ROSA right homology arm, present in pGATOR (Melidoni et al., 2013) using primers J61 and J62 to amplify a fragment with BstZ171 at one end and Sbf1 at the other. Primer 61 was positioned to exclude an endogenous Sbf1 site 65 bp up from ROSA ZFN cleavage site. FIG. 31 shows the sequences of ROSA26 left and right homology arms.

TABLE 11

Primers for nuclease-directed targeting of the mouse ROSA 26 locus

| J60 (SEQ ID NO: 129) | ACACACGGTACCGCGATCGCG CTGATTGGCTTCTTTTCCTC | AsiSI-rosa26-L-F |
| --- | --- | --- |
| 2706 (SEQ ID NO: 130) | TTTTTTATGCATTCTAGAAAG ACTGGAGTTGCAGA | NsiI-rosa26-L-R |

TABLE 11 -continued

Primers for nuclease-directed targeting of
the mouse ROSA 26 locus

| | | | |
|---|---|---|---|
| 2715 (SEQ ID NO: 131) | | GAGCGTCCGCCCACCCTC | ROSA-Left-NotI_knockout_F |
| 2716 (SEQ ID NO: 132) | | GAGGGTGGGCGGACGCTC | ROSA-Left-NotI_knockout_R |
| 2709 (SEQ ID NO: 133) | | TTTTTTATGCATTAAGGGATC TGTAGGGCGCAG | Splice_acceptor-F-NsiI |
| 2710 (SEQ ID NO: 134) | | GTGAATTCCTAGAGCGGCCTC | Splice_acceptor-R |
| 2745 (SEQ ID NO: 135) | | GAGGCCGCTCTAGGAATTCAC GCCGCCACCATGACCGAGTAC AAGCCCAC | Overlap-Puro-F+kozak |
| J59 (SEQ ID NO: 136) | | AAAAAAAGATCTGTGTGTTTC GAATCAGGCACCGGGCTTGCG GGTCAT | Bgl2-Puro-R |
| J61 (SEQ ID NO: 137) | | tttttGTATACGGGAATTGA ACAGGTGTAAAATTG | ROSA-Right_F-BstZ171 |
| J62 (SEQ ID NO: 138) | | TTTTTTCCTGCAGGAGGTTGG ATTCTCAATACATCTATTGTT G | ROSA-Right_R-SbfI |
| 2701 (SEQ ID NO: 139) | | GCCGACGTCTCGTCGCTGATG TTTT | |
| 2702 (SEQ ID NO: 140) | | ATCAGCGACGAGACGTCGGCC GGTG | |
| 2703 (SEQ ID NO: 141) | | CGCCCATCTTCTAGAAAGACG TTTT | |
| 2704 (SEQ ID NO: 142) | | GTCTTTCTAGAAGATGGCGC GGTG | |

Integration of pINT19, encoding antibody or alternative binding molecules, into the mouse ROSA26 locus could be achieved by nuclease-directed introduction of antibody libraries using CRISPR/Cas9 as described in Example 20. Here, nuclease-directed integration via CRISPR/Cas9 could be demonstrated using the "Geneart CRISPR nuclease vector kit" (Lifetech A21175). In this system, a U6 RNA polymerase III promoter drives expression of a target complementary CRIPSR RNA (crRNA) which is linked to a trans-activating crRNA (tracrRNA). The crRNA and tracrRNA together make up a guide RNA which directs the cleavage specificity of a Cas9 protein encoded on the same "GeneArt CRISPR nuclease vector" (see manufacturer's instructions). The vector is provided as a linearised plasmid into which a short double-stranded oligonucleotide with appropriate 3' overhangs is cloned. Cleavage specificity is then determined by the sequence of the cloned segment. 2 different targeting sequences were designed to direct cleavage to the mouse ROSA26 encoded by primers 2701/2702 and 2703/2704 (see Table 10).

As an alternative, Zinc finger nucleases which cleave within the ROSA26 locus have been described [34]. These could be constructed in an appropriate expression vector as described for Sce-I meganuclease (FIG. 16, example 11).

Nuclease-mediated integration of donor plasmid pINT19 would give rise to clones expressing secreted antibody which could bind endogenous receptor or ligand resulting in either antagonism [105,107] or agonism [47,106,108] of receptor signalling pathways. To enable the linkage between cellular phenotype and the functional activity of the secreted antibody, cells can be plated at a low density in semi-solid media so that individual colonies propagate and antibody expression can be initiated via an inducible promoter [105]. Alternatively, a constitutive promoter could be employed for antibody gene expression. The semi-solid media would maintain an elevated local concentration of the endogenously-expressed antibody, so that any phenotypic change specific to a colony arising from an individual cell would be caused by the unique antibody expressed from that particular clone. If a rapid response reporter, such as Rex or Nanog promoter fused to a reporter gene, was employed it would be possible to plate cells at a low density in semi-solid media, harvest and then screen by flow cytometry. Alternatively, the stop codon downstream of the antibody gene in pINT19 could be replaced by a transmembrane domain to enable tethering of the antibody to the cell surface. The stop codon downstream of the antibody gene in pINT19 could also be replaced by an endoplasmic reticulum (ER) retention signal sequence to enable retention of antibodies in the ER and potential down-regulation of an endogenously expressed target receptor or any secreted protein or peptide. pINT19 is designed specifically to target the mouse ROSA26 locus and can be employed for phenotypic screening of antibodies or alternative binding molecules in mouse ES cells. However, nuclease-directed antibody or binder molecule gene integration methods could also be applied to other functional screens such as those described using the lentiviral approach [47,106,107,108].

REFERENCES

All references listed below and others cited anywhere in this disclosure are incorporated herein by reference in their entire
1. Russell, S. J., Hawkins, R. E., & Winter, G. (1993). Retroviral vectors displaying functional antibody fragments. *Nucleic Acids Res,* 21(5), 1081-1085.
2. Boublik, Y., Di Bonito, P., & Jones, I. M. (1995). Eukaryotic virus display: Engineering the major surface glycoprotein of the *Autographa californica* nuclear polyhedrosis virus (AcNPV) for the presentation of foreign proteins on the virus surface. *Nature Biotechnology,* 13(10), 1079-1084.
3. Mottershead, D. G., Alfthan, K., Ojala, K., Takkinen, K., & Oker-Blom, C. (2000). Baculoviral display of functional scFv and synthetic IgG-binding domains. *Biochemical and Biophysical Research Communications,* 275(1), 84-90.
4. Oker-Blom, C., Airenne, K. J., & Grabherr, R. (2003). Baculovirus display strategies: Emerging tools for eukaryotic libraries and gene delivery. *Briefings in Functional Genomics and Proteomics,* 2(3), 244-253.
5. Edwards, B. M., Barash, S. C., Main, S. H., Choi, G. H., Minter, R., Ullrich, S., et al. (2003). The Remarkable Flexibility of the Human Antibody Repertoire; Isolation of Over One Thousand Different Antibodies to a Single Protein, BLyS. *Journal of Molecular Biology,* 334(1), 103-118. doi:10.1016/j.jmb.2003.09.054
6. Pershad, K., Pavlovic, J. D., Graslund, S., Nilsson, P., Colwill, K., Karatt-Vellatt, A., et al. (2010). Generating a panel of highly specific antibodies to 20 human SH2 domains by phage display. *Protein Engineering, Design and Selection,* 23(4), 279-288. doi:10.1093/protein/gzq003

7. Schofield, D. J., Pope, A. R., Clementel, V., Buckell, J., Chapple, S., Clarke, K. F., et al. (2007). Application of phage display to high throughput antibody generation and characterization. *Genome Biol,* 8(11), R254.

8. Salema, V., Marín, E., Martinez-Arteaga, R., Ruano-Gallego, D., Fraile, S., Margolies, Y., et al. (2013). Selection of Single Domain Antibodies from Immune Libraries Displayed on the Surface of *E. coli* Cells with Two β-Domains of Opposite Topologies. *PLoS ONE,* 8(9), e75126. doi:10.1371/journal.pone.0075126.s007

9. Chao, G., Lau, W. L., Hackel, B. J., Sazinsky, S. L., Lippow, S. M., & Wittrup, K. D. (2006). Isolating and engineering human antibodies using yeast surface display. *Nat Protoc,* 1(2), 755-768.

10. Higuchi, K., Araki, T., Matsuzaki, O., Sato, A., Kanno, K., Kitaguchi, N., & Ito, H. (1997). Cell display library for gene cloning of variable regions of human antibodies to hepatitis B surface antigen. *J Immunol Methods,* 202(2), 193-204.

11. Ho, M., Nagata, S., & Pastan, I. (2006). Isolation of anti-CD22 Fv with high affinity by Fv display on human cells. *Proc Natl Acad Sci USA,* 903(25), 9637-9642. doi:10.1073/pnas.0603653103

12. Ho, M., & Pastan, I. (2009). Display and selection of scFv antibodies on HEK-293T cells. *Methods Mol Biol,* 562, 99-113. doi:10.1007/978-1-60327-302-2_8

13. Akamatsu, Y., Pakabunto, K., Xu, Z., Zhang, Y., & Tsurushita, N. (2007). Whole IgG surface display on mammalian cells: Application to isolation of neutralizing chicken monoclonal anti-IL-12 antibodies. *Journal of Immunological Methods,* 327(1-2), 40-52. doi:10.1016/j.jim.2007.07.007

14. Beerli, R. R., Bauer, M., Buser, R. B., Gwerder, M., Muntwiler, S., Maurer, P., et al. Isolation of human monoclonal antibodies by mammalian cell display. Proc Natl Acad Sci USA. 2008 Sep. 23; 105(38):14336-41. doi: 10.1073/pnas.0805942105

15. Breous-Nystrom, E., Schultze, K., Meier, M., Flueck, L., Holzer, C., Boll, M., et al. (2013). Retrocyte Display® technology: Generation and screening of a high diversity cellular antibody library. *Methods,* 1-11. doi:10.1016/j.ymeth.2013.09.003

16. Grindley, Whiteson & Rice. Mechanisms of Site-Specific Recombination. Annu Rev Biochem 2006 75:567-605

17. Zhou, C., Jacobsen, F. W., Cai, L., Chen, Q., & Shen, W. D. (2010). Development of a novel mammalian cell surface antibody display platform. *mAbs,* 2(5), 508-518

18. Li, C. Z., Liang, Z. K., Chen, Z. R., Lou, H. B., Zhou, Y., Zhang, Z. H., et al. (2012). Identification of HBsAg-specific antibodies from a mammalian cell displayed full-length human antibody library of healthy immunized donor. Cellular and Molecular Immunology, 9(2), 184-190.

19. Buchholz, F., Ringrose, L., Angrand, P. O., Rossi, F., & Stewart, A. F. (1996). Different thermostabilities of FLP and Cre recombinases: Implications for applied site-specific recombination. *Nucleic Acids Res,* 24(21), 4256-4262.

20. Schaft, J., Ashery-Padan, R., Van Hoeven, F. D., Gruss, P., & Francis Stewart, A. (2001). Efficient FLP recombination in mouse ES cells and oocytes. *Genesis,* 31(1), 6-10.

21. Moehle, E. A., Moehle, E. A., Rock, J. M., Rock, J. M., Lee, Y.-L., Lee, Y. L., et al. (2007). Targeted gene addition into a specified location in the human genome using designed zinc finger nucleases. *Proc Natl Acad Sci USA,* 104(9), 3055-3060. doi:10.1073/pnas.0611478104

22. Cristea, S., Freyvert, Y., Santiago, Y., Holmes, M. C., Urnov, F. D., Gregory, P. D., & Cost, G. J. (2013). In vivo cleavage of transgene donors promotes nuclease-mediated targeted integration. *Biotechnology and Bioengineering,* 110(3), 871-880. doi:10.1002/bit.24733

23. Letourneur, F., & Malissen, B. (1989). Derivation of a T cell hybridoma variant deprived of functional T cell receptor alpha and beta chain transcripts reveals a nonfunctional alpha-mRNA of BW5147 origin. European Journal of Immunology, 19(12), 2269-2274. doi:10.1002/eji.1830191214

24. Kanayama, N., Todo, K., Reth, M., & Ohmori, H. (2005). Reversible switching of immunoglobulin hypermutation machinery in a chicken B cell line. Biochem Biophys Res Commun, 327(1), 70-75. doi:10.1016/j.bbrc.2004.11.143

25. Lin, W., Kurosawa, K., Murayama, A., Kagaya, E., & Ohta, K. (2011). B-cell display-based one-step method to generate chimeric human IgG monoclonal antibodies. Nucleic Acids Research, 39(3), e14-e14. doi:10.1093/nar/gkq1122

26. Adachi, N., So, S., Iiizumi, S., Nomura, Y., Murai, K., Yamakawa, C., et al. (2006). The human pre-B cell line Nalm-6 is highly proficient in gene targeting by homologous recombination. *DNA and Cell Biology,* 25(1), 19-24. doi:10.1089/dna.2006.25.19

27. Palacios, R., & Steinmetz, M. (1985). IL3-Dependent mouse clones that express B-220 surface antigen, contain Ig genes in germ-line configuration, and generate B lymphocytes in vivo. Cell, 41(3), 727-734

28. Barretina, J., Caponigro, G., Stransky, N., Venkatesan, K., Margolin, A. A., Kim, S., et al. (2012). The Cancer Cell Line Encyclopedia enables predictive modelling of anticancer drug sensitivity. *Nature,* 483(7391), 603-607. doi:10.1038/nature11003

29. Forbes, S. A., Bindal, N., Bamford, S., Cole, C., Kok, C. Y., Beare, D., et al. (2011). COSMIC: mining complete cancer genomes in the Catalogue of Somatic Mutations in Cancer. *Nucleic Acids Research,* 39(Database issue), D945-50. doi:10.1093/nar/gkq929

30. Silva, G., Poirot, L., Galetto, R., Smith, J., Montoya, G., Duchateau, P., & Pâques, F. (2011). Meganucleases and other tools for targeted genome engineering: Perspectives and challenges for gene therapy. *Current Gene Therapy,* 11(1), 11-27

31. Epinat, J. C., Silva, G. H., Paques, F., Smith, J., & Duchateau, P. (2013). *Engineered meganucleases for genome engineering purposes. Topics in Current Genetics* (Vol. 23, pp. 147-185).

32. Szczepek, M., Brondani, V., Büchel, J., Serrano, L., Segal, D. J., & Cathomen, T. (2007). Structure-based redesign of the dimerization interface reduces the toxicity of zinc-finger nucleases. *Nature Biotechnology,* 25(7), 786-793. doi:10.1038/nbt1317

33. Doyon, Y., Vo, T. D., Mendel, M. C., Greenberg, S. G., Wang, J., Xia, D. F., et al. (2011). Enhancing zinc-finger-nuclease activity with improved obligate heterodimeric architectures. *Nat Methods,* 8(1), 74-79. doi:10.1038/nmeth.1539

34. Perez-Pinera, P., Ousterout, D. G., Brown, M. T., & Gersbach, C. A. (2012). Gene targeting to the ROSA26 locus directed by engineered zinc finger nucleases. *Nucleic Acids Research,* 40(8), 3741-3752. doi:10.1093/nar/gkr1214

35. Urnov, F. D., Miller, J. C., Lee, Y.-L., Beausejour, C. M., Rock, J. M., Augustus, S., et al. (2005). Highly efficient endogenous human gene correction using designed zinc-finger nucleases. *Nature*, 435(7042), 646-651. doi:10.1038/nature03556
36 Maresca, M., Lin, V. G., Guo, N., & Yang, Y. (2013). Obligate ligation-gated recombination (ObLiGaRe): custom-designed nuclease-mediated targeted integration through nonhomologous end joining. *Genome Research*, 23(3), 539-546. doi:10.1101/gr.145441.112
37 Bogdanove, A. J., & Voytas, D. F. (2011). TAL effectors: customizable proteins for DNA targeting. *Science*, 333 (6051), 1843-1846. doi:10.1126/science.1204094
38 Reyon, D., Tsai, S. Q., Khgayter, C., Foden, J. A., Sander, J. D., & Joung, J. K. (2012). FLASH assembly of TALENs for high-throughput genome editing. *Nature Biotechnology*, 30(5), 460-465. doi:10.1038/nbt.2170
39 Boissel, S., Jarjour, J., Astrakhan, A., Adey, A., Gouble, A., Duchateau, P., et al. (2013). megaTALs: a rare-cleaving nuclease architecture for therapeutic genome engineering. *Nucleic Acids Research*. doi:10.1093/nar/gkt1224
40 Beurdeley, M., Bietz, F., Li, J., Thomas, S., Stoddard, T., Juillerat, A., et al. (2013). Compact designer TALENs for efficient genome engineering. *Nature Communications*, 4, 1762. doi:10.1038/ncomms2782
41 Sampson, T. R., & Weiss, D. S. (2014). Exploiting CRISPR/Cas systems for biotechnology. *BioEssays: News and Reviews in Molecular, Cellular and Developmental Biology*, 36(1), 34-38. doi:10.1002/bies.201300135
42 Shalem, O., Sanjana, N. E., Hartenian, E., Shi, X., Scott, D. A., Mikkelsen, T. S., et al. (2014). Genome-scale CRISPR-Cas9 knockout screening in human cells. *Science*, 343(6166), 84-87. doi:10.1126/science.1247005
43 Wang, T., Wei, J. J., Sabatini, D. M., & Lander, E. S. (2014). Genetic screens in human cells using the CRISPR-Cas9 system. *Science*, 343(6166), 80-84. doi:10.1126/science.1246981
44 Beard, C., Hochedlinger, K., Plath, K., Wutz, A., & Jaenisch, R. (2006). Efficient method to generate single-copy transgenic mice by site-specific integration in embryonic stem cells. *Genesis*, 44(1), 23-28.
45 Orlando, S. J., Santiago, Y., DeKelver, R. C., Freyvert, Y., Boydston, E. A., Moehle, E. A., et al. (2010). Zinc-finger nuclease-driven targeted integration into mammalian genomes using donors with limited chromosomal homology. *Nucleic Acids Research*, 38(15), e152. doi:10.1093/nar/gkq512
Cadinanos, J; Bradley, A. (2007) Nucleic Acids Res. 35(12): e87
47 Zhang, H., Yea, K., Xie, J., Ruiz, D., Wilson, I. A., & Lerner, R. A. (2013). Selecting agonists from single cells infected with combinatorial antibody libraries. *Chemistry & Biology*, 20(5), 734-741. doi:10.1016/j.chembiol.2013.04.012
48 Porteus, M. H., & Baltimore, D. (2003). Chimeric nucleases stimulate gene targeting in human cells. *Science*, 300(5620), 763. doi:10.1126/science.1078395
49 Rouet, P., Smih, F., & Jasin, M. (1994). Introduction of double-strand breaks into the genome of mouse cells by expression of a rare-cutting endonuclease. *Molecular and Cellular Biology*, 14(12), 8096-8106.
50 Jasin, M. (1996). Genetic manipulation of genomes with rare-cutting endonucleases. *Trends in Genetics*, 12(6), 224-228
51 Davis, L., & Maizels, N. (2011). DNA nicks promote efficient and safe targeted gene correction. *PLoS ONE*, 6(9), e23981. doi:10.1371/journal.pone.0023981
52 Fujioka, K., Aratani, Y., Kusano, K., & Koyama, H. (1993). Targeted recombination with single-stranded DNA vectors in mammalian cells. *Nucleic Acids Res*, 21(3), 407-412
53 Khan, I. F., Hirata, R. K., & Russell, D. W. (2011). AAV-mediated gene targeting methods for human cells. *Nat Protoc*, 6(4), 482-501. doi:10.1038/nprot.2011.301
54 Deyle, D. R., & Russell, D. W. (2009). Adeno-associated virus vector integration. *Current Opinion in Molecular Therapeutics*, 11(4), 442-447
55 Benatuil, L., Perez, J. M., Belk, J., & Hsieh, C. M. (2010). An improved yeast transformation method for the generation of very large human antibody libraries. *Protein Engineering, Design and Selection*, 23(4), 155-159.
56 Feldhaus, M. J., Siegel, R. W., Opresko, L. K., Coleman, J. R., Feldhaus, J. M., Yeung, Y. A., et al. (2003). Flow-cytometric isolation of human antibodies from a nonimmune *Saccharomyces cerevisiae* surface display library. *Nat Biotechnol*.
57 Zhao, A., Nunez-Cruz, S., Li, C., Coukos, G., Siegel, D. L., & Scholler, N. (2011). Rapid isolation of high-affinity human antibodies against the tumor vascular marker Endosialin/TEM1, using a paired yeast-display/secretory scFv library platform. *Journal of Immunological Methods*, 363(2), 221-232. doi:10.1016/j.jim.2010.09.001
58 Skerra, A. (2007). Alternative non-antibody scaffolds for molecular recognition. *Curr Opin Biotechnol*, 18(4), 295-304. doi:10.1016/j.copbio.2007.04.010
59 Gebauer, M., & Skerra, A. (2009). Engineered protein scaffolds as next-generation antibody therapeutics. *Current Opinion in Chemical Biology*, 13(3), 245-255. doi:10.1016/j.cbpa.2009.04.627
60 Haan & Maggos (2004) BioCentury, 12(5): A1-A6
61 Koide et al. (1998) Journal of Molecular Biology, 284: 1141-1151.
62 Nygren et al. (1997) Current Opinion in Structural Biology, 7: 463-469
63 Wess, L. In: BioCentury, The Bernstein Report on BioBusiness, 12(42), A1-A7, 2004
64 Chang, H.-J., Hsu, H.-J., Chang, C.-F., Peng, H.-P., Sun, Y.-K., Yu, H.-M., et al. (2009). Molecular Evolution of Cystine-Stabilized Miniproteins as Stable Proteinaceous Binders. *Structure*, 17(4), 620-631. doi:10.1016/j.str.2009.04.011
65 Ward, E. S. et al., *Nature* 341, 544-546 (1989)
66 McCafferty et al *Nature*, 348, 552-554 (1990)
67 Holt et al *Trends in Biotechnology* 21, 484-490 (2003)
68 Bird et al, Science, 242, 423-426, (1988)
69 Huston et al, PNAS USA, 85, 5879-5883, (1988)
70 Holliger, P. et al, PNAS USA 90 6444-6448, (1993)
71 Reiter, Y. et al, *Nature Biotech*, 14, 1239-1245, (1996)
72 Holliger & Hudson, *Nature Biotechnology* 23(9):1126-1136 (2005)
73 Knappik et al. *J. Mol. Biol.* 296, 57-86 (2000)
74 Krebs et al. *Journal of Immunological Methods* 254, 67-84 (2001)
75 Holliger and Bohlen *Cancer and metastasis rev.* 18: 411-419 (1999)
76 Holliger, P. and Winter G. *Current Opinion Biotechnol* 4, 446-449 (1993)
77 Glennie M J et al., *J. Immunol.* 139, 2367-2375 (1987)
78 Repp R. et al., *J. Hemat.* 377-382 (1995)
79 Staerz U. D. and Bevan M. *J. PNAS* 83 (1986)
80 Suresh M. R. et al., *Method Enzymol.* 121: 210-228 (1986)
81 Merchand et al., *Nature Biotech.* 16:677-681 (1998)
82 Ridgeway, J. B. B. et al, *Protein Eng.*, 9, 616-621, (1996)

83 Marks, J. D., Hoogenboom, H. R., Bonnert, T. P., McCafferty, J., Griffiths, A. D., & Winter, G. (1991). By-passing immunization. Human antibodies from V-gene libraries displayed on phage. *J Mol Biol*, 222(3), 581-597.

84 Gronwald, R. G. K., Grant, F. J., Haldeman, B. A., Hart, C. E., O'Hara, P. J., Hagen, F. S., et al. (1988). Cloning and expression of a cDNA coding for the human platelet-derived growth factor receptor: Evidence for more than one receptor class (Vol. 85, pp. 3435-3439). Presented at the Proceedings of the National Academy of Sciences of the United States of America.

85 Kumar, N., & Borth, N. (2012). Flow-cytometry and cell sorting: an efficient approach to investigate productivity and cell physiology in mammalian cell factories. *Methods*, 56(3), 366-374. doi:10.1016/j.ymeth.2012.03.004

86 Brezinsky, S. C. G., Chiang, G. G., Szilvasi, A., Mohan, S., Shapiro, R. I., MacLean, A., et al. (2003). A simple method for enriching populations of transfected CHO cells for cells of higher specific productivity. *J Immunol Methods*, 277(1-2), 141-155.

87 Pichler, J., Hesse, F., Wieser, M., Kunert, R., Galosy, S. S., Mott, J. E., & Borth, N. (2009). A study on the temperature dependency and time course of the cold capture antibody secretion assay. Journal of Biotechnology, 141(1-2), 80-83. doi:10.1016/j.jbiotec.2009.03.001

88 Anastassiadis, K., Fu, J., Patsch, C., Hu, S., Weidlich, S., Duerschke, K., et al. (2009). Dre recombinase, like Cre, is a highly efficient site-specific recombinase in *E. coli*, mammalian cells and mice. *Disease Models & Mechanisms*, 2(9-10), 508-515. doi:10.1242/dmm.003087

89 Horlick, R. A., Macomber, J. L., Bowers, P. M., Neben, T. Y., Tomlinson, G. L., Krapf, I. P., et al. (2013). Simultaneous surface display and secretion of proteins from mammalian cells facilitate efficient in vitro selection and maturation of antibodies. *J Biol Chem*, 288(27), 19861-19869. doi:10.1074/jbc.M113.452482

90 Biffi, G., Tannahill, D., McCafferty, J., & Balasubramanian, S. (2013). Quantitative visualization of DNA G-quadruplex structures in human cells. *Nature Chemistry*, 5(3), 182-186. doi:10.1038/nchem.1548

91 Gao, J., Sidhu, S. S., & Wells, J. A. (2009). Two-state selection of conformation-specific antibodies. *Proc Natl Acad Sci USA*, 106(9), 3071-3076. doi:10.1073/pnas.0812952106

92 Gu, G. J., Friedman, M., Jost, C., Johnsson, K., Kamali-Moghaddam, M., Plückthun, A., et al. (2013). Protein tag-mediated conjugation of oligonucleotides to recombinant affinity binders for proximity ligation. *N Biotechnol*, 30(2), 144-152. doi:10.1016/j.nbt.2012.05.005

93 Cho, Y. K., & Shusta, E. V. (2010). Antibody library screens using detergent-solubilized mammalian cell lysates as antigen sources. *Protein Eng Des Sel*, 23(7), 567-577. doi:10.1093/protein/gzq029

94 Tillotson, B. J., Cho, Y. K., & Shusta, E. V. (2013). Cells and cell lysates: a direct approach for engineering antibodies against membrane proteins using yeast surface display. Methods, 60(1), 27-37. doi:10.1016/j.ymeth.2012.03.010

95 Kunert, A., Straetemans, T., Govers, C., Lamers, C., Mathijssen, R., Sleijfer, S., & Debets, R. (2013). TCR-Engineered T Cells Meet New Challenges to Treat Solid Tumors: Choice of Antigen, T Cell Fitness, and Sensitization of Tumor Milieu. *Frontiers in Immunology*, 4, 363. doi:10.3389/fimmu.2013.00363

96 Liddy, N., Bossi, G., Adams, K. J., Lissina, A., Mahon, T. M., Hassan, N. J., et al. (2012). Monoclonal TCR-redirected tumor cell killing. *Nature Medicine*, 18(6), 980-987. doi:10.1038/nm.2764

97 Holler, P. D., Holman, P. O., Shusta, E. V., O'Herrin, S., Wittrup, K. D., & Kranz, D. M. (2000). In vitro evolution of a T cell receptor with high affinity for peptide/MHC. *Proc Natl Acad Sci USA*, 97(10), 5387-5392. doi:10.1073/pnas.080078297

98 Weber, K. S., Donermeyer, D. L., Allen, P. M., & Kranz, D. M. (2005). Class II-restricted T cell receptor engineered in vitro for higher affinity retains peptide specificity and function. *Proc Natl Acad Sci USA*, 102(52), 19033-19038. doi:10.1073/pnas.0507554102

99 Kessels, H. W., van Den Boom, M. D., Spits, H., Hooijberg, E., & Schumacher, T. N. (2000). Changing T cell specificity by retroviral T cell receptor display. *Proc Natl Acad Sci USA*, 97(26), 14578-14583. doi:10.1073/pnas.97.26.14578

100 Chervin, A. S., Aggen, D. H., Raseman, J. M., & Kranz, D. M. (2008). Engineering higher affinity T cell receptors using a T cell display system. *Journal of Immunological Methods*, 339(2), 175-184.

101 Crawford, F., Jordan, K. R., Stadinski, B., Wang, Y., Huseby, E., Marrack, P., et al. (2006). Use of baculovirus MHC/peptide display libraries to characterize T-cell receptor ligands. *Immunological Reviews*, 210, 156-170. doi:10.1111/j.0105-2896.2006.00365.x 102 Hinrichs, C. S., & Restifo, N. P. (2013). Reassessing target antigens for adoptive T-cell therapy. *Nat Biotechnol*, 31(11), 999-1008. doi:10.1038/nbt.2725

103 Sadelain, M., Brentjens, R., & Riviére, I. (2013). The basic principles of chimeric antigen receptor design. *Cancer Discovery*, 3(4), 388-398. doi:10.1158/2159-8290.CD-12-0548

104 Alonso-Camino, V., Sanchez-Martin, D., Compte, M., Sanz, L., & Alvarez-Vallina, L. (2009). Lymphocyte display: a novel antibody selection platform based on T cell activation. *PLoS ONE*, 4(9), e7174. doi:10.1371/journal.pone.0007174

105 Melidoni, A. N., Dyson, M. R., Wormald, S., & McCafferty, J. (2013). Selecting antagonistic antibodies that control differentiation through inducible expression in embryonic stem cells. *Proceedings of the National Academy of Sciences*, 110(44), 17802-17807. doi:10.1073/pnas.1312062110

106 Zhang, H., Wilson, I. A., & Lerner, R. A. (2012). Selection of antibodies that regulate phenotype from intracellular combinatorial antibody libraries. *Proceedings of the National Academy of Sciences*, 109(39), 15728-15733. doi:10.1073/pnas.1214275109

107 Xie, J., Yea, K., Zhang, H., Moldt, B., He, L., Zhu, J., & Lerner, R. A. (2014). Prevention of cell death by antibodies selected from intracellular combinatorial libraries. *Chemistry & Biology*, 21(2), 274-283.

108 Yea, K., Zhang, H., Xie, J., Jones, T. M., Yang, G., Song, B. D., & Lerner, R. A. (2013). Converting stem cells to dendritic cells by agonist antibodies from unbiased morphogenic selections (Vol. 110, pp. 14966-14971). Presented at the Proceedings of the National Academy of Sciences of the United States of America. doi:10.1073/pnas.1313671110

109 Kawahara, M., Kimura, H., Ueda, H., & Nagamune, T. (2004). Selection of genetically modified cell population using hapten-specific antibody/receptor chimera. *Biochem Biophys Res Commun*, 315(1), 132-138. doi:10.1016/j.bbrc.2004.01.030

110 Kawahara, M., Shimo, Y., Sogo, T., Hitomi, A., Ueda, H., & Nagamune, T. (2008). Antigen-mediated migration of murine pro-B Ba/F3 cells via an antibody/receptor chimera. *Journal of Biotechnology*, 133(1), 154-161. doi: 10.1016/j.jbiotec.2007.09.009

111 Sogo, T., Kawahara, M., Ueda, H., Otsu, M., Onodera, M., Nakauchi, H., & Nagamune, T. (2009). T cell growth control using hapten-specific antibody/interleukin-2 receptor chimera. *Cytokine*, 46(1), 127-136. doi:10.1016/j.cyto.2008.12.020

112 Kawahara, M., Chen, J., Sogo, T., Teng, J., Otsu, M., Onodera, M., et al. (2011). Growth promotion of genetically modified hematopoietic progenitors using an antibody/c-Mpl chimera. *Cytokine*, 55(3), 402-408. doi: 10.1016/j.cyto.2011.05.024

113 Ueda, H., Kawahara, M., Aburatani, T., Tsumoto, K., Todokoro, K., Suzuki, E., et al. (2000). Cell-growth control by monomeric antigen: the cell surface expression of lysozyme-specific Ig V-domains fused to truncated Epo receptor. *J Immunol Methods*, 241(1-2), 159-170.

114 Kerppola, T. K. (2009). Visualization of molecular interactions using bimolecular fluorescence complementation analysis: Characteristics of protein fragment complementation. *Chemical Society Reviews*, 38(10), 2876-2886.

115 Michnick, S. W., Ear, P. H., Manderson, E. N., Remy, I., & Stefan, E. (2007). Universal strategies in research and drug discovery based on protein-fragment complementation assays. *Nature Reviews Drug Discovery*, 6(7), 569-582. doi:10.1038/nrd231

116 Petschnigg, J., Groisman, B., Kotlyar, M., Taipale, M., Zheng, Y., Kurat, C. F., at al. (2014). The mammalian-membrane two-hybrid assay (MaMTH) for probing membrane-protein interactions in human cells. *Nat Methods*. doi:10.1038/nmeth.2895

117 Renaut, L., Monnet, C., Dubreuil, O., Zaki, O., Crozet, F., Bouayadi, K., et al. (2012). *Affinity maturation of antibodies: Optimized methods to generate high-quality scfv libraries and isolate igg candidates by high-throughput screening*. Methods in Molecular Biology (Vol. 907, pp. 451-461)

118 Dyson, M. R., Zheng, Y., Zhang, C., Colwill, K., Pershad, K., Kay, B. K., et al. (2011). Mapping protein interactions by combining antibody affinity maturation and mass spectrometry. *Anal Biochem*, 417(1), 25-35. doi:10.1016/j.ab.2011.05.005

119 de Felipe P (2002) Polycistronic viral vectors. Curr Gene Ther 2: 355-378. doi: 10.2174/1566523023347742.

120 Foote, J., & Winter, G. (1992). Antibody framework residues affecting the conformation of the hypervariable loops. *J Mol Biol*, 224(2), 487-499.

121 Massie, B., Dionne, J., Lamarche, N., Fleurent, J., & Langelier, Y. (1995). Improved adenovirus vector provides herpes simplex virus ribonucleotide reductase R1 and R2 subunits very efficiently. *Nature Biotechnology*, 13(6), 602-608.

122 Kim, D. W., Uetsuki, T., Kaziro, Y., Yamaguchi, N., & Sugano, S. (1990). Use of the human elongation factor 1 alpha promoter as a versatile and efficient expression system. *Gene*, 91(2), 217-223.

123 Holden, P., Keene, D. R., Lunstrum, G. P., Bachinger, H. P., & Horton, W. A. (2005). Secretion of cartilage oligomeric matrix protein is affected by the signal peptide. *J Biol Chem*, 280(17), 17172-17179.

124 Sadelain, M., Papapetrou, E. P., & Bushman, F. D. (2011). Safe harbours for the integration of new DNA in the human genome. *Nature Reviews Cancer*, 12(1), 51-58.

125 Sanjana, N. E., Cong, L., Zhou, Y., Cunniff, M. M., Feng, G., & Zhang, F. (2012). A transcription activator-like effector toolbox for genome engineering. *Nat Protoc*, 7(1), 171-192. doi:10.1038/nprot.2011.431

126 Falk, R., Falk, A., Dyson, M. R., Melidoni, A. N., Parthiban, K., Young, J. L., et al. (2012). Generation of anti-Notch antibodies and their application in blocking Notch signalling in neural stem cells. *Methods*, 58(1), 69-78. doi:10.1016/j.ymeth.2012.07.008

127 Martin, C. D., Rojas, G., Mitchell, J. N., Vincent, K. J., Wu, J., McCafferty, J., & Schofield, D. J. (2006). A simple vector system to improve performance and utilisation of recombinant antibodies. *BMC Biotechnology*, 6, 46.

128 Reyon, D., Tsai, S. Q., Khgayter, C., Foden, J. A., Sander, J. D., & Joung, J. K. (2012). FLASH assembly of TALENs for high-throughput genome editing. *Nature Biotechnology*, 30(5), 460-465. doi:10.1038/nbt.2170

129 Van Der Weyden, L., Adams, D. J., Harris, L. W., Tannahill, D., Arends, M. J., & Bradley, A. (2005). Null and conditional Semaphorin 3B alleles using a flexible puroΔtk LoxP/FRT vector. *Genesis*, 41(4), 171-178

130 de Felipe, P., & Ryan, M. D. (2004). Targeting of proteins derived from self-processing polyproteins containing multiple signal sequences. *Traffic*, 5(8), 616-626.

131 Raymond, C. S., & Soriano, P. (2007). High-efficiency FLP and PhiC31 site-specific recombination in mammalian cells. *PLoS ONE*, 2(1), e162. doi:10.1371/journal.pone.0000162

132 Kranz, A., Fu, J., Duerschke, K., Weidlich, S., Naumann, R., Stewart, A. F., & Anastassiadis, K. (2010). An improved Flp deleter mouse in C57Bl/6 based on Flpo recombinase. *Genesis*, 48(8), 512-520. doi:10.1002/dvg.20641

133 Szymczak A L, Vignali D A (2005) Development of 2A peptide-based strategies in the design of multicistronic vectors. Expert Opin Biol Ther 5: 627-638. doi: 10.1517/14712598.5.5.627

134 Chapple, S. D., Crofts, A. M., Shadbolt, S. P., McCafferty, J., and Dyson, M. R. (2006). Multiplexed expression and screening for recombinant protein production in mammalian cells. BMC biotechnology 6, 49.

135. Zhao, Y. at al. Multiple injections of electroporated autologous T cells expressing a chimeric antigen receptor mediate regression of human disseminated tumor. *Cancer Research* 70, 9053-9061 (2010).

136 Szymczak, A. L. et al. Correction of multi-gene deficiency in vivo using a single 'self-cleaving' 2A peptide-based retroviral vector. *Nature biotechnology* 22, 589-594 (2004).

137. Li, Y. et al. Directed evolution of human T-cell receptors with picomolar affinities by phage display. *Nat. Biotechnol.* 23, 349-354 (2005).

138. Zhao, Y. et al. High-affinity TCRs generated by phage display provide CD4+ T cells with the ability to recognize and kill tumor cell lines. *J. Immunol.* 179, 5845-5854 (2007).

139. Madura, F. at al. T-cell receptor specificity maintained by altered thermodynamics. The *Journal of biological chemistry* 288, 18766-18775 (2013).

140. Pierce, B. G. et al. Computational design of the affinity and specificity of a therapeutic T cell receptor. *PLoS Comput Biol* 10, e1003478 (2014).

141. Sebestyén, Z. et al. Human TCR that incorporate CD3zeta induce highly preferred pairing between TCRalpha and beta chains following gene transfer. *J. Immunol.* 180, 7736-7746 (2008).

142. Roszik, J. et al. T-cell synapse formation depends on antigen recognition but not CD3 interaction: studies with TCR:ζ, a candidate transgene for TCR gene therapy. *Eur. J. Immunol.* 41, 1288-1297 (2011).

143. Cohen, C. J., Zhao, Y., Zheng, Z., Rosenberg, S. A. & Morgan, R. A. Enhanced antitumor activity of murine-human hybrid T-cell receptor (TCR) in human lymphocytes is associated with improved pairing and TCR/CD3 stability. *Cancer Research* 66, 8878-8886 (2006).

144. Huovinen, T. et al. Primer extension mutagenesis powered by selective rolling circle amplification. *PLoS ONE* 7, e31817 (2012).

145. Cribbs, A. P., Kennedy, A., Gregory, B. & Brennan, F. M. Simplified production and concentration of lentiviral vectors to achieve high transduction in primary human T cells. *BMC biotechnology* 13, 98 (2013).

146. Oelke, M. et al. Ex vivo induction and expansion of antigen-specific cytotoxic T cells by HLA-Ig-coated artificial antigen-presenting cells. *Nat Med* 9, 619-624 (2003).

147. Wölfl, M. & Greenberg, P. D. Antigen-specific activation and cytokine-facilitated expansion of naive, human CD8+ T cells. *Nature Protocols* 9, 950-966 (2014).

148. Lipowska-Bhalla, G., Gilham, D. E., Hawkins, R. E. & Rothwell, D. G. Isolation of tumor antigen-specific single-chain variable fragments using a chimeric antigen receptor bicistronic retroviral vector in a Mammalian screening protocol. *Hum Gene Ther Methods* 24, 381-391 (2013).

149. Kelly, R. J., Sharon, E., Pastan, I. & Hassan, R. Mesothelin-targeted agents in clinical trials and in pre-clinical development. *Mol. Cancer Ther.* 11, 517-525 (2012).

150. Atanackovic, D. et al. Surface molecule CD229 as a novel target for the diagnosis and treatment of multiple myeloma. *Haematologica* 96, 1512-1520 (2011).

151. Bund, D., Mayr, C., Kofler, D. M., Hallek, M. & Wendtner, C.-M. Human Ly9 (CD229) as novel tumor-associated antigen (TAA) in chronic lymphocytic leukemia (B-CLL) recognized by autologous CD8+ T cells. *Exp. Hematol.* 34, 860-869 (2006).

152. Tiede, C. et al. Adhiron: a stable and versatile peptide display scaffold for molecular recognition applications. *Protein Eng. Des. Sel.* 27, 145-155 (2014).

153. Maresca, M., Lin, V. G., Guo, N. & Yang, Y. Obligate ligation-gated recombination (ObLiGaRe): custom-designed nuclease-mediated targeted integration through nonhomologous end joining. *Genome Res.* 23, 539-546 (2013).

154. McVey, M. & Lee, S. E. MMEJ repair of double-strand breaks (director's cut): deleted sequences and alternative endings. *Trends Genet.* 24, 529-538 (2008).

155. Nakade, S. et al. Microhomology-mediated end-joining-dependent integration of donor DNA in cells and animals using TALENs and CRISPR/Cas9. *Nat Commun* 5, 5560 (2014).

156. Chiche, L. et al. Squash inhibitors: From structural motifs to macrocyclic knottins. *Current Protein & Peptide Science* 5, 341-349.

What is claimed is:

1. A method of producing a library of at least $10^5$ mammalian cell clones containing DNA encoding a diverse repertoire of binders, wherein the binders are displayed on surfaces of the mammalian cell clones, wherein the binders comprise or are linked to membrane anchors, and wherein the library contains donor DNA integrated at a fixed locus or at duplicate fixed loci, the method comprising providing donor DNA molecules encoding the binders, and mammalian cells with a genome size of greater than $2 \times 10^7$ base pairs, introducing the donor DNA molecules into the cells and providing a site-specific nuclease within the cells, wherein the nuclease cleaves a recognition sequence in cellular DNA to create an integration site at which the donor DNA becomes integrated into the cellular DNA, integration occurring through DNA repair mechanisms endogenous to the cells, thereby creating recombinant cells containing the donor DNA integrated in the cellular DNA, and culturing the recombinant cells to produce clones, thereby providing a library of at least $10^5$ mammalian cell clones containing the donor DNA encoding the repertoire of binders, wherein the binders are displayed on the surface of their expressing cells.

2. The method of claim 1, wherein the site-specific nuclease cleaves cellular DNA to create a double strand break serving as an integration site.

3. The method of claim 1, wherein the binders are antibody molecules, T cell receptors, full length immunoglobulins, IgG, Fab, scFv-Fc or scFv.

4. The method of claim 1, wherein the binders are multimeric, comprising at least a first and a second subunit.

5. The method of claim 4, wherein the multimeric binders are antibody molecules comprising a heavy chain variable (VH) domain and a light chain variable (VL) domain as separate subunits.

6. The method of claim 5, wherein the antibody molecules further comprise one or more additional subunits, which may be introduced on the same donor DNA as the first or second subunit or which may be integrated at separate sites in the cellular DNA.

7. The method of claim 1, wherein the recognition sequence is in genomic DNA of the cells, or wherein the recognition sequence is in episomal DNA within the cells.

8. The method of claim 1, wherein the recognition sequence for the site-specific nuclease occurs only once or twice in the cellular DNA.

9. The method of claim 1, wherein the donor DNA is integrated into the cellular DNA by homologous recombination, non-homologous end joining or microhomology-directed end joining.

10. The method of claim 1, wherein the donor DNA comprises a genetic element for selection of cells into which the donor DNA is integrated.

11. The method of claim 1, wherein integration of the donor DNA into the cellular DNA places expression of the binder and/or expression of a genetic selection element under control of a promoter present within the cellular DNA.

12. The method of claim 1, wherein each clone contains integrated donor DNA encoding only one or two members of the repertoire of binders.

13. The method of claim 1, wherein the donor DNA molecules are sourced from rounds of phage display selection.

14. The method of claim 1, wherein the binders comprise transmembrane domains.

15. The method of claim 1, wherein the nuclease is a meganuclease, a zinc finger nuclease (ZFN) or a TALE nuclease.

* * * * *

UNITED STATES PATENT AND TRADEMARK OFFICE
CERTIFICATE OF CORRECTION

PATENT NO. : 11,286,477 B2  Page 1 of 1
APPLICATION NO. : 15/308570
DATED : March 29, 2022
INVENTOR(S) : McCafferty et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 125 days.

Signed and Sealed this
Eleventh Day of February, 2025

Coke Morgan Stewart
*Acting Director of the United States Patent and Trademark Office*

SEQUENCE LISTING

<160> NUMBER OF SEQ ID NOS: 142

<210> SEQ ID NO 1
<211> LENGTH: 5396
<212> TYPE: DNA
<213> ORGANISM: Artificial Sequence
<220> FEATURE:
<223> OTHER INFORMATION: pD1 dual promoter antibody expression cassette
      for surface expression

<400> SEQUENCE: 1

```
ggtaccgaat tccgtgaggc tccggtgccc gtcagtgggc agagcgcaca tcgcccacag      60
tccccgagaa gttgggggga ggggtcggca attgaaccgg tgcctagaga aggtggcgcg     120
gggtaaactg ggaaagtgat gtcgtgtact ggctccgcct ttttcccgag ggtggggag     180 aaccgtatat aagtgcagta gtcgccgtga acgttctttt tcgcaacggg tttgccgcca     240
gaacacaggt aagtgccgtg tgtggttccc gcgggcctgg cctcttacg ggttatggcc     300 cttgcgtgcc ttgaattact tccacctggc tccagtacgt gattcttgat cccgagctgg     360
agccaggggc gggccttgcg ctttaggagc cccttcgcct cgtgcttgag ttgaggcctg     420
gcctgggcgc tggggccgcc gcgtgcgaat ctggtggcac cttcgcgcct gtctcgctgc     480
tttcgataag tctctagcca tttaaatttt ttgatgacct gctgcgacgc ttttttctg     540 gcaagatagt cttgtaaatg cgggccagga tctgcacact ggtatttcgg tttttgggcc     600
cgcggccggc gacggggccc gtgcgtccca gcgcacatgt tcggcgaggc ggggcctgcg     660
agcgcggcca ccgagaatcg gacgggggta gtctcaagct ggccggcctg ctctggtgcc     720
tggcctcgcg ccgccgtgta tcgcccgcc ctgggcggca aggctggccc ggtcggcacc     780
agttgcgtga gcgaaagat ggccgcttcc cggccctgct ccaggggct caaaatggag     840 gacgcggcgc tcgggagagc gggcggtga gtcacccaca caaaggaaaa gggcctttcc     900
```

```
gtcctcagcc gtcgcttcat gtgactccac ggagtaccgg gcgccgtcca ggcacctcga    960
ttagttctgg agcttttgga gtacgtcgtc tttaggttgg ggggaggggt tttatgcgat   1020
ggagtttccc cacactgagt gggtggagac tgaagttagg ccagcttggc acttgatgta   1080
attctcgttg gaatttgccc tttttgagtt tggatcttgg ttcattctca gcctcagac    1140 agtggttcaa agttttttc ttccatttca ggtgtcgtga gacgtggcca ccatgagggc    1200
ctggatcttc tttctccttt gcctggccgg gagggctctg gcagctagcg acatccagat   1260
gacccagagc ccaagcagcc tgagcgccag cgtgggtgac agagtgacca tcacctgtag   1320
agccagcggt aacatccaca actacctggc ttggtaccag cagaagccag gtaaggctcc   1380
aaagctgctg atctactaca ccaccaccct ggctgacggt gtgccaagca gattcagcgg   1440
tagcggtagc ggtaccgact acaccttcac catcagcagc ctccagccag aggacatcgc   1500
cacctactac tgccagcact ctggagcac cccaaggacg ttcggccaag ggaccaaggt   1560
ggaaatcaaa cgtaccgcgg ccgcccttc cgtgttcatc ttccctccct ccgacgagca   1620
gctgaagtcc ggcaccgcct ctgtggtgtg cctgctgaac aacttctacc ctcgggaggc   1680
caaggtgcag tggaaggtgg acaacgccct gcagtccggc aactcccagg aatccgtcac   1740
cgagcaggac tccaaggact ctacctactc cctgtcctcc accctgaccc tgtccaaggc   1800
cgactacgag aagcacaagc tgtacgcctg cgaagtgacc caccagggcc tgtcctctcc   1860
cgtgaccaag tccttcaacc ggggcgagtg ctaataaaag cttacgacgt gatcagcctc   1920
gactgtgcct tctagttgcc agccatctgt tgtttgcccc tccccgtgc cttccttgac    1980 cctggaaggt gccactccca ctgtcctttc ctaataaaat gaggaaattg catcgcattg   2040
tctgagtagg tgtcattcta ttctgggggg tggggtgggg caggacagca agggggagga   2100
ttgggaagac aatagcaggc atgctgggga acattgatta ttgactagtt attaatagta   2160
atcaattacg gggtcattag ttcatagccc atatatggag ttccgcgtta cataacttac   2220
ggtaaatggc ccgcctggct gaccgcccaa cgacccccgc ccattgacgt caataatgac   2280
gtatgttccc atagtaacgc caatagggac tttccattga cgtcaatggg tggagtattt   2340
acggtaaact gcccacttgg cagtacatca agtgtatcat atgccaagtc cgccccctat   2400
tgacgtcaat gacggtaaat ggcccgcctg gcattatgcc cagtacatga ccttacggga   2460 cttttcctact tggcagtaca tctacgtatt agtcatcgct attaccatag tgatgcggtt   2520
ttggcagtac accaatgggc gtggatagcg gtttgactca cggggatttc caagtctcca   2580
ccccattgac gtcaatggga gtttgttttg gcaccaaaat caacgggact ttccaaaatg   2640
tcgtaataac cccgccccgt tgacgcaaat gggcggtagg cgtgtacggt gggaggtcta   2700
tataagcaga gctcgtttag tgaaccgtca gatcctcact ctcttccgca tcgctgtctg   2760
cgagggccag ctgttgggct cgcggttgag acaaactct cgcggtctt ccagtactc    2820 ttggatcgga aacccgtcgg cctccgaacg gtactccgcc accgagggac ctgagcgagt   2880
ccgcatcgac cggatcggaa aacctctcgt gaaaggcgtc taaccagtca cagtcgcaag   2940
gtaggctgag caccgtggcg ggcggcagcg ggtggcggtc ggggttgttt ctggcggagg   3000
tgctgctgat gatgtaatta agtaggcgg tcttgagacg gcggatggtc gaggtgaggt   3060
gtggcaggct tgagatccag ctgttgggt gagtactccc tctcaaaagc gggcattact   3120
tctgcgctaa gattgtcagt ttccaaaaac gaggaggatt tgatattcac ctggcccgat   3180
ctggccatac acttgagtga caatgacatc cactttgcct ttctctccac aggtgtccac   3240
```

```
tcccaggtcc aagtttgtgg aaattaatac gacgtggcca ccatgagttg gagctgtatc   3300
atcctcttct tggtagcaac agctacaggt aaggggttaa cagtagcagg cttgaggtct   3360
ggacatatat atgggtgaca atgacatcca ctttgccttt ctctccacag gcgccatggc   3420
ccaggtccaa ctgcaggaga gcggtccagg tcttgtgaga cctagccaga ccctgagcct   3480
gacctgcacc gtgtctggca gcaccttcag cggctatggt gtaaactggg tgagacagcc   3540
acctggacga ggtcttgagt ggattggaat gatttgggt gatggaaaca cagactataa   3600
ttcagctctc aaatccagag tgacaatgct ggtagacacc agcaagaacc agttcagcct   3660
gagactcagc agcgtgacag ccgccgacac cgcggtctat tattgtgcaa gagagagaga   3720
ttataggctt gactactggg gtcaaggcag cctcgtcaca gtctcgagtg ccagcaccaa   3780 gggcccagc gtgttccctc tggccccctg tagcagaagc accagcgaga gcacagccgc   3840
cctgggctgc ctggtcaagg actacttccc cgagcccgtg accgtgtcct ggaactctgg   3900
cgctctgacc agcggcgtgc acacctttcc agccgtgctg cagagcagcg gcctgtacag   3960
cctgagcagc gtggtcaccg tgcccagcag caacttcggc acccagacct acacctgtaa   4020
cgtggaccac aagcccagca acaccaaggt ggacaagacc gtggaacgga agtgctgcgt   4080
ggaatgcccc cctgtcccg ctcctccagt ggctggacct tccgtgttcc tgttcccccc   4140
aaagcccaag gacaccctga tgatcagccg gacccccgaa gtgacctgcg tggtggtgga   4200
cgtgtcccac gaggaccccg aggtgcagtt caattggtac gtggacggcg tggaagtgca   4260
caacgccaag accaagccca gagaggaaca gttcaacagc accttccggg tggtgtccgt   4320
gctgaccgtg gtgcaccagg actggctgaa cggcaaagag tacaagtgcg ccgtctccaa   4380
caagggcctg cctgccccca tcgagaaaac catcagcaag accaagggcc agcctcgcga   4440
gcctcaggtg tacacactgc cccccagccg ggaagagatg accaagaacc aggtgtgcct   4500
gacctgcctc gtgaagggct ctacccag cgatatcgcc gtggaatggg agagcaacgg   4560
ccagcccgag aacaactaca agaccacccc ccccatgctg gacagcgacg gctcattctt   4620
cctgtacagc aagctgacag tggacaagag ccggtggcag cagggcaacg tgttcagctg   4680
cagcgtgatg cacgaggccc tgcacaacca ctacacccag aagtccctga gcctgagccc   4740
cggcaaggga tccaaggtaa gtttaaacat atatataact ttaaataatt ggcattattt   4800
aaagttacta ctaactaacc ctgattattt aaattttcag gaacaaaaac tcatctcaga   4860
agaggatctg aatgctgtgg ccaggacac gcaggaggtc atcgtggtgc cacactcctt   4920
gccctttaag gtggtggtga tctcagccat cctggccctg gtggtgctca ccatcatctc   4980
ccttatcatc ctcatcatgc tttggcagaa gaagccacgt tagtaacagg taagagtgta   5040
actttaaata atgccaatta tttaaagtta ctgactctct ctgcttacga cgcttcttct   5100
tttttttttc ctgcaggggt agtaatcagc ctcgactgtg ccttctagtt gccagccatc   5160
tgttgtttgc ccctcccccg tgccttcctt gaccctggaa ggtgccactc ccactgtcct   5220
ttcctaataa aatgaggaaa ttgcatcgca ttgtctgagt aggtgtcatt ctattctggg   5280
gggtggggtg gggcaggaca gcaaggggga ggattgggaa gacaatagca ggcatgctgg   5340
ggatggcccg ggcatgataa cttcgtataa tgtatgctat acgaagttat gtatac         5396
```

<210> SEQ ID NO 2
<211> LENGTH: 233
<212> TYPE: PRT
<213> ORGANISM: Artificial sequence
<220> FEATURE:
<223> OTHER INFORMATION: BM40 Leader, Humanised D1.3 VL and Human C Kappa sequence

<400> SEQUENCE: 2

Met Arg Ala Trp Ile Phe Phe Leu Leu Cys Leu Ala Gly Arg Ala Leu
1               5                   10                  15

Ala Ala Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gly Asn Ile
        35                  40                  45

His Asn Tyr Leu Ala Trp Tyr Gln Gln Lys Pro Gly Lys Ala Pro Lys
    50                  55                  60

Leu Leu Ile Tyr Tyr Thr Thr Thr Leu Ala Asp Gly Val Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln His Phe Trp Ser
            100                 105                 110

Thr Pro Arg Thr Phe Gly Gln Gly Thr Lys Val Glu Ile Lys Arg Thr
        115                 120                 125

Ala Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Leu Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 3
<211> LENGTH: 15
<212> TYPE: PRT
<213> ORGANISM: Artificial sequence
<220> FEATURE:
<223> OTHER INFORMATION: Leader 1 sequence

<400> SEQUENCE: 3

Met Ser Trp Ser Cys Ile Ile Leu Phe Leu Val Ala Thr Ala Thr
1               5                   10                  15

<210> SEQ ID NO 4
<211> LENGTH: 449
<212> TYPE: PRT
<213> ORGANISM: Artificial sequence
<220> FEATURE:
<223> OTHER INFORMATION: Leader 2 and D1.3 VH sequence, CH1 domain,
      Hinge, CH2 and CH3 domains

<400> SEQUENCE: 4

Gly Ala Met Ala Gln Val Gln Leu Gln Glu Ser Gly Pro Gly Leu Val
1               5                   10                  15

Arg Pro Ser Gln Thr Leu Ser Leu Thr Cys Thr Val Ser Gly Ser Thr
            20                  25                  30

```
Phe Ser Gly Tyr Gly Val Asn Trp Val Arg Gln Pro Gly Arg Gly
        35                  40                  45

Leu Glu Trp Ile Gly Met Ile Trp Gly Asp Gly Asn Thr Asp Tyr Asn
 50                  55                  60

Ser Ala Leu Lys Ser Arg Val Thr Met Leu Val Asp Thr Ser Lys Asn
 65                  70                  75                  80

Gln Phe Ser Leu Arg Leu Ser Ser Val Thr Ala Ala Asp Thr Ala Val
                 85                  90                  95

Tyr Tyr Cys Ala Arg Glu Arg Asp Tyr Arg Leu Asp Tyr Trp Gly Gln
            100                 105                 110

Gly Ser Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Ala Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Ser
        435                 440                 445

Lys
```

<210> SEQ ID NO 5
<211> LENGTH: 60
<212> TYPE: PRT
<213> ORGANISM: Artificial
<220> FEATURE:
<223> OTHER INFORMATION: Myc epitope, PDGFR spacer and PDGFR
      Transmembrane region (TM)

<400> SEQUENCE: 5

Glu Gln Lys Leu Ile Ser Glu Glu Asp Leu Asn Ala Val Gly Gln Asp
1               5                   10                  15

Thr Gln Glu Val Ile Val Val Pro His Ser Leu Pro Phe Lys Val Val
            20                  25                  30

Val Ile Ser Ala Ile Leu Ala Leu Val Val Leu Thr Ile Ile Ser Leu
        35                  40                  45

Ile Ile Leu Ile Met Leu Trp Gln Lys Lys Pro Arg
    50                  55                  60

<210> SEQ ID NO 6
<211> LENGTH: 1542
<212> TYPE: DNA
<213> ORGANISM: Artificial Sequence
<220> FEATURE:
<223> OTHER INFORMATION: pD1-huD1.3 donor construct fragment containing
      AAVS1 left homology arm, splice acceptor site, Blasticidin gene,
      SV40 polyA

<400> SEQUENCE: 6
ggtaccgaat cgcccttttg ctttctctga cctgcattct ctcccctggg cctgtgccgc     60
tttctgtctg cagcttgtgg cctgggtcac ctctacggct ggcccagatc cttccctgcc    120
gcctccttca ggttccgtct tcctccactc cctcttcccc ttgctctctg ctgtgttgct    180
gcccaaggat gctctttccg gagcacttcc ttctcggcgc tgcaccacgt gatgtcctct    240
gagcggatcc tccccgtgtc tgggtcctct ccgggcatct ctcctccctc acccaacccc    300
atgccgtctt cactcgctgg gttccctttt ccttctcctt ctggggcctg tgccatctct    360
cgtttcttag gatggccttc tccgacggat gtctcccttg cgtcccgcct cccttcttg     420 taggcctgca tcatcaccgt ttttctggac aaccccaaag taccccgtct ccctggcttt    480
agccacctct ccatcctctt gctttctttg cctggacacc ccgttctcct gtggattcgg    540
gtcacctctc actcctttca tttgggcagc tcccctaccc ccttacctc tctagtctgt     600 gcaagctctt ccagcccct gtcatggcat cttccagggg tccagagct cagctagtct      660 tcttcctcca acccgggccc ctatgtccac ttcaggacag catgtttgct gcctccaggg    720
atcctgtgtc cccgagctgg gaccaccta ttcccagg gccggttaat gtggctctgg       780
ttctgggtac ttttatctgt cccctccacc ccacagtggg gcaagatgca tcttctgacc    840
tcttctcttc ctcccacagg gcatggcaaa acctctgagc caggaagaaa gcacactgat    900
tgaaagagca accgctacta tcaacagcat ccccatctcc gaagactatt ctgtggctag    960
tgccgctctg tccagcgacg ggagaatctt caccggtgtg aacgtctacc actttacagg    1020
cggaccatgc gcagagctgg tggtcctggg gactgcagcc gctgcagccg ctggtaatct    1080
gacctgtatc gtggccattg caacgaaaaa tagggggcatc ctgtccccat gcggcaggtg    1140
tcggcaggtg ctgctggatc tgcatcctg catcaaggca attgtcaaag actctgatgg    1200
acagcctacc gccgtcggta tccgtgaact gctgcctagc ggctatgtct gggagggata    1260
atgagcttgg cttcgaaatg accgaccaag cgacgcccaa cctgccatca cgagatttcg    1320

```
attccaccgc cgccttctat gaaaggttgg gcttcggaat cgttttccgg gacgccggct   1380
ggatgatcct ccagcgcggg gatctcatgc tggagttctt cgcccacccc aacttgttta   1440
ttgcagctta taatggttac aaataaagca atagcatcac aaatttcaca ataaagcat    1500 ttttttcact gcattctagt tgtggtttaa ttaagtcaat tc                      1542
```

<210> SEQ ID NO 7
<211> LENGTH: 924
<212> TYPE: DNA
<213> ORGANISM: Artificial Sequence
<220> FEATURE:
<223> OTHER INFORMATION: pD1-huD1.3 fragment containing AAVS1 right
      homology arm

<400> SEQUENCE: 7

```
tggcccgggc atgataactt cgtataatgt atgctatacg aagttatgta tacggcgcgc    60
ccactaggga caggattggt gacagaaaag ccccatcctt aggcctcctc cttcctagtc   120
tcctgatatt gggtctaacc cccacctcct gttaggcaga ttccttatct ggtgacacac   180
ccccatttcc tggagccatc tctctccttg ccagaacctc taaggtttgc ttacgatgga   240
gccagagagg atcctgggag ggagagcttg caggggggtg ggagggaagg gggggatgcg   300
tgacctgccc ggttctcagt ggccaccctg cgctacccte tcccagaacc tgagctgctc   360
tgacgcggct gtctggtgcg tttcactgat cctggtgctg cagcttcctt acacttccca   420
agaggagaag cagtttggaa aacaaaatc agaataagtt ggtcctgagt tctaactttg    480
gctcttcacc tttctagtcc ccaatttata ttgttcctcc gtgcgtcagt tttacctgtg   540
agataaggcc agtagccagc cccgtcctgg cagggctgtg gtgaggaggg gggtgtccgt   600
gtggaaaact ccctttgtga gaatggtgcg tcctaggtgt tcaccaggtc gtggccgcct   660
ctactccctt tctctttctc catccttctt tccttaaaga gtccccagtg ctatctggga   720
catattcctc cgcccagagc agggtcccgc ttccctaagg ccctgctctg gcttctgggg   780
tttgagtcct tggcaagccc aggagaggcg ctcaggcttc cctgtccccc ttcctcgtcc   840
accatctcat gccctggct ctcctgcccc ttccctacag gggttcctgg ctctgctctg    900
acgcgtgtat actcgatctt tccg                                           924
```

<210> SEQ ID NO 8
<211> LENGTH: 132
<212> TYPE: PRT
<213> ORGANISM: Artificial Sequence
<220> FEATURE:
<223> OTHER INFORMATION: Synthetic Blasticidin resistance gene

<400> SEQUENCE: 8

```
Met Ala Lys Pro Leu Ser Gln Glu Glu Ser Thr Leu Ile Glu Arg Ala
1               5                   10                  15

Thr Ala Thr Ile Asn Ser Ile Pro Ile Ser Glu Asp Tyr Ser Val Ala
            20                  25                  30

Ser Ala Ala Leu Ser Ser Asp Gly Arg Ile Phe Thr Gly Val Asn Val
        35                  40                  45

Tyr His Phe Thr Gly Gly Pro Cys Ala Glu Leu Val Val Leu Gly Thr
    50                  55                  60

Ala Ala Ala Ala Ala Ala Gly Asn Leu Thr Cys Ile Val Ala Ile Gly
65                  70                  75                  80

Asn Glu Asn Arg Gly Ile Leu Ser Pro Cys Gly Arg Cys Arg Gln Val
                85                  90                  95
```

Leu Leu Asp Leu His Pro Gly Ile Lys Ala Ile Val Lys Asp Ser Asp
            100                 105                 110

Gly Gln Pro Thr Ala Val Gly Ile Arg Glu Leu Leu Pro Ser Gly Tyr
        115                 120                 125

Val Trp Glu Gly
    130

<210> SEQ ID NO 9
<211> LENGTH: 734
<212> TYPE: DNA
<213> ORGANISM: Artificial Sequence
<220> FEATURE:
<223> OTHER INFORMATION: pD6 vector for scFv-Fc expression, fragment
      from NcoI site to PmeI site containing a fragment (last 4 amino
      acids) of the leader sequence, the complete CH2 domain and CH3
      domain

<400> SEQUENCE: 9
ggcgccatgg cccaggtcgc ggccgccgtg gaatgccccc cctgtcccgc tcctccagtg      60
gctggacctt ccgtgttcct gttccccccca aagcccaagg acaccctgat gatcagccgg    120 accccgaag tgacctgcgt ggtggtggac gtgtcccacg aggaccccga ggtgcagttc      180
aattggtacg tggacggcgt ggaagtgcac aacgccaaga ccaagcccag agaggaacag    240
ttcaacagca ccttccgggt ggtgtccgtg ctgaccgtgg tgcaccagga ctggctgaac    300
ggcaaagagt acaagtgcgc cgtctccaac aagggcctgc ctgcccccat cgagaaaacc    360
atcagcaaga ccaagggcca gcctcgcgag cctcaggtgt acacactgcc cccagccgg    420 gaagagatga ccaagaacca ggtgtccctg acctgcctcg tgaagggctt ctaccccagc    480
gatatcgccg tggaatggga gagcaacggc cagcccgaga caactacaa gaccaccccc    540 cccatgctgg acagcgacgg ctcattcttc ctgtacagca agctgacagt ggacaagagc    600
cggtggcagc agggcaacgt gttcagctgc agcgtgatgc acgaggccct gcacaaccac    660
tacacccaga gtccctgag cctgagcccc ggcaagggat ccaaggtaag tttaaacata    720
tatataactt taaa                                                       734

<210> SEQ ID NO 10
<211> LENGTH: 4
<212> TYPE: PRT
<213> ORGANISM: Artificial Sequence
<220> FEATURE:
<223> OTHER INFORMATION: Vector pD6, fragment at the end of leader
      sequence

<400> SEQUENCE: 10

Gly Ala Met Ala
1

<210> SEQ ID NO 11
<211> LENGTH: 219
<212> TYPE: PRT
<213> ORGANISM: Artificial Sequence
<220> FEATURE:
<223> OTHER INFORMATION: Vector pD6 CH2 and CH3 domains

<400> SEQUENCE: 11

Ala Pro Pro Val Ala Gly Pro Ser Val Phe Leu Phe Pro Lys Pro
1               5                   10                  15

Lys Asp Thr Leu Met Ile Ser Arg Thr Pro Glu Val Thr Cys Val Val
            20                  25                  30

```
Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
 50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Ala Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys Gly Ser Lys
    210                 215
```

<210> SEQ ID NO 12
<211> LENGTH: 60
<212> TYPE: DNA
<213> ORGANISM: Artificial Sequence
<220> FEATURE:
<223> OTHER INFORMATION: Fragment of sequence of pD4 vector preceding
      and including the start of the AAVS1 left homology arm

<400> SEQUENCE: 12

```
ggtaccgaat cgcccttttg ctttctctga cctgcattct ctccctggg cctgtgccgc   60
```

<210> SEQ ID NO 13
<211> LENGTH: 3933
<212> TYPE: DNA
<213> ORGANISM: Artificial sequence
<220> FEATURE:
<223> OTHER INFORMATION: Fragment of sequence of vector pD4 including
      the end of the AAVS1 LHA, FRT site, Lox2272 site, 1-SceI
      meganuclease site, GFP left TALEN binding site, GFP right TALEN
      binding site, T2A, GFP, PGK promoter, puromycin delta TK, loxP
      site and start of AAVS1 RHA

<400> SEQUENCE: 13

```
ttctgggtac ttttatctgt cccctccacc ccacagtggg gcaagatgca tgaagttcct    60
attccgaagt tcctattctc tagaaagtat aggaacttcg accataactt cgtataaagt   120
atcctatacg aagttatgcg atcgctcgcg cgtagggata acagggtaat aagtccaccg   180
gtcgccacca tggtgagcaa gggcgaggag ctgttcactt ctgacctctt ctcttcctcc   240
cacagggcct agagagatct ggcagcggag agggcagagg aagtcttcta acatgcggtg   300
acgtggagga gaatcccgga ccgatggtga gcaagggaga agaactcttc accggggtgg   360
tgcccatcct ggtcgagctg gacgcgacg tgaacggcca agttcagc gtgtccggcg      420 agggcgaggg cgatgccacc tacggcaagc tgaccctgaa gttcatctgc accaccggca   480
```

| | |
|---|---|
| agctgcccgt gccctggccc accctcgtga ccaccctgac ctacggcgtg cagtgcttca | 540 |
| gccgctaccc cgaccacatg aagcagcacg acttcttcaa gtccgccatg cccgaaggct | 600 |
| acgtccagga gcgcaccatc ttcttcaagg acgacggcaa ctacaagacc cgcgccgagg | 660 |
| tgaagttcga gggcgacacc ctggtgaacc gcatcgagct gaagggcatc gacttcaagg | 720 |
| aggacggcaa catcctgggg cacaagctgg agtacaacta caacagccac aacgtctata | 780 |
| tcatggccga caagcagaag aacggcatca aggtgaactt caagatccgc cacaacatcg | 840 |
| aggacggcag cgtgcagctc gccgaccact accagcagaa cacccccatc ggcgacggcc | 900 |
| ccgtgctgct gcccgacaac cactacctga gcacccagtc cgccctgagc aaagacccca | 960 |
| acgagaagcg cgatcacatg gtcctgctgg agttcgtgac cgccgccggg atcactcacg | 1020 |
| gcatggacga gctgtacaag aagctgagcc acggcttccc gccggcggtg cggcgcaggg | 1080 |
| atgatggcac gctgcccatg tcttgtgccc aggagagcgg gatggaccgt caccctgcag | 1140 |
| cctgtgcttc tgctaggatc aatgtgtagg tgatcagcct cgactgtgcc ttctagttgc | 1200 |
| cagccatctg ttgtttgccc ctcccccgtg ccttccttga ccctggaagg tgccactccc | 1260 |
| actgtccttt cctaataaaa tgaggaaatt gcatcgcatt gtctgagtag gtgtcattct | 1320 |
| attctggggg gtggggtggg gcaggacagc aaggggagg attgggaaga caatagcagg | 1380 |
| catgctgggg atggcccaat tctaccgggt aggggaggcg ctttcccaa ggcagtctgg | 1440 |
| agcatgcgct ttagcagccc cgctgggcac ttggcgctac acaagtggcc tctggcctcg | 1500 |
| cacacattcc acatccaccg gtaggcgcca accggctccg ttctttggtg gccccttcgc | 1560 |
| gccaccttct actcctcccc tagtcaggaa gttccccccc gccccgcagc tcgcgtcgtg | 1620 |
| caggacgtga caaatggaag tagcacgtct cactagtctc gtgcagatgg acagcaccgc | 1680 |
| tgagcaatga aagcgggtag gcctttgggg cagcggccaa tagcagcttt gctccttcgc | 1740 |
| tttctgggct cagaggctgg aaggggtgg gtccggggc gggctcaggg gcgggctcag | 1800 |
| gggcggggcg ggcgcccgaa ggtcctccgg aggcccggca ttctgcacgc ttcaaaagcg | 1860 |
| cacgtctgcc gcgctgttct cctcttcctc atctccgggc ctttcgacct gcagccaacg | 1920 |
| ccaccatggg gaccgagtac aagcccacgg tgcgcctcgc cacccgcgac gacgtccccc | 1980 |
| gggccgtacg caccctcgcc gccgcgttcg ccgactaccc cgccacgcgc cacaccgtcg | 2040 |
| acccggaccg ccacatcgag cgggtcaccg agctgcaaga actcttcctc acgcgcgtcg | 2100 |
| ggctcgacat cggcaaggtg tgggtcgcgg acgacggcgc cgcggtggcg gtctggacca | 2160 |
| cgccggagag cgtcgaagcg ggggcggtgt cgccgagat cggcccgcgc atggccgagt | 2220 |
| tgagcggttc ccggctggcc gcgcagcaac agatggaagg cctcctggcg ccgcaccggc | 2280 |
| ccaaggagcc gcgtggttc ctggccaccg tcggcgtctc gcccgaccac cagggcaagg | 2340 |
| gtctgggcag cgccgtcgtg ctccccggag tggaggcggc cgagcgcgcc ggggtgcccg | 2400 |
| ccttcctgga gacctccgcg cccgcaacc tccccttcta cgagcggctc ggcttcaccg | 2460 |
| tcaccgccga cgtcgaggtg cccgaaggac gcgcacctg gtgcatgacc gcaagcccg | 2520 |
| gtgccggatc catgcccacg ctactgcggg tttatataga cggtcctcac gggatgggga | 2580 |
| aaaccaccac cacgcaactg ctggtggccc tgggttcgcg cgacgatatc gtctacgtac | 2640 |
| ccgagccgat gacttactgg caggtgctgg ggcttccga caatcgcg aacatctaca | 2700 |
| ccacacaaca ccgcctcgac cagggtgaga tatcggccgg gacgcgcg gtggtaatga | 2760 |
| caagcgccca gataacaatg gcatgccttt atgccgtgac cgacgccgtt ctggctcctc | 2820 |
| atatcggggg ggaggctggg agctcacatg ccccgccccc ggccctcacc ctcatcttcg | 2880 |

```
accgccatcc catcgccgcc ctcctgtgct acccggccgc gcgataccct atgggcagca    2940
tgacccccca ggccgtgctg gcgttcgtgg ccctcatccc gccgaccttg cccggcacaa    3000
acatcgtgtt gggggcctt ccggaggaca gacacatcga ccgcctggcc aaacgccagc    3060
gccccggcga gcggcttgac ctggctatgc tggccgcgat tcgccgcgtt tacgggctgc    3120
ttgccaatac ggtgcggtat ctgcagggcg gcgggtcgtg gcgggaggat tggggacagc    3180
tttcggggac ggccgtgccg ccccagggtg ccgagcccca gagcaacgcg ggcccacgac    3240
cccatatcgg ggacacgtta tttaccctgt tcgggcccc cgagttgctg gcccccaacg    3300
gcgacctgta caacgtgttt gcctgggcct tggacgtctt ggccaaacgc ctccgtccca    3360
tgcacgtctt tatcctggat tacgaccaat cgcccgccgg ctgccgggac gccctgctgc    3420
aacttacctc cggggatggtc cagacccacg tcaccacccc cggctccata ccgacgatct    3480
gcgacctggc gcgcacgttt gcccgggaga tgggggaggc taactgagct ctagagctcg    3540
ctgatcagcc tcgactgtgc cttctagttg ccagccatct gttgtttgcc cctcccccgt    3600
gccttccttg accctggaag gtgccactcc cactgtcctt tcctaataaa atgaggaaat    3660
tgcatcgcat tgtctgagta ggtgtcattc tattctgggg ggtggggtgg ggcaggacag    3720
caagggggag gattgggaag acaatagcag gcatgctggg gatgcggtgg gctctatggc    3780
ttctgaggcg gaaagaacca gctggggctc gagatccact agttctagcc tcgaggctag    3840
agcggccggc cctataactt cgtataatgt atgctatacg aagttatcag gtaagttaac    3900
agggcgcgcc cactagggac aggattggtg aca                                 3933
```

<210> SEQ ID NO 14  
<211> LENGTH: 20  
<212> TYPE: DNA  
<213> ORGANISM: Artificial Sequence  
<220> FEATURE:  
<223> OTHER INFORMATION: Fragment of pD4 including the end of the AAVS1 right homology arm (RHA)

<400> SEQUENCE: 14

```
tctgctctga cgcgtgtata                                                  20
```

<210> SEQ ID NO 15  
<211> LENGTH: 53  
<212> TYPE: PRT  
<213> ORGANISM: Artificial Sequence  
<220> FEATURE:  
<223> OTHER INFORMATION: Fragment of pD4 comprising T2A and start of EGFP sequence

<400> SEQUENCE: 15

Gly Ser Gly Glu Gly Arg Gly Ser Leu Leu Thr Cys Gly Asp Val Glu
1               5                   10                  15

Glu Asn Pro Gly Pro Met Val Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly
    50

<210> SEQ ID NO 16  
<211> LENGTH: 69  
<212> TYPE: PRT  
<213> ORGANISM: Artificial Sequence  
<220> FEATURE:

<223> OTHER INFORMATION: Fragment of pD4 comprising terminal part of
      EGFP sequence and Mu ornithine decarboxylase PEST sequence

<400> SEQUENCE: 16

Asn Glu Lys Arg Asp His Met Val Leu Leu Glu Phe Val Thr Ala Ala
1               5                   10                  15

Gly Ile Thr His Gly Met Asp Glu Leu Tyr Lys Lys Leu Ser His Gly
            20                  25                  30

Phe Pro Pro Ala Val Ala Ala Gln Asp Asp Gly Thr Leu Pro Met Ser
        35                  40                  45

Cys Ala Gln Glu Ser Gly Met Asp Arg His Pro Ala Ala Cys Ala Ser
    50                  55                  60

Ala Arg Ile Asn Val
65

<210> SEQ ID NO 17
<211> LENGTH: 18
<212> TYPE: PRT
<213> ORGANISM: Artificial Sequence
<220> FEATURE:
<223> OTHER INFORMATION: Initial fragment of of purodelta TK sequence
      encoded by pD4

<400> SEQUENCE: 17

Met Gly Thr Glu Tyr Lys Pro Thr Val Arg Leu Ala Thr Arg Asp Asp
1               5                   10                  15

Val Pro

<210> SEQ ID NO 18
<211> LENGTH: 15
<212> TYPE: PRT
<213> ORGANISM: Artificial Sequence
<220> FEATURE:
<223> OTHER INFORMATION: Terminal fragment of puromycin delta TK
      sequence encoded by pD4

<400> SEQUENCE: 18

Cys Asp Leu Ala Arg Thr Phe Ala Arg Glu Met Gly Glu Ala Asn
1               5                   10                  15

<210> SEQ ID NO 19
<211> LENGTH: 1098
<212> TYPE: DNA
<213> ORGANISM: Artificial Sequence
<220> FEATURE:
<223> OTHER INFORMATION: Sequence of donor plasmid for integration into
      Flp/GFP TALEN sites (pD5), fragment preceding D1.3 antibody
      expression cassette

<400> SEQUENCE: 19
ggtaccgaat tcctagctct tccagccccc tgtcatggca tcttccaggg gtccgagagc      60
tcagctagtc ttcttcctcc aacccgggcc cctatgtcca cttcaggaca gcatgtttgc     120
tgcctccagg gatcctgtgt ccccgagctg ggaccaccct atattcccag ggccggttaa     180
tgtggctctg gttctgggta ctttttatctg tcccctccac cccacagtgg ggcaagatgc    240
atgaagttcc tattccgaag ttcctattct ctagaaagta taggaacttc gaccataact     300
tcgtataaag tatcctatac gaagttatgc gatcgctcgc gcgtagggat aacagggtaa     360
taagtccacc ggtcgccacc atggtcttct gacctcttct cttcctccca cagggcatgg     420
caaaacctct gagccaggaa gaaagcacac tgattgaaag agcaaccgct actatcaaca     480
gcatccccat ctccgaagac tattctgtgg ctagtgccgc tctgtccagc gacgggagaa     540

```
tcttcaccgg tgtgaacgtc taccacttta caggcggacc atgcgcagag ctggtggtcc      600
tggggactgc agccgctgca gccgctggta atctgacctg tatcgtggcc attggcaacg      660
aaaatagggg catcctgtcc ccatgcggca ggtgtcggca ggtgctgctg atctgcatc      720 ctggcatcaa ggcaattgtc aaagactctg atggacagcc taccgccgtc ggtatccgtg      780
aactgctgcc tagcggctat gtctgggagg gataatgaat gagcttggct tcgaaatgac      840
cgaccaagcg acgcccaacc tgccatcacg agatttcgat tccaccgccg ccttctatga      900
aaggttgggc ttcggaatcg ttttccggga cgccggctgg atgatcctcc agcgcgggga      960
tctcatgctg gagttcttcg cccaccccaa cttgtttatt gcagcttata atggttacaa     1020
ataaagcaat agcatcacaa atttcacaaa taaagcattt ttttcactgc attctagttg     1080
tggtttaatt aacaattc                                                   1098
```

<210> SEQ ID NO 20
<211> LENGTH: 931
<212> TYPE: DNA
<213> ORGANISM: Artificial Sequence
<220> FEATURE:
<223> OTHER INFORMATION: Sequence of donor plasmid for integration into
      Flp/GFP TALEN sites (pD5), fragment following D1.3 antibody
      expression cassette

<400> SEQUENCE: 20

```
caggcatgct ggggatggcc cgggcatgat aacttcgtat aatgtatgct atacgaagtt       60
atgtatacgg cgcgcccgag caagggcgag gagctgttca cttctgacct cttctcttcc      120
tcccacctga gcctagagag atctggcagc ggagagggca gaggaagtct tctaacatgc      180
ggtgacgtgg aggagaatcc cggaccgtga gtgagcaagg gagaagaact cttcaccggg      240
gtggtgccca tcctggtcga gctggacggc gacgtgaacg ccacaagttt cagcgtgtcc      300
ggcgagggcg agggcgatgc cacctacggc aagctgaccc tgaagttcat ctgcaccacc      360
ggcaagctgc ccgtgccctg gcccaccctc gtgaccaccc tgacctacgg cgtgcagtgc      420
ttcagccgct accccgacca catgaagcag cacgacttct tcaagtccgc catgcccgaa      480
ggctacgtcc aggagcgcac catcttcttc aaggacgacg gcaactacaa gacccgcgcc      540
gaggtgaagt tcgagggcga caccctggtg aaccgcatcg agctgaaggg catcgacttc      600
aaggaggacg gcaacatcct ggggcacaag ctggagtaca actacaacag ccacaacgtc      660
tatatcatgg ccgacaagca gaagaacggc atcaaggtga acttcaagat ccgccacaac      720
atcgaggacg gcagcgtgca gctcgccgac cactaccagc agaacacccc catcggcgac      780
ggccccgtgc tgctgcccga caaccactac ctgagcaccc agtccgccct gagcaaagac      840
cccaacgaga gcgcgatca catggtcctg ctggagttcg tgaccgccgc cgggatcact      900
cacggcatgg acgagcctga cgcgtgtata c                                    931
```

<210> SEQ ID NO 21
<211> LENGTH: 131
<212> TYPE: PRT
<213> ORGANISM: Artificial Sequence
<220> FEATURE:
<223> OTHER INFORMATION: Sequence of Blasticidin resistance protein
      encoded by donor plasmid for integration into FLP/GFP TALEN sites
      (pD5)

<400> SEQUENCE: 21

Ala Lys Pro Leu Ser Gln Glu Glu Ser Thr Leu Ile Glu Arg Ala Thr
1               5                   10                  15

Ala Thr Ile Asn Ser Ile Pro Ile Ser Glu Asp Tyr Ser Val Ala Ser
            20                  25                  30

Ala Ala Leu Ser Ser Asp Gly Arg Ile Phe Thr Gly Val Asn Val Tyr
        35                  40                  45

His Phe Thr Gly Gly Pro Cys Ala Glu Leu Val Val Leu Gly Thr Ala
    50                  55                  60

Ala Ala Ala Ala Ala Gly Asn Leu Thr Cys Ile Val Ala Ile Gly Asn
65                  70                  75                  80

Glu Asn Arg Gly Ile Leu Ser Pro Cys Gly Arg Cys Arg Gln Val Leu
                85                  90                  95

Leu Asp Leu His Pro Gly Ile Lys Ala Ile Val Lys Asp Ser Asp Gly
            100                 105                 110

Gln Pro Thr Ala Val Gly Ile Arg Glu Leu Leu Pro Ser Gly Tyr Val
        115                 120                 125

Trp Glu Gly
    130

<210> SEQ ID NO 22
<211> LENGTH: 813
<212> TYPE: DNA
<213> ORGANISM: Artificial Sequence
<220> FEATURE:
<223> OTHER INFORMATION: Sequence of I-Sce-1 meganuclease construct

<400> SEQUENCE: 22
ccatgggcta tccttacgat gtccctgatt acgccaacag tcctggtatc cctggtatgg      60
gtcctaaaaa gaagcgaaaa gtgggtagac tggaacccgg catgaagaac attaagaaaa     120
atcaggtgat gaacctggga cctaattcca agctgctgaa agagtacaag tctcagctga     180
tcgaactgaa cattgagcag tttgaagcag ggatcggtct gattctgggg gacgcctaca     240
tccggagcag ggatgagggc aagacttatt gcatgcagtt cgaatggaag aataaggcct     300
acatggacca cgtgtgtctg ctgtatgatc agtgggtcct gtctccccct cacaagaaag     360
agagagtgaa ccatctgggc aatctggtca ttacttgggg agcacagacc ttcaagcatc     420
aggcctttaa caaactggct aacctgttca tcgtgaacaa caagaaaacc atccctaaca     480
atctggtcga aaactacctg acaccaatga gtctggccta ttggttcatg gacgatggcg     540
gaaaatggga ctacaacaag aacagcacaa acaaaagcat cgtgctgaat cccagtcct      600 tcacatttga ggaagtggag tatctggtca agggcctgcg gaacaaattc cagctgaact     660
gctacgtgaa gatcaacaag aacaagccaa tcatctacat cgattctatg agttacctga     720
tcttttataa cctgattaag ccataccctga tcccccagat gatgtataaa ctgcccaata     780
caatcagctc cgagactttc ctgaaggtct aga                                   813

<210> SEQ ID NO 23
<211> LENGTH: 269
<212> TYPE: PRT
<213> ORGANISM: Artificial Sequence
<220> FEATURE:
<223> OTHER INFORMATION: Sequence encoded by I-Sce1 meganuclease
      construct: HA tag, NLS, and I-Sce1

<400> SEQUENCE: 23

Met Gly Tyr Pro Tyr Asp Val Pro Asp Tyr Ala Asn Ser Pro Gly Ile
1               5                   10                  15

Pro Gly Met Gly Pro Lys Lys Lys Arg Lys Val Gly Arg Leu Glu Pro
            20                  25                  30

```
Gly Met Lys Asn Ile Lys Lys Asn Gln Val Met Asn Leu Gly Pro Asn
         35                  40                  45
Ser Lys Leu Leu Lys Glu Tyr Lys Ser Gln Leu Ile Glu Leu Asn Ile
 50                  55                  60
Glu Gln Phe Glu Ala Gly Ile Gly Leu Ile Leu Gly Asp Ala Tyr Ile
 65                  70                  75                  80
Arg Ser Arg Asp Glu Gly Lys Thr Tyr Cys Met Gln Phe Glu Trp Lys
                 85                  90                  95
Asn Lys Ala Tyr Met Asp His Val Cys Leu Leu Tyr Asp Gln Trp Val
             100                 105                 110
Leu Ser Pro Pro His Lys Lys Glu Arg Val Asn His Leu Gly Asn Leu
             115                 120                 125
Val Ile Thr Trp Gly Ala Gln Thr Phe Lys His Gln Ala Phe Asn Lys
             130                 135                 140
Leu Ala Asn Leu Phe Ile Val Asn Asn Lys Lys Thr Ile Pro Asn Asn
145                 150                 155                 160
Leu Val Glu Asn Tyr Leu Thr Pro Met Ser Leu Ala Tyr Trp Phe Met
                 165                 170                 175
Asp Asp Gly Gly Lys Trp Asp Tyr Asn Lys Asn Ser Thr Asn Lys Ser
             180                 185                 190
Ile Val Leu Asn Thr Gln Ser Phe Thr Phe Glu Glu Val Glu Tyr Leu
             195                 200                 205
Val Lys Gly Leu Arg Asn Lys Phe Gln Leu Asn Cys Tyr Val Lys Ile
             210                 215                 220
Asn Lys Asn Lys Pro Ile Ile Tyr Ile Asp Ser Met Ser Tyr Leu Ile
225                 230                 235                 240
Phe Tyr Asn Leu Ile Lys Pro Tyr Leu Ile Pro Gln Met Met Tyr Lys
                 245                 250                 255
Leu Pro Asn Thr Ile Ser Ser Glu Thr Phe Leu Lys Val
             260                 265

<210> SEQ ID NO 24
<211> LENGTH: 67
<212> TYPE: DNA
<213> ORGANISM: Artificial Sequence
<220> FEATURE:
<223> OTHER INFORMATION: pINT20 Vector fragment showing NsiI site,
      splice acceptor site and start of Puromycin resistance gene
      sequence

<400> SEQUENCE: 24
atgcatcttc tgacctcttc tcttcctccc acagggcatg accgagtaca agcccacggt      60
gcgcctc                                                               67

<210> SEQ ID NO 25
<211> LENGTH: 10
<212> TYPE: PRT
<213> ORGANISM: Artificial Sequence
<220> FEATURE:
<223> OTHER INFORMATION: Initial fragment of puromycin resistance
      protein encoded by pINT20 vector

<400> SEQUENCE: 25

Met Thr Glu Tyr Lys Pro Thr Val Arg Leu
 1               5                  10

<210> SEQ ID NO 26
<211> LENGTH: 1125
```

<212> TYPE: DNA
<213> ORGANISM: Artificial Sequence
<220> FEATURE:
<223> OTHER INFORMATION: Sequence of T cell receptor clone c12/c2 alpha
      chain construct containing Nhe1, Not1 and Acc651 restriction sites

<400> SEQUENCE: 26

```
gctagcaagc aggaagtgac tcagatccca gccgctctga gcgtgcctga gggagaaaac    60
ctggtcctga attgcagttt caccgactca gccatctata acctgcagtg gtttcgccag   120
gatccaggca agggactgac ctccctgctg ctgattcaga gctcccagag ggaacagaca   180
tctggcagac tgaatgctag tctggacaaa tctagtggac ggtctaccct gtacatcgca   240
gccagccagc ctggagattc cgcaacatat ctgtgcgccg tgcgcccact acaggcgga    300
agctacattc ccaccttcgg gcgaggtaca agcctgatcg tgcacccaga catccagaat   360
ccggagcccg ccgtatacca gctgaaggac cccagaagcc aggacagcac cctgtgcctg   420
ttcaccgact cgacagcca gatcaacgtg cccaagacaa tggaaagcgg caccttcatc   480
accgacaaga ccgtgctgga catgaaggct atggacagca gagcaacgg cgccattgcc    540
tggtccaacc agaccagctt cacatgccag gacatcttca agagacaaa cgccacctac   600
cccagcagcg acgtgccctg tgatgccacc ctgaccgaga gtccttcga cagacatg     660
aacctgaact tccagaacct gtccgcggcc gcaggcctgc tggatcccaa gctgtgctac   720
ctgctggacg gatcctgtt catctacggt gtgatcctga ctgccctgtt cctgcgagtc   780
aaatttctc ggagtgccga cgctcctgca taccagcagg ggcagaacca gctgtataac    840
gagctgaatc tgggtcggag ggaggaatat gacgtgctgg ataagagacg cggcagggat   900
ccagaaatgg ggggcaagcc ccagcgacgg aaaaaccctc aggagggact gtataatgaa   960
ctgcagaagg acaaaatggc cgaggcttac tctgaaattg ggatgaaggg cgagaggaga  1020
cgcggcaaag gacacgatgg cctgtaccag ggactgagca ctgctaccaa ggacacatat  1080
gatgctctgc atatgcaggc actgccccct agataataag gtacc                  1125
```

<210> SEQ ID NO 27
<211> LENGTH: 369
<212> TYPE: PRT
<213> ORGANISM: Artificial Sequence
<220> FEATURE:
<223> OTHER INFORMATION: Sequence of T cell receptor clone c12/c2 alpha
      chain

<400> SEQUENCE: 27

```
Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Thr
                85                  90                  95

Gly Gly Ser Tyr Ile Pro Thr Phe Gly Arg Gly Thr Ser Leu Ile Val
            100                 105                 110

His Pro Asp Ile Gln Asn Pro Glu Pro Ala Val Tyr Gln Leu Lys Asp
```

```
            115                 120                 125
Pro Arg Ser Gln Asp Ser Thr Leu Cys Leu Phe Thr Asp Phe Asp Ser
    130                 135                 140

Gln Ile Asn Val Pro Lys Thr Met Glu Ser Gly Thr Phe Ile Thr Asp
145                 150                 155                 160

Lys Thr Val Leu Asp Met Lys Ala Met Asp Ser Lys Ser Asn Gly Ala
                165                 170                 175

Ile Ala Trp Ser Asn Gln Thr Ser Phe Thr Cys Gln Asp Ile Phe Lys
            180                 185                 190

Glu Thr Asn Ala Thr Tyr Pro Ser Ser Asp Val Pro Cys Asp Ala Thr
        195                 200                 205

Leu Thr Glu Lys Ser Phe Glu Thr Asp Met Asn Leu Asn Phe Gln Asn
    210                 215                 220

Leu Ser Ala Ala Ala Gly Leu Leu Asp Pro Lys Leu Cys Tyr Leu Leu
225                 230                 235                 240

Asp Gly Ile Leu Phe Ile Tyr Gly Val Ile Leu Thr Ala Leu Phe Leu
                245                 250                 255

Arg Val Lys Phe Ser Arg Ser Ala Asp Ala Pro Ala Tyr Gln Gln Gly
            260                 265                 270

Gln Asn Gln Leu Tyr Asn Glu Leu Asn Leu Gly Arg Arg Glu Glu Tyr
        275                 280                 285

Asp Val Leu Asp Lys Arg Arg Gly Arg Asp Pro Glu Met Gly Gly Lys
    290                 295                 300

Pro Gln Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg
```

<210> SEQ ID NO 28
<211> LENGTH: 1226
<212> TYPE: DNA
<213> ORGANISM: Artificial Sequence
<220> FEATURE:
<223> OTHER INFORMATION: Sequence of T cell receptor clone c12/c2 beta
      chain construct containing Nco1, Xho1 and Hind3 restriction sites

<400> SEQUENCE: 28

```
ccatggccaa cgctggagtg actcagaccc ctaagttcca ggtcctgaaa actgggcaga      60
gtatgaccct gcagtgcgca caggacatga atcacgagta catgtcatgg tatcggcagg     120
atccagggat gggtctgagg ctgatccatt acagcgtggg cgctggaact accgaccagg     180
gcgaggtgcc caacggatat aatgtctcaa gaagcaccac agaagatttc ccactgcgac     240
tgctgagcgc cgctcctagc cagacatccg tgtactttg cgccagctcc aatgtcggga     300
acaccggcga gctgttcttt ggggaaggtt cccgcctgac agtgctcgag acctgagaa     360 acgtgacccc ccccaaggtg tccctgttcg agcctagcaa ggccgagatc gccaacaagc     420
agaaagccac cctcgtgtgc ctggccagag gcttcttccc cgaccacgtg aactgtctt     480 ggtgggtcaa cggcaaagag gtgcacacgc gcgtgtccac cgatcccag cctacaaag     540 agagcaacta cagctactgc ctgagcagca gactgcgggt gtccgccacc ttctggcaca     600
```

```
acccccggaa ccacttcaga tgccaggtgc agtttcacgg cctgagcgaa gaggacaagt    660
ggcccgaggg cagccctaag cccgtgaccc agaatatctc tgccgaagcc tggggcagag    720
ccgactgtgg cattaccagc gccagctacc agcagggcgt gctgtctgcc accatcctgt    780
acgaggtcgc gagcggactg ctggaccaaa agctgtgcta cctgctggat gggatcctgt    840
tcatctacgg tgtgattctg acagccctgt cctgcgagt caagttcagc cggagcgccg     900
acgcaccagc ataccagcag ggcagaatc agctgtataa cgagctgaat ctgggtcgga    960
gggaggaata cgacgtgctg gataagagac gcggcaggga tcccgaaatg gcggaaagc    1020 ctcagcgacg gaaaaaccca caggagggac tgtacaatga actgcagaag gacaaaatgg    1080
ctgaggcata ttctgaaatc ggcatgaagg gagagaggag acgcggcaaa ggacacgatg    1140
ggctgtacca gggtctgagt acagccacta aggacaccta tgatgccctg catatgcagg    1200
ctctgccacc cagataataa aagctt                                         1226

<210> SEQ ID NO 29
<211> LENGTH: 404
<212> TYPE: PRT
<213> ORGANISM: Artificial Sequence
<220> FEATURE:
<223> OTHER INFORMATION: Sequence of T cell receptor clone c12/c2 beta
      chain construct

<400> SEQUENCE: 29

Met Ala Asn Ala Gly Val Thr Gln Thr Pro Lys Phe Gln Val Leu Lys
1               5                   10                  15

Thr Gly Gln Ser Met Thr Leu Gln Cys Ala Gln Asp Met Asn His Glu
            20                  25                  30

Tyr Met Ser Trp Tyr Arg Gln Asp Pro Gly Met Gly Leu Arg Leu Ile
        35                  40                  45

His Tyr Ser Val Gly Ala Gly Thr Thr Asp Gln Gly Glu Val Pro Asn
    50                  55                  60

Gly Tyr Asn Val Ser Arg Ser Thr Thr Glu Asp Phe Pro Leu Arg Leu
65                  70                  75                  80

Leu Ser Ala Ala Pro Ser Gln Thr Ser Val Tyr Phe Cys Ala Ser Ser
                85                  90                  95

Asn Val Gly Asn Thr Gly Glu Leu Phe Phe Gly Glu Gly Ser Arg Leu
            100                 105                 110

Thr Val Leu Glu Asp Leu Arg Asn Val Thr Pro Pro Lys Val Ser Leu
        115                 120                 125

Phe Glu Pro Ser Lys Ala Glu Ile Ala Asn Lys Gln Lys Ala Thr Leu
    130                 135                 140

Val Cys Leu Ala Arg Gly Phe Phe Pro Asp His Val Glu Leu Ser Trp
145                 150                 155                 160

Trp Val Asn Gly Lys Glu Val His Ser Gly Val Ser Thr Asp Pro Gln
                165                 170                 175

Ala Tyr Lys Glu Ser Asn Tyr Ser Tyr Cys Leu Ser Ser Arg Leu Arg
            180                 185                 190

Val Ser Ala Thr Phe Trp His Asn Pro Arg Asn His Phe Arg Cys Gln
        195                 200                 205

Val Gln Phe His Gly Leu Ser Glu Glu Asp Lys Trp Pro Glu Gly Ser
    210                 215                 220

Pro Lys Pro Val Thr Gln Asn Ile Ser Ala Glu Ala Trp Gly Arg Ala
225                 230                 235                 240
```

Asp Cys Gly Ile Thr Ser Ala Ser Tyr Gln Gln Gly Val Leu Ser Ala
            245                 250                 255

Thr Ile Leu Tyr Glu Val Ala Ser Gly Leu Leu Asp Pro Lys Leu Cys
        260                 265                 270

Tyr Leu Leu Asp Gly Ile Leu Phe Ile Tyr Gly Val Ile Leu Thr Ala
        275                 280                 285

Leu Phe Leu Arg Val Lys Phe Ser Arg Ser Ala Asp Ala Pro Ala Tyr
    290                 295                 300

Gln Gln Gly Gln Asn Gln Leu Tyr Asn Glu Leu Asn Leu Gly Arg Arg
305                 310                 315                 320

Glu Glu Tyr Asp Val Leu Asp Lys Arg Arg Gly Arg Asp Pro Glu Met
            325                 330                 335

Gly Gly Lys Pro Gln Arg Arg Lys Asn Pro Gln Glu Gly Leu Tyr Asn
        340                 345                 350

Glu Leu Gln Lys Asp Lys Met Ala Glu Ala Tyr Ser Glu Ile Gly Met
        355                 360                 365

Lys Gly Glu Arg Arg Arg Gly Lys Gly His Asp Gly Leu Tyr Gln Gly
        370                 375                 380

Leu Ser Thr Ala Thr Lys Asp Thr Tyr Asp Ala Leu His Met Gln Ala
385                 390                 395                 400

Leu Pro Pro Arg

<210> SEQ ID NO 30
<211> LENGTH: 677
<212> TYPE: DNA
<213> ORGANISM: Artificial Sequence
<220> FEATURE:
<223> OTHER INFORMATION: Sequence of T cell receptor clone 4JFH alpha
      chain construct with initial Nhe1 and terminal Not1 restriction
      sites

<400> SEQUENCE: 30
gctagccaga aagaggtgga acagaacagc ggccctctga gcgtgccaga aggcgctatc      60
gccagcctga actgcaccta cagctttctg ggcagccaga gcttcttctg gtacagacag     120
tacagcggca agagccccga gctgatcatg ttcacctaca gagagggcga caaagaggac     180
ggcagattca ccgcccagct gaacaaggcc agccagcacg tgtccctgct gatcagagac     240
agccagccta cgacagcgc cacctacctg tgcgccgtga atgatggcgg cagactgacc      300
tttggcgacg gcaccaccct gaccgtgaag cctgacatcc agaatccgga gcccgccgta     360
taccagctga aggaccccag aagccaggac agcaccctgt gcctgttcac cgacttcgac     420
agccagatca acgtgcccaa gacaatggaa agcggcacct tcatcaccga caagaccgtg     480
ctggacatga aggctatgga cagcaagagc aacggcgcca ttgcctggtc aaccagacc      540 agcttcacat gccaggacat cttcaaagag acaaacgcca cctaccccag cagcgacgtg     600
ccctgtgatg ccaccctgac cgagaagtcc ttcgagacag acatgaacct gaacttccag     660
aacctgtccg cggccgc                                                    677

<210> SEQ ID NO 31
<211> LENGTH: 221
<212> TYPE: PRT
<213> ORGANISM: Artificial Sequence
<220> FEATURE:
<223> OTHER INFORMATION: Sequence of T cell receptor clone 4JFH alpha
      chain construct

<400> SEQUENCE: 31

```
Gln Lys Glu Val Gln Asn Ser Gly Pro Leu Ser Val Pro Glu Gly
1               5                   10                  15

Ala Ile Ala Ser Leu Asn Cys Thr Tyr Ser Phe Leu Gly Ser Gln Ser
            20                  25                  30

Phe Phe Trp Tyr Arg Gln Tyr Ser Gly Lys Ser Pro Glu Leu Ile Met
        35                  40                  45

Phe Thr Tyr Arg Glu Gly Asp Lys Glu Asp Gly Arg Phe Thr Ala Gln
    50                  55                  60

Leu Asn Lys Ala Ser Gln His Val Ser Leu Leu Ile Arg Asp Ser Gln
65                  70                  75                  80

Pro Ser Asp Ser Ala Thr Tyr Leu Cys Ala Val Asn Asp Gly Gly Arg
                85                  90                  95

Leu Thr Phe Gly Asp Gly Thr Thr Leu Thr Val Lys Pro Asp Ile Gln
                100                 105                 110

Asn Pro Glu Pro Ala Val Tyr Gln Leu Lys Asp Pro Arg Ser Gln Asp
            115                 120                 125

Ser Thr Leu Cys Leu Phe Thr Asp Phe Asp Ser Gln Ile Asn Val Pro
130                 135                 140

Lys Thr Met Glu Ser Gly Thr Phe Ile Thr Asp Lys Thr Val Leu Asp
145                 150                 155                 160

Met Lys Ala Met Asp Ser Lys Ser Asn Gly Ala Ile Ala Trp Ser Asn
                165                 170                 175

Gln Thr Ser Phe Thr Cys Gln Asp Ile Phe Lys Glu Thr Asn Ala Thr
            180                 185                 190

Tyr Pro Ser Ser Asp Val Pro Cys Asp Ala Thr Leu Thr Glu Lys Ser
        195                 200                 205

Phe Glu Thr Asp Met Asn Leu Asn Phe Gln Asn Leu Ser
    210                 215                 220

<210> SEQ ID NO 32
<211> LENGTH: 353
<212> TYPE: DNA
<213> ORGANISM: Artificial Sequence
<220> FEATURE:
<223> OTHER INFORMATION: Sequence of T cell receptor clone4JFH beta
      chain construct with initial Ncol restriction site and terminal
      Xhol restriction site

<400> SEQUENCE: 32
ccatggccag ccagaccatc catcagtggc ctgccaccct ggtgcagcct gtgggatctc      60
ctctgagcct ggaatgcacc gtggaaggca ccagcaaccc caacctgtac tggtacagac     120
aggccgctgg cagaggcccc cagctgctgt tttactgggg cccctttggc cagatcagca     180
gcgaggtgcc ccagaacctg agcgccagca ccccagga ccggcagttt atcctgagca      240
gcaagaagct gctgctgagc gacagcggct tctacctgtg cgcttggagc gagacaggcc     300
tgggcatggg cggatggcag tttggcgagg gcagcagact gacagtgctc gag            353

<210> SEQ ID NO 33
<211> LENGTH: 117
<212> TYPE: PRT
<213> ORGANISM: Artificial Sequence
<220> FEATURE:
<223> OTHER INFORMATION: Sequence of T cell receptor clone 4JFH
      beta chain construct

<400> SEQUENCE: 33

Met Ala Ser Gln Thr Ile His Gln Trp Pro Ala Thr Leu Val Gln Pro
1               5                   10                  15
```

Val Gly Ser Pro Leu Ser Leu Glu Cys Thr Val Gly Thr Ser Asn
            20                  25                  30

Pro Asn Leu Tyr Trp Tyr Arg Gln Ala Ala Gly Arg Gly Pro Gln Leu
                35                  40                  45

Leu Phe Tyr Trp Gly Pro Phe Gly Gln Ile Ser Glu Val Pro Gln
 50                  55                  60

Asn Leu Ser Ala Ser Arg Pro Gln Asp Arg Gln Phe Ile Leu Ser Ser
 65                  70                  75                  80

Lys Lys Leu Leu Leu Ser Asp Ser Gly Phe Tyr Leu Cys Ala Trp Ser
                85                  90                  95

Glu Thr Gly Leu Gly Met Gly Gly Trp Gln Phe Gly Glu Gly Ser Arg
            100                 105                 110

Leu Thr Val Leu Glu
        115

<210> SEQ ID NO 34
<211> LENGTH: 53
<212> TYPE: DNA
<213> ORGANISM: Artificial Sequence
<220> FEATURE:
<223> OTHER INFORMATION: Primer for mutation of CDR3 of c12/c2 TCR alpha
      chain
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 34
cacgcggcac gcgggtgaan nsnnscctwc natgtaaggg tggaagcccg ctc        53

<210> SEQ ID NO 35
<211> LENGTH: 52
<212> TYPE: DNA
<213> ORGANISM: Artificial Sequence
<220> FEATURE:
<223> OTHER INFORMATION: Primer used to mutate CDR3 of c12/c2 TCR alpha
      chain
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t

<400> SEQUENCE: 35
ctcgcccgaa ggtgggaatg tangwtccsn nsnnaagtgg gcgcacggcg ca         52

<210> SEQ ID NO 36
<211> LENGTH: 17
<212> TYPE: PRT
<213> ORGANISM: Artificial Sequence
<220> FEATURE:
<223> OTHER INFORMATION: Strategy used to mutate CDR3 of c12/c2 TCR alpha chain
<220> FEATURE:
<221> NAME/KEY: misc_feature
<222> LOCATION: (7)..(8)
<223> OTHER INFORMATION: Xaa can be any naturally occurring amino acid

<400> SEQUENCE: 36

Cys Ala Val Arg Pro Leu Xaa Xaa Gly Ser Tyr Ile Pro Thr Phe Gly
1               5                   10                  15

Arg

<210> SEQ ID NO 37
<211> LENGTH: 17
<212> TYPE: PRT
<213> ORGANISM: Artificial Sequence
<220> FEATURE:
<223> OTHER INFORMATION: Strategy used to mutate CDR3 of c12/c2 TCR
      alpha chain
<220> FEATURE:
<221> NAME/KEY: misc_feature
<222> LOCATION: (7)..(8)
<223> OTHER INFORMATION: Xaa can be any naturally occurring amino acid

<400> SEQUENCE: 37

Cys Ala Val Arg Pro Leu Xaa Xaa Gly Thr Tyr Ile Pro Thr Phe Gly
1               5                   10                  15

Arg

<210> SEQ ID NO 38
<211> LENGTH: 50
<212> TYPE: DNA
<213> ORGANISM: Artificial Sequence
<220> FEATURE:
<223> OTHER INFORMATION: Primer used to mutate CDR3 of c12/c2 TCR beta
      chain
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 38 gtactttgc gccagctccn nsstcgggnn saccggcgag ctgttctttg           50

<210> SEQ ID NO 39
<211> LENGTH: 49
<212> TYPE: DNA
<213> ORGANISM: Artificial Sequence
<220> FEATURE:
<223> OTHER INFORMATION: Primer used to mutate CDR3 of c12/c2 TCR beta
      chain
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 39
caaagaacag ctcgccggts nncccgassn nggagctggc gcaaaagta           49

<210> SEQ ID NO 40
<211> LENGTH: 16
<212> TYPE: PRT

```
<213> ORGANISM: Artificial Sequence
<220> FEATURE:
<223> OTHER INFORMATION: Strategy used to mutate CDR3 of c12/c2 TCR beta
      chain

<400> SEQUENCE: 40

Tyr Phe Cys Ala Ser Ser Asn Val Gly Asn Thr Gly Glu Leu Phe Phe
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Strategy used to mutate CDR3 of c12/c2 TCR beta
      chain

<400> SEQUENCE: 41

Tyr Phe Cys Ala Ser Ser Asn Leu Gly Asn Thr Gly Glu Leu Phe Phe
1               5                   10                  15

<210> SEQ ID NO 42
<211> LENGTH: 462
<212> TYPE: DNA
<213> ORGANISM: Artificial Sequence
<220> FEATURE:
<223> OTHER INFORMATION: Sequence of CD3 zeta in pINT21 CAR1

<400> SEQUENCE: 42
ggcgccatgg cccaggtcgc ggccgcaagc ggactgctgg acccaaagct gtgctacctg      60
ctggatggga tcctgttcat ctacggtgtg attctgacag ccctgttcct gcgagtcaag     120
ttcagccgga gcgccgacgc accagcatac cagcaggggc agaatcagct gtataacgag     180
ctgaatctgg gtcggaggga ggaatacgac gtgctggata agagacgcgg cagggatccc     240
gaaatgggcg gaaagcctca gcgacggaaa aacccacagg agggactgta caatgaactg     300
cagaaggaca aaatggctga gcatattct gaaatcggca tgaagggaga gaggagacgc     360
ggcaaaggac acgatgggct gtaccagggt ctgagtacag ccactaagga cacctatgat     420
gccctgcata tgcaggctct gccacccaga taataaaagc tt                       462

<210> SEQ ID NO 43
<211> LENGTH: 4
<212> TYPE: PRT
<213> ORGANISM: Artificial Sequence
<220> FEATURE:
<223> OTHER INFORMATION: Fragment encoded by pINT21 CAR1 vector

<400> SEQUENCE: 43

Gly Ala Met Ala
1

<210> SEQ ID NO 44
<211> LENGTH: 141
<212> TYPE: PRT
<213> ORGANISM: Artificial Sequence
<220> FEATURE:
<223> OTHER INFORMATION: CDR3 zeta sequence encoded by pINT21 CAR1

<400> SEQUENCE: 44

Ser Gly Leu Leu Asp Pro Lys Leu Cys Tyr Leu Leu Asp Gly Ile Leu
1               5                   10                  15

Phe Ile Tyr Gly Val Ile Leu Thr Ala Leu Phe Leu Arg Val Lys Phe
            20                  25                  30
```

```
Ser Arg Ser Ala Asp Ala Pro Ala Tyr Gln Gln Gly Gln Asn Gln Leu
         35                  40                  45

Tyr Asn Glu Leu Asn Leu Gly Arg Arg Glu Glu Tyr Asp Val Leu Asp
 50                  55                  60

Lys Arg Arg Gly Arg Asp Pro Glu Met Gly Gly Lys Pro Gln Arg Arg
 65                  70                  75                  80

Lys Asn Pro Gln Glu Gly Leu Tyr Asn Glu Leu Gln Lys Asp Lys Met
                 85                  90                  95

Ala Glu Ala Tyr Ser Glu Ile Gly Met Lys Gly Glu Arg Arg Arg Gly
            100                 105                 110

Lys Gly His Asp Gly Leu Tyr Gln Gly Leu Ser Thr Ala Thr Lys Asp
        115                 120                 125

Thr Tyr Asp Ala Leu His Met Gln Ala Leu Pro Pro Arg
    130                 135                 140
```

<210> SEQ ID NO 45
<211> LENGTH: 705
<212> TYPE: DNA
<213> ORGANISM: Artificial Sequence
<220> FEATURE:
<223> OTHER INFORMATION: pINT21 CAR2 Sequence encoding CD3 zeta

<400> SEQUENCE: 45

```
gccatggccc aggtcgcggc cgcaacaaca accccagccc ccagacctcc taccccctgcc      60
cctacaattg ccagccagcc tctgagcctg aggcccgagg cttgtagacc agctgctggc     120
ggagccgtgc acaccagagg actggatttc gcctgcgaca tctacatctg gccccctctg     180
gccggcacat gtggcgtgct gctgctgagc ctcgtgatca ccctgtactg caagcggggc     240
agaaagaaac tgctgtacat ctttaagcag cccttcatgc ggcccgtgca gaccacccag     300
gaagaggacg gctgctcctg cagattcccc gaggaagaag aaggcggctg cgagctgaga     360
gtgaagttca gcagatccgc cgacgcccct gcctacaagc agggccagaa ccagctgtac     420
aacgagctga acctgggcag acgggaagag tacgacgtgc tggacaagcg agagaggccgg     480
gacccagaga tgggcggaaa gcccagaaga aagaaccccc aggaaggcct gtataacgaa     540
ctgcagaaag acaaaatggc cgaggcctac agcgagatcg gaatgaaggg cgagcggaga     600
agaggcaagg gcacgatgg cctgtaccag ggcctgagca ccgccaccaa ggacacctat     660
gacgccctgc acatgcaggc cctgccccct agataataaa agctt                     705
```

<210> SEQ ID NO 46
<211> LENGTH: 223
<212> TYPE: PRT
<213> ORGANISM: Artificial Sequence
<220> FEATURE:
<223> OTHER INFORMATION: Sequence encoded by pINT21 CAR2: CD8 hinge /
      transmembrane region, 4-1BB and CD3 zeta

<400> SEQUENCE: 46

```
Thr Thr Thr Pro Ala Pro Arg Pro Pro Thr Pro Ala Pro Thr Ile Ala
  1               5                  10                  15

Ser Gln Pro Leu Ser Leu Arg Pro Glu Ala Cys Arg Pro Ala Ala Gly
             20                  25                  30

Gly Ala Val His Thr Arg Gly Leu Asp Phe Ala Cys Asp Ile Tyr Ile
         35                  40                  45

Trp Ala Pro Leu Ala Gly Thr Cys Gly Val Leu Leu Leu Ser Leu Val
 50                  55                  60

Ile Thr Leu Tyr Cys Lys Arg Gly Arg Lys Lys Leu Leu Tyr Ile Phe
```

```
                65                  70                  75                  80
Lys Gln Pro Phe Met Arg Pro Val Gln Thr Thr Gln Glu Glu Asp Gly
                    85                  90                  95

Cys Ser Cys Arg Phe Pro Glu Glu Glu Gly Gly Cys Glu Leu Arg
                100                 105                 110

Val Lys Phe Ser Arg Ser Ala Asp Ala Pro Ala Tyr Lys Gln Gly Gln
            115                 120                 125

Asn Gln Leu Tyr Asn Glu Leu Asn Leu Gly Arg Arg Glu Glu Tyr Asp
        130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
        195                 200                 205

Lys Asp Thr Tyr Asp Ala Leu His Met Gln Ala Leu Pro Pro Arg
    210                 215                 220

<210> SEQ ID NO 47
<211> LENGTH: 750
<212> TYPE: DNA
<213> ORGANISM: Artificial Sequence
<220> FEATURE:
<223> OTHER INFORMATION: Sequence of FMC63 H-L (anti-CD19 antibody)

<400> SEQUENCE: 47
gccatggccg aagtgaaact gcaggagtct ggacccggcc tggtggcccc atctcagtct      60
ctgagcgtga cctgtaccgt gtccggcgtg tccctgcctg actatggcgt gtcctggatc     120
agacagcccc ccagaaaggg cctggaatgg ctgggagtga tctggggcag cgaaaccacc     180
tactacaaca gcgccctgaa gtcccggctg accatcatca aggacaactc caagagccag     240
gtgttcctga gatgaacag cctgcagacc gacgacaccg ccatctacta ctgcgccaag     300
cactactact acggcggcag ctacgctatg gactactggg gccagggcac ctcggtcacc     360
gtctcgagtg gtggaggcgg ttcaggcgga ggtggctctg gcggtggcgc tagcgacatc     420
cagatgaccc agaccaccag cagcctgagc gccagcctgg gcgatagagt gaccatcagc     480
tgcagagcca gccaggacat cagcaagtac ctgaactggt atcagcagaa acccgacggc     540
accgtgaagc tgctgatcta ccacaccagc agactgcaca gcggcgtgcc cagcagattt     600
tccggctctg gcagcggcac cgactacagc ctgaccatct ccaacctgga acaggaagat     660
atcgctacct acttctgtca gcaaggcaac accctgccct acaccttcgg cggagggacc     720
aagctggaga tcaaacgtac cgcggccgca                                      750

<210> SEQ ID NO 48
<211> LENGTH: 250
<212> TYPE: PRT
<213> ORGANISM: Artificial Sequence
<220> FEATURE:
<223> OTHER INFORMATION: Sequence of FMC63 H-L (anti-CD19 antibody)

<400> SEQUENCE: 48

Ala Met Ala Glu Val Lys Leu Gln Glu Ser Gly Pro Gly Leu Val Ala
1               5                   10                  15

Pro Ser Gln Ser Leu Ser Val Thr Cys Thr Val Ser Gly Val Ser Leu
```

```
                20                  25                  30
Pro Asp Tyr Gly Val Ser Trp Ile Arg Gln Pro Pro Arg Lys Gly Leu
            35                  40                  45
Glu Trp Leu Gly Val Ile Trp Gly Ser Glu Thr Thr Tyr Tyr Asn Ser
        50                  55                  60
Ala Leu Lys Ser Arg Leu Thr Ile Ile Lys Asp Asn Ser Lys Ser Gln
65                  70                  75                  80
Val Phe Leu Lys Met Asn Ser Leu Gln Thr Asp Thr Ala Ile Tyr
                85                  90                  95
Tyr Cys Ala Lys His Tyr Tyr Gly Gly Ser Tyr Ala Met Asp Tyr
                    100                 105                 110
Trp Gly Gln Gly Thr Ser Val Thr Val Ser Ser Gly Gly Gly Gly Ser
                115                 120                 125
Gly Gly Gly Gly Ser Gly Gly Gly Ala Ser Asp Ile Gln Met Thr Gln
            130                 135                 140
Thr Thr Ser Ser Leu Ser Ala Ser Leu Gly Asp Arg Val Thr Ile Ser
145                 150                 155                 160
Cys Arg Ala Ser Gln Asp Ile Ser Lys Tyr Leu Asn Trp Tyr Gln Gln
                    165                 170                 175
Lys Pro Asp Gly Thr Val Lys Leu Leu Ile Tyr His Thr Ser Arg Leu
                180                 185                 190
His Ser Gly Val Pro Ser Arg Phe Ser Gly Ser Gly Ser Gly Thr Asp
                195                 200                 205
Tyr Ser Leu Thr Ile Ser Asn Leu Glu Gln Glu Asp Ile Ala Thr Tyr
            210                 215                 220
Phe Cys Gln Gln Gly Asn Thr Leu Pro Tyr Thr Phe Gly Gly Gly Thr
225                 230                 235                 240
Lys Leu Glu Ile Lys Arg Thr Ala Ala Ala
                245                 250

<210> SEQ ID NO 49
<211> LENGTH: 327
<212> TYPE: DNA
<213> ORGANISM: Artificial Sequence
<220> FEATURE:
<223> OTHER INFORMATION: Sequence of lox1 binding Adhiron lox1A

<400> SEQUENCE: 49
gccatggctg ctacaggcgt gcgggctgtg cccggcaatg agaacagcct ggaaatcgag    60
gaactggcca gattcgccgt ggacgagcac aacaagaaag agaacgccct gctggaattc   120
gtgcgggtcg tgaaggccaa agagcagtgg agcgaggccg acaacgactg cacaccatg    180 tactacctga ccctggaagc caaggacggc ggcaagaaga agctgtacga ggccaaagtg   240
tgggtcaagc tggacctgga aacctggcag cacttcaact tcaaagagct ccaggaattc   300
aagcccgtgg cgacgctgc ggccgcg                                        327

<210> SEQ ID NO 50
<211> LENGTH: 109
<212> TYPE: PRT
<213> ORGANISM: Artificial Sequence
<220> FEATURE:
<223> OTHER INFORMATION: Sequence of Lox1 binding Adhiron lox1A

<400> SEQUENCE: 50

Ala Met Ala Ala Thr Gly Val Arg Ala Val Pro Gly Asn Glu Asn Ser
1               5                   10                  15
```

```
Leu Glu Ile Glu Glu Leu Ala Arg Phe Ala Val Asp Glu His Asn Lys
            20                  25                  30

Lys Glu Asn Ala Leu Leu Glu Phe Val Arg Val Lys Ala Lys Glu
        35                  40                  45

Gln Trp Ser Glu Ala Asp Asn Asp Trp His Thr Met Tyr Tyr Leu Thr
    50                  55                  60

Leu Glu Ala Lys Asp Gly Gly Lys Lys Leu Tyr Glu Ala Lys Val
65                  70                  75                  80

Trp Val Lys Leu Asp Leu Glu Thr Trp Gln His Phe Asn Phe Lys Glu
                85                  90                  95

Leu Gln Glu Phe Lys Pro Val Gly Asp Ala Ala Ala
            100                 105
```

<210> SEQ ID NO 51
<211> LENGTH: 333
<212> TYPE: DNA
<213> ORGANISM: Artificial Sequence
<220> FEATURE:
<223> OTHER INFORMATION: Sequence of lox1 binding Adhiron lox1B

<400> SEQUENCE: 51

```
gccatggctg ctacaggcgt gcgggctgtg cccggcaatg agaacagcct ggaaatcgag    60
gaactggcca gattcgccgt ggacgagcac aacaagaaag agaacgccct gctggaattc   120
gtgcgggtcg tgaaggccaa agagcaggaa cagcccatcg cgagcacccc cgtgaacgac   180
accatgtact acctgaccct ggaagccaag gacggcggca agaagaagct gtacgaggcc   240
aaagtgtggg tcaagcggtg gctgcggttc accgagatct acaacttcaa agagctccag   300
gaattcaagc ccgtgggcga cgctgcggcc gcg                                333
```

<210> SEQ ID NO 52
<211> LENGTH: 111
<212> TYPE: PRT
<213> ORGANISM: Artificial Sequence
<220> FEATURE:
<223> OTHER INFORMATION: Sequence of lox1 binding Adhiron lox1B

<400> SEQUENCE: 52

```
Ala Met Ala Ala Thr Gly Val Arg Ala Val Pro Gly Asn Glu Asn Ser
1               5                   10                  15

Leu Glu Ile Glu Glu Leu Ala Arg Phe Ala Val Asp Glu His Asn Lys
            20                  25                  30

Lys Glu Asn Ala Leu Leu Glu Phe Val Arg Val Lys Ala Lys Glu
        35                  40                  45

Gln Glu Gln Pro Ile Gly Glu His Pro Val Asn Asp Thr Met Tyr Tyr
    50                  55                  60

Leu Thr Leu Glu Ala Lys Asp Gly Gly Lys Lys Leu Tyr Glu Ala
65                  70                  75                  80

Lys Val Trp Val Lys Arg Trp Leu Arg Phe Thr Glu Ile Tyr Asn Phe
                85                  90                  95

Lys Glu Leu Gln Glu Phe Lys Pro Val Gly Asp Ala Ala Ala Ala
            100                 105                 110
```

<210> SEQ ID NO 53
<211> LENGTH: 54
<212> TYPE: DNA
<213> ORGANISM: Artificial Sequence
<220> FEATURE:
<223> OTHER INFORMATION: Adhiron_mut1 primer
<220> FEATURE:

```
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 53
cagggtcagg tagtacatgg tsnnsnnsnn snnctgctct ttggccttca cgac      54

<210> SEQ ID NO 54
<211> LENGTH: 48
<212> TYPE: DNA
<213> ORGANISM: Artificial Sequence
<220> FEATURE:
<223> OTHER INFORMATION: Adhiron_mut2 primer
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 54
ctggagctct ttgaagttsn nsnnsnnsnn cttgacccac actttggc      48

<210> SEQ ID NO 55
<211> LENGTH: 54
<212> TYPE: DNA
<213> ORGANISM: Artificial Sequence
<220> FEATURE:
<223> OTHER INFORMATION: Mutagenic primer for construction of library of
      binders within loop 1 (adhiron mut 1)
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 55
gtcgtgaagg ccaaagagca gnnsnnsnns nnsaccatgt actacctgac cctg      54

<210> SEQ ID NO 56
```

```
<211> LENGTH: 18
<212> TYPE: PRT
<213> ORGANISM: Artificial Sequence
<220> FEATURE:
<223> OTHER INFORMATION: Adhiron mut1 loop library variant sequence
<220> FEATURE:
<221> NAME/KEY: misc_feature
<222> LOCATION: (8)..(11)
<223> OTHER INFORMATION: Xaa can be any naturally occurring amino acid

<400> SEQUENCE: 56

Val Val Lys Ala Lys Glu Gln Xaa Xaa Xaa Xaa Thr Met Tyr Tyr Leu
1               5                   10                  15

Thr Leu

<210> SEQ ID NO 57
<211> LENGTH: 48
<212> TYPE: DNA
<213> ORGANISM: Artificial Sequence
<220> FEATURE:
<223> OTHER INFORMATION: Mutagenic primer for construction of library of
      binders within Adhiron mut2 loop
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 57
gccaaagtgt gggtcaagnn snnsnnsnns aacttcaaag agctccag            48

<210> SEQ ID NO 58
<211> LENGTH: 16
<212> TYPE: PRT
<213> ORGANISM: Artificial Sequence
<220> FEATURE:
<223> OTHER INFORMATION: Adhiron mut 2 loop library variant sequence
<220> FEATURE:
<221> NAME/KEY: misc_feature
<222> LOCATION: (7)..(10)
<223> OTHER INFORMATION: Xaa can be any naturally occurring amino acid

<400> SEQUENCE: 58

Ala Lys Val Trp Val Lys Xaa Xaa Xaa Xaa Asn Phe Lys Glu Leu Gln
1               5                   10                  15

<210> SEQ ID NO 59
<211> LENGTH: 105
<212> TYPE: DNA
<213> ORGANISM: Artificial sequence
<220> FEATURE:
<223> OTHER INFORMATION: Trypsin binding Knottin MCoTI-IIsequence

<400> SEQUENCE: 59
gccatggccg gtgtgtgccc caagatcttg aaaaagtgcc gccgtgacag cgattgtccc    60
ggcgcctgca tctgccgcgg caatggctat tgcggagcgg ccgca                 105

<210> SEQ ID NO 60
```

```
<211> LENGTH: 32
<212> TYPE: PRT
<213> ORGANISM: Artificial Sequence
<220> FEATURE:
<223> OTHER INFORMATION: Trypsin binding Knottin MCo-TI-II sequence

<400> SEQUENCE: 60

Ala Met Ala Gly Val Cys Pro Lys Ile Leu Lys Lys Cys Arg Arg Asp
1               5                   10                  15

Ser Asp Cys Pro Gly Ala Cys Ile Cys Arg Gly Asn Gly Tyr Cys Gly
                20                  25                  30

<210> SEQ ID NO 61
<211> LENGTH: 99
<212> TYPE: DNA
<213> ORGANISM: Artificial Sequence
<220> FEATURE:
<223> OTHER INFORMATION: Primer for creation of library of Knottin
      mutants
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 61
ggtgtgtgcv nsvnsvnsvn svnsvnsvns vnsvnsvnst gccgccgtga cagcgattgt    60
cccggcgcct gcatctgccg cggcaatggc tattgcgga                           99

<210> SEQ ID NO 62
<211> LENGTH: 99
<212> TYPE: DNA
<213> ORGANISM: Artificial Sequence
<220> FEATURE:
<223> OTHER INFORMATION: Sequence varied in library of knottin mutants
<220> FEATURE:
<221> NAME/KEY: misc_feature
<222> LOCATION: (62)..(62)
```

```
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t

<400> SEQUENCE: 62
tccgcaatag ccattgccgc ggcagatgca ggcgccggga caatcgctgt cacggcggca       60
snbsnbsnbs nbsnbsnbsn bsnbsnbsnb gcacacacc                              99

<210> SEQ ID NO 63
<211> LENGTH: 33
<212> TYPE: PRT
<213> ORGANISM: Artificial Sequence
<220> FEATURE:
<223> OTHER INFORMATION: Sequence of Knottin varied in library
<220> FEATURE:
<221> NAME/KEY: misc_feature
<222> LOCATION: (4)..(13)
<223> OTHER INFORMATION: Xaa can be any naturally occurring amino acid

<400> SEQUENCE: 63

Gly Val Cys Xaa Xaa Xaa Xaa Xaa Xaa Xaa Xaa Xaa Cys Arg Arg
1               5                   10                  15

Asp Ser Asp Cys Pro Gly Ala Cys Ile Cys Arg Gly Asn Gly Tyr Cys
            20                  25                  30

Gly

<210> SEQ ID NO 64
<211> LENGTH: 121
<212> TYPE: DNA
<213> ORGANISM: Artificial Sequence
<220> FEATURE:
<223> OTHER INFORMATION: pD7-Sce1 sequence nucleotides 1 - 120

<400> SEQUENCE: 64
ggtaccgaat tctagggata acagggtaat atgcatcttc tgacctcttc tcttcctccc       60
acagggcatg gcaaaacctc tgagccagga agaaagcaca ctgattgaaa gagcaaccgc      120
```

<210> SEQ ID NO 65
<211> LENGTH: 18
<212> TYPE: PRT
<213> ORGANISM: Artificial Sequence
<220> FEATURE:
<223> OTHER INFORMATION: Fragment of blasticidin resistance gene encoded by pD7-Sce1

<400> SEQUENCE: 65

```
Met Ala Lys Pro Leu Ser Gln Glu Glu Ser Thr Leu Ile Glu Arg Ala
1               5                   10                  15

Thr Ala
```

<210> SEQ ID NO 66
<211> LENGTH: 120
<212> TYPE: DNA
<213> ORGANISM: Artificial Sequence
<220> FEATURE:
<223> OTHER INFORMATION: pD7-ObLiGaRe sequence fragment

<400> SEQUENCE: 66

```
ggtaccgaat tcttttctgt caccaatcct ggggccacta gggacactgt ggggtggagg      60
aaatgcatct tctgacctct tctcttcctc ccacagggca tggcaaaacc tctgagccag     120
```

<210> SEQ ID NO 67
<211> LENGTH: 7
<212> TYPE: PRT
<213> ORGANISM: Artificial Sequence
<220> FEATURE:
<223> OTHER INFORMATION: Fragment of Blasticidin resistance gene encoded by pD7-ObLiGaRe

<400> SEQUENCE: 67

```
Met Ala Lys Pro Leu Ser Gln
1               5
```

<210> SEQ ID NO 68
<211> LENGTH: 1061
<212> TYPE: DNA
<213> ORGANISM: Artificial Sequence
<220> FEATURE:
<223> OTHER INFORMATION: ROSA 26 left homology arm sequence

<400> SEQUENCE: 68

```
gcgatcgcgc tgattggctt cttttcctcc cgccgtgtgt gaaaacacaa atggcgtgtt      60
ttggttggcg taaggcgcct gtcagttaac ggcagccgga gtgcgcagcc gccggcagcc     120
tcgctctgcc cactgggtgg ggcgggaggt aggtgggggtg aggcgagctg acgtgcggg     180
cgcggtcggc ctctggcggg gcggggggagg ggagggaggg tcagcgaaag tagctcgcgc     240
gcgagcggcc gcccaccctc cccttcctct ggggagtcg ttttaccgc cgccggccgg     300
gcctcgtcgt ctgattggct ctcggggccc agaaaactgg cccttgccat ggctcgtgt     360
tcgtgcaagt tgagtccatc cgccggccag cggggcggc gaggaggcgc tcccaggttc     420
cggccctccc ctcggccccg cgccgcagag tctggccgcg cgcccctgcg caacgtggca     480
ggaagcgcgc gctgggggcg gggacgggca gtagggctga gcggctgcgg ggcgggtgca     540
agcacgtttc cgacttgagt tgcctcaaga ggggcgtgct gagccagacc tccatcgcgc     600
actccgggga gtggagggaa ggagcgaggg ctcagttggg ctgttttgga ggcaggaagc     660
```

| | |
|---|---|
| acttgctctc ccaaagtcgc tctgagttgt tatcagtaag ggagctgcag tggagtaggc | 720 |
| ggggagaagg ccgcaccctt ctccggaggg gggaggggag tgttgcaata cctttctggg | 780 |
| agttctctgc tgcctcctgg cttctgagga ccgccctggg cctgggagaa tcccttcccc | 840 |
| ctcttccctc gtgatctgca actccagtct ttctagaatg cattaaggga tctgtagggc | 900 |
| gcagtagtcc agggtttcct tgatgatgtc atacttatcc tgtccttttt ttttccacag | 960 |
| ctcgcggttg aggacaaact cttcgcggtc tttccagtgg ggatcgacgg tatcgtagag | 1020 |
| tcgaggccgc tctaggaatt cacgccgcca ccatgaccga g | 1061 |

<210> SEQ ID NO 69
<211> LENGTH: 703
<212> TYPE: DNA
<213> ORGANISM: Artificial Sequence
<220> FEATURE:
<223> OTHER INFORMATION: ROSA 26 right homology arm sequence

<400> SEQUENCE: 69

| | |
|---|---|
| gtatacggga attgaacagg tgtaaaattg gagggacaag acttcccaca gattttcggt | 60 |
| tttgtcggga agttttttaa taggggcaaa taaggaaaat gggaggatag gtagtcatct | 120 |
| ggggttttat gcagcaaaac tacaggttat tattgcttgt gatccgcctc ggagtatttt | 180 |
| ccatcgaggt agattaaaga catgctcacc cgagttttat actctcctgc ttgagatcct | 240 |
| tactacagta tgaaattaca gtgtcgcgag ttagactatg taagcagaat tttaatcatt | 300 |
| tttaaagagc ccagtacttc atatccattt ctcccgctcc ttctgcagcc ttatcaaaag | 360 |
| gtatttaga acactcattt tagccccatt ttcatttatt atactggctt atccaacccc | 420 |
| tagacagagc attggcattt tccctttcct gatcttagaa gtctgatgac tcatgaaacc | 480 |
| agacagatta gttacataca ccacaaatcg aggctgtagc tggggcctca acactgcagt | 540 |
| tcttttataa ctccttagta cacttttttgt tgatcctttg ccttgatcct taattttcag | 600 |
| tgtctatcac ctctcccgtc aggtggtgtt ccacatttgg gcctattctc agtccaggga | 660 |
| gttttacaac aatagatgta ttgagaatcc aacctcctgc agg | 703 |

<210> SEQ ID NO 70
<211> LENGTH: 18
<212> TYPE: DNA
<213> ORGANISM: Artificial Sequence
<220> FEATURE:
<223> OTHER INFORMATION: Left TALEN recognition sequence

<400> SEQUENCE: 70

| | |
|---|---|
| tccctccac cccacagt | 18 |

<210> SEQ ID NO 71
<211> LENGTH: 15
<212> TYPE: DNA
<213> ORGANISM: Artificial Sequence
<220> FEATURE:
<223> OTHER INFORMATION: TALEN spacer

<400> SEQUENCE: 71

| | |
|---|---|
| ggggccacta gggac | 15 |

<210> SEQ ID NO 72
<211> LENGTH: 18
<212> TYPE: DNA
<213> ORGANISM: Artificial Sequence
<220> FEATURE:
<223> OTHER INFORMATION: Right TALEN target sequence

```
<400> SEQUENCE: 72
aggattggtg acagaaaa                                            18

<210> SEQ ID NO 73
<211> LENGTH: 18
<212> TYPE: DNA
<213> ORGANISM: Artificial Sequence
<220> FEATURE:
<223> OTHER INFORMATION: Right TALEN sequence

<400> SEQUENCE: 73
ttttctgtca ccaatcct                                            18

<210> SEQ ID NO 74
<211> LENGTH: 20
<212> TYPE: DNA
<213> ORGANISM: Artificial Sequence
<220> FEATURE:
<223> OTHER INFORMATION: AAVS-Left-arm-junction-PCR-Forw (9625) primer

<400> SEQUENCE: 74
ccggaactct gccctctaac                                          20

<210> SEQ ID NO 75
<211> LENGTH: 23
<212> TYPE: DNA
<213> ORGANISM: Artificial Sequence
<220> FEATURE:
<223> OTHER INFORMATION: BSD_Junction PCR-rev (9626) primer

<400> SEQUENCE: 75
tagccacaga atagtcttcg gag                                      23

<210> SEQ ID NO 76
<211> LENGTH: 21
<212> TYPE: DNA
<213> ORGANISM: Artificial Sequence
<220> FEATURE:
<223> OTHER INFORMATION: Donor_plasmid_seq_PDGFRTM-2 Forw  primer

<400> SEQUENCE: 76
acacgcagga ggccatcgtg g                                        21

<210> SEQ ID NO 77
<211> LENGTH: 20
<212> TYPE: DNA
<213> ORGANISM: Artificial Sequence
<220> FEATURE:
<223> OTHER INFORMATION: AAVS1_right arm_junction_PCR_rev primer

<400> SEQUENCE: 77
tcctgggata ccccgaagag                                          20

<210> SEQ ID NO 78
<211> LENGTH: 54
<212> TYPE: DNA
<213> ORGANISM: Artificial Sequence
<220> FEATURE:
<223> OTHER INFORMATION: Primer 2598

<400> SEQUENCE: 78 tttttttaa ttaagattat tgactagtta ttaatagtaa tcaattacgg ggtc      54

<210> SEQ ID NO 79
```

```
<211> LENGTH: 52
<212> TYPE: DNA
<213> ORGANISM: Artificial Sequence
<220> FEATURE:
<223> OTHER INFORMATION: Primer 2619

<400> SEQUENCE: 79 tttttttgttt aaacttacct tggatcccett gccggggctc aggctcaggg ac          52

<210> SEQ ID NO 80
<211> LENGTH: 33
<212> TYPE: DNA
<213> ORGANISM: Artificial Sequence
<220> FEATURE:
<223> OTHER INFORMATION: M13Leadseq primer

<400> SEQUENCE: 80
aaattattat tcgcaattcc tttggttgtt cct                                 33

<210> SEQ ID NO 81
<211> LENGTH: 30
<212> TYPE: DNA
<213> ORGANISM: Artificial Sequence
<220> FEATURE:
<223> OTHER INFORMATION: Notmycseq primer

<400> SEQUENCE: 81
ggccccattc agatcctctt ctgagatgag                                     30

<210> SEQ ID NO 82
<211> LENGTH: 22
<212> TYPE: DNA
<213> ORGANISM: Artificial Sequence
<220> FEATURE:
<223> OTHER INFORMATION: Primer 2623

<400> SEQUENCE: 82
taaagtaggc ggtcttgaga cg                                             22

<210> SEQ ID NO 83
<211> LENGTH: 22
<212> TYPE: DNA
<213> ORGANISM: Artificial Sequence
<220> FEATURE:
<223> OTHER INFORMATION: Primer 2624

<400> SEQUENCE: 83
gaaggtgctg ttgaactgtt cc                                             22

<210> SEQ ID NO 84
<211> LENGTH: 19
<212> TYPE: DNA
<213> ORGANISM: Artificial Sequence
<220> FEATURE:
<223> OTHER INFORMATION: Primer 2595

<400> SEQUENCE: 84
gagggctctg gcagctagc                                                 19

<210> SEQ ID NO 85
<211> LENGTH: 20
<212> TYPE: DNA
<213> ORGANISM: Artificial Sequence
<220> FEATURE:
<223> OTHER INFORMATION: Primer 2597

<400> SEQUENCE: 85
```

```
tcgagactgt gacgaggctg                                                    20

<210> SEQ ID NO 86
<211> LENGTH: 19
<212> TYPE: DNA
<213> ORGANISM: Artificial Sequence
<220> FEATURE:
<223> OTHER INFORMATION: Primer 2625

<400> SEQUENCE: 86
ccttggtgct ggcactcga                                                     19

<210> SEQ ID NO 87
<211> LENGTH: 40
<212> TYPE: DNA
<213> ORGANISM: Artificial Sequence
<220> FEATURE:
<223> OTHER INFORMATION: Primer 1999

<400> SEQUENCE: 87
aaaaagcagg ctaccatgag ggcctggatc ttctttctcc                              40

<210> SEQ ID NO 88
<211> LENGTH: 44
<212> TYPE: DNA
<213> ORGANISM: Artificial Sequence
<220> FEATURE:
<223> OTHER INFORMATION: TALEN recognition sequence

<400> SEQUENCE: 88
tccaccggtc gccaccatgg tgagcaaggg cgaggagctg ttca                         44

<210> SEQ ID NO 89
<211> LENGTH: 33
<212> TYPE: DNA
<213> ORGANISM: Artificial Sequence
<220> FEATURE:
<223> OTHER INFORMATION: AAVS1_HA-L_Nested_Forw1 primer

<400> SEQUENCE: 89
gtgcccttgc tgtgccgccg gaactctgcc ctc                                     33

<210> SEQ ID NO 90
<211> LENGTH: 23
<212> TYPE: DNA
<213> ORGANISM: Artificial Sequence
<220> FEATURE:
<223> OTHER INFORMATION: EGFP_Synthetic_gene_Rev_Assembly primer

<400> SEQUENCE: 90
ttcacgtcgc cgtccagctc gac                                                23

<210> SEQ ID NO 91
<211> LENGTH: 21
<212> TYPE: DNA
<213> ORGANISM: Artificial Sequence
<220> FEATURE:
<223> OTHER INFORMATION: Purotk_seq_fow2 primer

<400> SEQUENCE: 91
tccataccga cgatctgcga c                                                  21

<210> SEQ ID NO 92
<211> LENGTH: 27
<212> TYPE: DNA
```

```
<213> ORGANISM: Artificial Sequence
<220> FEATURE:
<223> OTHER INFORMATION: J44 primer

<400> SEQUENCE: 92
aaaagcgcct cccctacccg gtagaat                                        27

<210> SEQ ID NO 93
<211> LENGTH: 27
<212> TYPE: DNA
<213> ORGANISM: Artificial Sequence
<220> FEATURE:
<223> OTHER INFORMATION: J46 primer

<400> SEQUENCE: 93
ggcgacacgg aaatgttgaa tactcat                                        27

<210> SEQ ID NO 94
<211> LENGTH: 27
<212> TYPE: DNA
<213> ORGANISM: Artificial Sequence
<220> FEATURE:
<223> OTHER INFORMATION: J48 primer

<400> SEQUENCE: 94
cactacaccc agaagtccct gagcctg                                        27

<210> SEQ ID NO 95
<211> LENGTH: 20
<212> TYPE: DNA
<213> ORGANISM: Artificial Sequence
<220> FEATURE:
<223> OTHER INFORMATION: pSANG10pelB primer

<400> SEQUENCE: 95
cgctgcccag ccggccatgg                                                20

<210> SEQ ID NO 96
<211> LENGTH: 26
<212> TYPE: DNA
<213> ORGANISM: Artificial Sequence
<220> FEATURE:
<223> OTHER INFORMATION: Primer 2097

<400> SEQUENCE: 96
gatggtgatg atgatgtgcg gatgcg                                         26

<210> SEQ ID NO 97
<211> LENGTH: 38
<212> TYPE: DNA
<213> ORGANISM: Artificial Sequence
<220> FEATURE:
<223> OTHER INFORMATION: Primer 2423

<400> SEQUENCE: 97 tttttccat gggccggccc tccttcagtt tagttgag                             38

<210> SEQ ID NO 98
<211> LENGTH: 39
<212> TYPE: DNA
<213> ORGANISM: Artificial Sequence
<220> FEATURE:
<223> OTHER INFORMATION: Primer 2437

<400> SEQUENCE: 98 tttttttgcgg ccgcggaagc cgtgatctcc ttctctctc                          39
```

<210> SEQ ID NO 99
<211> LENGTH: 20
<212> TYPE: DNA
<213> ORGANISM: Artificial Sequence
<220> FEATURE:
<223> OTHER INFORMATION: Primer 2622

<400> SEQUENCE: 99
gaacaggaac acggaaggtc                                               20

<210> SEQ ID NO 100
<211> LENGTH: 22
<212> TYPE: DNA
<213> ORGANISM: Artificial Sequence
<220> FEATURE:
<223> OTHER INFORMATION: Primer 41679

<400> SEQUENCE: 100
atgagttgga gctgtatcat cc                                            22

<210> SEQ ID NO 101
<211> LENGTH: 18
<212> TYPE: DNA
<213> ORGANISM: Artificial Sequence
<220> FEATURE:
<223> OTHER INFORMATION: Primer 2621

<400> SEQUENCE: 101
gcattccacg gcggccgc                                                 18

<210> SEQ ID NO 102
<211> LENGTH: 9
<212> TYPE: PRT
<213> ORGANISM: Artificial Sequence
<220> FEATURE:
<223> OTHER INFORMATION: Peptide SLLMWITQV (NY-ESO-1 157-165) recognised
      by c12c2

<400> SEQUENCE: 102

Ser Leu Leu Met Trp Ile Thr Gln Val
1               5

<210> SEQ ID NO 103
<211> LENGTH: 10
<212> TYPE: PRT
<213> ORGANISM: Artificial Sequence
<220> FEATURE:
<223> OTHER INFORMATION: Peptide MART-1 26-35 recognised by MEL5 TCR

<400> SEQUENCE: 103

Glu Leu Ala Gly Ile Gly Ile Leu Thr Val
1               5                   10

<210> SEQ ID NO 104
<211> LENGTH: 30
<212> TYPE: DNA
<213> ORGANISM: Artificial Sequence
<220> FEATURE:
<223> OTHER INFORMATION: Primer 4JFH-Valpha-F

<400> SEQUENCE: 104
acacacgcta gccagaaaga ggtggaacag                                    30

<210> SEQ ID NO 105
<211> LENGTH: 50

```
<212> TYPE: DNA
<213> ORGANISM: Artificial Sequence
<220> FEATURE:
<223> OTHER INFORMATION: Primer 2770
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 105
caaagaacag ctcgccggts nncccgassn nggagctggc gcaaaagtac         50

<210> SEQ ID NO 106
<211> LENGTH: 53
<212> TYPE: DNA
<213> ORGANISM: Artificial Sequence
<220> FEATURE:
<223> OTHER INFORMATION: Primer 2771
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t

<400> SEQUENCE: 106
ctcgcccgaa ggtgggaatg tangwtccsn nsnnaagtgg gcgcacggcg cac       53

<210> SEQ ID NO 107
<211> LENGTH: 22
<212> TYPE: DNA
<213> ORGANISM: Artificial Sequence
<220> FEATURE:
<223> OTHER INFORMATION: Primer 2780

<400> SEQUENCE: 107
ctggcagcta gcaagcagga ag                                       22

<210> SEQ ID NO 108
<211> LENGTH: 22
<212> TYPE: DNA
<213> ORGANISM: Artificial Sequence
<220> FEATURE:
<223> OTHER INFORMATION: Primer 2781

<400> SEQUENCE: 108
tacattccca ccttcgggcg ag                                       22

<210> SEQ ID NO 109
<211> LENGTH: 26
<212> TYPE: DNA
<213> ORGANISM: Artificial Sequence
<220> FEATURE:
<223> OTHER INFORMATION: Primer 2782

<400> SEQUENCE: 109 tttttttgcgg ccgcggacag gttctg                                  26

<210> SEQ ID NO 110
```

<210> SEQ ID NO 110
<211> LENGTH: 27
<212> TYPE: DNA
<213> ORGANISM: Artificial Sequence
<220> FEATURE:
<223> OTHER INFORMATION: Primer 2783

<400> SEQUENCE: 110
cgtaagctgg taccttatta tctaggg                                        27

<210> SEQ ID NO 111
<211> LENGTH: 27
<212> TYPE: DNA
<213> ORGANISM: Artificial Sequence
<220> FEATURE:
<223> OTHER INFORMATION: Primer 2785

<400> SEQUENCE: 111
ccctagataa taaggtacca gcttacg                                        27

<210> SEQ ID NO 112
<211> LENGTH: 19
<212> TYPE: DNA
<213> ORGANISM: Artificial Sequence
<220> FEATURE:
<223> OTHER INFORMATION: Primer 2787

<400> SEQUENCE: 112
accggcgagc tgttctttg                                                 19

<210> SEQ ID NO 113
<211> LENGTH: 26
<212> TYPE: DNA
<213> ORGANISM: Artificial Sequence
<220> FEATURE:
<223> OTHER INFORMATION: Primer 2788

<400> SEQUENCE: 113
agtgacaagc ttttattatc tgggtg                                         26

<210> SEQ ID NO 114
<211> LENGTH: 19
<212> TYPE: DNA
<213> ORGANISM: Artificial Sequence
<220> FEATURE:
<223> OTHER INFORMATION: Primer 2789

<400> SEQUENCE: 114
caggtcctcg agcactgtc                                                 19

<210> SEQ ID NO 115
<211> LENGTH: 25
<212> TYPE: DNA
<213> ORGANISM: Artificial Sequence
<220> FEATURE:
<223> OTHER INFORMATION: CRISPR1 double-stranded DNA insert strand

<400> SEQUENCE: 115
ggggccacta gggacaggat gtttt                                          25

<210> SEQ ID NO 116
<211> LENGTH: 26
<212> TYPE: DNA
<213> ORGANISM: Artificial Sequence
<220> FEATURE:
<223> OTHER INFORMATION: CRISPR1 double-stranded DNA insert strand

<400> SEQUENCE: 116

```
catcctgtcc ctagtggccc ccggtg                                              26

<210> SEQ ID NO 117
<211> LENGTH: 25
<212> TYPE: DNA
<213> ORGANISM: Artificial Sequence
<220> FEATURE:
<223> OTHER INFORMATION: CRISPR2 double-stranded DNA insert strand

<400> SEQUENCE: 117
gtcaccaatc ctgtccctag gtttt                                               25

<210> SEQ ID NO 118
<211> LENGTH: 25
<212> TYPE: DNA
<213> ORGANISM: Artificial Sequence
<220> FEATURE:
<223> OTHER INFORMATION: CRISPR2 double-stranded DNA insert strand

<400> SEQUENCE: 118
ctagggacag gattggtgac cggtg                                               25

<210> SEQ ID NO 119
<211> LENGTH: 102
<212> TYPE: RNA
<213> ORGANISM: Artificial Sequence
<220> FEATURE:
<223> OTHER INFORMATION: CRISPR 1 RNA

<400> SEQUENCE: 119 gggggggccac uagggacagg auguuuuaga gcuagaaaua gcaaguuaaa auaaggcuag        60
uccguuauca acuugaaaaa guggcaccga gucggugcuu uu                           102

<210> SEQ ID NO 120
<211> LENGTH: 102
<212> TYPE: RNA
<213> ORGANISM: Artificial Sequence
<220> FEATURE:
<223> OTHER INFORMATION: CRISPR 2 RNA

<400> SEQUENCE: 120
gggucaccaa uccugucccu agguuuuaga gcuagaaaua gcaaguuaaa auaaggcuag         60
uccguuauca acuugaaaaa guggcaccga gucggugcuu uu                           102

<210> SEQ ID NO 121
<211> LENGTH: 25
<212> TYPE: DNA
<213> ORGANISM: Artificial Sequence
<220> FEATURE:
<223> OTHER INFORMATION: Primer 2723

<400> SEQUENCE: 121
cgcgccagaa gtctcaccaa gccca                                               25

<210> SEQ ID NO 122
<211> LENGTH: 25
<212> TYPE: DNA
<213> ORGANISM: Artificial Sequence
<220> FEATURE:
<223> OTHER INFORMATION: Primer 2724

<400> SEQUENCE: 122
cgcgtgggct tggtgagact tctgg                                               25
```

<210> SEQ ID NO 123
<211> LENGTH: 60
<212> TYPE: DNA
<213> ORGANISM: Artificial Sequence
<220> FEATURE:
<223> OTHER INFORMATION: Primer 2768

<400> SEQUENCE: 123
aattctcccc tccaccccac agtagggaca gtggggccag gattggtgac agaaaatgca          60

<210> SEQ ID NO 124
<211> LENGTH: 52
<212> TYPE: DNA
<213> ORGANISM: Artificial Sequence
<220> FEATURE:
<223> OTHER INFORMATION: Primer 2769

<400> SEQUENCE: 124
ttttctgtca ccaatcctgg ccccactgtc cctactgtgg ggtggagggg ag                  52

<210> SEQ ID NO 125
<211> LENGTH: 28
<212> TYPE: DNA
<213> ORGANISM: Artificial Sequence
<220> FEATURE:
<223> OTHER INFORMATION: Primer 2778

<400> SEQUENCE: 125
aattctaggg ataacagggt aatatgca                                             28

<210> SEQ ID NO 126
<211> LENGTH: 20
<212> TYPE: DNA
<213> ORGANISM: Artificial Sequence
<220> FEATURE:
<223> OTHER INFORMATION: Primer 2779

<400> SEQUENCE: 126
tattaccctg ttatccctag                                                      20

<210> SEQ ID NO 127
<211> LENGTH: 60
<212> TYPE: DNA
<213> ORGANISM: Artificial Sequence
<220> FEATURE:
<223> OTHER INFORMATION: Primer 2808

<400> SEQUENCE: 127
aattcttttc tgtcaccaat cctggggcca ctagggacac tgtggggtgg aggggatgca          60

<210> SEQ ID NO 128
<211> LENGTH: 57
<212> TYPE: DNA
<213> ORGANISM: Artificial Sequence
<220> FEATURE:
<223> OTHER INFORMATION: Primer 2809

<400> SEQUENCE: 128
tcccctccac cccacagtgt ccctagtggc cccaggattg gtgacagaaa agaattg             57

<210> SEQ ID NO 129
<211> LENGTH: 41
<212> TYPE: DNA
<213> ORGANISM: Artificial Sequence
<220> FEATURE:
<223> OTHER INFORMATION: Primer J60

```
<400> SEQUENCE: 129
acacacggta ccgcgatcgc gctgattggc ttcttttcct c                          41

<210> SEQ ID NO 130
<211> LENGTH: 35
<212> TYPE: DNA
<213> ORGANISM: Artificial Sequence
<220> FEATURE:
<223> OTHER INFORMATION: Primer 2706

<400> SEQUENCE: 130 tttttatgc attctagaaa gactggagtt gcaga                                  35

<210> SEQ ID NO 131
<211> LENGTH: 18
<212> TYPE: DNA
<213> ORGANISM: Artificial Sequence
<220> FEATURE:
<223> OTHER INFORMATION: Primer 2715

<400> SEQUENCE: 131
gagcgtccgc ccaccctc                                                    18

<210> SEQ ID NO 132
<211> LENGTH: 18
<212> TYPE: DNA
<213> ORGANISM: Artificial Sequence
<220> FEATURE:
<223> OTHER INFORMATION: Primer 2716

<400> SEQUENCE: 132
gagggtgggc ggacgctc                                                    18

<210> SEQ ID NO 133
<211> LENGTH: 33
<212> TYPE: DNA
<213> ORGANISM: Artificial Sequence
<220> FEATURE:
<223> OTHER INFORMATION: Primer 2709

<400> SEQUENCE: 133 tttttatgc attaagggat ctgtagggcg cag                                    33

<210> SEQ ID NO 134
<211> LENGTH: 21
<212> TYPE: DNA
<213> ORGANISM: Artificial Sequence
<220> FEATURE:
<223> OTHER INFORMATION: Primer 2710

<400> SEQUENCE: 134
gtgaattcct agagcggcct c                                                21

<210> SEQ ID NO 135
<211> LENGTH: 50
<212> TYPE: DNA
<213> ORGANISM: Artificial Sequence
<220> FEATURE:
<223> OTHER INFORMATION: Primer 2745

<400> SEQUENCE: 135
gaggccgctc taggaattca cgccgccacc atgaccgagt acaagcccac                 50

<210> SEQ ID NO 136
```

<211> LENGTH: 48
<212> TYPE: DNA
<213> ORGANISM: Artificial Sequence
<220> FEATURE:
<223> OTHER INFORMATION: Primer J59

<400> SEQUENCE: 136
aaaaaaagat ctgtgtgttt cgaatcaggc accgggcttg cgggtcat              48

<210> SEQ ID NO 137
<211> LENGTH: 36
<212> TYPE: DNA
<213> ORGANISM: Artificial Sequence
<220> FEATURE:
<223> OTHER INFORMATION: Primer J61

<400> SEQUENCE: 137 tttttttgtat acgggaattg aacaggtgta aaattg                          36

<210> SEQ ID NO 138
<211> LENGTH: 43
<212> TYPE: DNA
<213> ORGANISM: Artificial Sequence
<220> FEATURE:
<223> OTHER INFORMATION: Primer J62

<400> SEQUENCE: 138 tttttttcctg caggaggttg gattctcaat acatctattg ttg                   43

<210> SEQ ID NO 139
<211> LENGTH: 25
<212> TYPE: DNA
<213> ORGANISM: Artificial Sequence
<220> FEATURE:
<223> OTHER INFORMATION: Primer 2701

<400> SEQUENCE: 139
gccgacgtct cgtcgctgat gtttt                                       25

<210> SEQ ID NO 140
<211> LENGTH: 25
<212> TYPE: DNA
<213> ORGANISM: Artificial Sequence
<220> FEATURE:
<223> OTHER INFORMATION: Primer 2702

<400> SEQUENCE: 140
atcagcgacg agacgtcggc cggtg                                       25

<210> SEQ ID NO 141
<211> LENGTH: 25
<212> TYPE: DNA
<213> ORGANISM: Artificial Sequence
<220> FEATURE:
<223> OTHER INFORMATION: Primer 2703

<400> SEQUENCE: 141
cgcccatctt ctagaaagac gtttt                                       25

<210> SEQ ID NO 142
<211> LENGTH: 25
<212> TYPE: DNA
<213> ORGANISM: Artificial Sequence

```
<220> FEATURE:
<223> OTHER INFORMATION: Primer 2704

<400> SEQUENCE: 142
gtctttctag aagatgggcg cggtg                                          25
```